US011326173B2

(12) United States Patent
Jach et al.

(10) Patent No.: US 11,326,173 B2
(45) Date of Patent: May 10, 2022

(54) METHOD OF FERMENTATIVE ALPHA-IONONE PRODUCTION

(71) Applicant: PHYTOWELT GREENTECHNOLOGIES GMBH, Nettetal (DE)

(72) Inventors: Guido Jach, Konigswinter (DE); Sanae Azdouffal, Dusseldorf (DE); Katrin Schullehner, Cologne (DE); Peter Welters, Nettetal (DE); Angela Goergen, Cologne (DE)

(73) Assignee: PHYTOWELT GREENTECHNOLOGIES GMBH, Nettetal (DE)

(*) Notice: Subject to any disclaimer, the term of this patent is extended or adjusted under 35 U.S.C. 154(b) by 92 days.

(21) Appl. No.: 15/755,976

(22) PCT Filed: Aug. 28, 2015

(86) PCT No.: PCT/EP2015/069751

§ 371 (c)(1),
(2) Date: Feb. 27, 2018

(87) PCT Pub. No.: WO2017/036495

PCT Pub. Date: Mar. 9, 2017

(65) Prior Publication Data

US 2018/0251796 A1 Sep. 6, 2018

(51) Int. Cl.

*C12P 5/00* (2006.01)
*C12N 1/20* (2006.01)

(Continued)

(52) U.S. Cl.

CPC ........... *C12N 15/63* (2013.01); *C12N 9/0069* (2013.01); *C12N 9/10* (2013.01); *C12N 9/90* (2013.01);

(Continued)

(58) Field of Classification Search

CPC ........ C12N 9/001; C12N 9/1085; C12N 9/90; C12N 9/0069; C12P 23/00

See application file for complete search history.

(56) References Cited

U.S. PATENT DOCUMENTS 6,989,257 B2 * 1/2006 Berry .................. C12N 9/0006 435/189
10,030,258 B2 * 7/2018 Kim .......................... C12R 1/15

(Continued)

FOREIGN PATENT DOCUMENTS

WO 9961399 A1 12/1999
WO 02061050 A2 8/2002

(Continued)

OTHER PUBLICATIONS

Schwartz. Characterization of a novel carotenoid cleavage dioxygenase from Plants. J. Biol. Chem. 276:25208-25211(2001).*

(Continued)

*Primary Examiner* — Yong D Pak
(74) *Attorney, Agent, or Firm* — Leber IP Law; Narendra K. Vaish

(57) ABSTRACT

The present invention concerns a method of producing and enantiomerically pure alpha-ionone. Further, the invention concerns a nucleic acid that comprises a sequence that encodes a lycopene-epsilon-cyclase (EC), a lycopene-epsilon-cyclase (EC), plasmids, which encode components of the alpha-ionone biosynthesis and a microorganism that contains heterologous nucleotide sequences which encode the enzymes geranylgeranyl-diphosphate-synthase, isopentenyl-diphosphate-isomerase (IPI), phytoene desaturase-dehydrogenase (crtI), phytoene synthase (crtB), lycopene-epsilon-cyclase (EC) and carotenoid-cleavage-dioxygenase (Continued)

The coding sequences of the labeled proteins are depicted as arrows. Regulatory DNA-sequences are depicted as boxes. The positions of singular restriction sites are indicated. The exact positions of the labeled elements and their functions are listed in the following table:

| Sequence name | Start | Stop | Characteristic |
|---|---|---|---|
| pTet-m1 | 9 | 65 | Tetracycline-promoter(modified) |
| idsA | 75 | 1174 | Geranylgeranyl-pyrophosphate synthase |
| IPI | 1238 | 2281 | type2 isopentenyl diphosphate isomerase |
| crtI | 2294 | 3772 | Phytoene-desaturase |
| crtB | 3769 | 4698 | Phytoene Synthase |
| newTerm | 4699 | 4725 | artificial terminator |
| CmR | 5556 | 4897 | Chlorampenicol-resistance gene |
| aP12 | 6148 | 6171 | artificial promoter (aP12) |
| ECmut3.3 | 6202 | 7680 | Lycopene epsilon cyclase (muted; incl. HIS Tag) |
| OfCCD1 | 7696 | 9354 | Carotenoid-cleavage dioxygenase (from O. fragrans; incl. HIS-Tag |
| aTerm5 | 9375 | 9402 | artificial terminator |
| P15A | 9433 | 4 | Origin of replication |

(CCD1). Further, the invention concerns a method of producing highly pure epsilon-carotene.

4 Claims, 17 Drawing Sheets

Specification includes a Sequence Listing.

(51) Int. Cl.

| | |
|---|---|
| ***C12N 15/00*** | (2006.01) |
| ***C12N 9/10*** | (2006.01) |
| ***C12N 9/90*** | (2006.01) |
| ***C12N 9/02*** | (2006.01) |
| ***C12N 15/63*** | (2006.01) |
| ***C12P 23/00*** | (2006.01) |
| ***C12N 15/74*** | (2006.01) |
| *C12R 1/01* | (2006.01) |

(52) U.S. Cl.

CPC .............. *C12N 15/74* (2013.01); *C12P 5/007* (2013.01); *C12P 23/00* (2013.01); *C12N 1/205* (2021.05); *C12R 2001/01* (2021.05); *C12Y 103/9903* (2013.01); *C12Y 104/99* (2013.01); *C12Y 202/01007* (2013.01); *C12Y 205/01029* (2013.01); *C12Y 205/01032* (2013.01); *C12Y 503/03002* (2013.01); *C12Y 505/01018* (2013.01)

(56) References Cited

U.S. PATENT DOCUMENTS

| | | | | |
|---|---|---|---|---|
| 10,059,974 B2 * | 8/2018 | Wurtzel | ......... | C12Y 114/99045 |
| 10,364,434 B2 * | 7/2019 | Wang | ........................ | C12P 7/26 |
| 2009/0216039 A1 | 8/2009 | Yamamoto et al. | | |
| 2014/0170720 A1 * | 6/2014 | Kim | .......................... | C12P 7/24<br>435/147 |

FOREIGN PATENT DOCUMENTS

| | | | | |
|---|---|---|---|---|
| WO | 2005087942 A1 | 9/2005 | | |
| WO | WO-2014/204058 A1 * | 12/2014 | ............... | C12R 1/15 |

OTHER PUBLICATIONS

Studer. Residue mutations and their impact on protein structure and function: detecting beneficial and pathogenic changes. Biochem. J. (2013) 449, 581-594.*

Bai et al. , "Novel Lycopene Epsilon Cyclase Activities in Maize Revealed Through Perturbation of Carotenoid Biosynthesis," The Plant Journal, Aug. 2009, vol. 59 (4), pp. 588-599.

Baldermann et al., "Functional Characterization of a Carotenoid Cleavage Dioxygenase 1 and Its Relation to the Carotenoid Accumulation and Volatile Emission During the Floral Development of Osmanthus Fragrans Lour," Journal of Experimental Botany, Jun. 2010, vol. 61 (11), pp. 2967-2977.

Bovolenta et al., "A Simple and Efficient Highly Enantioselective Synthesis of alpha-Ionone and alpha-Damascone," The Journal of Organic Chemistry, Dec. 2004, vol. 69 (25), pp. 8959-8962.

Cunningham et al., "A Portfolio of Plasmids for Identification and Analysis of Carotenoid Pathway Enzymes: Adonis Aestivalis as a Case Study," Photosynthesis Research, May 2007, vol. 92 (2), pp. 245-259.

Cunningham et al., "A Study in Scarlet: Enzymes of Ketocarotenoid Biosynthesis in the Flowers of Adonis Aestivalis," Plant Journal, Feb. 2005, vol. 41 (3), pp. 478-492.

Cunningham et al., "Functional Analysis of the Beta and Epsilon Lycopene Cyclase Enzymes of *Arabidopsis* Reveals a Mechanism for Control of Cyclic Carotenoid Formation," The Plant Cell, Sep. 1996, vol. 8 (9), pp. 1613-1626.

Cunningham et al., "Molecular Structure and Enzymatic Function of Lycopene Cyclase From the *Cyanobacterium synechococcus* sp Strain PCC7942," The Plant cell, Aug. 1994, vol. 6 (8), pp. 1107-1121.

Cunningham et al., "One Ring or Two? Determination of Ring Number in Carotenoids by Lycopene Epsilon-Cyclases," Proceedings of the National Academy of Sciences of the United States of America, Feb. 2001, vol. 98 (5), pp. 2905-2910.

International Patent Application No. PCT/EP2015/069751, International Preliminary Report on Patentability dated Mar. 15, 2018.

International Patent Application No. PCT/EP2015/069751, International Search Report and Written Opinion dated Feb. 29, 2016.

Jach et al., "An Improved mRFP1 Adds Red to Bimolecular Fluorescence Complementation," Nature Methods, Aug. 2006, vol. 3 (8), pp. 597-600.

Misawa et al., "Elucidation of the Erwinia Uredovora Carotenoid Biosynthetic Pathway by Functional Analysis of Gene Products Expressed in *Escherichia coli*," Journal of Bacteriology, Dec. 1990, vol. 172 (12), pp. 6704-6712.

Perry et al., "Cloning and Regulation of Erwinia Herbicola Pigment Genes," Journal of Bacteriology, Nov. 1986, vol. 168 (2), pp. 607-612.

Soorukram et al., "Enantioselective Synthesis of alpha-Ionone Derivatives Using an Anti SN2' Substitution of Functionalized Zinc Organometallics," Organic Letters, Jun. 2004, vol. 6 (14), pp. 2409-2411.

Vogel et al., "The Carotenoid Cleavage Dioxygenase 1 Enzyme Has Broad Substrate Specificity, Cleaving Multiple Carotenoids at Two Different Bond Positions," Journal of Biological Chemistry, Apr. 2008, vol. 283 (17), pp. 11364-11373.

Yahyaa et al., "Formation of Norisoprenoid Flavor Compounds in Carrot (*Daucus carota*L.) Roots: Characterization of a Cyclic-Specific Carotenoid Cleavage Dioxygenase 1 Gene," Journal of Agricultural and Food Chemistry, Nov. 2013, vol. 61 (50), pp. 12244-12252.

Zhang et al., "Reconstruction of the Carotenoid Biosynthetic Pathway of Cronobacter sakazakii BAA894 in *Escherichia coli*," PLoS One, Jan. 2014, vol. 9 (1), pp. e86739.

Baldermann et al., "Biosynthesis of alpha- and beta-Ionone, Prominent Scent Compounds, in Flowers of Osmanthus Fragrans," Acta Biochimica Polonica, 2012, vol. 59 (1), pp. 79-81.

Gao et al., "Molecular Cloning, Characterization and Functional Analysis of a New Isopentenyl Diphosphate Isomerase Gene (IPI) From Curcuma Wenyujin," Journal of Medicinal Plants Research, Apr. 2012, vol. 6 (16), pp. 3148-3155.

Ibdah et al., "Functional Characterization of CmCCD1, a Carotenoid Cleavage Dioxygenase From Melon," Phytochemistry, Aug. 2006, vol. 67 (15), pp. 1579-1589.

Yoon et al., "Combinatorial Expression of Bacterial Whole Mevalonate Pathway for the Production of Beta-Carotene in *E. coli*," Journal of Biotechnology, Mar. 2009, vol. 140 (3-4), pp. 218-226.

Canadian Patent Application No. CA2996711, Office Action dated Feb. 28, 2020.

* cited by examiner

| Sequence name | Start | Stop | Characteristic |
|---|---|---|---|
| p15A | 1 | 913 | Origin of replication |
| crtE | 1002 | 1925 | Geranylgeranyl-pyrophosphate synthase |
| IPI | 1988 | 3031 | type2 isopentenyl diphosphate isomerase |
| crtI | 3044 | 4522 | Phytoene-desaturase |
| crtB | 4519 | 5448 | Phytoene synthase |
| aTerm5 | 5449 | 5476 | Artificial terminator |
| CmR | 6306 | 5647 | Chloramphenicol-resistance gene |

Figure 4:

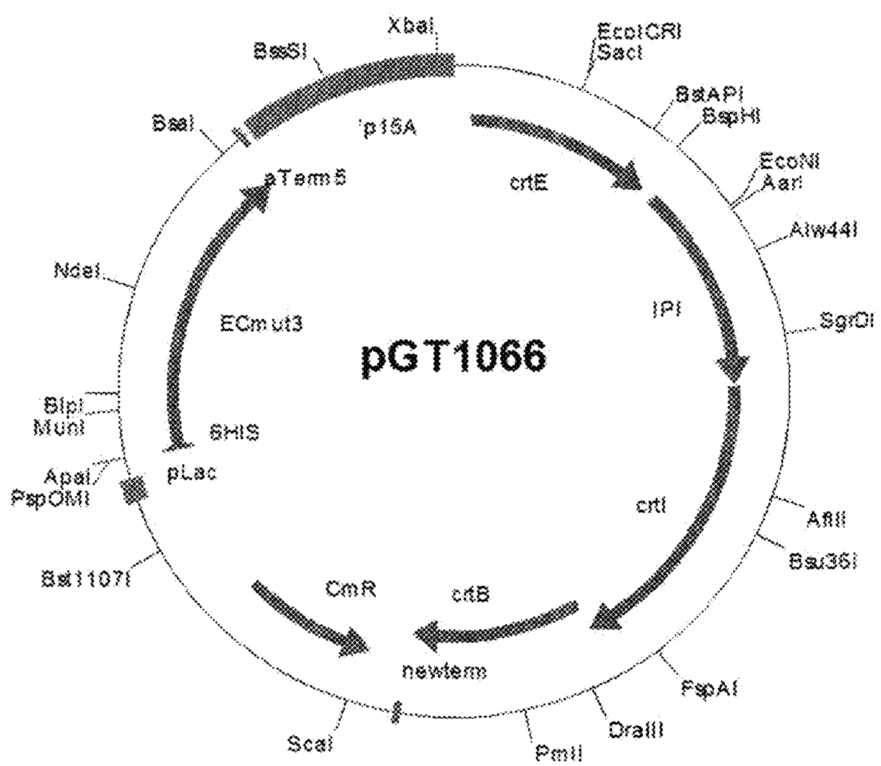

| Sequence name | Start | Stop | Characteristic |
|---|---|---|---|
| crtE | 93 | 1016 | Geranylgeranyl-pyrophosphate synthase |
| IPI | 1079 | 2122 | type2 isopentenyl diphosphate isomerase |
| crtI | 2135 | 3613 | Phytoene-desaturase |
| crtB | 3610 | 4539 | Phytoene-synthase |
| newTerm | 4550 | 4566 | Artificial terminator |
| CmR | 5397 | 4738 | Chloramphenicol-resistance gene |
| pLac | 6004 | 6101 | Lactose-Promoter |
| ECmut3 | 6183 | 7661 | Lycopene epsilon cyclase (mutated; incl. HIS-Tag) |
| aTerm5 | 7682 | 7709 | Artificial Terminator |
| P15A | 7740 | 4 | Origin of replication |

Figure 5:

AtEC
AtEC-del
AtECmut3
LsEC
ZmEC

Pos. 403(447)
Pos. 404(448)

LsEC(457)
ZmEC(461)

Pos. 445(489)

LsEC(498)
ZmEC(502)

Figure 7:

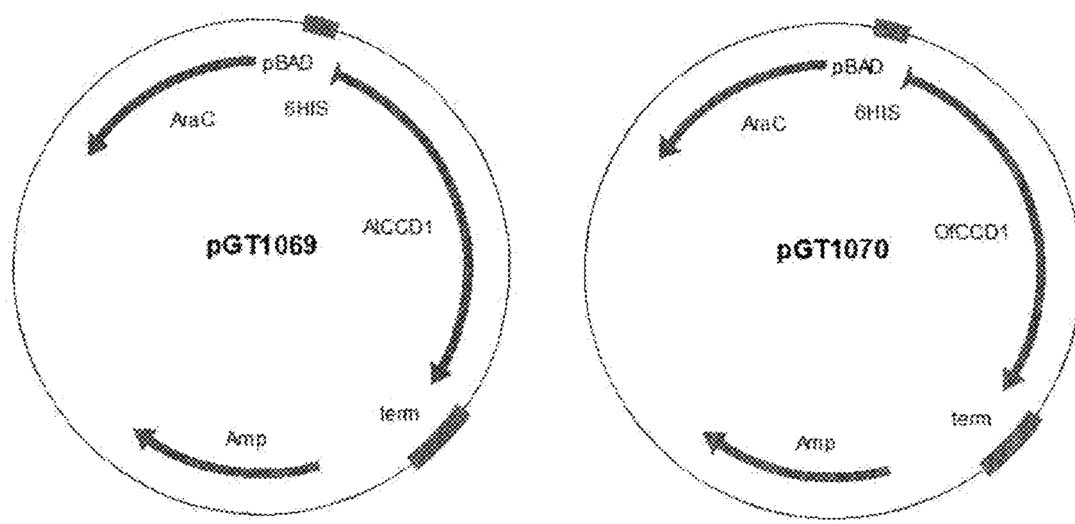

pGT1069

| Sequence name | Start | Stop | Characteristic |
|---|---|---|---|
| pBAD | 158 | 282 | Promoter |
| 6HIS | 328 | 362 | HIS-TAG |
| AtCCD1 | 364 | 1980 | AtCCD1-gene (coding region) |
| term | 1988 | 2265 | Terminator |
| Amp | 2607 | 3467 | Ampicillin-resistance gene |
| AraC | 5688 | 4810 | Repressor of the pBAD-promoter |

pGT1070

| Sequence name | Start | Stop | Characteristic |
|---|---|---|---|
| pBAD | 158 | 282 | Promoter |
| 6HIS | 328 | 362 | HIS-TAG |
| OfCCD1 | 364 | 1995 | OfCCD1-gene (coding region) |
| term | 2003 | 2280 | Terminator |
| Amp | 2622 | 3482 | Ampicillin-resistance gene |
| AraC | 5703 | 4825 | Repressor of the pBAD-promoter |

Figure 9:

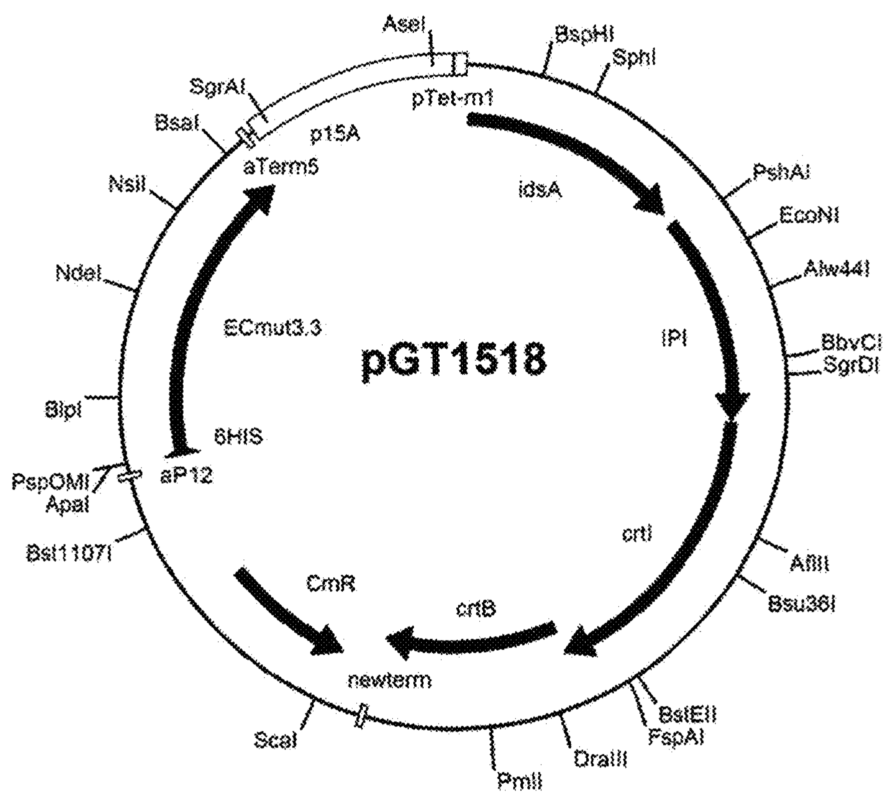

The coding sequences of the labeled proteins are depicted as arrows. Regulatory DNA-sequences are depicted as boxes. The positions of singular restriction sites are indicated. The exact positions of the labeled elements and their functions are listed in the following table:

| Sequence name | Start | Stop | Characteristic |
|---|---|---|---|
| pTet-m1 | 9 | 55 | Tetracycline-Promoter (modified) |
| idsA | 75 | 1174 | Geranylgeranyl-pyrophosphate synthase |
| IPI | 1238 | 2281 | type2 isopentenyl diphosphate isomerase |
| crtI | 2294 | 3772 | Phytoene-desaturase |
| crtB | 3769 | 4698 | Phytoene synthase |
| newTerm | 4699 | 4725 | artificial terminator |
| CmR | 5556 | 4897 | Chlorampenicol-restistance gene |
| aP12 | 6148 | 6171 | artificial promoter (aP12) |
| ECmut3.3 | 6202 | 7680 | Lycopene epsilon cyclase (muted; incl. HIS-Tag) |
| aTerm5 | 7701 | 7728 | artificial terminator |
| P15A | 7759 | 4 | Origin of replication |

Figure 10:

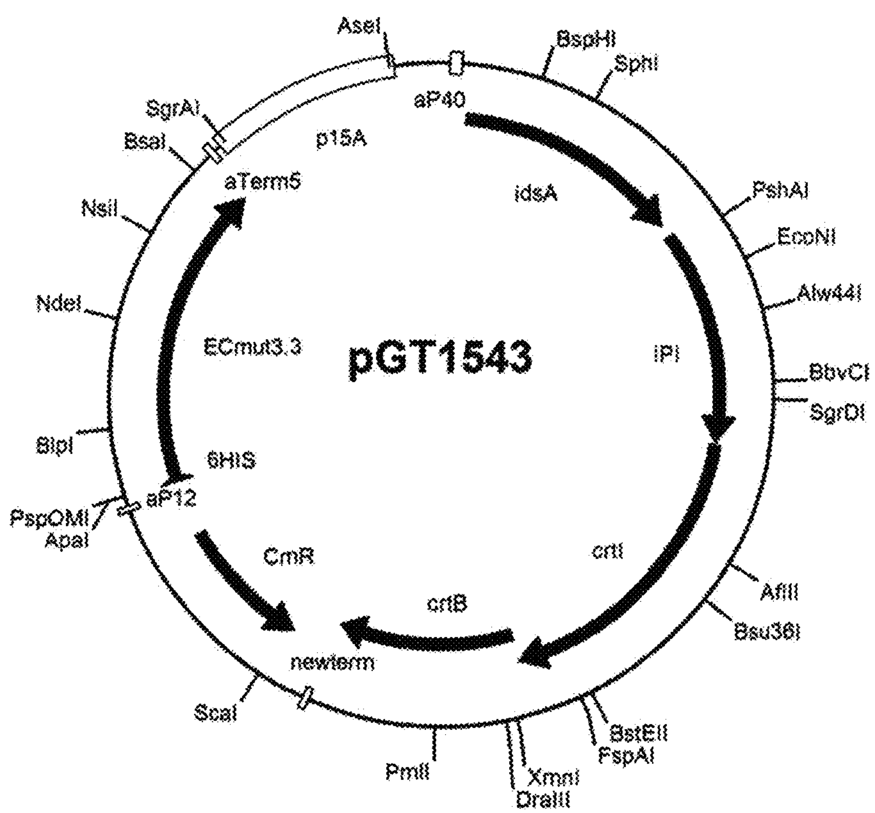

The coding sequences of the labeled proteins are depicted as arrows. Regulatory DNA-sequences are depicted as boxes. The positions of singular restriction sites are indicated. The exact positions of the labeled elements and their functions are listed in the following table:

| Sequence name | Start | Stop | Characteristic |
|---|---|---|---|
| aP40 | 41 | 90 | artificial Promoter (PHY-collection) |
| idsA | 123 | 1222 | Geranylgeranyl-pyrophosphate synthase |
| IPI | 1286 | 2329 | type2 isopentenyl diphosphate isomerase |
| crtI | 2342 | 3820 | Phytoene-desaturase |
| crtB | 3817 | 4746 | Phytoene synthase |
| newTerm | 4747 | 4773 | artificial terminator |
| CmR | 5604 | 4945 | Chloramphenicol-resistance gene |
| aP12 | 5824 | 5847 | artificial promoter (aP12) |
| ECmut3.3 | 5914 | 7356 | Lycopene epsilon cyclase (muted; incl. HIS-Tag) |
| aTerm5 | 7377 | 7404 | artificial terminator |
| P15A | 7433 | 8215 | Origin of replication |

Figure 11:

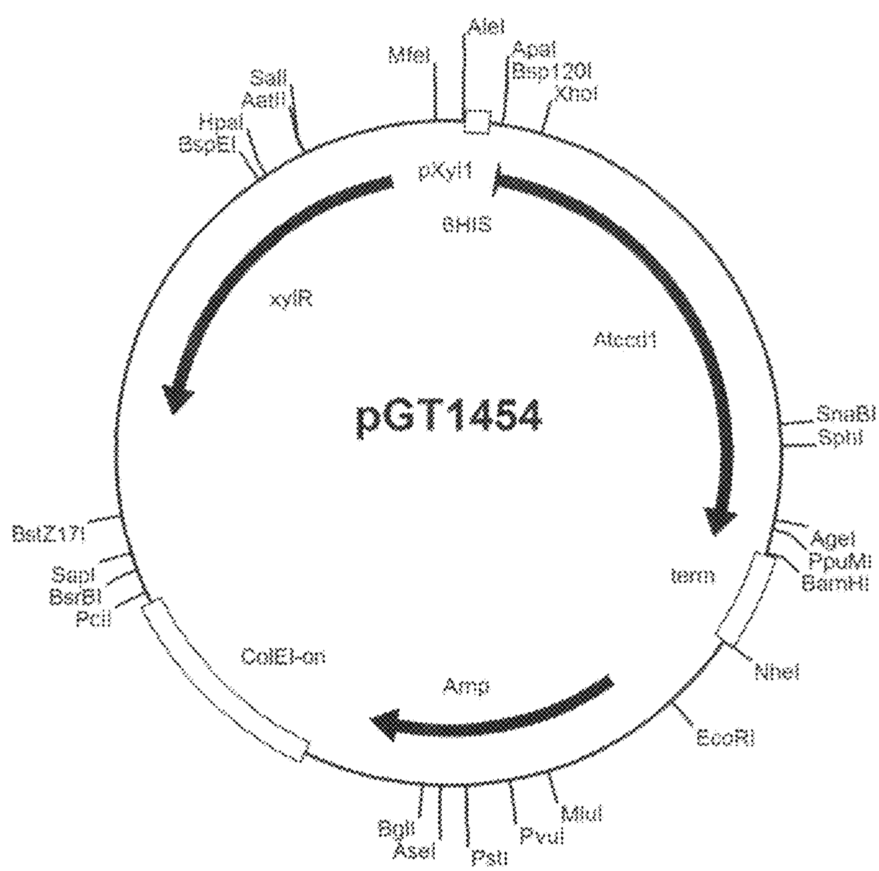

The coding sequences of the labeled proteins are depicted as arrows. Regulatory DNA-sequences are depicted as boxes. The positions of singular restriction sites are indicated. The exact positions of the labeled elements and their functions are listed in the following table:

| **Sequence name** | **Start** | **Stop** | **Characteristic** |
|---|---|---|---|
| pXyl1 | 46 | 117 | Xylose-inducible promoter (PHY-collection) |
| AtCCD1 | 160 | 1797 | Carotenoid-cleavage dioxygenase from *A.thaliana* |
| term | 1805 | 2082 | Terminator |
| Amp | 2424 | 3284 | Amipicillin-resistance gene |
| ColE1-ori | 3440 | 4070 | Origin of replication |
| xylR | 5827 | 4652 | pXyl-regulator |

Figure 12:

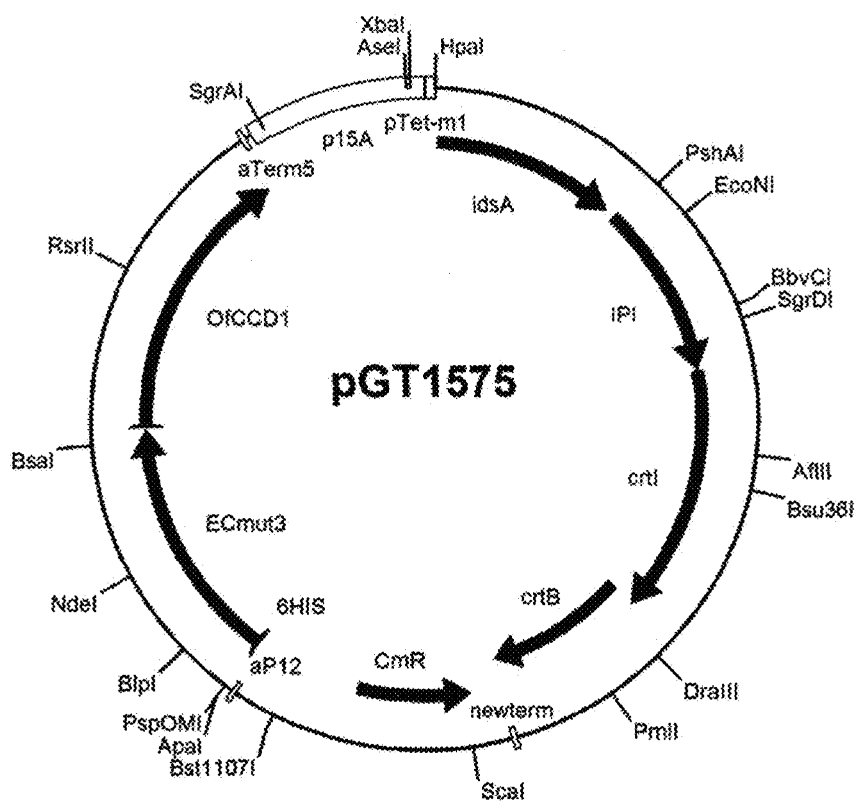

The coding sequences of the labeled proteins are depicted as arrows. Regulatory DNA-sequences are depicted as boxes. The positions of singular restriction sites are indicated. The exact positions of the labeled elements and their functions are listed in the following table:

| Sequence name | Start | Stop | Characteristic |
|---|---|---|---|
| pTet-m1 | 9 | 55 | Tetracycline-promoter(modified) |
| idsA | 75 | 1174 | Geranylgeranyl-pyrophosphate synthase |
| IPI | 1238 | 2281 | type2 isopentenyl diphosphate isomerase |
| crtI | 2294 | 3772 | Phytoene-desaturase |
| crtB | 3769 | 4698 | Phytoene Synthase |
| newTerm | 4699 | 4725 | artificial terminator |
| CmR | 5556 | 4897 | Chlorampenicol-resistance gene |
| aP12 | 6148 | 6171 | artificial promoter (aP12) |
| ECmut3.3 | 6202 | 7680 | Lycopene epsilon cyclase (muted; incl. HIS-Tag) |
| OfCCD1 | 7696 | 9354 | Carotenoid-cleavage dioxygenase (from O. fragrans; incl. HIS-Tag |
| aTerm5 | 9375 | 9402 | artificial terminator |
| P15A | 9433 | 4 | Origin of replication |

Figure 13:

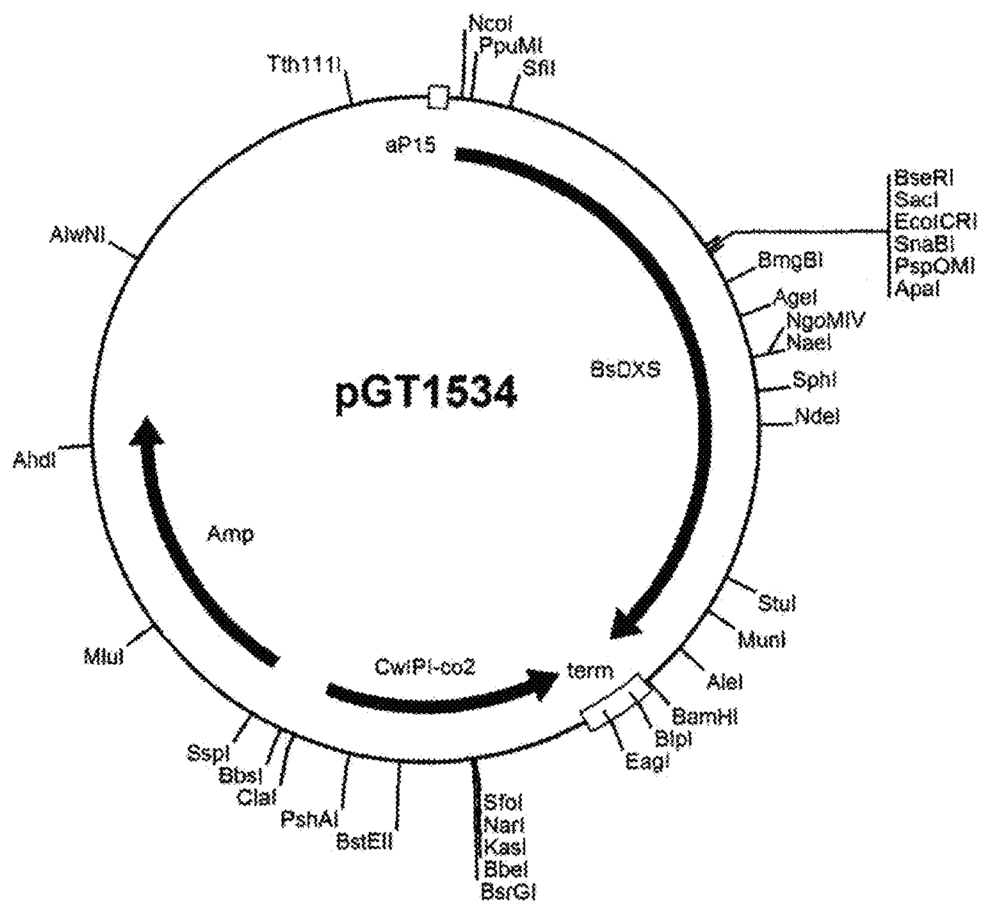

The coding sequences of the labeled proteins are depicted as arrows. Regulatory DNA-sequences are depicted as boxes. The positions of singular restriction sites are indicated. The exact positions of the labeled elements and their functions are listed in the following table:

| Sequence name | Start | Stop | Characteristic |
|---|---|---|---|
| aP15 | 11 | 58 | artificial promoter (PHY-collection) |
| BsDXS | 95 | 1999 | DX-synthase from B. subtilis |
| term | 2007 | 2182 | Terminator |
| CwIPI-co2 | 2893 | 2186 | isopentenyl pyrophosphate isomerase |
| Amp | 3066 | 3927 | Ampicillin resistance gene |

Figure 14:

| | Expression cassette | | | | | | | | | | | | | | | | | | |
|---|---|---|---|---|---|---|---|---|---|---|---|---|---|---|---|---|---|---|---|
| | polycistronic | | | | | | polycistronic | | | | monocistronic | | | monocistronic | | | | | |
| Plasmid | | Gene | | | | Terminator | | Gene | | erminato | Prom | Gen | Term | Prom | Gen | Term | Type | Fig. | SEQ ID No. |
| pAC-BETA(pi-d-crtY | | | | | | | | | | | | | | | | | LYC synthesis LYC synthesis | | 28 |
| pGT1036 | pTet | crtE | IPI | crtI | crtB | newTerm | | | | | | | | | | | eCaro synthesis | 3 | 11 |
| pGT1066 | pTet | crtE | IPI | crtI | crtB | newTerm | | | | | plac | EC mut 3 | aTerm5 | | | | | 4 | 17 |
| pGT1066* | pTet | crtE | IPI | crtI | crtB | newTerm | | | | | plac | AtEC-del-Mut 403, 404, 445 | aTerm5 | | | | eCaro synthesis | | 18 |
| pGT1182 (ist ein pGT1066*) | pTet | crtE | IPI | crtI | crtB | newTerm | | | | | plac | EC mut 3.3 | aTerm5 | | | | eCaro synthesis eCaro synthesis | | 30 |
| pGT1464 | pTet | crtE | IPI | crtI | crtB | newTerm | | | | | aP12 | EC mut 3.3 | aTerm5 | | | | eCaro synthesis | | 31 |
| pGT1484 | pTet | idsA | IPI | crtI | crtB | newTerm | | | | | aP12 | EC mut 3.3 | aTerm5 | | | | eCaro synthesis | | 32 |
| pGT1518 | pTet-m1 | idsA | IPI | crtI | crtB | newTerm | | | | | aP12 | EC mut 3.3 | aTerm5 | | | | eCaro synthesis | 9 | 33 |
| pGT1543 | aP40 | idsA | IPI | crtI | crtB | newTerm | | | | | aP12 | EC mut 3.3 | aTerm5 | | | | eCaro synthesis | 10 | 34 |
| pGT1544 | aP32 | idsA | IPI | crtI | crtB | newTerm | | | | | aP12 | EC mut 3.3 | aTerm5 | | | | eCaro synthesis | | 35 |
| pGT1546 | aP47.2 | idsA | IPI | crtI | crtB | newTerm | | | | | aP12 | EC mut 3.3 | aTerm5 | | | | eCaro cleavage | | 36 |
| pGT1069 | | | | | | | | | | | pBAD | AtCCD1 | Term | | | | eCaro cleavage | 7 | 21 |
| pGT1070 | | | | | | | | | | | pBAD | OfCCD1 | Term | | | | eCaro cleavage | 7 | 24 |
| pGT1454 | | | | | | | | | | | pXYL1 | AtCCD1 | Term | | | | eCaro cleavage | 11 | 37 |
| pGT1455 | | | | | | | | | | | pXYL2 | AtCCD1 | Term | | | | eCaro cleavage | | 38 |
| pGT1557 | | | | | | | | | | | aP5 | OfCCD1 | Term | | | | eCaro cleavage | | 39 |
| pGT1560 | | | | | | | | | | | aP15 | OfCCD1 | Term | | | | eCaro cleavage | | 40 |
| pGT1584 | | | | | | | | | | | pXYL1 | OfCCD1 | Term | | | | eCaro cleavage | | 41 |
| pGT1586 | | | | | | | | | | | pXYL2 | OfCCD1 | Term | | | | eCaro cleavage | | 42 |
| pGT1574 | pTet-m1 | idsA | IPI | crtI | crtB | newTerm | aP12 | ECmut3.3 | AtCCD1 | aTerm5 | | | | | | | ionone synthesis | | 43 |
| pGT1575 | pTet-m1 | idsA | IPI | crtI | crtB | newTerm | aP12 | ECmut3.3 | OfCCD1 | aTerm5 | | | | | | | ionone synthesis | 12 | 44 |
| pGT1534 | | | | | | | | | | | aP15 | dxs | Term | pTet-m1 | CwIPI-co2 | Term | MEP pathway | 13 | 45 |
| pGT1579 | | | | | | | pTet-m1 | CxIPI-co2 | ispG | | aP15 | dxs | Term | | | | MEP pathway | | 46 |
| pGT1582 | | | | | | | aP15 | ispDF | dxs | Term | | | | pTet-m1 | CwIPI-co2 | Term | MEP pathway | | 47 |

Figure 15:

| Promoter | Plasmid | SEQ-ID | Position |
|---|---|---|---|
| pTet-m1 | pGT1518 | 33 | 9-55 |
| aP5 | pGT1557 | 39 | 11-57 |
| aP12 | pGT1464 | 31 | 5989-6012 |
| aP15 | pGT1560 | 40 | 11-58 |
| aP32 | pGT1544 | 35 | 41-88 |
| aP40 | pGT1543 | 34 | 41-90 |
| aP47.2 | pGT1546 | 36 | 41-93 |
| pXYL1 | pGT1454 | 37 | 46-117 |
| pXYL2 | pGT1455 | 38 | 46-117 |

METHOD OF FERMENTATIVE ALPHA-IONONE PRODUCTION

TECHNICAL AREA OF THE INVENTION

The present invention concerns a method of producing enantiomerically pure alpha-ionone. Further, the invention concerns a nucleic acid, which comprises a sequence, which encodes a lycopene-epsilon-cyclase (EC), plasmids, which encode components of the alpha-ionone biosynthesis, and a microorganism, which contains heterologous nucleotide sequences, which encode the enzymes geranylgeranyl-diphosphate-synthase, isopentenyl-diphosphate-isomerase (IPI), phytoene-desaturase/dehydrogenase (crtI), phytoene synthase (crtB), and lycopene-epsilon-cyclase (EC) or geranylgeranyl-diphosphate-synthase, isopentenyl-diphosphate-isomerase (IPI), phytoene-desaturase/dehydrogenase (crtI), phytoene synthase (crtB), lycopene-epsilon-cyclase (EC) and carotenoid-cleavage-dioxygenase (CCD1). Additionally, the invention concerns a method of producing highly pure epsilon-carotene.

BACKGROUND OF THE INVENTION

Nowadays fragrances are used in many products, such as detergents and cleaning agents, but also in numerous cosmetic skin and body care products, deodorants and perfumes. These fragrances do not only have to be produced in sufficient amounts and affordably, but also have to be available in highly pure form. The latter is necessary to prevent unwanted side effects, but also to have maximal freedom with regard to the formulation of fragrance mixtures.

The ionones are a group of ubiquitous natural products that belong to the terpenes, which are produced in many plants through the conversion of carotenoids. Ionones are used in the fragrance industry in great amounts as fragrances. The substance group comprises the individual substances alpha-, beta-, and gamma-ionone, which differ in the position of the double bond in the ionone-ring structure. For both alpha- and gamma-ionone two enantiomers exist: (R)-alpha-ionone and (S)-alpha-ionone or (R)-gamma-ionone and (S)-gamma-ionone (FIG. 1). All individual substances differ in their scent. In particular, this is true for the enantiomers. In this regard, the scent of (S)-alpha-ionone is described as cedar like/raspberry like, whereas the corresponding (R)-enantiomer has a fruity-bloomy violet scent. Due to these characteristics (R)-alpha-ionone is particularly interesting for the fragrance industry.

In natural sources the ionones always exist as mixtures of different composition. The most common representatives are alpha- and beta-ionone wherein beta-ionone is the main product and alpha-ionone exists in lower amounts as additional component. Gamma-ionone is produced only by a few plants. Therefore, to obtain the individual substances in pure form from nature and to provide them for industrial use laborious and costly enrichment and purification steps are necessary. This is particularly true for the industrially highly relevant but very rare (R)-alpha-ionone.

In plants the formation of the ionones occurs through a multistep synthetic pathway: initially the linear carotenoid lycopene is produced, which is subsequently transformed in different further mono- or bi-cyclic carotenoids through the activity of different lycopene-cyclases (FIG. 2A). The main product is most often beta-carotene. Subsequently, the ionone-formation occurs in a further step through oxidative cleavage of the generated carotenoids through carotenase enzymes, which are also referred to as carotenoid-cleavage-dioxygenase (CCD) (FIG. 2A).

In plants, the transformation of different carotenes through carotenases (CCD) leads to the formation of alpha-ionone (FIG. 2A). In most cases, alpha-carotene is transformed, which leads to a mixture of alpha- and beta-ionone. In contrast, the exclusive formation of alpha-ionone occurs through the CCD-catalytic cleavage of epsilon-carotene or its precursor delta-carotene. This pathway hardly contributes to the generated total amount of alpha-ionone, since delta-carotene and epsilon-carotene are not produced in most plants or only in trace amounts.

Alpha-ionone can also be chemically synthesized. A method of synthesizing alpha- and beta-ionone from citral has already been developed and patented in 1893. This chemically synthesized alpha-ionone exists as racemic mixture and thus contains enantiomers with different scent. The utility for the fragrance industry is therefore limited. More recently enantio-selective synthetic methods for (S)-alpha-ionone (Bovolenta et al., 2004) or (R)-alpha-ionone (Soorukram and Knochel, 2004) have been described. The enantiomeric purity of the so produced (R)-alpha-ionone is 97%. Thus, substantial amounts of the (5)-enantiomer are still contained. The yield is 61%.

For a sustainable and environment friendly ionone-production fermentative production systems, in particular involving the use of the recombinant microorganisms, are preferred.

In general, recombinant delta-carotene and epsilon-carotene producing microorganisms are suitable for the production of alpha-ionone. The use of delta-carotene as starting material for an efficient alpha-ionone production is however not sensible, since only one molecule ionone per starting molecule can be obtained from this monocyclic substrate. A biosynthesis using epsilon-carotene is preferred, since the yield of alpha-ionone per starting molecule epsilon-carotene can be doubled.

The recombinant systems described so far with proven ionone-synthesis mostly resulted from the biochemical characterization of different CCD1-enzymes. The natural processes were imitated by additionally inserting the CCD1-enzymes to be tested in recombinant bacterial strains, in which prior to this the synthetic genes for different carotenoids had been implemented (Misawa et al., 1990, Cunningham et al., 1996). In doing so it has been shown that CCD1-enzymes have a broad spectrum of substrates and that they transform the substrates with different preferences. Preferably, CCD1-enzymes were tested in strains that provide lycopene, beta-carotene or zeaxanthin.

Carotenoids are ubiquitous lipophilic pigments that belong to the class of tetraterpenes. Most carotenoids can be formally derived from acyclic lycopene and are formed through cyclization of the end groups, hydrogenation or dehydrogenation or also through the introduction of oxygen.

Starting materials of the carotenoid synthesis are the isoprene derivative isopentenyl-diphosphate (IPP) and the corresponding isomer dimethyl-allyl-diphosphate (DMAPP), which, depending on the host organism, are produced via the so called non-mevalonate pathway (MEP-pathway) and/or the so called mevalonate pathway (MVA-pathway). In plants, both synthetic pathways are active. Through the coupling of multiple IPP and DMAPP-molecules initially the important intermediate geranylgeranyl-diphosphate (GGPP) is formed. Through the condensation of 2 GGPP-units the first tetraterpene compound is formed, phytoene. The colorless phytoene is then through repeated desaturation and isomerisation transformed into the red lycopene, which is the essential intermediate, from which through different cyclization reactions the carotenoids alpha-, beta-, gamma-, delta- and epsilon-carotene are formed. An overview is depicted in FIG. 2A.

Carotenoid biosynthesis pathways have not only been identified for plants, but also for different microorganisms (bacteria and yeast) and the corresponding genes or gene clusters have been isolated. As early as 1986 a corresponding bacterial gene cascade was cloned by Perry and coworkers from *Erwinia herbicola* for the expression in *E. coli* (Perry et al, 1986). The analogous expression cassette from *Erwinia uredovora* was described for the first time in 1990 (Misawa et al., 1990). Subsequently, Cunningham and coworkers described a recombinant microbial system for the synthesis of carotenoids in *E. coli*, which used the biosynthesis genes of the above mentioned known *Erwinia* species, *E. uredovora* and *E. herbicola* (Cunningham et al., 1996).

Since then many research groups have used the plasmid described by Perry et al (1986) as basis for investigating the functionality of individual bacterial or plant enzymes of the carotenoid biosynthesis through complementation experiments (Cunningham et al., 1994, 1996). In doing so always the original cassette from *E. herbicola* with the original promoter, terminator and the transitions between the individual genes including original ribosome binding sites (Shine-Dalgarno-sequences; SD) were used.

Recently, an additional gene cluster for carotenoid-synthesis was reported which is expressed in *E. coli*. The heterologous expression of the genes of *Cronobacter sakazakii* leads to a yellow coloration of the colonies. The individual genes have been identified as idi, crtE, crtX, crtY, crtI, crtB and crtZ (Zhang et al., 2014). These have been cloned in different combinations with optimized SD-sequences in the target vector pWSK29.

To date different clusters have been identified and heterologously expressed; however, the publications do not report optimizing the yields of carotenes.

Several essential enzymes are involved in the synthesis of epsilon-carotene from lycopene and the release of ionones from carotenoids, which are described in the following.

Lycopene-epsilon-cyclases catalyze the formation of alpha-ionone-ring structures at the ends of the lycopene molecule, wherein initially the monocyclic delta-carotene is produced as an intermediate, which is then transformed to epsilon-carotene through several lycopene-epsilon-cyclases (EC) under formation of a second alpha-ionone ring. Accordingly, two classes of lycopene-epsilon-cyclases can be distinguished: one class of which can only produce a single ring and therefore exclusively synthesize delta-carotene. The epsilon-cyclase of *Arabidopsis thaliana* and the absolute majority of plant EC-enzymes that have been investigated and described to date belong to this class. The second EC-class can also generate a second ring at the same molecule (or the monocyclic intermediate) and thus can also produce epsilon-carotene. The EC-enzyme of *Lactuca sativa* (salad) belongs to this class. It predominantly produces epsilon-carotene.

The described EC-enzymes of *Zea mays* (corn) and *Adonis aestivalis* synthesize a mixture of equal amounts of delta-carotene and epsilon-carotene (Bai et al., 2009; Cunningham und Gantt, 2001).

Cunningham und Gantt (2001) were able to show that the exchange of a single amino acid leads to a change in the product of the enzymatic reaction. For the enzyme of salad (*Lactuca sativa*) the exchange of histidine of leucine at position 457 leads to the formation of a monocyclic product, while the complementary mutation at the corresponding position in the EC-enzyme of *A. thaliana* (L448H) leads to a bicyclic product, i.e. the formation of epsilon-carotene is preferred. This work also showed the introduction of a hexapeptide sequence from the salad-EC in the enzyme of *Arabidopsis*, which leads to an exchange of four amino acids in this enzyme (A447F/L448H/Q451L/F452M). This mutated enzyme synthesized the bicyclic epsilon-carotene as main product.

More recent work also shows for the EC of corn that the change of the amino acid sequence at one position (L461H) leads to an increase in the fraction of bicyclic epsilon-carotene to 80%. A mutation of alanine to serine at position 502, however, leads to an increased fraction of the monocyclic delta-carotene (Bai et al., 2009).

Carotenases are plant enzymes that are able to cleave mono and bicyclic carotenoids in the area of the linear central molecule structure. The reaction occurs under $O_2$ consumption. According to the reaction mechanism, the enzymes are also referred to as carotenoid-cleaving-dioxygenases, CCD. The respective CCD-enzyme determines in which position the substrate molecules are cleaved—this is a fundamental enzyme characteristic. Only CCD-enzymes that are able to cleave carotene substrates between the positions 9, 10 and 9', 10' are able to release ionones.

The carotenoid-cleavage-dioxygenase 1 of *A. thaliana* (AtCCD1) accepts a broad spectrum of linear and cyclic carotenoid-substrates, as do its homologues of corn and tomato, and can cleave lycopene in addition to alpha- and beta-carotene (Vogel et al., 2008). The authors also show the cleavage of ζ-carotene for the corn-CCD1. For CCD1 of *Osmanthus fragrans* (OfCCD1) it has been shown that it in vitro transforms alpha- and beta-carotene and in doing so produces beta- and alpha-ionone (Baldermann et al., 2010). The CCD of *Daucus carota* has greater substrate specificity and cannot transform lycopene, phytoene or GGPP, but is able to transform zeaxanthin, beta-carotene and delta-carotene (Yahyaa et al., 2013).

As described above, alpha-ionone and in particular (R)-alpha-ionone is an important raw material for the fragrance industry. The presently available methods of producing alpha-ionone by means of isolation from natural sources or chemical synthesis provide only insufficient access to this important raw material in insufficient quantity and purity. Furthermore, against the background of an environment friendly and sustainable production an alternative to classical chemical synthesis is desirable.

Accordingly, it is a problem of the present invention to produce alpha-ionone and in particular (R)-alpha-ionone by means of an environment friendly and sustainable method in sufficient quantity and purity.

DESCRIPTION OF THE INVENTION

The above formulated problem is solved by the provision of a method of producing enantiomerically pure alpha-ionone, comprising the culturing of a microorganism, which contains heterologous nucleotide sequences, which encode the following enzymes: geranylgeranyl-diphosphate-synthase, isopentenyl-diphosphate-isomerase (IPI), phytoene-desaturase/dehydrogenase (crtI), phytoene synthase (crtB), lycopene-epsilon-cyclase (EC) and carotenoid-cleavage-dioxygenase (CCD1).

The above formulated problem is also solved by the provision of a nucleic acid, which comprises a sequence, which encodes a lycopene-epsilon-cyclase (EC), which catalyzes the transformation of lycopene to epsilon-carotene, wherein the lycopene-epsilon-cyclase (EC) leads to a greater epsilon-carotene yield than a reference lycopene-epsilon-cyclase (EC) with a sequence according to SEQ ID No. 26. Further, the problem is solved by the provision of the lycopene-epsilon-cyclase (EC) itself that is encoded by the nucleic acid.

Further, the provided plasmid contributes to the solution of the problem, wherein the plasmid is characterized in that it comprises nucleotide sequences that encode the enzymes geranylgeranyl-diphosphate-synthase, isopentenyl-diphosphate-isomerase (IPI), phytoene-desaturase/dehydrogenase (crtI) and phytoene synthase (crtB), wherein the heterologous expression of the lycopene-biosynthetic pathway that is encoded by the plasmid leads to a grater lycopene-yield compared to the heterologous expression of the lycopene-biosynthetic pathway that is encoded by the plasmid pAC-BETAipi-ΔcrtY (SEQ ID No. 28).

Further, the microorganism provided by the invention contributes to the solution of the problem, wherein the microorganism comprises heterologous nucleotide sequences that encode the following enzymes: geranylgeranyl-diphosphate-synthase, isopentenyl-diphosphate-isomerase (IPI), phytoene-desaturase/dehydrogenase (crtI), phytoene synthase (crtB), and lycopene-epsilon-cyclase (EC) or geranylgeranyl-diphosphate-synthase, isopentenyl-diphosphate-isomerase (IPI), phytoene-desaturase/dehydrogenase (crtI), phytoene synthase (crtB), lycopene-epsilon-cyclase (EC) and carotenoid-cleavage-dioxygenase (CCD1).

The method of producing highly pure epsilon-carotene provided by the present invention also contributes to the solution of the problem, wherein the method comprises the culturing of a microorganism, which comprises heterologous nucleotide sequences, which encode the following enzymes: geranylgeranyl-diphosphate-synthase, isopentenyl-diphosphate-isomerase (IPI), phytoene-desaturase/dehydrogenase (crtI), phytoene synthase (crtB) and lycopene-epsilon-cyclase (EC).

Finally, the provided plasmid also contributes to the solution of the problem, wherein the plasmid is characterized in that it comprises nucleotide sequences that encode the following enzyme: 1-desoxy-D-xylulose-5-phosphate-synthase (DXS) and isopentenyl-pyrophosphate-isomerase (CwIPI).

The nucleic acids, lycopene-epsilon-cyclases, plasmids, microorganisms and methods according to the present invention enable the efficient fermentative production of lycopene with clearly improved yields compared to the state of the art, as well as epsilon-carotene, with clearly improved yields of epsilon-carotene compared to the state of the art. Both, lycopene as well as epsilon-carotene are intermediates in the production of alpha-ionone.

The present invention is, among other things, characterized by an improved production of the two intermediates of the alpha-ionone biosynthesis compared to the state of the art, lycopene and epsilon-carotene (FIG. 2B). This aspect of the present invention considerably contributes to the production of alpha-ionone, and in particular (R)-alpha-ionone, by means of an environment friendly and sustainable method in sufficient quantity and purity.

A further advantage of the present invention compared to the state of the art is the provision of (R)-alpha-ionone in enantiomerically pure form in sufficient quantity and purity.

Further, the fermentative methods of the present invention are more environment friendly and more sustainable than the traditional chemical synthetic methods of the state of the art.

BRIEF DESCRIPTION OF THE FIGURES

FIG. 4: Plasmid map pGT1066 ("eCaro-synthesis" plasmid, expression plasmid). The coding sequences of the indicated proteins are depicted as arrows. Regulatory DNA sequences are depicted as box. The positions of unique restriction enzyme sites are indicated. The exact positions of the labeled genetic elements and their functions are listed in the table.

FIG. 5: Homology comparison of AtECmut3 and position of the point mutations. The comparison of the database protein sequence for the lycopene-epsilon-cyclase of *A. thaliana* (AtEC) with the sequences AtEC-del and AtECmut3 according to the present invention and the homologous enzymes of salad (LsEC) and corn (ZmEC). The chloroplast targeting signal (N-terminal 44 amino acids), which was detected in the wild type enzyme AtEC is underscored. AtEC-del is the protein variant that has been cloned from *A. thaliana* and shortened at the N-terminus by 44 amino acids, and which is the common basis for the generated mutants (AtECmut) of the present invention. The mutated positions 403, 404 and 445 are indicated (boxes). The corresponding positions for the full length-wild type-AtEC-protein are added in parentheses. The positions of the mutations that have been described for the salad- or corn-enzyme are indicated.

FIG. 7: Plasmid maps of the plasmids pGT1069 und pGT1070 (expression plasmids for AtCCD1 und OfCCD1). The coding sequences of the labeled proteins are depicted as arrows. Regulatory DNA sequences are depicted as box. The exact positions of the labeled elements are listed in both tables.

FIG. 9: Plasmid map pGT1518 ("eCaro-synthesis" plasmid, expression plasmid). This plasmid codes for the lycopene biosynthetic pathway according to the present invention (idsA, IPI, crtI und crtB) under der control of the pTet-ml promoter and for the lycopene-epsilon-cyclase (EC) with the mutation combination ECmut 3.3 under the control of the aP12 promoter. The coding sequences of the labeled proteins are depicted as arrows. Regulatory DNA sequences are depicted as box. The positions of unique restriction enzyme sites are indicated. The exact positions of the labeled genetic elements and their functions are listed in the table.

FIG. 10: Plasmid map pGT1543 ("eCaro-synthesis" plasmid, expression plasmid). This plasmid encodes the lycopene biosynthetic pathway according to the present invention (idsA, IPI, crtI und crtB) under the control of the aP40 promoter and for the lycopene-epsilon-cyclase (EC) with the mutation combination ECmut3.3 under the control of the aP12 promoter. The coding sequences of the labeled proteins are depicted as arrows. Regulatory DNA sequences are depicted as box. The positions of unique restriction enzyme sites are indicated. The exact positions of the labeled genetic elements and their functions are listed in the table.

FIG. 11: Plasmid map pGT1454 ("eCaro-cleavage" plasmid, expression plasmid). This plasmid encodes the carotenoid-cleavage-dioxygenase (CCD1) from *Arabidopsis thaliana* (AtCCD1). The coding sequences of the labeled proteins are depicted as arrows. Regulatory DNA sequences are depicted as box. The positions of unique restriction enzyme sites are indicated. The exact positions of the labeled genetic elements and their functions are listed in the table.

FIG. 12: Plasmid map pGT1575 ("ionone-synthesis" plasmid, expression plasmid). This plasmid encodes the lycopene biosynthetic pathway according to the present invention (idsA, IPI, crtI und crtB) under the control of pTet-ml promoter and for the lycopene-epsilon-cyclase (EC) with the mutation combination ECmut 3.3 as well as for the carotenoid-cleavage-dioxygenase (CCD1) of *Osmanthus fragrans* (OfCCDI), both under the control of the aP12 promoter. The coding sequences of the labeled proteins are depicted as arrows. Regulatory DNA sequences are depicted as box. The positions of unique restriction enzyme sites are indicated. The exact positions of the labeled genetic elements and their functions are listed in the table.

FIG. 13: Plasmid map pGT1534 ("MEP-pathway" plasmid, expression plasmid). This plasmid encodes the 1-desoxy-D-xylulose-5-phosphate-synthase (DXS) according to the present invention under the control of the aP15 promoter and the isopentenyl-diphosphate-Isomerase (CwIPI-co2), a codon optimized variant of the isopentenyl-diphosphate-Isomerase (CwIPI) from *Curcuma wenyujin,* according to the present invention, under the control of the pTet-ml promoter. The coding sequences of the labeled proteins are depicted as arrows. Regulatory DNA sequences are depicted as box. The positions of unique restriction enzyme sites are indicated. The exact positions of the labeled genetic elements and their functions are listed in the table.

FIG. 14: The table shows a selection of plasmids according to the present invention, namely "Lyc-synthesis" plasmids, "eCaro-synthesis" plasmids, "eCaro-cleavage" plasmids, “ionone-synthesis” plasmids and “MEP-pathway” plasmids. The table shows the respective expression cassettes of the plasmids according to the present invention, which are organized either polycistronically or monocistronically. aP5, aP12, aP15, aP32, aP40 and aP47.2 denominate the constitutive promoters according to the present invention. pTet: tetracycline-promoter of *E. coli* plasmid pBR332. pLac: Lac-promoter; promoter region of the genomic *E. coli* Lac operon. pBAD: arabinose inducible promoter; promoter region of the genomic *E. coli* Arabinose operon. pXyl: xylose inducible promoter; regulatory sequences of the *E.coli* xylose operon consisting of the bidirectional promoter region (cis-regulatory sequences), which controls the polycistronic operons xylA/xylB and xylF/xylG/xylH/xylR, wherein its activity is regulated through the xylR gene product of the xylFGHR operon. pTet-ml: 12 bp deletion in the promoter of LYC operon; promotor activity is improved by the factor 2.8. pXyl0: synthetic xylose inducible promoter. Resulting from the direct coupling of the xylR gene with the cis-regulatory sequences (by means of deletion of the xylF-, xylG- and xylH gene sequences). Basic construct. Inducibility: 25×; relative expression strength (max): 2.5% of the reference promoter (pLac). pXyl1: Combination of pXyl0 with an optimized ribosomen binding site (Shine-Dalgarno-sequence) for the efficient translation of targeted genes. pXyl1 Promoter 3-4× more active than pXyl0 (maximally 10% of the pLac activity). pXyl2: Based on pXyl1, the sequence of the −10 region (binding site of the RNA-polymerase) of the downstream-directed promoter element was modified. Promoter 3-4× more active than pXyl0 (maximally 36% of the pLac activity).

FIG. 15: The promoters according to the present invention.

DETAILED DESCRIPTION OF THE INVENTION

Figure 1A:
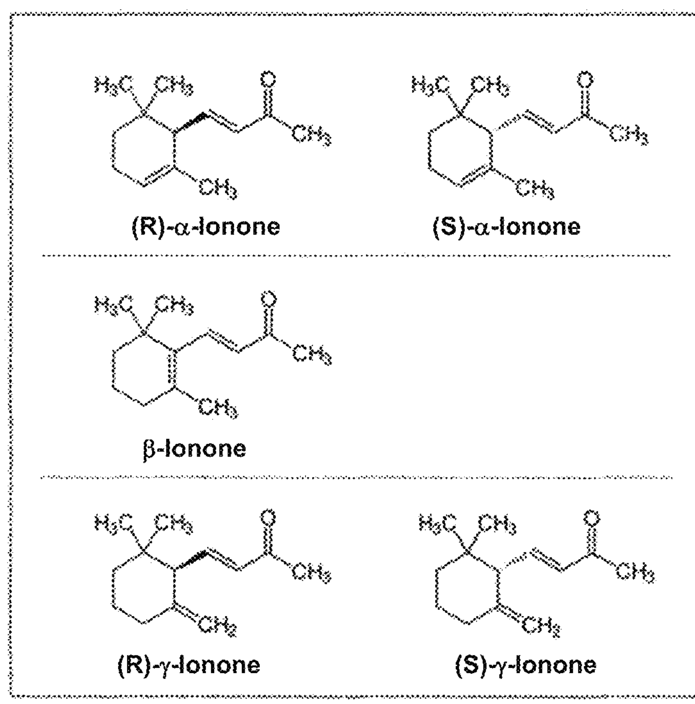
FIG. 1A: Ionone-structures including the structure of the (R)- and (S)-enantiomer of alpha-ionone.
Figure 1B:
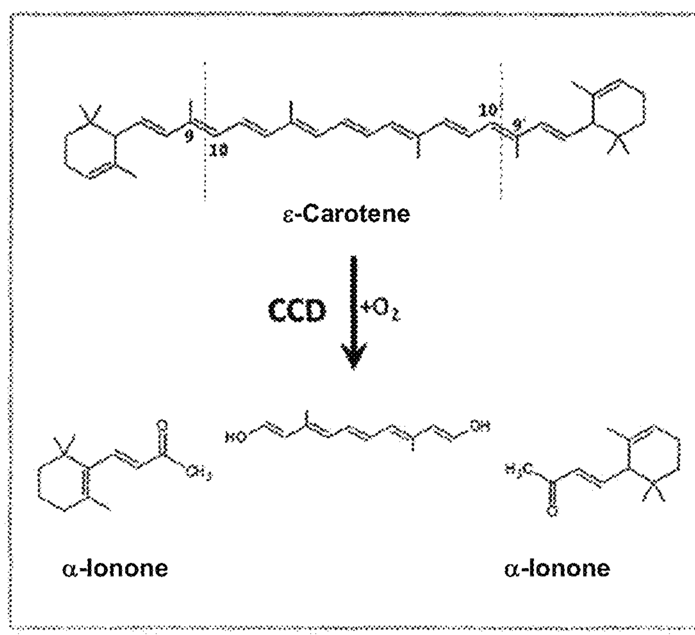
FIG. 1B: Reaction scheme of the CCD-catalyzed-ionone formation through carotene-cleavage. The positions of the cleaved double bonds are numbered. CCD=carotenoid-cleavage-dioxygenase.
Figure 2A:
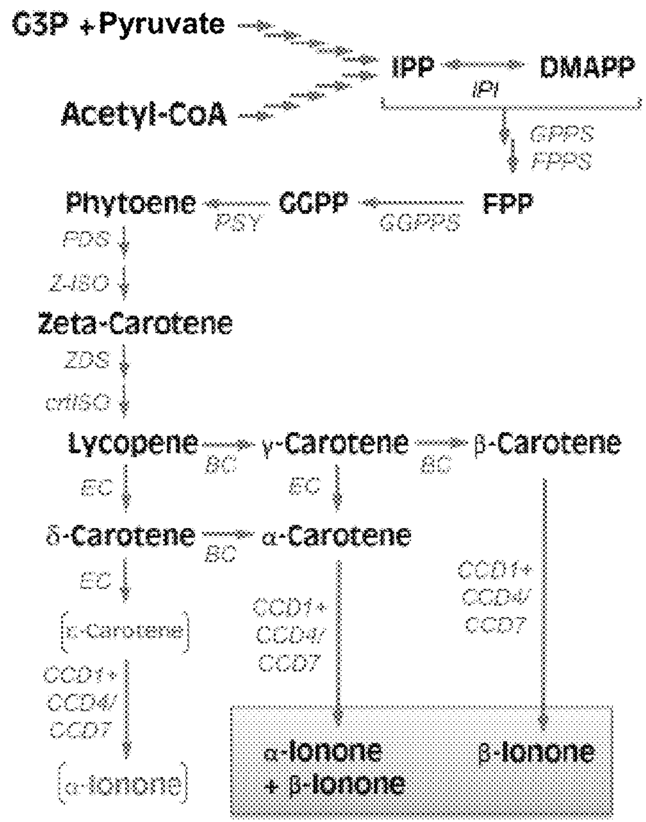
FIG. 2A: Ionone-synthetic pathway in plants. Starting materials of the carotenoid synthesis are the isoprene derivatives isopentenyl-diphosphate (IPP) and its isomer dimethylallyl-diphosphate (DMAPP), which, in plants are produced via the so called non-mevalonate pathway (MEP pathway) and/or the so called mevalonate pathway (MVA pathway). Through the coupling of multiple IPP and DMAPP molecules initially the important intermediate geranylgeranyl-diphosphate (GGPP) is formed. Through the condensation of two GGPP units then the first tetraterpene compound is produced, phytoene. Plants require four different enzymes to transform phytoene into lycopene, whereas according to the synthetic pathway of the present invention only the bacterial enzyme crtI is required (FIG. 2B). In the natural plant system both the enzyme lycopene-epsilon-cyclase (EC) and the lycopene-beta-cyclase (BC) are encompassed. Thus, a mixture of alpha-, beta- and epsilon-carotene is generated, wherein epsilon-carotene has been detected only in a small number of plants in very small amounts. Beta-carotene is the main product. Alpha-carotene is mostly produced in small amounts. The cleavage of carotenoids to ionones occurs in two steps through the combination of the enzymes CCD1 and CCD4 or CCD1 and CCD7. According to the present substrate distribution predominantly beta-ionone is generated. The additionally, in small amounts, present alpha-carotene is cleaved in equal amounts to alpha- and beta-ionone. Accordingly, alpha-ionone is always present in small amounts as an additive compared to the predominantly produced beta-ionone. The names of the required enzymes are represented in italics and are assigned to the corresponding reaction arrows. IPI: isopentenyl diphosphate isomerase; GGPPS: geranylgeranyl-diphosphate-synthase; PSY: phytoene synthase; PDS: phytoene-desaturase; Z-ISO: zeta-carotene-isomerase; ZDS: zeta-carotene-desaturase; crtISO: cis-lycopene-isomerase; EC: lycopene-epsilon-cyclase; BC: lycopene-beta-cyclase; CCD1: carotenoid-cleavage-dioxygenase 1 (cytosolic); CCD4: carotenoid-cleavage-dioxygenase 4 (plastidic); CCD7: carotenoid-cleavage-dioxygenase 7 (plastidic).
Figure 2B:
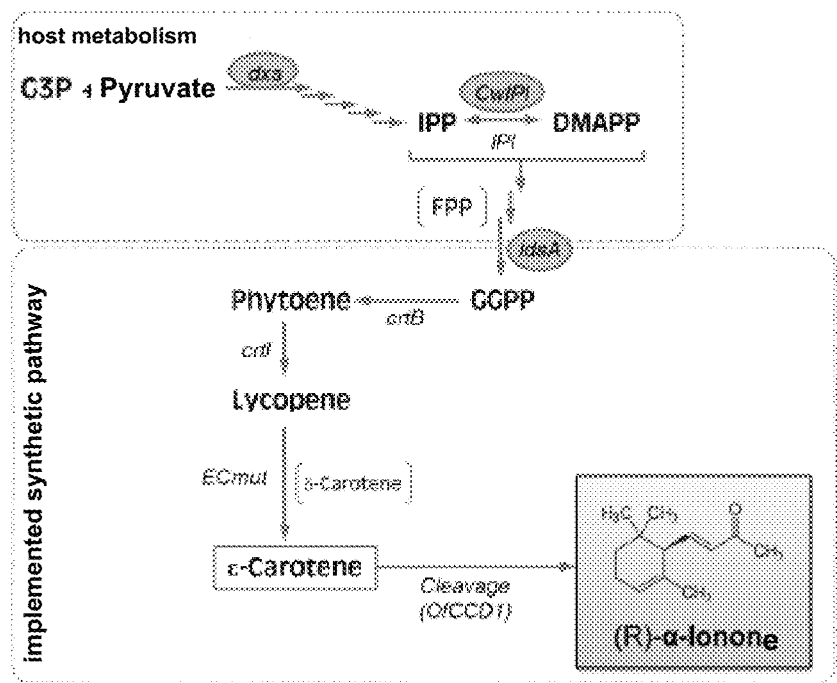
FIG. 2B: An example of the ionone synthetic pathway according to the present invention. By means of preventing beta-cyclase activity and using a mutated lycopene-epsilon-cyclase exclusively epsilon-carotene is generated (the δ-carotene intermediate can be detected in traces, if at all). Only one enzyme is required for cleavage and pure alpha-ionone is generated. The names of the used enzymes are depicted in italics and are assigned to the corresponding reaction arrow. dxs: desoxy-D-xylulose-5-phosphate-synthase; IPI: isopentenyl diphosphate Isomerase; CwIPI: isopentenyl diphosphate Isomerase from *Curcuma wenyujin;* idsA: geranylgeranyl-diphosphate-synthase; crtI: phytoen-desaturase/dehydrogenase; crtB: phytoenesynthase; ECmut: mutated lycopene-epsilon-cyclase according to the invention; CCD1: carotenoid-cleavage-dioxygenase (AtCCD1 or OfCCD1). The connection of the synthetic pathway, implemented in the microbial host, to the host's basic metabolism is indicated.
Figure 3:
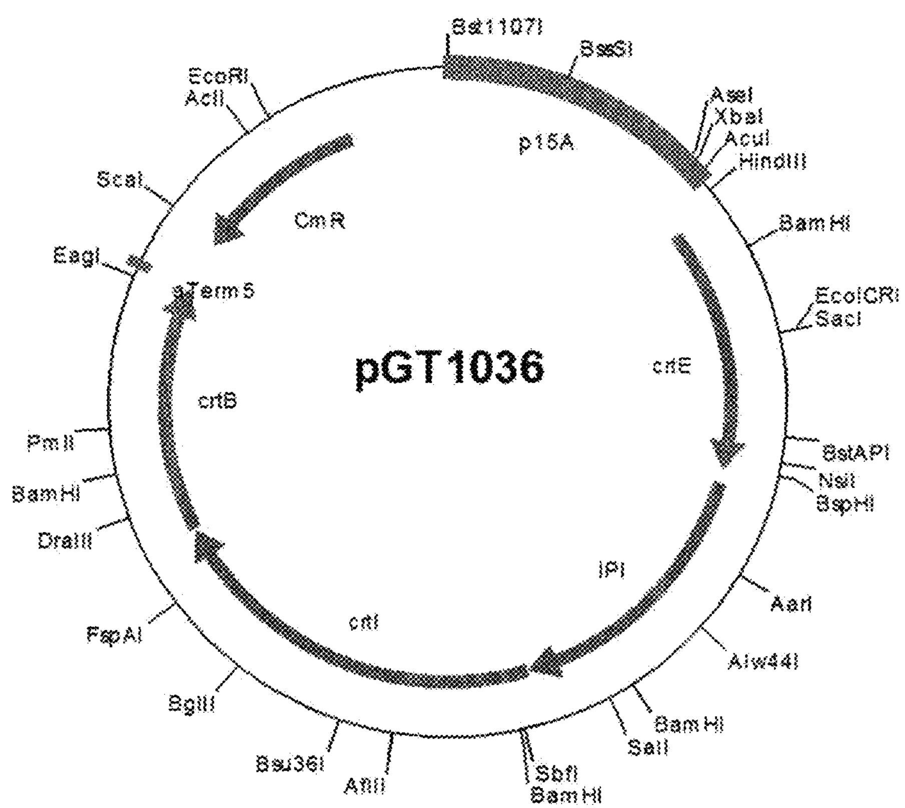
FIG. 3: Plasmid map pGT1036 ("Lyc-synthesis" plasmid, expression plasmid). The coding sequences of the indicated proteins are depicted as arrows. Regulatory DNA sequences are depicted as box. The positions of unique restriction enzyme sites are indicated. The exact positions of the labeled genetic elements and their functions are listed in the table.

The present invention is not limited to the specifically mentioned products and methods herein, but provides a general technical teaching, which enables the skilled person to achieve the advantages described herein. The used terminology should not limit the general technical teaching described herein in any form, but serves merely to describe the specific embodiments.

The used EC-classification numbers (EC-numbers) classify enzymes according to the reactions that they catalyze. These EC-numbers are issued by the International Union of Biochemistry and Molecular Biology (UIBMB) and can be searched by the skilled person on the internet.

The “accession numbers” used herein (GenBank accession number—GenBank) serve for the unambiguous characterization of nucleotide sequences or amino acid sequences and are taken from the webpage of the NCBI (National Center for Biotechnology Information).

The term “AtEC” as used herein describes the *Arabidopsis thaliana* lycopene-epsilon-cyclase (EC) with the GenBank accession number GenBank: AAL85102.1.

The term “LsEC” as used herein describes the *Lactuca sativa* lycopene-epsilon-cyclase (EC) with the GenBank accession number GenBank: AAK07434.1.

The term “ZmEC” as used herein describes the *Zea mays* lycopene-epsilon-cyclase (EC) with the GenBank accession number GenBank: ABU93262.1.

The term “lycopene” as used herein describes a linear carotenoid that is known to the skilled person, which is also known to the skilled person under the name “lycopin” and “leukopin” or “all-trans-lycopene”. These terms can be used interchangeably.

The term “lycopene-biosynthetic pathway” as used herein describes the combination of the enzymes geranylgeranyl-diphosphate-synthase, isopentenyl-diphosphate-isomerase (IPI), phytoene-desaturase/dehydrogenase (crtI) and phytoene synthase (crtB).

The term “AtECmut” as used herein describes the mutants of the *Arabidopsis thaliana* lycopene-epsilon-cyclase according to the present invention, wherein the term may refer to the entire protein or only to the specific mutation, which is appended to the term as a number (e.g. AtECmut3). The meaning of the term follows for the skilled person unambiguously from the respective context. The term “AtECmut” is used herein equivalently with the term “ECmut”.

The term “yield” as used herein describes the amount of a produced material based on a determined culture volume (liquid culture of a microorganism) or the isolated dry matter from a determined culture volume or based on a different reference value. The term “amount” as used herein describes the amount of substance of a material or a different measure, whose value is directly dependent on the amount of substance of the material, for example the peak area of an HPLC absorption chromatogram.

The term “sequence identity” as used herein describes the agreement of two nucleotide sequences or amino acid sequences, given in percent, and depends on the number of identical positions between the two sequences, wherein the number and length of gaps that need to be introduced to achieve an optimal sequence alignment is taken into account. As used herein, the sequence identity is determined according to the BLAST-algorithm (Altschul et al., 1990). As known to the skilled person, the sequence identity can be determined according to the BLAST-algorithm for nucleotide sequences (blastn) or amino acid sequences (blastp) simply on the NCBI webpage (http://blast.ncbi.nlm.nih.gov/Blast.cgi).

The term “geranylgeranyl-diphosphate-synthase” as used herein describes an enzyme with the EC-number EC 2.5.1.29, which catalyzes the condensation of farnesyl-diphosphate and isopentenyl-diphosphate to geranylgeranyl-diphosphate. Preferred embodiments are the geranylgeranyl-diphosphate-synthase crtE and idsA.

The term “1-desoxy-D-xylulose-5-phosphate-synthase (DXS)” as used herein describes an enzyme with EC-number EC 2.2.1.7, which catalyzes the condensation of pyruvate and glycerinaldehyd-3-phosphate to 1-desoxy-D-xylulose-5-phosphate (DXP).

The term “isopentenyl-diphosphate-isomerase (IPI)” as used herein describes an enzyme with the EC-number EC 5.3.3.2, which catalyzes the rearrangement of isopentenyl-diphosphate (IPP) to dimethylallyl-diphosphate (DMAPP), or the converse reaction. Also the enzymes CwIPI or the codon-optimized variant CwIPI-co2 are isopentenyl-diphosphate-isomerases with an enzymatic activity according to the EC-number EC 5.3.3.2.

The term “phytoene-desaturase/dehydrogenase (crtI)” as used herein describes an enzyme with the EC-number EC 1.3.99.31, which catalyzes the desaturation (oxidation) of phytoene to all-trans-lycopene.

The term “phytoene synthase (crtB)” as used herein describes an enzyme with the EC-number EC 2.5.1.32, which catalyzes the condensation of two molecules of geranylgeranyl-diphosphate to phytoene.

Lycopene-Epsilon-Cyclase

An aspect of the invention concerns a nucleic acid, which encodes lycopene-epsilon-cyclase.

The nucleic acid according to the present invention is characterized in that it comprises a sequence which encodes lycopene-epsilon-cyclase (EC), which catalyzes the transformation of lycopene to epsilon-carotene, wherein the lycopene-epsilon-cyclase (EC) leads to a greater epsilon-carotene yield as a reference lycopene-epsilon-cyclase with a sequence according to SEQ ID NO: 26 (AtECmut1).

In a preferred embodiment of the nucleic acid according to the present invention, which may be combined with any of the preceding or subsequent embodiments, the lycopene-epsilon-cyclase (EC) leads to a greater epsilon-carotene yield, wherein the lycopene-epsilon-cyclase (EC) is a expressed in a microorganism. To be able to compare the lycopene yield of the lycopene-epsilon-cyclase (EC) with the reference lycopene-epsilon-cyclase, both cyclases are expressed in the same microorganism under the same conditions. For the expression of the lycopene-epsilon-cyclase (EC) and the reference lycopene-epsilon-cyclase in the microorganism, a plasmid that encodes the lycopene-epsilon-cyclase (EC) or a reference lycopene-epsilon-cyclase can be introduced into a microorganism by means of transformation.

In a preferred embodiment of the nucleic acid according to the present invention, which can be combined with any of the preceding or subsequent embodiments, the encoded lycopene-epsilon-cyclase has a sequence with at least 80% or at least 85%, 90%, 91%, 92%, 93%, 94%, 95%, 96%, 97%, 98%, 99% or 100% sequence identity with the sequence according to SEQ ID NO: 19 (AtEC-del).

SEQ ID NO: 19 (AtEC-del) defines the sequence of the lycopene-epsilon-cyclase of *Arabidopsis thaliana* having the N-terminal 44 amino acids (not including the N-terminal methionine) of the wildtype sequence removed. This N-terminal peptide is a chloroplast import signal (transit peptide) which affects the transport of the newly synthesized proteins into the chloroplasts in the plant. The positions of the amino acids of the mutations according to the present invention of the different lycopene-epsilon-cyclase variants are indicated relative to this N-terminal truncated version of the lycopene-epsilon-cyclase of *A. thaliana* (SEQ ID NO: 19). The corresponding positions in the wildtype sequence of the lycopene-epsilon-cyclase of *A. thaliana* are therefore shifted by 44 positions. Thus, position 403 in the truncated version (SEQ ID NO: 19) corresponds to position 447 in the wildtype sequence (AAL85102.1), position 404 corresponds to position 448, and position 445 corresponds to position 489.

In a further embodiment of the nucleic acid according to the invention, which can be combined with any of the preceding or subsequent embodiments, the sequence of the encoded lycopene-epsilon-cyclase differs in at least one of the positions 403, 404 and 445 from the sequence according to SEQ ID NO: 19 (AtEC-del).

In an embodiment of the nucleic acid according to the present invention, which can be combined with any of the preceding or subsequent embodiments, the encoded lycopene-epsilon-cyclase comprises one of the following mutations or mutation combinations: ECmut2 (A445S), ECmut9 (L404S), ECmut3 (L404H/A445S), ECmut3.10 (A403C/A445S), ECmut3.12 (L404T/A445S), ECmut4 (A403S/L404H), ECmut5 (A403F/L404W), ECmut6 (A403G/L404G), ECmut7 (A403K/L404D), ECmut8 (A403W/L404R), ECmut10 (A403S/L404T), ECmut11 (A403F/L404S), ECmut12 (A403C/L404S), ECmut13 (A403I/L404T), ECmut14 (A403T/L404R), ECmut15 (A403F/L404R), ECmut16 (A403W/L404G), ECmut17 (A403C/A404C), ECmut18 (A403L/L404V), ECmut19 (A403K/L404R), ECmut20 (A403Y/L404K), ECmut21 (A403Q/L404K), ECmut22 (A403G/L404Q), ECmut3.1 (A403S/L404H/A445S), ECmut3.2 (A403C/L404C/A445S), ECmut3.3 (A403E/L404A/A445S), ECmut3.4 (A403W/L404R/A445S), ECmut3.5 (A403M/L404A/A445S), ECmut3.6 (A403N/L404T/A445S), ECmut3.7 (A403N/L404A/A445S), ECmut3.8 (A403H/L404S/A445S), ECmut3.9 (A403E/L404G/A445S), ECmut3.11 (A403K/L404G/A445S), ECmut3.13 (A403R/L404S/A445S), ECmut3.14 (A403G/L404R/A445S), ECmut3.15 (A403F/L404V/A445S) and ECmut3.16 (A403G/L404G/A445S).

In a preferred embodiment of the nucleic acid according to the present invention, which can be combined with any of the preceding or subsequent embodiments, the encoded lycopene-epsilon-cyclase comprises one of the mutations or mutation combinations: ECmut16 (A403W/L404G), ECmut3.12 (L404T/A445S), ECmut3.3 (A403E/L404A/A445S), ECmut3.5 (A403M/L404A/A445S), ECmut3.8 (A403H/L404S/A445S), ECmut3.9 (A403E/L404G/A445S), ECmut3.16 (A403G/L404G/A445S), ECmut9 (L404S), ECmut10 (A403S/L404T) and ECmut3.2 (A403C/L404C/A445S).

In a particularly preferred embodiment of the nucleic acid according to the present invention, which can be combined with any of the preceding or subsequent embodiments, the encoded lycopene-epsilon-cyclase comprises one of the following mutations or mutation combinations: ECmut9 (L404S), ECmut10 (A403S/L404T) and ECmut3.2 (A403C/L404C/A445S).

In a further particularly preferred embodiment of the nucleic acid according to the present invention, which can be combined with any of the preceding or subsequent embodiments, the encoded lycopene-epsilon-cyclase consists of a sequence according to SEQ ID NO: 19 and has one of the above-mentioned mutations or mutation combinations. Particularly preferred in this context are embodiments with a mutation combination selected from the group consisting of ECmut16 (A403W/L404G), ECmut3.12 (L404T/A445S), ECmut3.3 (A403E/L404A/A445S), ECmut3.5 (A403M/L404A/A445S), ECmut3.8 (A403H/L404S/A445S), ECmut3.9 (A403E/L404G/A445S) and ECmut3.16 (A403G/L404G/A445S) and particularly preferred are embodiments with a mutation or a mutation combination selected from the group consisting of ECmut9 (L404S), ECmut10 (A403S/L404T) and ECmut3.2 (A403C/L404C/A445S).

A further aspect of the invention concerns the lycopene-epsilon-cyclase itself.

The lycopene-epsilon-cyclase according to the present invention is characterized in that it is encoded by one of the above-described nucleic acids.

In a particularly preferred embodiment of the nucleic acid according to the present invention, which can be combined with any of the preceding or subsequent embodiments, the encoded lycopene-epsilon-cyclase consists of a sequence according to SEQ ID NO: 19 and has one of the mutations or mutation combinations according to the present invention. Particularly preferred in this context are embodiments with a mutation combination selected from the group consisting of ECmut16 (A403W/L404G), ECmut3.12 (L404T/A445S), ECmut3.3 (A403E/L404A/A445S), ECmut3.5 (A403M/L404A/A445S), ECmut3.8 (A403H/L404S/A445S), ECmut3.9 (A403E/L404G/A445S) and ECmut3.16 (A403G/L404G/A445S) and particularly preferred are embodiments with a mutation or a mutation combination selected from the group consisting of ECmut9 (L404S), ECmut10 (A403S/L404T) and ECmut3.2 (A403C/L404C/A445S).

Plasmids

Part of the invention also are different plasmids, which comprise nucleotide sequences which encode the components of the present invention of the lycopene, epsilon-carotene and/or alpha-ionone biosynthesis. Particularly preferred embodiments of these plasmids according to the present invention are listed in FIG. 14.

Part of the invention is a plasmid which comprises nucleotide sequences which encode components according to the present invention of the lycopene biosynthesis geranylgeranyl-diphosphate-synthase, isopentenyl-diphosphate-isomerase (IPI), phytoene-desaturase/dehydrogenase (crtI) and phytoene synthase (crtB) ("Lyc-synthesis" plasmid). Part of the invention is further a plasmid which comprises a nucleotide sequence which encodes components according to the present invention of the epsilon-carotene biosynthesis, geranylgeranyl-diphosphate-synthase, isopentenyl-diphosphate-isomerase (IPI), phytoene-desaturase/dehydrogenase (crtI), phytoene synthase (crtB) and lycopene-epsilon-cyclase (EC) ("eCaro-synthesis" plasmid). Further, part of the invention is a plasmid which comprises nucleotide sequences which encode the components according to the present invention for cleaving epsilon-carotene to alpha-ionone carotenoid-cleavage-dioxygenase (CCD1) ("eCaro-cleavage" plasmid). Part of the invention is also a plasmid which comprises nucleotide sequences which encode the components according to the present invention of the alpha-ionone biosynthesis geranylgeranyl-diphosphate-synthase, isopentenyl-diphosphate-isomerase (IPI), phytoene-desaturase/dehydrogenase (crtI), phytoene synthase (crtB), lycopene-epsilon-cyclase (EC) and carotenoid-cleavage-dioxygenase (CCD1) ("ionone synthesis" plasmid). Equally part of the invention is a plasmid which comprises nucleotide sequences which encode the components according to the present invention for connecting the non-mevalonate pathway (MEP pathway) to the lycopene, epsilon-carotene and/or alpha-ionone biosynthesis, namely 1-desoxy-D-xylulose-5-phosphat-synthase (DXS) ("MEP pathway" plasmid).

In a preferred embodiment of the plasmids according to the present invention, which can be combined with any of the preceding or subsequent embodiments, the heterologous expression of the lycopene biosynthetic pathway that is encoded by the plasmid (geranylgeranyl-diphosphate-synthase, isopentenyl-diphosphate-Isomerase (IPI), phytoen-desaturase/dehydrogenase (crtI) and phytoene synthase (crtB)) leads to an increased lycopene yield in a microorganism, preferably a bacterium. A preferred bacterium is *E. coli*. Particularly preferred in this context are the *E. coli* strains, XL1-blue, TOP10, XL10 blue, DH5-alpha, JM109, C41, BL21gold (DE3) and W3110. In particular, the microorganism according to the present invention can be the *E. coli* strain TOP10. Particularly preferred is the *E. coli* strain BL21gold (DE3).

In a preferred embodiment of the plasmids according to the present invention, which can be combined with any of the preceding or subsequent embodiments, the enzymes geranylgeranyl-diphosphate-synthase, isopentenyl-diphosphate-Isomerase (IPI), phytoene-desaturase/dehydrogenase (crtI) and phytoene synthase (crtB) are the corresponding enzymes of *Erwinia herbicola*.

In a preferred embodiment of the plasmids according to the present invention, which can be combined with any of the preceding or subsequent embodiments, the enzymes encoded by the plasmid are under the control of an inducible promoter. Particularly preferred are the inducible promoters pTet, pBAD, pLac, and pXyl, which are also described in more detail in Example 10 and FIG. 15. Particularly preferred are the inducible promoters pTet-m1, pXyl0, pXyl1 and pXyl2 (Example 10 and FIG. 15).

In a preferred embodiment of the plasmids according to the present invention, which can be combined with any of the preceding or subsequent embodiments, the enzymes encoded by the plasmid are under the control of a constitutive promoter. Particularly preferred are the constitutive promoters according to the present invention aP5, aP12, aP15, aP32 and aP47.2 (Example 10 and FIG. 15).

"Lyc-Synthesis" Plasmid

The "Lyc-synthesis" plasmid according to the present invention is characterized in that it comprises nucleotide sequences that encode the following enzymes: geranylgeranyl-diphosphate-synthase, isopentenyl-diphosphate-Isomerase (IPI), phytoene-desaturase/dehydrogenase (crtI) and phytoene synthase (crtB), wherein the heterologous expression of the lycopene-biosynthetic pathway that is encoded by the plasmid leads to an increased lycopene yield compared to the heterologous expression of the lycopene biosynthetic pathway that is encoded by the plasmid pAC-BETAipi-ΔcrtY (SEQ ID Nr. 28).

In a further embodiment of the plasmid according to the present invention, which can be combined with any of the previous or subsequent embodiments, the plasmid comprises a sequence or preferably consists of this sequence, which has at least 80% or at least 85%, 90%, 91%, 92%, 93%, 94%, 95%, 96%, 97%, 98%, 99% or 100% sequence identity with a reference sequence.

In a further embodiment of the plasmid according to the present invention, which can be combined with any of the previous or subsequent embodiments, the reference sequence is a sequence according to SEQ ID Nr. 28, wherein the reference sequence has a deletion of the bases 984-1394 and 3432-4198 relative to the sequence according to SEQ ID Nr. 28 (pAC-BETAipi-ΔcrtY).

In a further embodiment of the plasmid according to the present invention, which can be combined with any of the previous and subsequent embodiments, the reference sequence has a deletion of the bases 984-1394, 3432-4198 and 6605-7242 relative to the sequence according to SEQ ID Nr. 28 (pAC-BETAipi-ΔcrtY).

In a preferred embodiment of the plasmid according to the present invention, which can be combined with any of the previous and subsequent embodiments, the reference sequence is a sequence according to SEQ ID Nr. 11 (pGT1036). Particularly, the sequence of the plasmid according to the invention can comprise a sequence, which is identical to the sequence according to SEQ ID Nr. 11. In a particularly preferred embodiment, the plasmid consists of a sequence that is identical to the sequence according to SEQ ID Nr. 11.

"eCaro-Synthesis" Plasmid

The "eCaro-synthesis" plasmid according to the present invention is characterized in that it comprises nucleotide sequences that encode the following enzymes: geranylgeranyl-diphosphate-synthase, isopentenyl-diphosphate-Isomerase (IPI), phytoene-desaturase/dehydrogenase (crtI) and phytoene synthase (crtB) and lycopene-epsilon-cyclase (EC), wherein the heterologous expression of the lycopene biosynthetic pathway that is encoded by the plasmid leads to an increased lycopene yield compared to the heterologous expression of the lycopene biosynthetic pathway that is encoded by the plasmid pAC-BETAIPI-ΔcrtY (SEQ ID Nr. 28).

The "eCaro-synthesis" plasmid according to the present invention comprises particularly also all embodiments of the "Lyc-synthesis" plasmids according to the present invention and of the lycopene-epsilon-cyclase (EC) according to the present invention.

In a preferred embodiment of the "eCaro-synthesis" plasmid according to the present invention, which can be combined with any of the preceding and subsequent embodiments, the reference sequence (characterized in the passage "Lyc-synthesis" plasmid) is a sequence according to SEQ ID Nr. 18 (pGT1066*, corresponding to pGT1066, however with n, corresponding to a, t, c or g, for the nucleotides of the codons that encode for amino acid positions 403, 404 and 445 of the AtEC-del-enzyme). In particular, the sequence of the plasmid according to the present invention can also comprise a sequence that is identical to the sequence according to SEQ ID Nr. 18. In a particularly preferred embodiment, the plasmid consists of a sequence that is identical to the sequence according to SEQ ID Nr. 18.

In a particularly preferred embodiment of the "eCaro-synthesis" plasmid according to the present invention, which can be combined with any of the previous and subsequent embodiments, the reference sequence is a sequence according to SEQ ID No. 29 (pGT1066-AtEC-del), wherein the lycopene-epsilon-cyclase (EC) that is encoded by the plasmid comprises or has one of the following mutations or mutation combinations: ECmut2 (A445S), ECmut9 (L404S), ECmut3 (L404H/A445S), ECmut3.10 (A403C/A445S), ECmut3.12 (L404T/A445S), ECmut4 (A403S/L404H), ECmut5 (A403F/L404W), ECmut6 (A403G/L404G), ECmut7 (A403K/L404D), ECmut8 (A403W/L404R), ECmut10 (A403S/L404T), ECmut11 (A403F/L404S), ECmut12 (A403C/L404S), ECmut13 (A403I/L404T), ECmut14 (A403T/L404R), ECmut15 (A403F/L404R), ECmut16 (A403W/L404G), ECmut17 (A403C/A404C), ECmut18 (A403L/L404V), ECmut19 (A403K/L404R), ECmut20 (A403Y/L404K), ECmut21 (A403Q/L404K), ECmut22 (A403G/L404Q), ECmut3.1 (A403S/L404H/A445S), ECmut3.2 (A403C/L404C/A445S), ECmut3.3 (A403E/L404A/A445S), ECmut3.4 (A403W/L404R/A445S), ECmut3.5 (A403M/L404A/A445S), ECmut3.6 (A403N/L404T/A445S), ECmut3.7 (A403N/L404A/A445S), ECmut3.8 (A403H/L404S/A445S), ECmut3.9 (A403E/L404G/A445S), ECmut3.11 (A403K/L404G/A445S), ECmut3.13 (A403R/L404S/A445S), ECmut3.14 (A403G/L404R/A445S), ECmut3.15 (A403F/L404V/A445S) and ECmut3.16 (A403G/L404G/A445S). Particularly preferred mutation combinations are ECmut16 (A403W/L404G), ECmut3.12 (L404T/A445S), ECmut3.3 (A403E/L404A/A445S), ECmut3.5 (A403M/L404A/A445S), ECmut3.8 (A403H/L404S/A445S), ECmut3.9 (A403E/L404G/A445S) and ECmut3.16 (A403G/L404G/A445S). Particularly preferred are the mutations or mutation combinations ECmut9 (L404S), ECmut10 (A403S/L404T) and ECmut3.2 (A403C/L404C/A445S).

In a particularly preferred embodiment of "eCaro-Synthese" plasmid according to the present invention, which can be combined with any of the previous and subsequent embodiments, the plasmid consists of a sequence according to SEQ ID No. 29 (pGT1066-AtEC-del), wherein the lycopene-epsilon-cyclase (EC) that is encoded by the plasmid has one of the following mutations or mutation combinations: ECmut9 (L404S), ECmut10 (A403S/L404T), ECmut3.2 (A403C/L404C/A445S) and ECmut3.3 (A403E/L404A/A445S).

In a particularly preferred embodiment of "eCaro-synthesis" plasmid according to the present invention, which can be combined with any of the previous and subsequent embodiments, the plasmid has at least 80% or at least 85%, 90%, 91%, 92%, 93%, 94%, 95%, 96%, 97%, 98%, 99% oder 100% sequence identity with a sequence according to SEQ ID No. 30, 31, 32, 33, 34, 35 or 36.

"eCaro-Cleavage" Plasmid

The "eCaro-cleavage" plasmid according to the present invention is characterized in that it comprises a nucleotide sequence that encodes the enzyme carotenoid-cleavage-dioxygenase (CCD1).

In a preferred embodiment of the "eCaro-cleavage" plasmid according to the present invention, the carotenoid-cleavage-dioxygenase (CCD1) is a carotenoid-cleavage-dioxygenase 30 (CCD1) of *Arabidopsis thaliana* or *Osmanthus fragrans*.

In a preferred embodiment of the "eCaro-cleavage" plasmid according to the present invention, which can be combined with any of the previous and subsequent embodiments, the plasmid has at least 80% or at least 85%, 90%, 91%, 92%, 93%, 94%, 95%, 96%, 97%, 98%, 99% or 100% sequence identity with a sequence according to SEQ ID No. 21, 24, 37, 38, 39, 40, 41 or 42. Particularly preferred are the sequences according to SEQ ID No. 37 and 41.

"Ionone Synthesis" Plasmid

The "ionone synthesis" plasmid according to the present invention characterized in that it comprises nucleotide sequences that encode the following enzymes: geranylgeranyl-diphosphate-synthase, isopentenyl-diphosphate-Isomerase (IPI), phytoene-desaturase/dehydrogenase (crtI) and phytoene synthase (crtB) and lycopene-epsilon-cyclase (EC) and carotenoid-cleavage-dioxygenase (CCD1), wherein the heterologous expression of the lycopene biosynthetic pathway that is encoded by the plasmid leads to an increased lycopene yield compared to heterologous expression of the lycopene biosynthetic pathway that is encoded by the plasmid pAC-BETAIPI-ΔcrtY (SEQ ID No. 28).

The "ionone synthesis" plasmid according to the present invention comprises also in particular all embodiments of the "Lyc-synthesis" plasmids according to the present invention, the lycopene-epsilon-cyclase (EC) according to the present invention and the "eCaro-Synthesis" plasmids according to the present invention.

In a preferred embodiment of the "ionone synthesis" plasmid according to the present invention, which can be combined with any of the preceding and subsequent embodiments, the plasmid has at least 80% or at least 85%, 90%, 91%, 92%, 93%, 94%, 95%, 96%, 97%, 98%, 99% or 100% sequence identity with a sequence according to SEQ ID No. 43 or 44, wherein die sequence according to SEQ ID No. 44 is particularly preferred. In particular preferred is a plasmid that has a sequence according to SEQ ID No. 44.

"MEP Pathway" Plasmid

The "MEP pathway" plasmid according to the present invention is characterized in that it comprises nucleotide sequences that encode the following enzyme: 1-desoxy-D-xylulose-5-phosphate-synthase (DXS).

In a preferred embodiment of the "MEP pathway" plasmid according to the present invention, which can be combined with any of the preceding and subsequent embodiments, the plasmid comprises nucleotide sequences that encode the isopentenyl-diphosphate-Isomerase (CwIPI) of Curcuma wenyujin. Particularly preferred is a codon optimized synthetic gene sequence of the isopentenyl-diphosphate-Isomerase (CwIPI-co2). The isopentenyl-diphosphate-Isomerase (CwIPI) is per se not necessary for the coupling of the lycopene-epsilon-carotene and/or alpha-ionone biosynthesis to the MEP pathway. In a particularly preferred embodiment of the "MEP pathway" plasmid according to the present invention, which can be combined with any of the preceding and subsequent embodiments, the "MEP pathway" plasmid has at least 80% or at least 85%, 90% 91%, 92%, 93%, 94%, 95%, 96%, 97%, 98%, 99% or 100% sequence identity with a sequence according to SEQ ID No. 45, 46 or 47, wherein the sequence according to SEQ ID No. 45 is particularly preferred. Particularly preferred is a plasmid that has a sequence according to SEQ ID No. 45.

Expression Cassettes

A further aspect of the invention concerns the expression cassettes according to the present invention, which the skilled person can take from the figures, in particular FIGS. 3, 4, 7 and 9 to 14, as well as the sequence protocol. The expression cassettes according to the present invention can be present in a way that it is integrated in the genome of the microorganism according to the present invention. The expression cassettes can be integrated into the genome of a microorganism with methods that are known to the skilled person, in particular with homologous recombination. In a preferred embodiment, the expression cassettes according to the present invention can be present in an *E. coli* strain, in particular in XL1-blue, TOP10, XL10 blue, DH5-alpha, JM109, C41, BL21gold (DE3) and W3110. In particular the microorganism according to the present invention can be an *E. coli* strain TOP10. Particularly preferred is the *E. coli* strain BL21gold (DE3).

The expression cassettes according to the present invention comprise particularly the expression cassettes as listed in FIG. 14.

In particular, the expression cassettes according to the present invention, which preferably are present in the genome of a microorganism, such as *E. coli*, comprise expression cassettes that have at least 80% or at least 85%, 90%, 91%, 92%, 93%, 94%, 95%, 96%, 97%, 98%, 99% or 100% sequence identity with the expression cassettes according to FIG. 14.

In a preferred embodiment of the expression cassettes according to the present invention, which can be combined with any of the preceding and subsequent embodiments, the enzymes that are encoded by the expression cassettes according to the present invention are under the control of a constitutive promoter. The particularly preferred constitutive promoters according to the present invention are aP5, aP12, aP15, aP32 and aP47.2.

In a preferred embodiment of the expression cassettes according to the present invention, which can be combined with any of the preceding and subsequent embodiments, the enzymes that are encoded by the expression cassettes are under the control of an inducible promoter. Particularly preferred are the inducible promoters pTet, pBAD, pLac, and pXyl, which are also described in detail in Example 10. Particularly preferred are the inducible promoters pTet-m1, pXyl0, pXyl1 and pXyl2 (Example 10).

Microorganisms

The microorganism according to the present invention is characterized in that it contains heterologous nucleotide sequences that encode the following enzymes: geranylgeranyl-diphosphate-synthase, isopentenyl-diphosphate-Isomerase (IPI), phytoene- desaturase/dehydrogenase (crtI), phytoene synthase (crtB) and lycopene-epsilon-cyclase (EC), or geranylgeranyl-diphosphate-synthase, isopentenyl-diphosphate-Isomerase (IPI), phytoene-desaturase/dehydrogenase (crtI), phytoene synthase (crtB), lycopene-epsilon-cyclase (EC) and carotenoid-cleavage-dioxygenase (CCD1).

In a preferred embodiment of the microorganism according to the present invention, which can be combined with any of the preceding and subsequent embodiments, the enzymes are encoded on one or more plasmids. Particularly preferred embodiments of the microorganism according to the present invention contain one or multiple plasmids according to the present invention. Particularly preferred are the "Lyc-synthesis", "eCaro-synthesis", "eCaro-cleavage", "ionone-synthesis" and "MEP pathway" plasmids.

In a further preferred embodiment of the microorganism according to the present invention, which can be combined with any of the preceding and subsequent embodiments, the enzymes geranylgeranyl-diphosphate-synthase, isopentenyl-diphosphate-Isomerase (IPI), phytoene-desaturase/dehydrogenase (crtI) and phytoene synthase (crtB) are the corresponding enzymes of *Erwinia herbicola*.

In a preferred embodiment of the microorganism according to the present invention, which can be combined with any of the preceding and subsequent embodiments, the plasmid or the plasmids are present in the microorganism as individual structures or are integrated into the genome of the microorganism.

In a further preferred embodiment of the microorganism according to the present invention, which can be combined with any of the preceding and subsequent embodiments, the expression of the carotenoid-cleavage-dioxygenase (CCD1) is under the transcriptional control of an inducible promoter. In a further preferred embodiment, which can be combined with any of the preceding and subsequent embodiments, the inducible promoter is the arabinose inducible promoter pBAD. Particularly preferred are furthermore the constitutive and/or inducible promoters pXYL1, pXYL2, aP5 and aP15.

In a further preferred embodiment of the microorganism according to the present invention, which can be combined with any of the preceding and subsequent embodiments, the microorganism contains the nucleic acid according to the present invention that encodes a lycopene-epsilon-cyclase.

In a further preferred embodiment of the microorganism according to the present invention, which can be combined with any of the preceding and subsequent embodiments, the carotenoid-cleavage-dioxygenase (CCD1) oxidatively cleaves the 9, 10- and 9', 10'-double bonds of the epsilon-carotene.

In a particularly preferred embodiment of the microorganism according to the present invention, which can be combined with any of the preceding and subsequent embodiments, the microorganism contains the "eCaro-synthesis" plasmid according to the present invention, which comprises a sequence or consists of it, which has at least 80% or at least 85%, 90%, 91%, 92%, 93%, 94%, 95%, 96%, 97%, 98%, 99% or 100% sequence identity with a sequence according to SEQ ID No. 29 (pGT1066-AtEC-del), wherein the lycopene-epsilon-cyclase (EC) that is encoded by the plasmid has one of the following mutations or mutation combinations: ECmut16 (A403W/L404G), ECmut3.12 (L404T/A445S), ECmut3.3 (A403E/L404A/A445S), ECmut3.5 (A403M/L404A/A445S), ECmut3.8 (A403H/L404S/A445S), ECmut3.9 (A403E/L404G/A445S), ECmut3.16 (A403G/L404G/A445S), ECmut9 (L404S), ECmut10 (A403S/L404T) and ECmut3.2 (A403C/L404C/A445S). Particularly preferred are the mutations or mutation combinations ECmut9 (L404S), ECmut10 (A403S/L404T) andECmut3.2 (A403C/L404C/A445S).

In a particularly preferred embodiment of the microorganism according to the present invention, which can be combined with any of the preceding and subsequent embodiments, the microorganism contains the "eCaro-synthesis" plasmid according to the present invention, which consists of a sequence according to SEQ ID No. 29, wherein the lycopene-epsilon-cyclase (EC) that is encoded by the plasmid has one of the following mutations or mutation combinations: ECmut9 (L404S), ECmut10 (A403S/L404T) and ECmut3.2 (A403C/L404C/A445S).

In a particularly preferred embodiment of the microorganism according to the present invention, which can be combined with any of the preceding and subsequent embodiments, the microorganism is an *E. coli* strain. Particularly preferred in this context are the *E. coli* strains XL1-blue, TOP10, XL10 blue, DH5-alpha, JM109, C41, BL21gold (DE3) and W3110. In particular, the microorganism according to the present invention can be the *E. coli* strain TOP10. Particularly preferred is the *E. coli* strain BL21gold (DE3).

In a particularly preferred embodiment of the microorganism according to the present invention, which can be combined with any of the preceding and subsequent embodiments, the microorganism contains the "eCaro-synthesis" plasmid according to the present invention and the "eCaro-cleavage" plasmid, which has at least 80% or at least 85%, 90%, 91%, 92 according to SEQ ID No. 21 (pGT1069) or according to SEQ ID No. 24 (pGT1070). Particularly preferred embodiments of the microorganism contain the "eCaro-synthesis" plasmid according to the present invention and the "eCaro-cleavage" plasmid with a sequence according to SEQ ID Nr. 21 (pGT1069) or according to SEQ ID Nr. 24 (pGT1070), wherein the "eCaro-synthesis" plasmid according to the present invention preferably consists of a sequence according to SEQ ID No. 29 (pGT1066-AtEC-del), wherein the lycopene-epsilon-cyclase (EC) that is encoded by the plasmid has one of the following mutations or mutation combinations: ECmut9 (L404S), ECmut10 (A403S/L404T) and ECmut3.2 (A403C/L404C/A445S).

In a further particularly preferred embodiment of the microorganism according to the present invention, the microorganism corresponds to the microorganism that is cultivated in the method according to the present invention of producing a highly epsilon-carotene or in the method according to the present invention of producing enantiomerically pure alpha-ionone.

Method of Producing Highly Pure Epsilon-Carotene

The method of producing highly pure epsilon-carotene from lycopene according to the present invention comprises the culturing of a microorganism that contains heterologous nucleotide sequences that encode the following enzymes: geranylgeranyl-diphosphate-synthase, isopentenyl-diphosphate-Isomerase (IPI), phytoene-desaturase/dehydrogenase (crtI), phytoene synthase (crtB) and lycopene-epsilon-cyclase (EC).

In a particularly preferred embodiment of the method of producing highly pure epsilon-carotene from lycopene according to the present invention, which can be combined with any of the preceding and subsequent embodiments, the microorganism according to the present invention is cultured.

In a preferred embodiment of the method of producing highly pure epsilon-carotene from lycopene according to the present invention, which can be combined with any of the preceding and subsequent embodiments, the geranylgeranyl-diphosphate-synthase is the geranylgeranyl-diphosphate-synthase crtE or the geranylgeranyl-diphosphate-synthase idsA.

In a preferred embodiment of the method of producing highly pure epsilon-carotene from lycopene according to the present invention, which can be combined with any of the preceding and subsequent embodiments, the lycopene-epsilon-cyclase (EC) is the lycopene-epsilon-cyclase (EC) according to the present invention. Particularly preferred in this context are embodiments, in which the lycopene-epsilon-cyclase (EC) has at least 80% or at least 85%, 90%, 91%, 92%, 93%, 94%, 95%, 96%, 97%, 98%, 99% or 100% sequence identity with a sequence according to SEQ ID No. 19 and in which it deviates at least at one of Positions 403, 404 and 445 from the sequence according to SEQ ID No. 19. Particularly preferred are embodiments in which the lycopene-epsilon-cyclase (EC) according to the present invention comprises one of the following mutations: ECmut9 (L404S), ECmut10 (A403S/L404T), ECmut3.3 (A403E/L404A/A445S) and ECmut3.2 (A403C/L404C/A445S).

In a preferred embodiment of the method of producing highly pure epsilon-carotene from lycopene according to the present invention, which can be combined with any of the preceding and subsequent embodiments, the enzymes are encoded on one or multiple plasmids. These plasmids can be present as individual structures in the microorganisms or be integrated into the genome of the microorganism. These enzymes can be co-expressed.

In a preferred embodiment of the method of producing highly pure epsilon-carotene from lycopene according to the present invention, which can be combined with any of the previous and subsequent embodiments, the microorganism contains a Plasmid with at least 80% or at least 85%, 90%, 91%, 92%, 93%, 94%, 95%, 96%, 97%, 98%, 99% or 100 sequence identity with a sequence according to SEQ ID No. 30, 31, 32, 33, 34, 35 or 36.

In a preferred embodiment of the method of producing highly pure epsilon-carotene from lycopene according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 45, 46 or 47.

In a particularly preferred embodiment of the method of producing highly pure epsilon-carotene from lycopene according to the present invention, which can be combined with any of the preceding and subsequent embodiments, the microorganism according to the present invention is cultured, which contains the "eCaro-synthesis" plasmid according to present invention, which comprises a sequence or consists of it, which has at least 80% or at least 85%, 90%, 91%, 92%, 93%, 94%, 95%, 96%, 97%, 98%, 99% or 100% sequence identity with a sequence according to SEQ ID No. 29 (pGT1066-AtEC-del), wherein the lycopene-epsilon-cyclase (EC) that is encoded by the plasmid comprises or has one of the following mutations or mutation combinations: ECmut2 (A445S), ECmut9 (L404S), ECmut3 (L404H/A445S), ECmut3.10 (A403C/A445S), ECmut3.12 (L404T/A445S), ECmut4 (A403S/L404H), ECmut5 (A403F/L404W), ECmut6 (A403G/L404G), ECmut7 (A403K/L404D), ECmut8 (A403W/L404R), ECmut10 (A403S/L404T), ECmut11 (A403F/L404S), ECmut12 (A403C/L404S), ECmut13 (A403I/L404T), ECmut14 (A403T/L404R), ECmut15 (A403F/L404R), ECmut16 (A403W/L404G), ECmut17 (A403C/A404C), ECmut18 (A403L/L404V), ECmut19 (A403K/L404R), ECmut20 (A403Y/L404K), ECmut21 (A403Q/L404K), ECmut22 (A403G/L404Q), ECmut3.1 (A403S/L404H/A445S), ECmut3.2 (A403C/L404C/A445S), ECmut3.3 (A403E/L404A/

A445S), ECmut3.4 (A403W/L404R/A445S), ECmut3.5 (A403M/L404A/A445S), ECmut3.6 (A403N/L404T/A445S), ECmut3.7 (A403N/L404A/A445S), ECmut3.8 (A403H/L404S/A445S), ECmut3.9 (A403E/L404G/A445S), ECmut3.11 (A403C/L404C/A445S), ECmut3.13 (A403R/L404S/A445S), ECmut3.14 (A403G/L404R/A445S), ECmut3.15 (A403F/L404V/A445S) and ECmut3.16 (A403G/L404G/A445S). Particularly preferred are mutations and mutation combinations ECmut9 (L404S), ECmut10 (A403S/L404T) and ECmut3.2 (A403C/L404C/A445S).

In a particularly preferred embodiment of the method of producing highly pure epsilon-carotene from lycopene according to the present invention, which can be combined with any of the preceding and subsequent embodiments, the microorganism according to the present invention is cultured, which contains the "eCaro-synthesis" plasmid according to the present invention, which consists of a sequence according to SEQ ID No. 29 (pGT1066-AtEC-del), wherein the lycopene-epsilon-cyclase (EC) that is encoded by the plasmid has one of the following mutations or mutation combinations: ECmut9 (L404S), ECmut10 (A403S/L404T), ECmut3.2 (A403C/L404C/A445S) and ECmut3.3 (A403E/L404A/A445S).

In a particularly preferred embodiment of the method of producing highly pure epsilon-carotene from lycopene according to the present invention, which can be combined with any of the preceding and subsequent embodiments, the microorganism according to the present invention is *E. coli*. Particularly preferred in this context are the *E. coli* strains XL1-blue, TOP10, XL10 blue, DH5-alpha, JM109, C41, BL21gold (DE3) and W3110. In particular, the microorganism can be the *E. coli* strain TOP10. Particularly preferred is the *E. coli* strain BL21gold (DE3).

In a particularly preferred embodiment of the method of producing highly pure epsilon-carotene from lycopene according to the present invention, which can be combined with any of the preceding and subsequent embodiments, the microorganism according to the present invention contains heterologous nucleotide sequences, which encode the enzyme 1-desoxy-D-xylulose-5-phosphate-synthase (DXS).

In a particularly preferred embodiment of the method of producing highly pure epsilon-carotene from lycopene according to the present invention, which can be combined with any of the previous and subsequent embodiments, the microorganism contains heterologous nucleotide sequences that encode the enzyme isopentenyl-diphosphate-isomerase (CwIPI).

In a particularly preferred embodiment of the method of producing highly pure epsilon-carotene from lycopene, which can be combined with any of the previous and subsequent embodiments, the microorganism contains a plasmid that has at least 80% or at least 85%, 90%, 91%, 92%, 93%, 94%, 95%, 96%, 97%, 98%, 99% or 100% sequence identity with a sequence according to SEQ ID No. 45, 46 or 47, wherein the sequence according to SEQ ID No. 45 is particularly preferred. In particular, preferred is a plasmid that has a sequence according to SEQ ID No. 45.

Method of Producing Enantiomerically Pure Alpha-Ionone

The method of producing enantiomerically pure alpha-ionone according to the present invention comprises the culturing of a microorganism that contains heterologous nucleotide sequences, which encode the following enzymes: geranylgeranyl-diphosphate-synthase, isopentenyl-diphosphate-Isomerase (IPI), phytoene-desaturase/dehydrogenase (crtI), phytoene synthase (crtB), lycopene-epsilon-cyclase (EC) and carotenoid-cleavage-dioxygenase (CCD1).

In a preferred embodiment of the method of producing enantiomerically pure alpha-ionone according to the present invention, which can be combined with any of the preceding and subsequent embodiments, the microorganism according to the present invention is cultured.

In a preferred embodiment of the method of producing enantiomerically pure alpha-ionone according to the present invention, which can be combined with any of the preceding and subsequent embodiments, (R)-alpha-ionone is produced.

In a preferred embodiment of the method of producing enantiomerically pure alpha-ionone according to the present invention, which can be combined with any of the preceding and subsequent embodiments, the geranylgeranyl-diphosphate-synthase is the geranylgeranyl-diphosphate-synthase crtE or the geranylgeranyl-diphosphate-synthase idsA.

In a preferred embodiment of the method of producing enantiomerically pure alpha-ionone according to the present invention, which can be combined with any of the preceding and subsequent embodiments, the lycopene-epsilon-cyclase (EC) is the lycopene-epsilon-cyclase (EC) according to the present invention. Particularly preferred in this context are embodiments in which the lycopene-epsilon-cyclase (EC) has at least 80% or at least 85%, 90%, 91%, 92%, 93%, 94%, 95%, 96%, 97%, 98%, 99% or 100% sequence identity with a sequence according to SEQ ID No. 19 and deviates at least at one of the positions 403, 404 and 445 from the sequence according to SEQ ID No. 19. Particularly preferred are embodiments in which the lycopene-epsilon-cyclase (EC) according to the present invention comprises one of the following mutations or mutation come nations: ECmut9 (L404S), ECmut10 (A403S/L404T), ECmut3.3 (A403E/L404A/A445S) and ECmut3.2 (A403C/L404C/A445S).

In a preferred embodiment of the method of producing enantiomerically pure alpha-ionone according to the present invention, which can be combined with any of the preceding and subsequent embodiments, the carotenoid-cleavage-dioxygenase (CCD1) is a carotenoid-cleavage-dioxygenase (CCD1) of *Arabidopsis thaliana* or *Osmanthus fragrans.*

In a preferred embodiment of the method of producing enantiomerically pure alpha-ionone according to the present invention, which can be combined with any of the preceding and subsequent embodiments, the enzymes are encoded by one or multiple plasmids. These plasmids can be present in the microorganism as individual structures or can be integrated into the genome des microorganism. These enzymes can be co-expressed.

In a particularly preferred embodiment of the method of producing enantiomerically pure alpha-ionone according to the present invention, preferably (R)-alpha-ionone, which can be combined with any of the preceding and subsequent embodiments, the microorganism is cultured, which contains the "eCaro-synthesis" plasmid and the "eCaro-cleavage" plasmid according to the present invention, wherein the "eCaro-synthesis" plasmid according to the present invention comprises a sequence or consists of it, which has at least 80% or at least 85%, 90%, 91%, 92%, 93%, 94%, 95%, 96%, 97%, 98%, 99% or 100% sequence identity with a sequence according to SEQ ID No. 29 (pGT1066-AtEC-del), wherein the lycopene-epsilon-cyclase (EC) that is encoded by the plasmid comprises or has one of the following mutations or mutation combinations: ECmut2 (A445S), ECmut9 (L404S), ECmut3 (L404H/A445S), ECmut3.10 (A403C/A445S), ECmut3.12 (L404T/A445S), ECmut4 (A403S/L404H), ECmut5 (A403F/L404W), ECmut6

(A403G/L404G), ECmut7 (A403K/L404D), ECmut8 (A403W/L404R), ECmut10 (A403S/L404T), ECmut11 (A403F/L404S), ECmut12 (A403C/L404S), ECmut13 (A403I/L404T), ECmut14 (A403T/L404R), ECmut15 (A403F/L404R), ECmut16 (A403W/L404G), ECmut17 (A403C/A404C), ECmut18 (A403L/L404V), ECmut19 (A403K/L404R), ECmut20 (A403Y/L404K), ECmut21 (A403Q/L404K), ECmut22 (A403G/L404Q), ECmut3.1 (A403S/L404H/A445S), ECmut3.2 (A403C/L404C/A445S), ECmut3.3 (A403E/L404A/A445S), ECmut3.4 (A403W/L404R/A445S), ECmut3.5 (A403M/L404A/A445S), ECmut3.6 (A403N/L404T/A445S), ECmut3.7 (A403N/L404A/A445S), ECmut3.8 (A403H/L404S/A445S), ECmut3.9 (A403E/L404G/A445S), ECmut3.11 (A403K/L404G/A445S), ECmut3.13 (A403R/L404S/A445S), ECmut3.14 (A403G/L404R/A445S), ECmut3.15 (A403F/L404V/A445S) and ECmut3.16 (A403G/L404G/A445S). Particularly preferred are the mutations or mutation combinations ECmut9 (L404S), ECmut10 (A403S/L404T) and ECmut3.2 (A403C/L404C/A445S). The “eCaro-cleavage” plasmid is preferably a plasmid that has at least 80% or at least 85%, 90%, 91%, 92%, 93%, 94%, 95%, 96%, 97%, 98%, 99 or 100% sequence identity with a sequence according to SEQ ID No. 21 (pGT1069) or according to SEQ ID No. 24 (pGT1070). Particularly preferred is a further plasmid that has a sequence that is identical with a sequence according to SEQ ID Nr. 21 (pGT1069) or according to SEQ ID No. 24 (pGT1070).

In a particularly preferred embodiment of the method of producing enantiomerically pure alpha-ionone according to the present invention, preferably (R)-alpha-ionone, which can be combined with any of the preceding and subsequent embodiments, the microorganism according to the present invention is cultured, which contains the “eCaro-synthesis” plasmid and the “eCaro-cleavage” plasmid according to the present invention, wherein the “eCaro-synthesis” plasmid consists of a sequence according to SEQ ID No. 29 (pGT1066-AtEC-del) and the lycopene-epsilon-cyclase (EC) that is encoded by the plasmid has one of the following mutations or mutation combinations: ECmut9 (L404S), ECmut10 (A403S/L404T), ECmut3.2 (A403C/L404C/A445S) and ECmut3.3 (A403E/L404A/A445S).

In a particularly preferred embodiment of the method of producing enantiomerically pure alpha-ionone according to the present invention, preferably (R)-alpha-ionone, which can be combined with any of the preceding and subsequent embodiments, the “eCaro-cleavage” plasmid consists of a sequence according to SEQ ID NO. 21 (pGT1069) or according to SEQ ID NO. 24 (pGT1070).

In a particularly preferred embodiment of the method of producing enantiomerically pure alpha-ionone according to the present invention, preferably (R)-alpha-ionone, which can be combined with any of the preceding and subsequent embodiments, the microorganism according to the present invention is cultured, which contains the “eCaro-synthesis” plasmid and the “eCaro-cleavage” plasmid, wherein the “eCaro-cleavage” plasmid consists of a sequence according to SEQ ID No. 21 (pGT1066-AtEC-del) or according to SEQ ID Nr. 24 (pGT1070) and wherein the “eCaro-synthesis” plasmid according to the present invention consists of a sequence according to SEQ ID Nr. 29 (pGT1066-AtEC-del), wherein the lycopene-epsilon-cyclase (EC) that is encoded by the plasmid according to the present invention has one of the following mutations or mutation combinations: ECmut9 (L404S), ECmut10 (A403S/L404T), ECmut3.2 (A403C/L404C/A445S) and ECmut3.3 (A403E/L404A/A445S).

In a particularly preferred embodiment of the method of producing enantiomerically pure alpha-ionone according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 30, 31, 32, 33, 34, 35 or 36.

In a preferred embodiment of the method of producing enantiomerically pure alpha-ionone according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 21, 24, 37, 38, 39, 40, 41 or 42.

In a preferred embodiment of the method of producing enantiomerically pure alpha-ionone according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 43 or 44.

In a preferred embodiment of the method of producing enantiomerically pure alpha-ionone according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 45, 46 or 47.

In a preferred embodiment of the method of producing enantiomerically pure alpha-ionone according to the present invention, which can be combined with any of the preceding and subsequent embodiments, the microorganism contains a plasmid with at least 80% or at least 85%, 90%, 91%, 92%, 93%, 94%, 95%, 96%, 97%, 98%, 99% or 100 sequence identity with a sequence according to SEQ ID No. 33 and a plasmid with at least 80% or at least 85%, 90%, 91%, 92%, 93%, 94%, 95%, 96%, 97%, 98%, 99% oder 100% sequence identity with a sequence according to SEQ ID Nr. 37. In a equally preferred embodiment the microorganism contains a plasmid with at least 80% or at least 85%, 90%, 91%, 92%, 93%, 94%, 95%, 96%, 97%, 98%, 99% or 100% sequence identity with a sequence according to SEQ ID No. 33 and a plasmid with at least 80% or at least 85%, 90%, 91%, 92%, 93%, 94%, 95%, 96%, 97%, 98%, 99% or 100% sequence identity with a sequence according to SEQ ID No. 41. In a further particularly preferred embodiment, the microorganism contains a plasmid with at least 80% or at least 85%, 90%, 91%, 92%, 93%, 94%, 95%, 96%, 97%, 98%, 99% or 100% sequence identity with a sequence according to SEQ ID No. 44 and a plasmid with at least 80% or at least 85%, 90%, 91%, 92%, 93%, 94%, 95%, 96%, 97%, 98%, 99% or 100% sequence identity with a sequence according to SEQ ID No. 45.

In a particularly preferred embodiment of the method of producing enantiomerically pure alpha-ionone according to the present invention, which can be combined with any of the preceding and subsequent embodiments, the microorganism contains a plasmid with a sequence according to SEQ ID No. 33 and a plasmid with a sequence according to SEQ ID No. 37, or a plasmid with a sequence according to SEQ ID Nr. 33 and a plasmid with a sequence according to SEQ ID No. 41, or a plasmid with a sequence according to SEQ ID No. 44 and a plasmid with a sequence according to SEQ ID Nr. 45.

In a particularly preferred embodiment of the method of producing enantiomerically pure alpha-ionone according to the present invention, which can be combined with any of the preceding and subsequent embodiments, the microorganism is an *E. coli* strain. Particularly preferred in this context is die *E. coli* strains, XL1-blue, TOP10, XL10 blue, DH5-alpha, JM109, C41, BL21gold (DE3) and W3110. In particular, the microorganism according to the present invention can be the *E. coli* strain TOP10. Particularly preferred is the *E. coli* strain BL21gold (DE3).

In a particularly preferred embodiment of the method of producing enantiomerically pure alpha-ionone according to the present invention, which can be combined with any of the preceding and subsequent embodiments, the microorganism contains heterologous nucleotide sequences that encode the enzyme 1-desoxy-D-xylulose-5-phosphat-synthase (DXS).

In a particularly preferred embodiment of the method of producing enantiomerically pure alpha-ionone according to the present invention, which can be combined with any of the preceding and subsequent embodiments, the microorganism contains heterologous nucleotide sequences that encode the enzyme isopentenyl-diphosphate-Isomerase (CwIPI).

In a particularly preferred embodiment of the method of producing enantiomerically pure alpha-ionone according to the present invention, which can be combined with any of the preceding and subsequent embodiments, the microorganism contains a plasmid that has at least 80% or at least 85%, 90%, 91%, 92%, 93%, 94%, 95%, 96%, 97%, 98%, 99% or 100% sequence identity with a sequence according to SEQ ID Nr. 45, 46 or 47, wherein the sequence according to SEQ ID No. 45 is particularly preferred. In particular, preferred is a plasmid that has a sequence according to SEQ ID No. 45.

Further Embodiments of the Invention:

In the following further embodiments of the present invention are described, which can be combined with any of the preceding and subsequent embodiments.

Embodiment 1: Nucleic acid characterized in that it comprises a sequence that encodes a lycopene-epsilon-cyclase (EC), which catalyzes the transformation of lycopene to epsilon-carotene, wherein the encoded lycopene-epsilon-cyclase (EC) leads to greater epsilon- carotene yield compared to a reference lycopene-epsilon-cyclase (EC) with a sequence according to SEQ ID No. 26.

Embodiment 2: Nucleic acid according to Embodiment 1, wherein the encoded lycopene-epsilon-cyclase (EC) has a sequence that has at least 80% sequence identity with a sequence according to SEQ ID No. 19.

Embodiment 3: Nucleic acid according to Embodiment 2, wherein the sequence of the encoded lycopene-epsilon-cyclase (EC) deviates at least at one of the Positions 403, 404 and 445 of the sequence according to SEQ ID No. 19.

Embodiment 4: Nucleic acid according to one of the Embodiments 1 to 3, wherein the encoded lycopene-epsilon-cyclase (EC) comprises one of the following mutations or mutation combinations: ECmut9 (L404S), ECmut10 (A403S/L404T), ECmut3.2 (A403C/L404C/A445S) and ECmut3.3 (A403E/L404A/A445S), Embodiment 5: Nucleic acid according to one of the Embodiments 1 to 4, wherein the encoded lycopene-epsilon-cyclase (EC) consists of a sequence according to SEQ ID No. 19, which has one of the following mutations or mutation combinations: ECmut9 (L404S), ECmut10 (A403S/L404T), ECmut3.2 (A403C/L404C/A445S) and ECmut3.3 (A403E/L404A/A445S), Embodiment 6: Lycopene-epsilon-cyclase (EC) encoded by a nucleic acid according to one of Embodiments 1 to 5.

Embodiment 7: Plasmid characterized in that it comprises nucleotide sequences that encode the following enzymes:

a. geranylgeranyl-diphosphate-synthase, b. isopentenyl-diphosphate-Isomerase (IPI), c. phytoene-desaturase/dehydrogenase (crtI) and d. phytoene synthase (crtB), wherein the heterologous Expression of the lycopene-biosynthetic pathway that is encoded by the plasmid leads to an increased lycopene yield compared to the heterologous expression of the lycopene-biosynthetic pathway that is encoded by the plasmid pAC-BETAIPI-ΔcrtY (SEQ ID No. 28).

Embodiment 8: Plasmid according to Embodiment 7, comprising a sequence that has at least 80% sequence identity with a reference sequence, wherein the reference sequence is a sequence according to SEQ ID No. 28, wherein the reference sequence has, relative to the sequence according to SEQ ID No. 28, a deletion of the Bases 984-1394 and 3432-4198.

Embodiment 9: Plasmid according to Embodiment 8, wherein the reference sequence relative to the sequence according to SEQ ID No. 28 has a deletion of the Bases 984-1394, 3432-4198 and 6605-7242.

Embodiment 10: Plasmid according to Embodiment 7, comprising a sequence that has at least 80% sequence identity with a reference sequence, wherein the reference sequence is a sequence according to SEQ ID No. 11.

Embodiment 11: Plasmid according to one of the Embodiments 7 to 10, wherein the plasmid further comprises a nucleic acid sequence according to one of the Embodiments 1 to 5.

Embodiment 12: Plasmid according to Embodiment 7, comprising a sequence that has at least 80% sequence identity with a reference sequence, wherein the reference sequence is a sequence according to SEQ ID No. 18.

Embodiment 13: Plasmid according to Embodiment 7, comprising a sequence that has at least 80% sequence identity with a reference sequence, wherein the reference sequence is a sequence according to SEQ ID No. 29, wherein the lycopene-epsilon-cyclase (EC) that is encoded by the plasmid has one of the following mutations or mutation combinations: ECmut9 (L404S), ECmut10 (A403S/L404T), ECmut3.2 (A403C/L404C/A445S) and ECmut3.3 (A403E/L404A/A445S).

Embodiment 14: Microorganism characterized in that it contains heterologous nucleotide sequences, which encode the following enzymes:

a. geranylgeranyl-diphosphate-synthase, isopentenyl-diphosphate-Isomerase (IPI), phytoene-desaturase/dehydrogenase (crtI), phytoene synthase (crtB), and lycopene-epsilon-cyclase (EC), or b. geranylgeranyl-diphosphate-synthase, isopentenyl-diphosphate-Isomerase (IPI), phytoene-desaturase/dehydrogenase (crtI), phytoene synthase (crtB), lycopene-epsilon-cyclase (EC) and carotenoid-cleavage-dioxygenase (CCD1).

Embodiment 15: Microorganism according to Embodiment 14, wherein the enzymes are encoded on one or multiple plasmids.

Embodiment 16: Microorganism according to Embodiment 14 or 15, wherein the one or multiple plasmids are present in the microorganism as individual structures or are integrated into the genome of the microorganism.

Embodiment 17: Microorganism according to one of the Embodiments 14 to 16, wherein the encoded enzymes are co-expressed.

Embodiment 18: Microorganism according to one of the Embodiments 14 to 17, wherein the expression of the carotenoid-cleavage-dioxygenase (CDD1) is under the transcriptional control of an inducible promoter, preferably under the control of the arabinose inducible promoter pBAD.

Embodiment 19: Microorganism according to one of the Embodiments 14 to 18, wherein the microorganism contains a nucleic acid according to one of Embodiments 1 to 5.

Embodiment 20: Microorganism according to one of the Embodiments 14 to 19, wherein the microorganism contains the plasmid according to one of Embodiments 7 to 13.

Embodiment 21: Microorganism according to one of the Embodiments 14 to 20, wherein the carotenoid-cleavage-dioxygenase (CDD1) oxidatively cleaves the 9, 10- and 9', 10'-double bonds of the epsilon-Carotene.

Embodiment 22: Microorganism according to one of the Embodiments 14 to 21, wherein the microorganism contains the plasmid pGT1069 (SEQ ID Nr. 21) or pGT1070 (SEQ ID Nr. 24).

Embodiment 23: Method of producing highly pure epsilon-Carotene from lycopene, characterized in that a microorganism is cultured that contains a heterologous nucleotide sequences that encode the following enzymes:

a. geranylgeranyl-diphosphate-synthase,
b. isopentenyl-diphosphate-Isomerase (IPI),
c. phytoene-desaturase/dehydrogenase (crtI),
d. phytoene synthase (crtB), and
e. lycopene-epsilon-cyclase (EC).

Embodiment 24: Method according to Embodiment 23, wherein the cultivated microorganism is a microorganism according to one of Embodiments 14 to 22.

Embodiment 25: Method of producing enantiomerically pure alpha-ionone, characterized in that a microorganism is cultured that contains heterologous nucleotide sequences that encode the following enzymes:

a. geranylgeranyl-diphosphate-synthase,
b. isopentenyl-diphosphate-Isomerase (IPI),
c. phytoene-desaturase/dehydrogenase (crtI),
d. phytoene synthase (crtB),
e. lycopene-epsilon-cyclase (EC) and
f. carotenoid-cleavage-dioxygenase (CCD1).

Embodiment 26: Method according to Embodiment 25, wherein the cultivated microorganism is a microorganism according to one of Embodiments 14 to 22.

EXAMPLES

Example 1: Optimization of an Expression Plasmid

Starting for optimizing the expression vector was the plasmid pAC-BET Aipi (Cunningham et al., 2007), which carries carotenoid genes of *E. herbicola* (crtE, IPI, crtB and crtl). Among other things, plasmid pAC-BET Aipi was modified as follows, so as to produce the plasmid pGT1036 (SEQ ID No. 11) using Molecular Biology standard methods known to the skilled person (Sambrook J, Fritsch E F, Maniatis T. in: Molecular Cloning, A Laboratory Manual, 1989 (Nolan C, Ed.), Cold Spring Harbor Laboratory Press, Cold Spring Harbor, N.Y.): Deletion 984-1394, Deletion 3432-5356 and Deletion 7761-8399. A plasmid map of the resulting plasmids pGT1036 is depicted in FIG. 3A and FIG. 3B lists the complete acid nucleic sequence of pGT1036.

The analysis of the lycopene yield was conducted analogously to the analysis described in Example 6 for the epsilon-Carotene yield. Briefly: The HPLC analysis of the bacterial carotenoid extracts was conducted using an HP-Series II 1090 liquid chromatograph (Agilent Technologies, Boblingen) with ternary pump system and diode-array-detector. For resolution, a Zorbax SB-C18 separation column (3.5 μm, 4.6×150 mm, Agilent Technologies, Boblingen) at a column temperature of 40° C. The separation of the carotenoids initially took place over a course of 2 minutes, isocratically with 20% ethyl acetate (EtAc) in acetonitrile (AcN), subsequently with a gradient of 20% EtAc in AcN to 50% EtAc in AcN for 10 minutes, and subsequently for 3 minutes isocratically at 50% EtAc in AcN with a flow rate of 1 ml per minute. The analysis was conducted with HP ChemStation for LC Version A.05.02 and was performed for lycopene at a wavelength of 450 nm. The HPLC conditions were as follows: Column—Zorbax C18 3,5 μm 150-4.6 (Agilent), column temperature—40° C., solvent A—acetonitrile, solvent B—ethyl acetate, flow rate—1 ml/min, and gradient—2 minutes isocratically at 20% B, in 10 minutes up to 50% B, 3 minutes isocratically at 50% B.

The analysis/detection was performed by means of absorption measurement. lycopene was detected at a wavelength of 450 nm.

For determining the amount of lycopene, the area of the corresponding peaks in the chromatogram is calculated. It is directly proportional to the amount of substance. For the generation of a reference curve, increasing amounts of pure reference substances in this manner. By using this reference curve, the given amount of substance (in g) can be calculated from the peak area.

The above-described changes to the plasmid pAC-BETAipi lead to a significant increase of lycopene yield. Compared to the reference plasmid pAC-BETAipi-ΔcrtY, the plasmid pGT1036 has a 4.2-fold increased lycopene yield.

Example 2: Cloning of an Artificial Terminator Sequence aTerm5

Starting from the expression plasmid pGJ2720 (Jach et al. 2006) a short DNA sequence, consisting of a random sequence of 18 bp that is flanked by 10 bp inverted repeats was introduced at the 3'-end of the reporter gene RFP (Red Fluorescent Protein). The following primers were used for the PCR reaction (N=random nucleotide):

```
SEQ ID No. 1:
NNNNNNNNNAACGGGATTTTTTGCTGAAAGGAGGAACTATATCC

SEQ ID No. 2:
NNNNNNNNNNNAACGGGCTTTGTTAGCAGCCGG
```

The PCR reaction (50 μl end volume) contained the following in bidest. water dissolved components: 5ng pGJ2720 plasmid (template), 20 μmol each of primers P2750 and P2751, 10 nmol each of nucleotides dATP, dCTP, dGTP, dTTP and 5 μl Q5-Puffer(10×). The following program was used: 2 minutes at 98° C., then 30 cycles each with 30 seconds at 98° C., 30 seconds at 65° C. and 90 seconds 72° C., followed by 5 minutes at 72° C.

After addition of 10 units of the restriction enzyme Dpnl, the PCR reaction was then incubated for 1 hour at 37° C. Subsequently, the resulting PCR product, in accordance with the manufacturer's instructions, was purified in a column (PCR Purification-Kit; Maschery and Nagel). For the phosphorylating the 5'-end of the PCR product, the eluate (50 μl) was combined with 2 μl 10 mM ATP and 1 μl polynucleotide-kinase and incubated for 15 minutes at 37° C. and then for 20 minutes at 65° C. 5 μl of this preparation were then added to a standard ligation reaction (Sambrook et al.; final volume 20 μl). The ligation products were then introduced into *E. coli* cells using standard transformation methods. The identification of functional terminator sequences was subsequent performed via the analysis of the reported gene expression of the resulting clones. A collection of functional clones was prepared, the corresponding plasmid DNA isolated and the sequence of the corresponding terminator sequence identified via DNA sequencing.

Example 3: Cloning of the Lycopene-Epsilon-Cyclase (EC) of *A. Thaliana*

An in-silico analysis of the lycopene-epsilon-cyclase (EC) encoded by the *Arabidopsis thaliana* gene At5g57030 was conducted, which showed that the first 44 amino acids (excluding the N-terminal Methionine) of the protein sequence constitute a chloroplast localization signal (transit peptide). Using PCR, the determined coding region of the mature protein (AtEC-del, SEQ ID No. 19) from *A. thaliana* cDNA was amplified, since the genomic gene sequence contains multiple Introns and is therefore not suitable for the microbial expression of the enzyme. Subsequently, it was sub-cloned in the expression plasmid pGJ2720, and the resulting DNA sequence was verified.

Example 4: Lycopene-Epsilon-Cyclase (EC) Mutations

Figure 5:
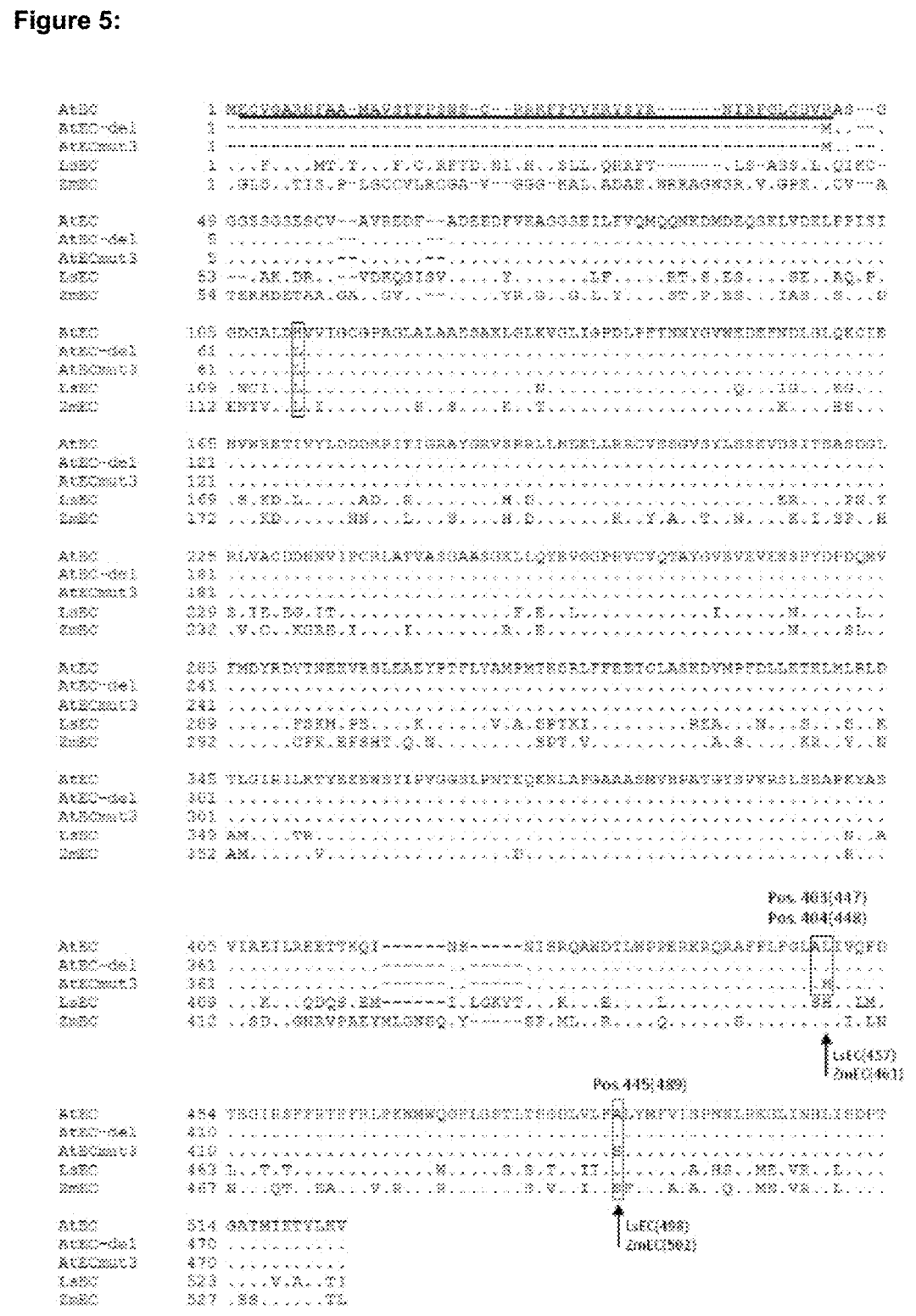

Using Molecular Biology standard procedures, a lycopene-epsilon-cyclase (EC) expression cassette was generated. The generated EC-expression cassette consisting of Lac promoter (pLac), the sequence that encodes AtEC-del (SEQ ID No. 19) and the terminator aTerm5 (see Example 2), was amplified using PCR reaction and introduced into the generated plasmid pGT1036 (FIG. 3A, SEQ ID No. 11). FIG. 4 shows exemplarily the plasmid map and the nucleotide sequence for an expression plasmid containing the gene for ECmut3 (pGT1066, SEQ ID No. 17). Using the following oligonucleotide primers, the targeted mutations (L404H, A445S, L404H/A445S, A403S/L404H) or random mutations were introduced by means of a PCR reaction into Positions 403/404 and/or 445 of the AtEC-del-amino acid sequence (see FIG. 5):

```
SEQ ID No. 3:
GTCTTGCACACATAGTTCAATTCG

SEQ ID No. 4:
CTATGTGTGCAAGACCAAAGAGAAAGAATGCTCTCTG

SEQ ID No. 5:
CTCTTTTCTTTATACATGTTCGTCATTTCACC

SEQ ID No. 6:
GTATAAAGAAAAGAGAACGAGATCTCCTG

SEQ ID No. 7:
GTCTTTCACACATAGTTCAATTCGATACCG

SEQ ID No. 8:
CTATGTGTGAAAGACCAAAGAGAAAGAATGCTC

SEQ ID No. 9:
GCATTCTTTCTCTTTGGTCTTNNKNNKATAGTTCAATTCGATACCGA

AGGC

SEQ ID No. 10:
CCAAAGAGAAAGAATGCTCTCTG
```

The PCR reactions (50 μl final volume) contain the following in bidest. water dissolved components: 5 ng pGJ2720 plasmid (template), 20 μmol each of one of the primer combinations (SEQ ID No. 3/SEQ ID No. 4, SEQ ID No. 5/SEQ ID No. 6, SEQ ID No. 7/SEQ ID No. 8 or SEQ ID No. 9/SEQ ID No. 10), 10 μmol each of the nucleotides dATP, dCTP, dGTP, dTTP and 5 μl Q5 buffer (10×). The following program was used: 2 minutes at 98° C., then 30 cycles each with 30 seconds at 98° C., 30 seconds at 60° C. and 4 minutes at 72° C., and finally 5 minutes at 72° C. After an addition of 10 units of the restriction enzyme Dpnl, the PCR reaction was then incubated for 1 hour at 37° C. Subsequently, the resulting PCR product was purified by a column following the manufacturer's instructions (PCR Purification-Kit; Maschery and Nagel). For the PCR products, LIC reactions (ligation independent cloning) were conducted and the reaction products were transformed in *E. coli* XL1-blue cells using standard methods.

The screening of the AtEC-del-random mutants was performed by plating the transformants on solid medium (LB+Chloramphenicol), incubation for 24 hours at 28° C. and the subsequent selection from colonies with the most intense yellow coloration due to the epsilon-carotenoid content. For determining the resulting mutation, the plasmid DNA of the selected clone was isolated and analyzed by means of DNA sequencing.

The following mutants were selected on the basis of their intense yellow coloration:

Single Mutants:

ECmut2 (A445S), ECmut9 (L404S)

Double Mutants:

ECmut4 (A403S/L404H), ECmut5 (A403F/L404W), ECmut6 (A403G/L404G),

ECmut7 (A403K/L404D), ECmut8 (A403W/L404R), ECmut10 (A403S/L404T), ECmut11 (A403F/L404S), ECmut12 (A403C/L404S), ECmut13 (A403I/L404T), ECmut14 (A403T/L404R), ECmut15 (A403F/L404R), ECmut16 (A403W/L404G), ECmut17 (A403C/A404C), ECmut18 (A403L/L404V), ECmut19 (A403K/L404R), ECmut20 (A403Y/L404K), ECmut21 (A403Q/L404K), ECmut22 (A403G/L404Q), Triple Mutants:

ECmut3.1 (A403S/L404H/A445S), ECmut3.2 (A403C/L404C/A445S),

ECmut3.3 (A403E/L404A/A445S), ECmut3.4 (A403W/L404R/A445S),

ECmut3.5 (A403M/L404A/A445S), ECmut3.6 (A403N/L404T/A445S),

ECmut3.7 (A403N/L404A/A445S), ECmut3.8 (A403H/L404S/A445S),

ECmut3.9 (A403E/L404G/A445S), ECmut3.11 (A403K/L404G/A445S),

ECmut3.13 (A403R/L404S/A445S), ECmut3.14 (A403G/L404R/A445S),

ECmut3.15 (A403F/L404V/A445S), ECmut3.16 (A403G/L404G/A445S)

Example 5: Transformation of Host Cells

All expression plasmids were introduced into *E. coli* TOP10 cells using transformation. The transformation of host cells was conducted following standard methods (Sambrook J, Fritsch EF, Maniatis T. in: Molecular Cloning, A Laboratory Manual, 1989 (Nolan C, Ed.), Cold Spring Harbor Laboratory Press, Cold Spring Harbor, N.Y.).

Example 6: Detection of Epsilon-Carotene

The recombinant strains were analyzed concerning their synthesized carotenoids using HPLC.

The recombinant strains were generated by transforming an *E. coli* strain with different expression plasmids, which contain, in addition to crtE, IPI, crtI and crtB, the nucleic acid for one of the different lycopene-epsilon-cyclase mutants (ECmut).

Die culturing of the recombinant strains was performed at 24 hours at 28° C. in dYT medium (+chloramphenicol and ampicillin). The cells were then pelleted using centrifugation (10 minutes, 4,000 g), the medium supernatant was removed and the formed carotenoids were quantitatively extracted from the cell pellet using acetone. The extracts were evaporated in vacuum to dryness and the resulting carotenoid pellets were dissolved in equal volumes of Acetonitril (1 ml) and directly used for HPLC analysis.

The HPLC analysis of the bacterial carotenoid extracts was performed by using the HP Series II 1090 Liquid Chromatograph (Agilent Technologies, Boblingen) with ternary pump system and diode-array-detector. For separation, a Zorbax SB-C18 separation column (3.5 μm, 4.6×150 mm, Agilent Technologies, Boblingen) was used at a column temperature of 40° C. The separation of the carotenoids was performed initially over 2 minutes isocratically with 20% ethyl acetate (EtAc) in acetonitrile (AcN), subsequently via a gradient from 20% EtAc in AcN to 50% EtAc in AcN for 10 minutes, and subsequently for 3 minutes, isocratically at 50% EtAc in AcN with a flow rate of 1 ml per minute.

The analysis was conducted using the HP ChemStation for LC Version A.05.02 and was performed for alpha-, β-, delta-, and epsilon-carotene at a wavelength of 450 nm.

Figure 6:
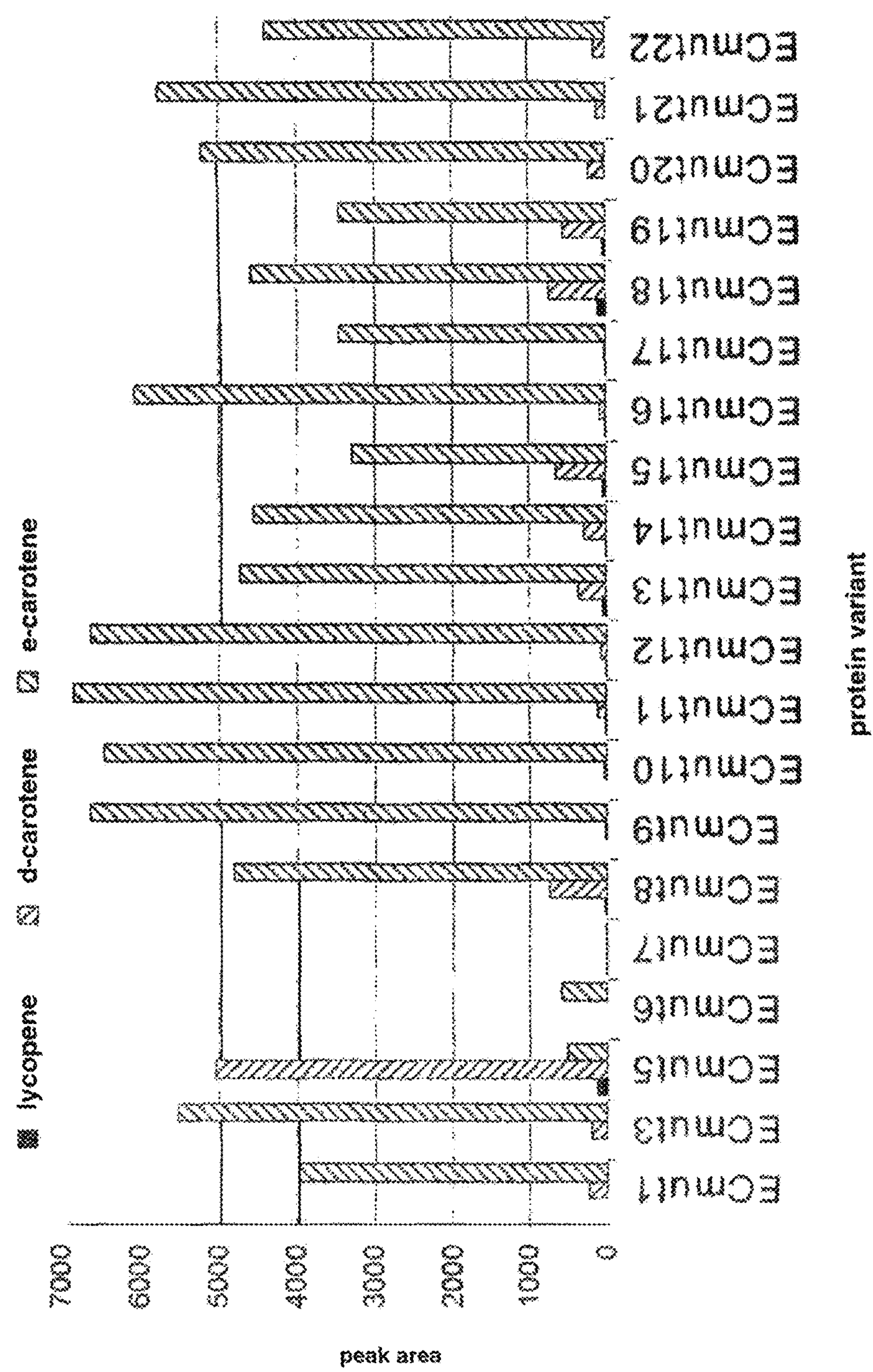
FIG. 6: Quantitative HPLC analysis of the AtECmut product profiles. Measurement of the yields of lycopene, delta-carotene and epsilon-carotene for the differently obtained mutants of the lycopene-epsilon-cyclase (ECmut). The corresponding expression vectors were introduced in *E. coli* TOP10 cells and the resulting strains were analyzed concerning the synthesized carotenoids per HPLC. The cells were cultured for 24 hours at 28° C. in dYT-medium (+chloramphenicol and ampicillin). The generated carotenoids were quantitatively extracted with acetone and transferred into the HPLC solvent. Absolute values of the determined peak areas are indicated for equal cell numbers of the different strains. Almost all strains almost completely transformed lycopene; delta-carotene was not completely transformed by only a few strains. Most strains show an efficient production of epsilon-carotene, the starting material for the transformation to an enantiomerically pure alpha-ionone. The variant ECmut1 corresponds to mutants that were previously described in the literature (Cunningham & Gantt, 2001) und serves as reference. The mutants ECmut 9, 10, 11, 12, 16, 21, 3.2, 3.3, 3.8 und 3.16 are significantly better than the reference in terms of the product amount and product purity.
Figure 6:
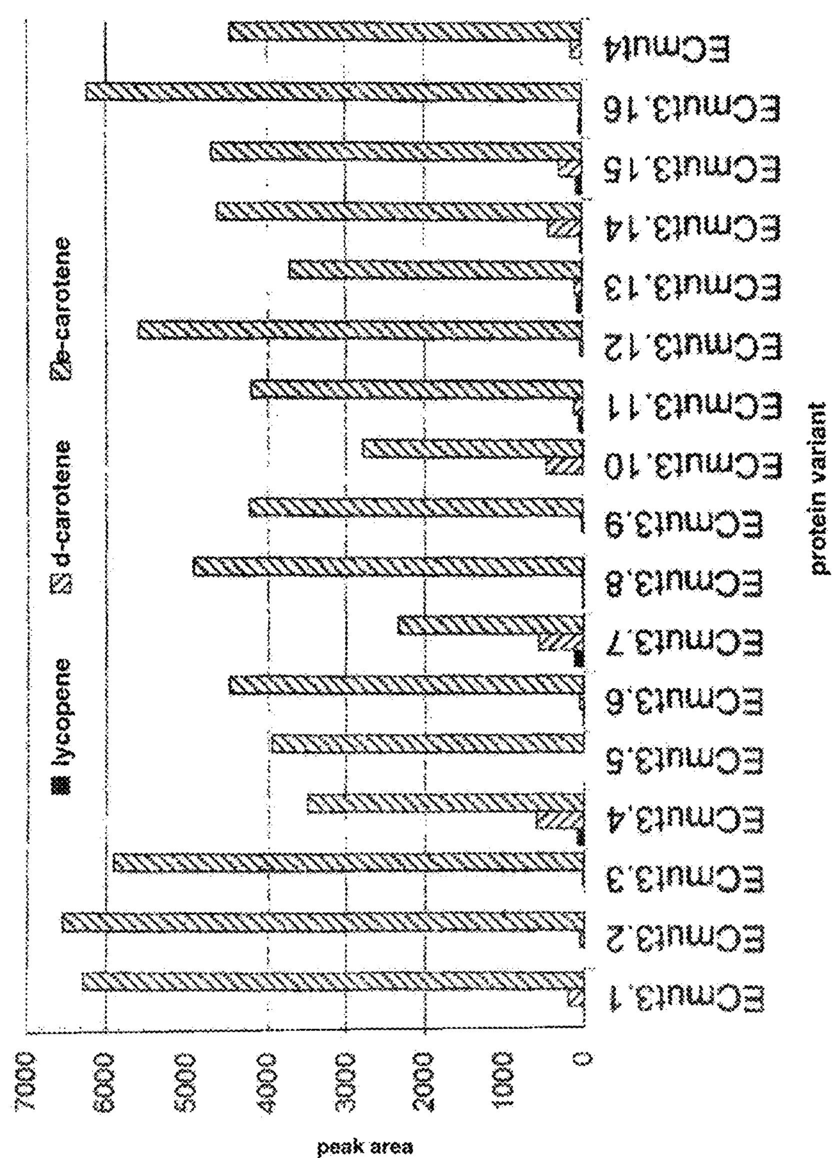

The HPLC analysis indicated that with the exception of ECmut5, all generated mutants essentially completely converted the starting material lycopene and produced epsilon-Carotene as a main product (Table 1, FIGS. 6A and 6B). Variant ECmut1 corresponds to the mutant that is already being described in the literature (AtEC-L448H; Cunningham & Gantt, 2001) and served as reference.

The mutants ECmut9, -10, -11, -12, -16, -21, -3.2, -3.3, -3.5, -3.8, -3.9, -3.12 and -3.16 are significantly better than the reference concerning the product purity and amount of product. The proportion of the epsilon-Carotene synthesized by the EC mutants compared to the total carotenoid content of the cells is 97.7% to 100% (see Table 1), whereas for the reference (ECmut1), a proportion of 94.3% was determined, which is thus slightly above the published reference value (92%; Cunningham et al., 2001).

The best mutants (ECmut9, -10, -3.2, -3.3, -3.5, -3.8, -3.9, -3.12) yielded epsilon-Carotene contents of 99.3%-100%. The ratio of epsilon-Carotene to its precursor delta-Carotene for the indicated mutants lies within 147:1 to 492:1 and is thus 3 to 10 times higher than the best amount ratios published so far, which ranged from 10:1 to 49:1 (see Table 1 and Cunningham et al., 2001, Bai et al. 2009). For ECmut3.5 the delta-Carotene amount was below the detection threshold, so that due to the total conversion, no quotient could be determined here or it is infinitely large.

Surprisingly, the analysis showed that not only the purity of the formed epsilon-Carotene, but also the amount of product depends on the used EC mutant (Table 1, FIGS. 6A and 6B).

TABLE 1

Comparison of the carotenoid yields of known lycopene-epsilon-cyclases (EC) with the mutants according to the present invention (ECmut)

| Enzyme | Mutation | Carotinoid yield (% of the total yield) | | | | | e-Caro/ | e-Caro- | |
|---|---|---|---|---|---|---|---|---|---|
| | | Lyc | a-Caro | g-Caro | d-Caro | e-Caro | d-Caro | yield (%) | Ref. |
| AtEC | — | 1 | | | 98 | 1 | 0.01 | | Cunningham 2001 |
| | — | 2 | 0 | 13.6 | 84.2 | 0.2 | 0.00 | | Bai 2009 |
| | A447S/L448H/Q451L/F452M | 0 | | | 2 | 98 | 49 | | Cunningham 2001 |
| | L448H | 0 | | | 8 | 92 | 11.5 | | Cunningham 2001 |
| | L448R | 0 | | | 8 | 92 | 11.5 | | Cunningham 2001 |
| | L448D | 37 | | | 56 | 8 | 0.14 | | Cunningham 2001 |
| | A447D | 1 | | | 98 | 1 | 0.01 | | Cunningham 2001 |
| LsEC | — | 3 | | | 8 | 90 | 11.25 | | Cunningham 2001 |
| | — | 6.3 | 12 | 4.2 | 7.1 | 70.3 | 9.90 | | Bai 2009 |
| | H457R | 3 | | | 6 | 91 | 15.17 | | Cunningham 2001 |
| | H457D | 22 | | | 18 | 60 | 3.33 | | Cunningham 2001 |
| | H457L | 17 | | | 73 | 10 | 0.14 | | Cunningham 2001 |
| AaEC | | 0 | | | 44 | 56 | 1.27 | | Cunningham 2001 |
| ZmEC | — | 5.5 | 3.4 | 9.3 | 42.6 | 39.2 | 0.92 | | Bai 2009 |
| | L461H | 4 | 9.5 | 5 | 5.4 | 76.1 | 14.09 | | Bai 2009 |
| | S502A | 2.9 | 0.2 | 11.8 | 80.6 | 4.5 | 0.06 | | Bai 2009 |
| ECmut1 (Re) | L448H | 0 | | | 5.7 | 94.3 | 16.48 | 100 | |
| ECmut9 | L448S | 0 | | | 0.4 | 99.6 | 221.7 | 167 | |
| ECmut10 | A447S/L448T | 0 | | | 0.6 | 99.4 | 170.1 | 162 | |
| ECmut3.12 | L448T/A489S | 0 | | | 0.7 | 99.3 | 147.1 | 140 | |
| ECmut3.2 | A447C/L448C/A489S | 0 | | | 0.7 | 99.3 | 133.8 | 164 | |
| ECmut3.3 | A447E/L448A/A489S | 0 | | | 0.2 | 99.8 | 492.5 | 148 | |
| ECmut3.5 | A447M/L448A/A489S | 0 | | | 0 | 100 | nb | 99 | |
| ECmut3.8 | A447H/L448S/A489S | 0.2 | | | 0.2 | 99.6 | 410.7 | 124 | |
| ECmut3.9 | A447E/L448G/A489S | 0 | | | 0.5 | 99.5 | 184.3 | 106 | |
| ECmut3.16 | A447G/L448G/A489S | 0.8 | | | 0.6 | 98.6 | 152.2 | 156 | |

The first two columns name the enzyme or the enzyme mutant and the corresponding amino acid exchanges. For better comparison with the literature data, the mutations of the ECmut enzymes according to the present invention are indicated according to the full length enzymes. Positions 447, 448 and 489 of the wild type *A. thaliana* enzyme lycopene-epsilon-cyclase (AtEC) correspond to the positions 403, 404 and 445 of the mutants AtEC-del according to the present invention (SEQ ID No. 19) (see FIG. 5) The described carotenoid yields in percent for Lyc, a-Caro, g-Caro, d-Caro, e-Caro depict the percental proportion of the respective carotenoid compared to the total amount of the mentioned carotenoids. The described e-Carotene yield indicates the ratio expressed in percent between the amount of formed epsilon-Carotene of the reference mutant ECmut1 (L448H) and the respective EC mutant according to the present invention, wherein reference value (ECmut1 (L448H)) was fixed as 100%.

Lyc=lycopene, a-Caro=alpha-Carotene, g-Caro=gamma-Carotene, d-Caro=delta-carotene, e-Caro=epsilon-Carotene;

At=*Arabidopsis thaliana,* Ls=*Latuca sativa,* Zm=*Zea mays,* EC=lycopene-epsilon-cyclase.

Example 7: Method for Obtaining Alpha-Ionone

For the production of alpha-ionone in shaking flask cultures initially the expression plasmids (e.g. pGT1066 coding for ECmut3 and a CCD1 expression plasmid pGT1069 or pGT1070) according to the present invention were introduced together into *E. coli*-TOP10 using standard transformation protocols, which were then cultured under selective conditions (selection with chloramphenicol (25 mg/L) and ampicillin (100 mg/L)) on agar plates with LB Medium (incubation for 24 hours at 28-30° C.). For the production of the substrate epsilon-carotene, liquid medium (dYT+ chloramphenicol (25 mg/L) and ampicillin (100 mg/L)) was inoculated with a single colony from the obtained plates and the culture was cultured for 24 hours and 28-30° C. under shaking (200 rpm). Subsequently the expression of the carotenoid-cleavage-dioxygenase (CCD) and thus the transformation of the formed epsilon-carotene to alpha-ionone was started by addition of the induction medium (dYT+0.5% arabinose+chloramphenicol (25 mg/L) and ampicillin (100 mg/L)). ⅕ of the original volume was added. The culture was then incubated for additional 4hours at 28° C. For extracting the formed alpha-ionone the bacterial cells were separated by centrifugation (10 minutes; 5000 rpm), subsequently lysed and the lysate shaken with diethyl ether.

Example 8: Detection of Alpha-Ionone

Figure 8:
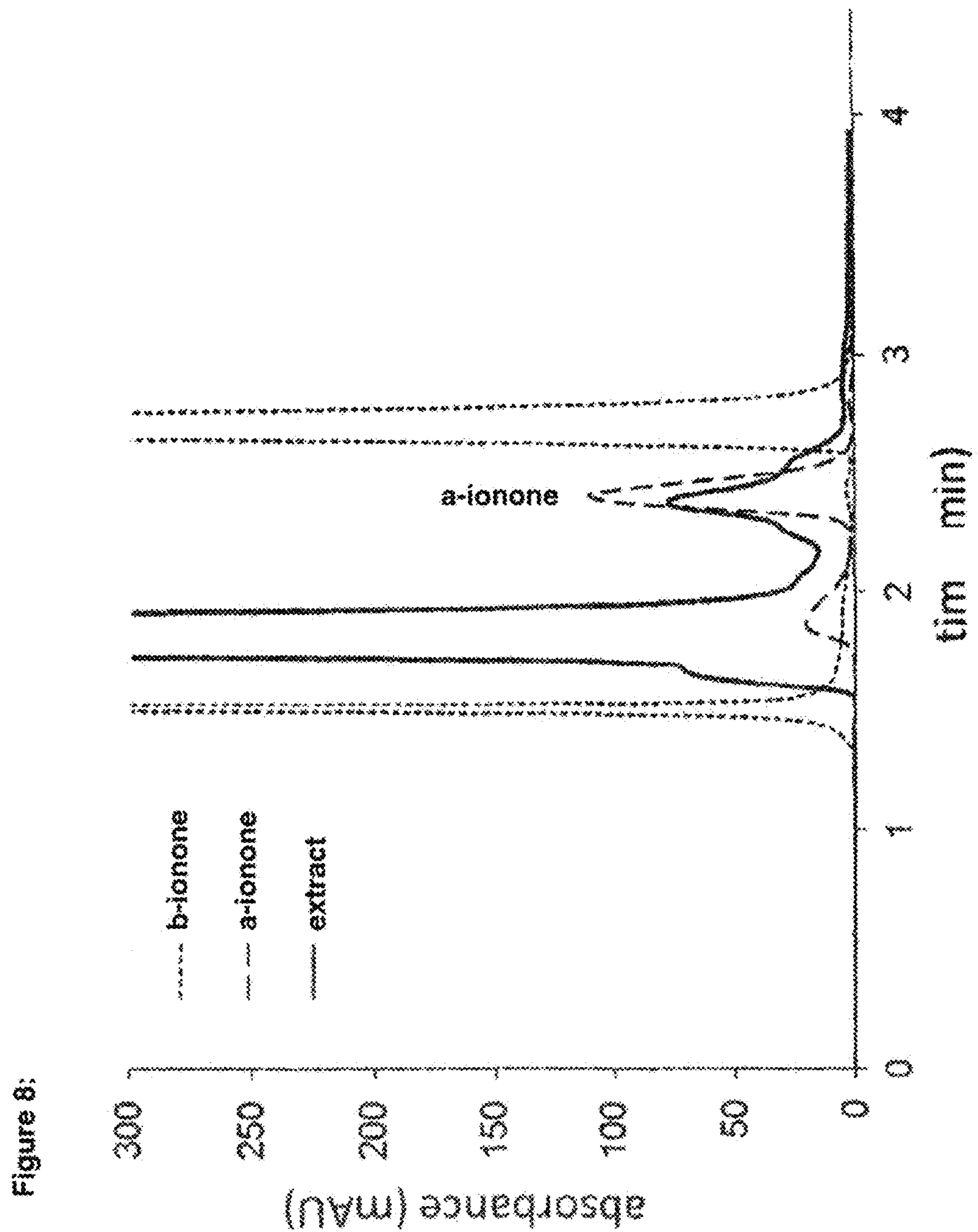
FIG. 8: Detection of alpha-ionone production. An HPLC chromatogram and a LC-MS-spectrum are depicted. A multitransgenic *E. coli* strain with the enzymes crtE, IPI, crtB, crtI, ECmut3, AtCCD1 was incubated for 24 hours at 28° C. in LB medium while shaking same and the expression of the AtCCD1 enzyme was induced by the addition of arabinose for 4 hours (final concentration: 0.1% (w/v)). The resulting epsilon-carotene-degradation products were subsequent to lyses of the cells extracted with diethyl ether and then analyzed by HPLC. The chromatograms for the added ionone reference substances and the obtained diethyl ether extract are depicted (dotted line: 11- ionone reference, broken line: alpha-ionone-reference; continuous line: chromatogram of the extract). In the same way, generated diethyl ether extracts were measured mass spectrometrically by LC-MS. The mass corresponding to alpha-ionone of 192.9 was unambiguously detected.
Figure 8:
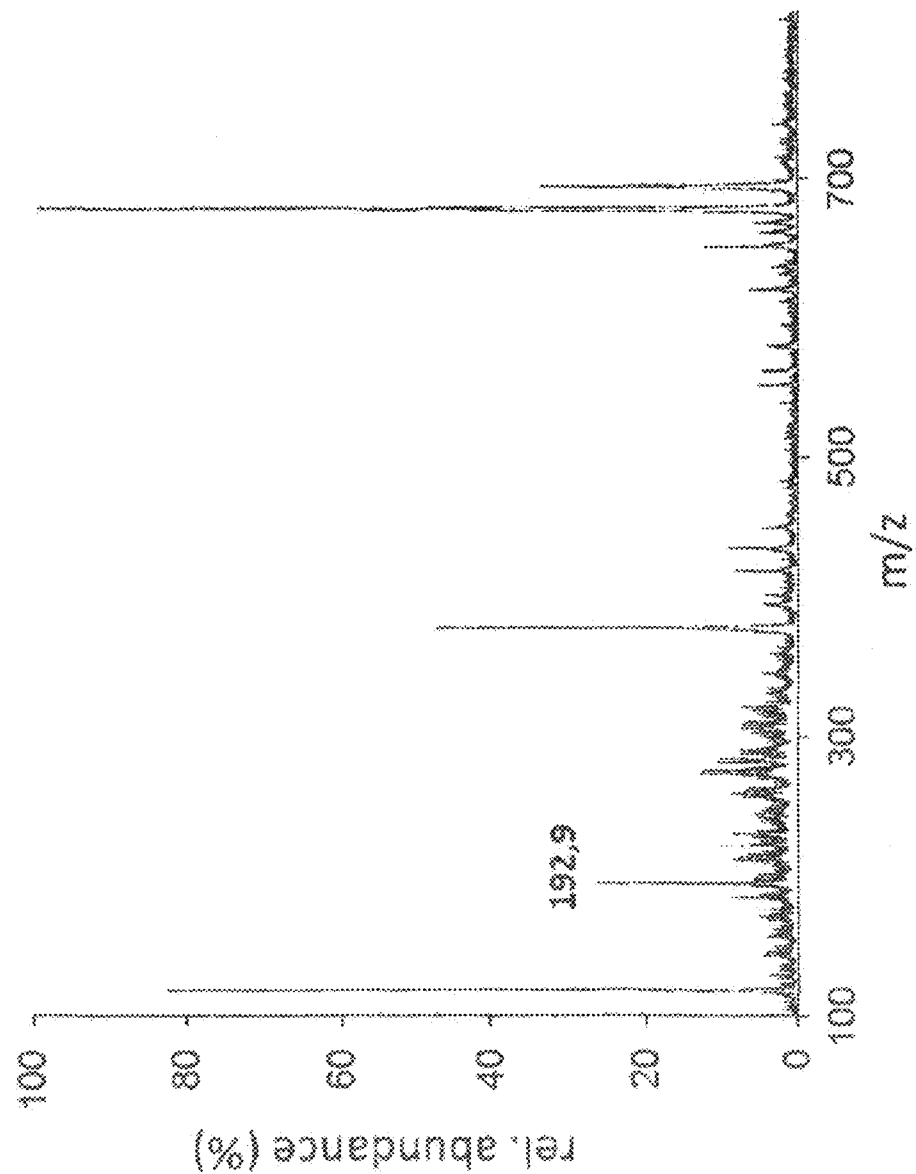

The produced epsilon-carotene was quantitatively transformed, which was already macroscopically visible based on the discoloration of the cells. For extracting the formed alpha-ionone the bacterial cells were separated by centrifugation (10 minutes; 5000 g), subsequently lysed and the lysate shaken with diethyl ether, as already described in Example 7. The resulting preparations were analyzed did HPLC and LC-MS (FIG. 8). The HPLC analysis of the bacterial carotenoid extracts was done with a HP Series II 1090 Liquid Chromatograph (Agilent Technologies, Boblingen) with a ternary pump system and a diode-array-detector. For separation a Zorbax SB-C18 separation column (3.5 μm, 4.6×150 mm, Agilent Technologies, Boblingen) at a column temperature of 40° C. The separation of the carotenoids was done initially at 2 minutes, isocratic with 20% ethyl acetate (EtAc) in acetonitrile (AcN), subsequently via a gradient of 20% EtAc in AcN to 50% EtAc in AcN for 10 minutes and subsequently for 3 minutes isocratic at 50% EtAc in can with a flow rate of 1 ml per minute. The analysis was conducted with a HP ChemStation for LC version A.05.02 and was done for alpha-, beta-, delta-and epsilon-carotene at a wavelength of 450 nm and for alpha-and beta-ionone at 280 nm.

Example 9: Analysis of the Enantiomer Distribution

The analysis of the fermentatively produced alpha-ionone with regard to the enantiomer distribution/purity was done by GC-mass spectrometry. For preparation, the diethyl ether extracts (see Example 8) were evaporated to dryness, to remove the diethyl ether, and the obtained dry substance was dissolved in acetonitrile. This sample was then used for GC-mass spectrometry without dilution.

Determination of the Enantiomer Distribution:

To this end, an enantiomer selective gas chromatography/mass spectrometry (GC/MS) was conducted as follows: the mass spectra were generated at a gas chromatograph Varian 3800 (Varian, Darmstadt), which was coupled to a mass spectrometer Saturn 2000 (Varian, Darmstadt). For determining the enantiomer distribution of alpha-ionone mass spectra were recorded in Cl-mode with an ionization energy of 70 eV. The following capillary column was used: BGB174, 30 m x 0.25 mm inner diameter (ID), 0.25 μm film thickness, Phenomenex. The following conditions for the GC/MS were used:

- Sample injection: on column, 40° C., 1 μl injection volume
- Carrier gas: helium, flow rate 35 cm/s
- Mass spectrometer: ion trap Saturn 2000-2000 R, Varian, Darmstadt
- Temperature program: temperature gradient 70-220° C. with 0 minutes at 70° C., 4° C. per minute increase, 5 minutes at 220° C.

Determination of the Beta-Ionone Content:

To this end, semi quantitative gas chromatography/mass spectrometry (GC/MS) was performed with a gas chromatograph Varian 3800 (Varian, Darmstadt) that was coupled to a mass spectrometer Saturn 2000 (Varian, Darmstadt). For the semi quantitative determination of beta-ionone mass specter there recorded in El-mode with an ionization energy of 70 eV. The following capillary column was used: FFAP, 30 m x 0.25 mm inner diameter (ID), 0.25 μm film thickness, Phenomenex.

The conditions for the GC/MS were as follows:

- Sample injection: on column, 40° C., 1 μl injection volume
- Carrier gas: helium, flow rate 35 cm/s
- Mass spectrometer: ion trap Saturn 2000-2000 R, Varian, Darmstadt
- temperature program: temperature gradient 40-240° C. with 1 minute at 40° C., 60° C. per minute increase, 5 minutes at 240° C.

Results:

For the alpha-ionone-sample and enantiomer distribution of 100% [R] 0% [S] was determined. The sample contains enantiomer pure (R)-alpha-ionone.

The content of beta-ionone was below the detection threshold (<2 μg/l). The sample contains pure alpha-ionone.

Example 10: Promoters

With the selection of the promoters the synthesis of the intermediates (lycopene, epsilon-carotene) and the end product (alpha-ionone) can be fine-tuned. To this end, inducible or constitutive promoters can be used. Depending on the construction of the microorganism with many, free plasmids or the integration of one expression cassette, respectively, in the microbial genome different promoter strengths are desirable.

Promoters of the Prior Art:

- pTet, tetracycline promoter from *E. coli* plasmid pBR332( ), constitutive
- pLac: Lac promoter, promoter region of the genomic *E. coli* Lac-operon
- pBAD: arabinose inducible promoter; promoter region of the genomic *E. coli* arabinose-operon
- pXyl promoter: xylose inducible promoter; regulatory sequences from the *E. coli* xylose-operon consisting of the bidirectional promoter region (cis-regulatory sequences), which control the polycistronic operons xylA/xylB and xylF/xylG/xylH/xylR, wherein its activity is regulated through the xylR gene product of the xylFGHR operon.

Inducible promoters according to the present invention:

- pTet-m1: 12 bp-deletion in promoter before Lyc operon, promoter activity is increased by the factor 2.8
- pXyl0: synthetic xylose inducible promoter. Generated through direct coupling of the xylR gene with the cis-regulatory sequences (by way of deletion of the xylF-, xylG- and xylH-gene sequences). Base construct. Inducibility: 25×; relative expression strength (max): 2.5% of the reference promoter (pLac)

pXyl1: combination of pXyl0 with an optimized ribosome binding site (Shine-Dalgarno-sequence) for the efficient translation of target genes. Promoter3-4× more active than pXyl0 (max 10% of the pLac activity)

pXyl2: based on pXyl1 the sequence of the −10-region (binding site for the RNA polymerase) of the downstream oriented promoter element was modified. Promoter 3-4× more active than pXyl0 (max 36% of the pLac activity)

Constitutive Promoters According to the Present Invention:

The used promoters were derived from a collection of constitutive expressing promoters, which were generated via a PCR-based approach. A promoter free RFP reporter construct (pGJ2720del) served in this context as template. With an inverted PCR approach the entire plasmid sequence is amplified with a proofreading polymerase, wherein the DNA fragment is extended by the additional sequences contained in the oligonucleotide primers. Primer 1 (−10-primer) binds to the template DNA in the area of the ribosome binding site before the reporter gene. Its extension consists of 9 random bases followed by the sequence TATAAT and 6 additional random bases. Primer 2 binds (in reverse orientation) directly before the binding site of primer 1. The primer 2 extension (−35-primer) consists of 9 random bases followed by the sequence TGTCAA and 6 further random bases. Primer 1 and 2 have annealing temperatures of 60° C. The primers were phosphorylated with the enzyme polynucleotide kinase (New England Biolabs) according to the manufacturer's instructions and then used for the amplification of the template with the following PCR program: 2 minutes at 98° C., followed by 30 cycles with 45 seconds at 98° C., 30 seconds at 60° C. and 2 minutes at 72° C. The resulting PCR fragment was separated electrophoretically on an agarose gel and the DNA band was isolated from the gel (PCR and gel extraction kit, Machery & Nagel). Using the enzyme T4-DNA-ligase and autoligation of the isolated DNA fragments was performed. The ligation products were transformed into *E. coli* XL1 cells using standard transformation methods and recombinant cells were cultured on selective media. The selection of the resulting functional promoters was done macroscopically based on the RFP reporter gene expression (red coloration) and in comparison to a corresponding microorganism, which expresses the RFP reporter gene under the control of a maximally induced pLac promoter. Loans with different expression levels were selected, the plasmid DNA isolated and the respectively obtained promoter sequence identified by DNA sequencing. The denomination was done according to the scheme aPxx according to the clone selection. The promoter number does not correlate with the expression strength.

aP12: activity: 35% of the pLac promoter (induced)

aP15: activity: 39% of the pLac promoter (induced)

pP32: activity: 51% of the pLac promoter (induced)

aP47.2: activity: 180% of the pLac promoter (induced)

Example 11: Carotenoid Yield

The carotenoid-producing *E. coli* strain is cultured in liquid dYT medium for 18 to 48 hours at 28° C. The cell density of the resulting culture (=OD600) is determined by measuring the absorption at 600 nm in a photometer. If necessary the culture is appropriately diluted (usually 1:10) with dYT medium to give extinction values in the range of 0.1 to 0.8. Based on the results the cultures are adjusted to OD600/ml=4 (dilution with fresh medium). The cells from 1 mL of these cultures are pelleted by centrifugation (1 minute, 13,000 rpm) and the supernatant is transferred. If the pellet still contains carotenoids (coloration still visible) extraction is repeated and the supernatants of the extractions are combined. The carotenoid concentrations of the extracts are determined photometrically (in g/L) by recording absorption spectra (against acetone as reference) and by converting the measured extinctions at 474 nm (lycopene) or 442 nm (e-carotene) based on the specific extinction coefficients (lycopene: 3450 (L*g-1*cm-1); e-carotene: 2900 (L*g-1*cm-1)). The dry weight of the extracted cell mass is calculated with the following empirically determined formula from the measured cell densities: TGw (g/L)=0.35×OD600. For assessing the carotenoid synthesis performance the carotenoid amount per biomass (mg carotenoid/g TGw) is determined.

TABLE 2

| Plasmid | Change | Rel. yield* Carotenoid |
|---|---|---|
| pAC-BETAipi-d-crtY | — | 1.0x |
| pGT1036** | 1. Deletion bases 984-1394 (formation new crtE-Shine-Dalgarno-Sequenz)<br>2. Deletion bases 3432-4198<br>3. Insertion of sequence GGAGGTACAAC at this position and modification 3418-3432 (formation of new crtl-Shine-Dalgarno)<br>4. Deletion bases 6605-7242<br>5. Insertion terminator sequence | 4.2x |
| pGT1066 | Integration pLac:ECmutX.x cassette | 4.2x |
| pGT1182 | =pGT1066 with ECmut3.3 | 4.2x |
| pGT1464*** | Replacement of bases 5183-6146 with aP12-sequence (−>exchange pLac-promoter before ECmut3.3 for PHY-promoter aP12) | 8.0x |
| pGT1484*** | Replacement der Basen 96-1015 durch idsA- Sequenz (−>exchange crtE for idsA) | 10.0x |
| pGT1518**** | Deletion of bases 123-140 (17 bp) in pTet-promoter (−>pTet-m1 (activity 2.8x higher!)) | 11.8x |
| pGT1543**** | Deletion of bases 8669-141 and insertion of aP30-promoters | 12.5x |

*Relative to equal biomass amounts
**Position information relate to pAC-BETAipi-d-crtY
***Position information relate to pGT1182
****Position information relate to pGT1484

TABLE 3

| Plasmid Combinations | Relative alpha-lonone-Yield |
|---|---|
| pGT1182/pGT1454 | 1x |
| pGT1464/pGT1454 | 1.6x |
| pGT1484/pGT1454 | 1.8x |
| pGT1518/pGT1454 | 2.4x |
| pGT1518/pGT1584 | 3.0x |
| pGT1575/pGT1534 | 4.8x |

BIBLIOGRAPHY

Bai L, Kim E-H, DellaPenna D, Brutnell T P (2009) Novel lycopene epsilon cyclase activities in maize revealed through perturbation of carotenoid biosynthesis. The Plant Journal 59: 588-599.

Baldermann S, Kato M, Kurosawa M, Kurobayashi Y, Fujita A, Fleischmann P, Watanabe N (2010) Functional characterization of a carotenoid cleavage dioxygenase 1 and its relation to the carotenoid accumulation and volatile emission during the floral development of *Osmanthus fragrans* Lour. Journal of Experimental Botany 61: 2967-2977.

Bovolenta M, Castronovo F, VadalàA, Zanoni G, Vidari G (2004) A Simple and Efficient Highly Enantioselective Synthesis of α-lonone and α-Damascone. The Journal of Organic Chemistry 69: 8959-8962.

Cunningham F X, Gantt E (2001) One ring or two? Determination of ring number in carotenoids by lycopene ?-cyclases. Proceedings of the National Academy of Sciences 98: 2905-2910.

Cunningham F X, Gantt E (2007) A portfolio of plasmids for identification and analysis of carotenoid pathway enzymes: Adonis aestivalis as a case study. Photosynthesis Research 92: 245-259.

Cunningham F X, Pogson B, Sun Z, McDonald K A, DellaPenna D, Gantt E (1996) Functional analysis of the beta and epsilon lycopene cyclase enzymes of *Arabidopsis* reveals a mechanism for control of cyclic carotenoid formation. The Plant Cell Online 8: 1613-1626.

Cunningham F X, Sun Z, Chamovitz D, Hirschberg J, Gantt E (1994) Molecular structure and enzymatic function of lycopene cyclase from the cyanobacterium *Synechococcus* sp strain PCC7942. The Plant Cell Online 6: 1107-1121.

Jach G, Pesch M, Richter K., Frings S and Uhrig J (2006) An improved mRFP1 adds red to bimolecular fluorescence complementation. Nature Methods 3 No8: 597-600

Misawa N, Nakagawa M, Kobayashi K, Yamano S, Izawa Y, Nakamura K, Harashima K (1990) Elucidation of the *Erwinia uredovora* carotenoid biosynthetic pathway by functional analysis of gene products expressed in *Escherichia coli.* Journal of Bacteriology 172: 6704-6712.

Perry K L, Simonitch T A, Harrison-Lavoie K J, Liu S T (1986) Cloning and regulation of *Erwinia herbicola* pigment genes. Journal of Bacteriology 168: 607-612.

Sambrook J, Fritsch E F, Maniatis T. in: Molecular Cloning, A Laboratory Manual, 1989 (Nolan C, Ed.), Cold Spring Harbor Laboratory Press, Cold Spring Harbor, N.Y.

Soorukram D, Knochel P (2004) Enantioselective Synthesis of adonone Derivatives Using an Anti SN2' Substitution of Functionalized Zinc Organometallics. Organic Letters 6: 2409-2411.

Vogel J T, Tan B-C, McCarty D R, Klee H J (2008) The Carotenoid Cleavage Dioxygenase 1 Enzyme Has Broad Substrate Specificity, Cleaving Multiple Carotenoids at Two Different Bond Positions. Journal of Biological Chemistry 283: 11364-11373.

Yahyaa M, Bar E, Dubey N K, Meir A, Davidovich-Rikanati R, Hirschberg J, Aly R, Tholl D, Simon P W, Tadmor Y, Lewinsohn E, Ibdah M (2013) Formation of Norisoprenoid Flavor Compounds in Carrot (*Daucus carota* L.) Roots: Characterization of a Cyclic-Specific Carotenoid Cleavage Dioxygenase 1 Gene. Journal of Agricultural and Food Chemistry 61: 12244-12252.

Zhang W, Hu X, Wang L, Wang X (2014) Reconstruction of the Carotenoid Biosynthetic Pathway of *Cronobacter sakazakii* BAA894 in *Escherichia coli.* PLoS ONE 9: e86739.

The invention claimed is:

1. A method of producing enantiomerically pure alpha-ionone comprising culturing an *Escherichia coli* that produces isopentenyldiphosphate (IPP) and a corresponding isomer dimethyl-allyl-diphosphate (DMAPP) as starting materials for the production of enantiomerically pure alpha-ionone, and wherein the *Escherichia coli* further comprises one or more expression cassettes having a sequence according to one of SEQ ID NO. 43 or 44 that encode the following enzymes:

a. geranylgeranyl-diphosphate-synthase idsA, b. isopentenyl-diphosphate-isomerase (ipi), c. phytoene-desaturase/dehydrogenase (crtl), d. phytoene synthase (crtB), e. lycopene-epsilon-cyclase (EC) and f. carotenoid-cleavage-dioxygenase (CCD1), wherein the lycopene-epsilon-cyclase (EC) comprises substitutions A403E/L404A/A445S (ECmut3.3) relative to a sequence according to SEQ ID NO: 19, and the carotenoid-cleavage-dioxygenase (CCD1) comprises a carotenoid-cleavage-dioxygenase 1 of *A. thaliana* (AtCCD1) or a carotenoid-cleavage-dioxygenase 1 of *Osmanthus fragrans* (OfCCD1).

2. The method according to claim 1, wherein the enzymes are encoded on one or multiple plasmids.

3. The method according to claim 2, wherein the one or the multiple plasmids are present in the *Escherichia coli* as individual structures or integrated into the genome of the *Escherichia coli*.

4. The method according to claim 1, wherein the encoded enzymes are co-expressed.

* * * * *

SEQUENCE LISTING

```
<160> NUMBER OF SEQ ID NOS: 47

<210> SEQ ID NO 1
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1..8
<223> OTHER INFORMATION: /note="n is a, c, g, or t"

<400> SEQUENCE: 1

nnnnnnnnaa cgggattttt tgctgaaagg aggaactata tcc                        43


<210> SEQ ID NO 2
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1..10
<223> OTHER INFORMATION: /note="n is a, c, g, or t"

<400> SEQUENCE: 2

nnnnnnnnnn aacgggcttt gttagcagcc gg                                    32


<210> SEQ ID NO 3
<211> LENGTH: 24
<212> TYPE: DNA
<213> ORGANISM: Artificial Sequence
<220> FEATURE:
<223> OTHER INFORMATION: Primer
```

<400> SEQUENCE: 3
gtcttgcaca catagttcaa ttcg 24

<210> SEQ ID NO 4
<211> LENGTH: 37
<212> TYPE: DNA
<213> ORGANISM: Artificial Sequence
<220> FEATURE:
<223> OTHER INFORMATION: Primer

<400> SEQUENCE: 4
ctatgtgtgc aagaccaaag agaaagaatg ctctctg 37

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
ctcttttctt tatacatgtt cgtcatttca cc 32

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
gtataaagaa aagagaacga gatctcctg 29

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gtctttcaca catagttcaa ttcgataccg 30

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
ctatgtgtga aagaccaaag agaaagaatg ctc 33

<210> SEQ ID NO 9
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22..23
<223> OTHER INFORMATION: /note="n is a, c, g, or t"
<220> FEATURE:
<221> NAME/KEY: misc_feature
<222> LOCATION: 25..26
<223> OTHER INFORMATION: /note="n is a, c, g, or t"

<400> SEQUENCE: 9
gcattctttc tctttggtct tnnknnkata gttcaattcg ataccgaagg c 51

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ccaaagagaa agaatgctct ctg 23

<210> SEQ ID NO 11
<211> LENGTH: 6667
<212> TYPE: DNA
<213> ORGANISM: Artificial Sequence
<220> FEATURE:
<223> OTHER INFORMATION: Nucleotide Sequence of pGT1036

<400> SEQUENCE: 11
gcgctagcgg agtgtatact ggcttactat gttggcactg atgagggtgt cagtgaagtg 60
cttcatgtgg caggagaaaa aaggctgcac cggtgcgtca gcagaatatg tgatacagga 120
tatattccgc ttcctcgctc actgactcgc tacgctcggt cgttcgactg cggcgagcgg 180
aaatggctta cgaacggggc ggagatttcc tggaagatgc caggaagata cttaacaggg 240
aagtgagagg gccgcggcaa agccgttttt ccataggctc cgcccccctg acaagcatca 300
cgaaatctga cgctcaaatc agtggtggcg aaacccgaca ggactataaa gataccaggc 360 gtttcccccct ggcggctccc tcgtgcgctc tcctgttcct gcctttcggt ttaccggtgt 420
cattccgctg ttatggccgc gtttgtctca ttccacgcct gacactcagt tccgggtagg 480
cagttcgctc caagctggac tgtatgcacg aacccccgt tcagtccgac cgctgcgcct 540
tatccggtaa ctatcgtctt gagtccaacc cggaaagaca tgcaaaagca ccactggcag 600
cagccactgg taattgattt agaggagtta gtcttgaagt catgcgccgg ttaaggctaa 660
actgaaagga caagttttgg tgactgcgct cctccaagcc agttacctcg gttcaaagag 720
ttggtagctc agagaacctt cgaaaaaccg ccctgcaagg cggttttttc gttttcagag 780
caagagatta cgcgcagacc aaaacgatct caagaagatc atcttattaa tcagataaaa 840
tatttctaga tttcagtgca atttatctct tcaaatgtag cacctgaagt cagccccata 900
cgatataagt tgtaattctc atgtttgaca gcttatcatc gataagcttt aatgcggtag 960
tttatcacag ttaaattgct aacgcagtca ggaaccttgc aatggtgagt ggcagtaaag 1020
cgggcgtttc gcctcatcgc gaaatagaag taatgagaca atccattgac gatcacctgg 1080
ctggcctgtt acctgaaacc gacagccagg atatcgtcag ccttgcgatg cgtgaaggcg 1140
tcatggcacc cggtaaacgg atccgtccgc tgctgatgct gctggccgcc cgcgacctcc 1200
gctaccaggg cagtatgcct acgctgctcg atctcgcctg cgccgttgaa ctgacccata 1260
ccgcgtcgct gatgctcgac gacatgccct gcatggacaa cgccgagctg cgccgcggtc 1320
agcccactac ccacaaaaaa tttggtgaga gcgtggcgat ccttgcctcc gttgggctgc 1380
tctctaaagc ctttggtctg atcgccgcca ccggcgatct gccgggggag aggcgtgccc 1440
aggcggtcaa cgagctctct accgccgtgg gcgtgcaggg cctggtactg gggcagtttc 1500
gcgatcttaa cgatgccgcc ctcgaccgta cccctgacgc tatcctcagc accaaccacc 1560

```
tcaagaccgg cattctgttc agcgcgatgc tgcagatcgt cgccattgct tccgcctcgt   1620
cgccgagcac gcgagagacg ctgcacgcct tcgccctcga cttcggccag gcgtttcaac   1680
tgctggacga tctgcgtgac gatcacccgg aaaccggtaa agatcgcaat aaggacgcgg   1740
gaaaatcgac gctggtcaac cggctgggcg cagacgcggc ccggcaaaag ctgcgcgagc   1800
atattgattc cgccgacaaa cacctcactt ttgcctgtcc gcagggcggc gccatccgac   1860
agtttatgca tctgtggttt ggccatcacc ttgccgactg gtcaccggtc atgaaaatcg   1920
cctgataccg cccttttggg ttcaagcagt acataacgat ggaaccacat tacaggagta   1980
gtgatgaatg aaggacgagc gccttgttca gcgtaagaac gatcatctgg atatcgttct   2040
cgacccccgt cgcgccgtaa ctcaggctag cgcaggtttt gagcgctggc gctttaccca   2100
ctgcgccctg ccagagctga attttagcga catcacgctg gaaaccacct tcctgaatcg   2160
gcagctacag gctccgctgc tgatcagctc catgaccggc ggcgttgagc gctcgcgcca   2220
tatcaaccgc cacctcgccg aggcggcgca ggtgctaaaa attgcgatgg gggtgggctc   2280
ccagcgcgtc gccattgaga gcgacgcggg cttagggctg gataaaaccc tgcggcagct   2340
ggctccggac gtgccgctgc tggcgaacct cggcgcggcg cagctgaccg gcagaaaagg   2400
tattgattac gcccgacggg ccgtggagat gatcgaggcg gatgcgctga ttgtgcacct   2460
aaacccgctg caggaggcgc tacagcccgg cggcgatcgc gactggcgcg gacggctggc   2520
ggctattgaa actctggtcc gcgagctgcc cgttccgctg gtggtgaaag aggtgggagc   2580
cggtatctcc cgaaccgtgg ccgggcagct gatcgatgcc ggcgttaccg tgattgacgt   2640
cgcgggcgcg ggcggcacca gctgggccgc cgttgaaggc gagcgggcgg ccaccgagca   2700
gcagcgcagc gtggccaacg tctttgccga ctgggggatc ccaccgctg aggcgctggt   2760
tgacattgcc gaggcctggc cgcagatgcc ccttattgcc tcgggcggga ttaaaaacgg   2820
cgtcgacgcg gcgaaagcgc tgcggctcgg cgcgtgcatg gtagggcagg ccgccgccgt   2880
gctcggcagc gcaggcgtct ccacggagaa ggtgatcgat cacttcaacg tgattattga   2940
gcagctgcgg gtggcctgct tctgcaccgg cagccgcagc ctgagcgatc taaagcaggc   3000
tgatatccgc tatgttcgtg atacgccata aggaggtaca accatgaaga aaaccgttgt   3060
gattggcgca ggctttggtg gcctggcgct ggcgattcgc ctgcaggcgg cagggatccc   3120
aaccgtactg ctggagcagc gggacaagcc cggcggtcgg gcctacgtct ggcatgacca   3180
gggctttacc tttgacgccg ggccgacggt gatcaccgat cctaccgcgc ttgaggcgct   3240
gttcaccctg gccggcaggc gcatggagga ttacgtcagg ctgctgccgg taaaaccctt   3300
ctaccgactc tgctgggagt ccgggaagac cctcgactat gctaacgaca gcgccgagct   3360
tgaggcgcag attacccagt tcaacccccg cgacgtcgag ggctaccggc gctttctggc   3420
ttactcccag gcggtattcc aggagggata tttgcgcctc ggcagcgtgc cgttcctctc   3480
ttttcgcgac atgctgcgcg ccgggccgca gctgcttaag ctccaggcgt ggcagagcgt   3540
ctaccagtcg gtttcgcgct ttattgagga tgagcatctg cggcaggcct tctcgttcca   3600
ctccctgctg gtaggcggca acccccttcac cacctcgtcc atctacaccc tgatccacgc   3660
ccttgagcgg gagtgggggg tctggttccc tgagggcggc accggggcgc tggtgaacgg   3720
catggtgaag ctgtttaccg atctgggcgg ggagatcgaa ctcaacgccc gggtcgaaga   3780
gctggtggtg gccgataacc gcgtaagcca ggtccggctg gcggatggtc ggatctttga   3840
caccgacgcc gtagcctcga acgctgacgt ggtgaacacc tataaaaagc tgctcggcca   3900
ccatccggtg gggcagaagc gggcggcagc gctggagcgc aagagcatga gcaactcgct   3960
```

```
gtttgtgctc tacttcggcc tgaaccagcc tcattcccag ctggcgcacc ataccatctg   4020
ttttggtccc cgctaccggg agctgatcga cgagatcttt accggcagcg cgctggcgga   4080
tgacttctcg ctctacctgc actcgccctg cgtgaccgat ccctcgctcg cgcctcccgg   4140
ctgcgccagc ttctacgtgc tggccccggt gccgcatctt ggcaacgcgc cgctggactg   4200
ggcgcaggag gggccgaagc tgcgcgaccg catctttgac taccttgaag agcgctatat   4260
gcccggcctg cgtagccagc tggtgaccca gcggatcttt accccggcag acttccacga   4320
cacgctggat gcgcatctgg gatcggcctt ctccatcgag ccgctgctga cccaaagcgc   4380
ctggttccgc ccgcacaacc gcgacagcga cattgccaac ctctacctgg tgggcgcagg   4440
tactcaccct ggggcgggca ttcctggcgt agtggcctcg gcgaaagcca ccgccagcct   4500
gatgattgag gatctgcaat gagccaaccg ccgctgcttg accacgccac gcagaccatg   4560
gccaacggct cgaaaagttt tgccaccgct gcgaagctgt tcgacccggc cacccgccgt   4620
agcgtgctga tgctctacac ctggtgccgc cactgcgatg acgtcattga cgaccagacc   4680
cacggcttcg ccagcgaggc cgcggcggag gaggaggcca cccagcgcct ggcccggctg   4740
cgcacgctga ccctggcggc gtttgaaggg gccgagatgc aggatccggc cttcgctgcc   4800
tttcaggagg tggcgctgac ccacggtatt acgccccgca tggcgctcga tcacctcgac   4860
ggctttgcga tggacgtggc tcagacccgc tatgtcacct ttgaggatac gctgcgctac   4920
tgctatcacg tggcgggcgt ggtgggtctg atgatggcca gggtgatggg cgtgcgggat   4980
gagcgggtgc tggatcgcgc ctgcgatctg gggctggcct tccagctgac gaatatcgcc   5040
cgggatatta ttgacgatgc ggctattgac cgctgctatc tgcccgccga gtggctgcag   5100
gatgccgggc tgaccccgga gaactatgcc gcgcgggaga atcgggccgc gctggcgcgg   5160
gtggcggagc ggcttattga tgccgcagag ccgtactaca tctcctccca ggccgggcta   5220
cacgatctgc cgccgcgctg cgcctgggcg atcgccaccg cccgcagcgt ctaccgggag   5280
atcggtatta aggtaaaagc ggcgggaggc agcgcctggg atcgccgcca gcacaccagc   5340
aaaggtgaaa aaattgccat gctgatggcg gcaccggggc aggttattcg ggcgaagacg   5400
acgagggtga cgccgcgtcc ggccggtctt tggcagcgtc ccgtttagcc cgttctgttt   5460
aagaacggga tttttttgcgc ttgtttcggc gtgggtatgg tggcaggccc cgtggccggg   5520
ggactgttgg gcgccatctc cttggggtcg aatttgcttt cgaatttctg ccattcatcc   5580
gcttattatc acttattcag gcgtagcacc aggcgtttaa gggcaccaat aactgcctta   5640
aaaaaattac gccccgccct gccactcatc gcagtactgt tgtaattcat taagcattct   5700
gccgacatgg aagccatcac agacggcatg atgaacctga atcgccagcg gcatcagcac   5760
cttgtcgcct tgcgtataat atttgcccat ggtgaaaacg ggggcgaaga agttgtccat   5820
attggccacg tttaaatcaa aactggtgaa actcacccag ggattggctg agacgaaaaa   5880
catattctca ataaaccctt tagggaaata ggccaggttt tcaccgtaac acgccacatc   5940
ttgcgaatat atgtgtagaa actgccggaa atcgtcgtgg tattcactcc agagcgatga   6000
aaacgtttca gtttgctcat ggaaaacggt gtaacaaggg tgaacactat cccatatcac   6060
cagctcaccg tctttcattg ccatacggaa ttccggatga gcattcatca ggcgggcaag   6120
aatgtgaata aaggccggat aaaacttgtg cttatttttc tttacggtct ttaaaaaggc   6180
cgtaatatcc agctgaacgg tctggttata ggtacattga gcaactgact gaaatgcctc   6240
aaaatgttct ttacgatgcc attgggatat atcaacggtg gtatatccag tgattttttt   6300
```

```
ctccatttta gcttccttag ctcctgaaaa tctcgataac tcaaaaaata cgcccggtag   6360

tgatcttatt tcattatggt gaaagttgga acctcttacg tgccgatcaa cgtctcattt   6420

tcgccaaaag ttggcccagg gcttcccggt atcaacaggg acaccaggat ttatttattc   6480

tgcgaagtga tcttccgtca caggtattta ttcggcgcaa agtgcgtcgg gtgatgctgc   6540

caacttactg atttagtgta tgatggtgtt tttgaggtgc tccagtggct tctgtttcta   6600

tcagctgtcc ctcctgttca gctactgacg ggtggtgcg taacggcaaa agcaccgccg    6660

gacatca                                                             6667


<210> SEQ ID NO 12
<211> LENGTH: 307
<212> TYPE: PRT
<213> ORGANISM: Erwinia herbicola
<220> FEATURE:
<223> OTHER INFORMATION: crtE

<400> SEQUENCE: 12

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205

Ser Thr Arg Glu Thr Leu His Ala Phe Ala Leu Asp Phe Gly Gln Ala
    210                 215                 220

Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
                245                 250                 255

Ala Asp Ala Ala Arg Gln Lys Leu Arg Glu His Ile Asp Ser Ala Asp
            260                 265                 270

Lys His Leu Thr Phe Ala Cys Pro Gln Gly Gly Ala Ile Arg Gln Phe
        275                 280                 285

Met His Leu Trp Phe Gly His His Leu Ala Asp Trp Ser Pro Val Met
```

```
    290                 295                 300

Lys Ile Ala
305


<210> SEQ ID NO 13
<211> LENGTH: 347
<212> TYPE: PRT
<213> ORGANISM: Erwinia herbicola
<220> FEATURE:
<223> OTHER INFORMATION: IPI

<400> SEQUENCE: 13

Met Lys Asp Glu Arg Leu Val Gln Arg Lys Asn Asp His Leu Asp Ile
1               5                   10                  15

Val Leu Asp Pro Arg Arg Ala Val Thr Gln Ala Ser Ala Gly Phe Glu
            20                  25                  30

Arg Trp Arg Phe Thr His Cys Ala Leu Pro Glu Leu Asn Phe Ser Asp
        35                  40                  45

Ile Thr Leu Glu Thr Thr Phe Leu Asn Arg Gln Leu Gln Ala Pro Leu
    50                  55                  60

Leu Ile Ser Ser Met Thr Gly Gly Val Glu Arg Ser Arg His Ile Asn
65                  70                  75                  80

Arg His Leu Ala Glu Ala Ala Gln Val Leu Lys Ile Ala Met Gly Val
                85                  90                  95

Gly Ser Gln Arg Val Ala Ile Glu Ser Asp Ala Gly Leu Gly Leu Asp
            100                 105                 110

Lys Thr Leu Arg Gln Leu Ala Pro Asp Val Pro Leu Leu Ala Asn Leu
        115                 120                 125

Gly Ala Ala Gln Leu Thr Gly Arg Lys Gly Ile Asp Tyr Ala Arg Arg
    130                 135                 140

Ala Val Glu Met Ile Glu Ala Asp Ala Leu Ile Val His Leu Asn Pro
145                 150                 155                 160

Leu Gln Glu Ala Leu Gln Pro Gly Gly Asp Arg Asp Trp Arg Gly Arg
                165                 170                 175

Leu Ala Ala Ile Glu Thr Leu Val Arg Glu Leu Pro Val Pro Leu Val
            180                 185                 190

Val Lys Glu Val Gly Ala Gly Ile Ser Arg Thr Val Ala Gly Gln Leu
        195                 200                 205

Ile Asp Ala Gly Val Thr Val Ile Asp Val Ala Gly Ala Gly Gly Thr
    210                 215                 220

Ser Trp Ala Ala Val Glu Gly Glu Arg Ala Ala Thr Glu Gln Gln Arg
225                 230                 235                 240

Ser Val Ala Asn Val Phe Ala Asp Trp Gly Ile Pro Thr Ala Glu Ala
                245                 250                 255

Leu Val Asp Ile Ala Glu Ala Trp Pro Gln Met Pro Leu Ile Ala Ser
            260                 265                 270

Gly Gly Ile Lys Asn Gly Val Asp Ala Ala Lys Ala Leu Arg Leu Gly
        275                 280                 285

Ala Cys Met Val Gly Gln Ala Ala Ala Val Leu Gly Ser Ala Gly Val
    290                 295                 300

Ser Thr Glu Lys Val Ile Asp His Phe Asn Val Ile Ile Glu Gln Leu
305                 310                 315                 320

Arg Val Ala Cys Phe Cys Thr Gly Ser Arg Ser Leu Ser Asp Leu Lys
                325                 330                 335

Gln Ala Asp Ile Arg Tyr Val Arg Asp Thr Pro
```

```
            340                 345


<210> SEQ ID NO 14
<211> LENGTH: 492
<212> TYPE: PRT
<213> ORGANISM: Erwinia herbicola
<220> FEATURE:
<223> OTHER INFORMATION: crtI

<400> SEQUENCE: 14

Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110

Phe Asn Pro Arg Asp Val Glu Gly Tyr Arg Arg Phe Leu Ala Tyr Ser
        115                 120                 125

Gln Ala Val Phe Gln Glu Gly Tyr Leu Arg Leu Gly Ser Val Pro Phe
    130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
            180                 185                 190

Asn Pro Phe Thr Thr Ser Ser Ile Tyr Thr Leu Ile His Ala Leu Glu
        195                 200                 205

Arg Glu Trp Gly Val Trp Phe Pro Glu Gly Gly Thr Gly Ala Leu Val
    210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
        275                 280                 285

Val Gly Gln Lys Arg Ala Ala Ala Leu Glu Arg Lys Ser Met Ser Asn
    290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                325                 330                 335

Glu Ile Phe Thr Gly Ser Ala Leu Ala Asp Asp Phe Ser Leu Tyr Leu
            340                 345                 350

His Ser Pro Cys Val Thr Asp Pro Ser Leu Ala Pro Pro Gly Cys Ala
```

```
        355                 360                 365

Ser Phe Tyr Val Leu Ala Pro Val Pro His Leu Gly Asn Ala Pro Leu
    370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415

Arg Ile Phe Thr Pro Ala Asp Phe His Asp Thr Leu Asp Ala His Leu
            420                 425                 430

Gly Ser Ala Phe Ser Ile Glu Pro Leu Leu Thr Gln Ser Ala Trp Phe
        435                 440                 445

Arg Pro His Asn Arg Asp Ser Asp Ile Ala Asn Leu Tyr Leu Val Gly
    450                 455                 460

Ala Gly Thr His Pro Gly Ala Gly Ile Pro Gly Val Val Ala Ser Ala
465                 470                 475                 480

Lys Ala Thr Ala Ser Leu Met Ile Glu Asp Leu Gln
                485                 490


<210> SEQ ID NO 15
<211> LENGTH: 309
<212> TYPE: PRT
<213> ORGANISM: Erwinia herbicola
<220> FEATURE:
<223> OTHER INFORMATION: crtB

<400> SEQUENCE: 15

Met Ser Gln Pro Pro Leu Leu Asp His Ala Thr Gln Thr Met Ala Asn
1               5                   10                  15

Gly Ser Lys Ser Phe Ala Thr Ala Ala Lys Leu Phe Asp Pro Ala Thr
            20                  25                  30

Arg Arg Ser Val Leu Met Leu Tyr Thr Trp Cys Arg His Cys Asp Asp
        35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
            100                 105                 110

Leu Asp Gly Phe Ala Met Asp Val Ala Gln Thr Arg Tyr Val Thr Phe
        115                 120                 125

Glu Asp Thr Leu Arg Tyr Cys Tyr His Val Ala Gly Val Val Gly Leu
    130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175

Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
    210                 215                 220

Pro Tyr Tyr Ile Ser Ser Gln Ala Gly Leu His Asp Leu Pro Pro Arg
```

```
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
            260                 265                 270

Thr Ser Lys Gly Glu Lys Ile Ala Met Leu Met Ala Ala Pro Gly Gln
        275                 280                 285

Val Ile Arg Ala Lys Thr Thr Arg Val Thr Pro Arg Pro Ala Gly Leu
    290                 295                 300

Trp Gln Arg Pro Val
305


<210> SEQ ID NO 16
<211> LENGTH: 219
<212> TYPE: PRT
<213> ORGANISM: Escherichia coli
<220> FEATURE:
<223> OTHER INFORMATION: CmR

<400> SEQUENCE: 16

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215


<210> SEQ ID NO 17
<211> LENGTH: 8632
<212> TYPE: DNA
<213> ORGANISM: Artificial Sequence
<220> FEATURE:
<223> OTHER INFORMATION: Nucleotide Sequence of pGT1066 (ECmut3)

<400> SEQUENCE: 17
```

-continued

```
ttgtaattct catgtttgac agcttatcat cgataagctt taatgcggta gtttatcaca      60
gttaaattgc taacgcagtc aggaaccttg caatggtgag tggcagtaaa gcgggcgttt     120
cgcctcatcg cgaaatagaa gtaatgagac aatccattga cgatcacctg gctggcctgt     180
tacctgaaac cgacagccag gatatcgtca gccttgcgat gcgtgaaggc gtcatggcac     240
ccggtaaacg gatccgtccg ctgctgatgc tgctggccgc ccgcgacctc cgctaccagg     300
gcagtatgcc tacgctgctc gatctcgcct gcgccgttga actgacccat accgcgtcgc     360
tgatgctcga cgacatgccc tgcatggaca acgccgagct gcgccgcggt cagcccacta     420
cccacaaaaa atttggtgag agcgtggcga tccttgcctc cgttgggctg ctctctaaag     480
cctttggtct gatcgccgcc accggcgatc tgccgggggga gaggcgtgcc caggcggtca     540
acgagctctc taccgccgtg ggcgtgcagg gcctggtact ggggcagttt cgcgatctta     600
acgatgccgc cctcgaccgt acccctgacg ctatcctcag caccaaccac ctcaagaccg     660
gcattctgtt cagcgcgatg ctgcagatcg tcgccattgc ttccgcctcg tcgccgagca     720
cgcgagagac gctgcacgcc ttcgccctcg acttcggcca ggcgtttcaa ctgctggacg     780
atctgcgtga cgatcacccg gaaaccggta aagatcgcaa taaggacgcg ggaaaatcga     840
cgctggtcaa ccggctgggc gcagacgcgg cccggcaaaa gctgcgcgag catattgatt     900
ccgccgacaa acacctcact tttgcctgtc cgcagggcgg cgccatccga cagtttatgc     960
atctgtggtt tggccatcac cttgccgact ggtcaccggt catgaaaatc gcctgatacc    1020
gcccttttgg gttcaagcag tacataacga tggaaccaca ttacaggagt agtgatgaat    1080
gaaggacgag cgccttgttc agcgtaagaa cgatcatctg gatatcgttc tcgacccccg    1140
tcgcgccgta actcaggcta gcgcaggttt tgagcgctgg cgctttaccc actgcgccct    1200
gccagagctg aattttagcg acatcacgct ggaaaccacc ttcctgaatc ggcagctaca    1260
ggctccgctg ctgatcagct ccatgaccgg cggcgttgag cgctcgcgcc atatcaaccg    1320
ccacctcgcc gaggcggcgc aggtgctaaa aattgcgatg ggggtgggct cccagcgcgt    1380
cgccattgag agcgacgcgg gcttagggct ggataaaacc ctgcggcagc tggctccgga    1440
cgtgccgctg ctggcgaacc tcggcgcggc gcagctgacc ggcagaaaag gtattgatta    1500
cgcccgacgg gccgtggaga tgatcgaggc ggatgcgctg attgtgcacc taaacccgct    1560
gcaggaggcg ctacagcccg gcggcgatcg cgactggcgc ggacggctgg cggctattga    1620
aactctggtc cgcgagctgc ccgttccgct ggtggtgaaa gaggtgggag ccggtatctc    1680
ccgaaccgtg gccgggcagc tgatcgatgc cggcgttacc gtgattgacg tcgcgggcgc    1740
gggcggcacc agctgggccg ccgttgaagg cgagcgggcg gccaccgagc agcagcgcag    1800
cgtggccaac gtctttgccg actgggggat ccccaccgct gaggcgctgg ttgacattgc    1860
cgaggcctgg ccgcagatgc cccttattgc ctcgggcggg attaaaaacg gcgtcgacgc    1920
ggcgaaagcg ctgcggctcg gcgcgtgcat ggtagggcag gccgccgccg tgctcggcag    1980
cgcaggcgtc tccacggaga aggtgatcga tcacttcaac gtgattattg agcagctgcg    2040
ggtggcctgc ttctgcaccg gcagccgcag cctgagcgat ctaaagcagg ctgatatccg    2100
ctatgttcgt gatacgccat aaggaggtac aaccatgaag aaaaccgttg tgattggcgc    2160
aggctttggt ggcctggcgc tggcgattcg cctgcaggcg gcagggatcc caaccgtact    2220
gctggagcag cgggacaagc ccggcggtcg ggcctacgtc tggcatgacc agggctttac    2280
ctttgacgcc gggccgacgg tgatcaccga tcctaccgcg cttgaggcgc tgttcaccct    2340
ggccggcagg cgcatggagg attacgtcag gctgctgccg gtaaaaccct tctaccgact    2400
```

```
ctgctgggag tccgggaaga ccctcgacta tgctaacgac agcgccgagc ttgaggcgca   2460

gattacccag ttcaaccccc gcgacgtcga gggctaccgg cgctttctgg cttactccca   2520

ggcggtattc caggagggat atttgcgcct cggcagcgtg ccgttcctct cttttcgcga   2580

catgctgcgc gccgggccgc agctgcttaa gctccaggcg tggcagagcg tctaccagtc   2640

ggtttcgcgc tttattgagg atgagcatct gcggcaggcc ttctcgttcc actccctgct   2700

ggtaggcggc aaccccttca ccacctcgtc catctacacc ctgatccacg cccttgagcg   2760

ggagtggggg gtctggttcc ctgagggcgg caccggggcg ctggtgaacg gcatggtgaa   2820

gctgtttacc gatctgggcg gggagatcga actcaacgcc cgggtcgaag agctggtggt   2880

ggccgataac cgcgtaagcc aggtccggct ggcggatggt cggatctttg acaccgacgc   2940

cgtagcctcg aacgctgacg tggtgaacac ctataaaaag ctgctcggcc accatccggt   3000

ggggcagaag cgggcggcag cgctggagcg caagagcatg agcaactcgc tgtttgtgct   3060

ctacttcggc ctgaaccagc ctcattccca gctggcgcac cataccatct gttttggtcc   3120

ccgctaccgg gagctgatcg acgagatctt taccggcagc gcgctggcgg atgacttctc   3180

gctctacctg cactcgccct gcgtgaccga tccctcgctc gcgcctcccg gctgcgccag   3240

cttctacgtg ctggccccgg tgccgcatct tggcaacgcg ccgctggact gggcgcagga   3300

ggggccgaag ctgcgcgacc gcatctttga ctaccttgaa gagcgctata tgcccggcct   3360

gcgtagccag ctggtgaccc agcggatctt taccccggca gacttccacg acacgctgga   3420

tgcgcatctg ggatcggcct tctccatcga gccgctgctg acccaaagcg cctggttccg   3480

cccgcacaac cgcgacagcg acattgccaa cctctacctg gtgggcgcag gtactcaccc   3540

tggggcgggc attcctggcg tagtggcctc ggcgaaagcc accgccagcc tgatgattga   3600

ggatctgcaa tgagccaacc gccgctgctt gaccacgcca cgcagaccat ggccaacggc   3660

tcgaaaagtt ttgccaccgc tgcgaagctg ttcgacccgg ccacccgccg tagcgtgctg   3720

atgctctaca cctggtgccg ccactgcgat gacgtcattg acgaccagac ccacggcttc   3780

gccagcgagg ccgcggcgga ggaggaggcc acccagcgcc tggcccggct gcgcacgctg   3840

accctggcgg cgtttgaagg ggccgagatg caggatccgg ccttcgctgc ctttcaggag   3900

gtggcgctga cccacggtat tacgccccgc atggcgctcg atcacctcga cggctttgcg   3960

atggacgtgg ctcagacccg ctatgtcacc tttgaggata cgctgcgcta ctgctatcac   4020

gtggcgggcg tggtgggtct gatgatggcc agggtgatgg gcgtgcggga tgagcgggtg   4080

ctggatcgcg cctgcgatct ggggctggcc ttccagctga cgaatatcgc ccgggatatt   4140

attgacgatg cggctattga ccgctgctat ctgcccgccg agtggctgca ggatgccggg   4200

ctgaccccgg agaactatgc cgcgcgggag aatcgggccg cgctggcgcg ggtggcggag   4260

cggcttattg atgccgcaga gccgtactac atctcctccc aggccgggct acacgatctg   4320

ccgccgcgct gcgcctgggc gatcgccacc gcccgcagcg tctaccggga gatcggtatt   4380

aaggtaaaag cggcgggagg cagcgcctgg gatcgccgcc agcacaccag caaaggtgaa   4440

aaaattgcca tgctgatggc ggcaccgggg caggttattc gggcgaagac gacgagggtg   4500

acgccgcgtc cggccggtct ttggcagcgt cccgtttaga ccgactccaa acgagtcggt   4560

tttttgcgc ttgtttcggc gtgggtatgg tggcaggccc cgtggccggg ggactgttgg   4620

gcgccatctc cttggggtcg aatttgcttt cgaatttctg ccattcatcc gcttattatc   4680

acttattcag gcgtagcaac caggcgttta agggcaccaa taactgcctt aaaaaaatta   4740
```

```
cgccccgccc tgccactcat cgcagtactg ttgtaattca ttaagcattc tgccgacatg   4800
gaagccatca cagacggcat gatgaacctg aatcgccagc ggcatcagca ccttgtcgcc   4860
ttgcgtataa tatttgccca tggtgaaaac gggggcgaag aagttgtcca tattggccac   4920
gtttaaatca aaactggtga aactcaccca gggattggct gagacgaaaa acatattctc   4980
aataaaccct ttagggaaat aggccaggtt ttcaccgtaa cacgccacat cttgcgaata   5040
tatgtgtaga aactgccgga aatcgtcgtg gtattcactc cagagcgatg aaaacgtttc   5100
agtttgctca tggaaaacgg tgtaacaagg gtgaacacta tcccatatca ccagctcacc   5160
gtctttcatt gccatacgga attccggatg agcattcatc aggcgggcaa gaatgtgaat   5220
aaaggccgga taaaacttgt gcttattttt ctttacggtc tttaaaaagg ccgtaatatc   5280
cagctgaacg gtctggttat aggtacattg agcaactgac tgaaatgcct caaaatgttc   5340
tttacgatgc cattgggata tatcaacggt ggtatatcca gtgatttttt tctccatttt   5400
agcttcctta gctcctgaaa atctcgataa ctcaaaaaat acgcccggta gtgatcttat   5460
ttcattatgg tgaaagttgg aacctcttac gtgccgatca acgtctcatt ttcgccaaaa   5520
gttggcccag ggcttcccgg tatcaacagg gacaccagga tttatttatt ctgcgaagtg   5580
atcttccgtc acaggtattt attcggcgca aagtgcgtcg ggtgatgctg ccaacttact   5640
gatttagtgt atgatggtgt ttttgaggtg ctccagtggc ttctgtttct atcagctgtc   5700
cctcctgttc agctactgac ggggtggtgc gtaacggcaa aagcaccgcc ggacatcagc   5760
gctagcggag tgtatacact ccgctatcgc tacgtgactg ggtcatggct gcgccccgac   5820
acccgccaac acccgctgac gcgccctgac gggcttgtct gctcccggca tccgcttaca   5880
gacaagctgt gaccgtctcc gggagctgca tgtgtcagag gttttcaccg tcatcaccga   5940
aacgcgcgag gcagctggca cgacaggttt cccgactgga aagcgggcag tgagcgcaac   6000
gcaattaatg tgagttagct cactcattag gcaccccagg ctttacactt tatgcttccg   6060
gctcgtatgt tgtgtggaat tgtgagcgga taacaatttc acacaggaaa cagctatgac   6120
catgattacg ccaagctcta gctagaaata attttgttta actttaagaa ggagatatac   6180
ccatgacaca gagggcccac catcaccatc accattccat ggctagcggc ggcggaagtt   6240
ccggtagtga gagttgtgta gcggtgagag aagatttcgc tgacgaagaa gattttgtga   6300
aagctggtgg ttctgagatt ctatttgttc aaatgcagca gaacaaagat atggatgaac   6360
agtctaagct tgttgataag ttgcctccta tatcaattgg tgatggtgct ttggatctag   6420
tggttattgg ttgtggtcct gctggtttag ccttggctgc agaatcagct aagcttggat   6480
taaaagttgg actcattggt ccagatcttc cttttactaa caattacggt gtttgggaag   6540
atgaattcaa tgatcttggg ctgcaaaaat gtattgagca tgtttggaga gagactattg   6600
tgtatctgga tgatgacaag cctattacca ttggccgtgc ttatggaaga gttagtcgac   6660
gtttgctcca tgaggagctt ttgaggaggt gtgtcgagtc aggtgtctcg taccttagct   6720
cgaaagttga cagcataaca gaagcttctg atggccttag acttgttgct tgtgacgaca   6780
ataacgtcat tccctgcagg cttgccactg ttgcttctgg agcagcttcg ggaaagctct   6840
tgcaatacga agttggtgga cctagagtct gtgtgcaaac tgcatacggc gtggaggttg   6900
aggtggaaaa tagtccatat gatccagatc aaatggtttt catggattac agagattata   6960
ctaacgagaa agttcggagc ttagaagctg agtatccaac gtttctgtac gccatgccta   7020
tgacaaagtc aagactcttc ttcgaggaga catgtttggc ctcaaaagat gtcatgccct   7080
ttgatttgct aaaaacgaag ctcatgttaa gattagatac actcggaatt cgaattctaa   7140
```

```
agacttacga agaggagtgg tcctatatcc cagttggtgg ttccttgcca aacaccgaac   7200

aaaagaatct cgcctttggt gctgccgcta gcatggtaca tcccgcaaca ggctattcag   7260

ttgtgagatc tttgtctgaa gctccaaaat atgcatcagt catcgcagag atactaagag   7320

aagagactac caaacagatc aacagtaata tttcaagaca agcttgggat actttatggc   7380

caccagaaag gaaaagacag agagcattct ttctctttgg tcttgcacac atagttcaat   7440

tcgataccga aggcattaga agcttcttcc gtactttctt ccgccttcca aaatggatgt   7500

ggcaagggtt tctaggatca acattaacat caggagatct cgttctcttt tctttataca   7560

tgttcgtcat ttcaccaaac aatttgagaa aaggtctcat caatcatctc atctctgatc   7620

caaccggagc aaccatgata aaaacctatc tcaaagtatg aggatccggc tgctaacaaa   7680

gcccgttctg tttaagaacg ggatttttg ctgaaaggag gaactatatc cggccggatt   7740

actggcttac tatgttggca ctgatgaggg tgtcagtgaa gtgcttcatg tggcaggaga   7800

aaaaaggctg caccggtgcg tcagcagaat atgtgataca ggatatattc cgcttcctcg   7860

ctcactgact cgctacgctc ggtcgttcga ctgcggcgag cggaaatggc ttacgaacgg   7920

ggcggagatt tcctggaaga tgccaggaag atacttaaca gggaagtgag agggccgcgg   7980

caaagccgtt tttccatagg ctccgccccc ctgacaagca tcacgaaatc tgacgctcaa   8040

atcagtggtg gcgaaacccg acaggactat aaagatacca ggcgtttccc cctggcggct   8100

ccctcgtgcg ctctcctgtt cctgcctttc ggtttaccgg tgtcattccg ctgttatggc   8160

cgcgtttgtc tcattccacg cctgacactc agttccgggt aggcagttcg ctccaagctg   8220

gactgtatgc acgaaccccc cgttcagtcc gaccgctgcg ccttatccgg taactatcgt   8280

cttgagtcca acccggaaag acatgcaaaa gcaccactgg cagcagccac tggtaattga   8340

tttagaggag ttagtcttga agtcatgcgc cggttaaggc taaactgaaa ggacaagttt   8400

tggtgactgc gctcctccaa gccagttacc tcggttcaaa gagttggtag ctcagagaac   8460

cttcgaaaaa ccgccctgca aggcggtttt ttcgttttca gagcaagaga ttacgcgcag   8520

accaaaacga tctcaagaag atcatcttat taatcagata aaatatttct agatttcagt   8580

gcaatttatc tcttcaaatg tagcacctga agtcagcccc atacgatata ag           8632
```

```
<210> SEQ ID NO 18
<211> LENGTH: 8632
<212> TYPE: DNA
<213> ORGANISM: Artificial Sequence
<220> FEATURE:
<223> OTHER INFORMATION: Nucleotide Sequence of pGT1066*
<220> FEATURE:
<221> NAME/KEY: misc_feature
<222> LOCATION: 7425..7430
<223> OTHER INFORMATION: /note="n is a, c, g, or t"
<220> FEATURE:
<221> NAME/KEY: misc_feature
<222> LOCATION: 7551..7553
<223> OTHER INFORMATION: /note="n is a, c, g, or t"

<400> SEQUENCE: 18
```

```
ttgtaattct catgtttgac agcttatcat cgataagctt taatgcggta gtttatcaca     60

gttaaattgc taacgcagtc aggaaccttg caatggtgag tggcagtaaa gcgggcgttt    120

cgcctcatcg cgaaatagaa gtaatgagac aatccattga cgatcacctg gctggcctgt    180

tacctgaaac cgacagccag gatatcgtca gccttgcgat gcgtgaaggc gtcatggcac    240

ccggtaaacg gatccgtccg ctgctgatgc tgctggccgc ccgcgacctc cgctaccagg    300
```

```
gcagtatgcc tacgctgctc gatctcgcct gcgccgttga actgacccat accgcgtcgc    360
tgatgctcga cgacatgccc tgcatggaca acgccgagct gcgccgcggt cagcccacta    420
cccacaaaaa atttggtgag agcgtggcga tccttgcctc cgttgggctg ctctctaaag    480
cctttggtct gatcgccgcc accggcgatc tgccgggggga gaggcgtgcc caggcggtca    540
acgagctctc taccgccgtg ggcgtgcagg gcctggtact ggggcagttt cgcgatctta    600
acgatgccgc cctcgaccgt acccctgacg ctatcctcag caccaaccac ctcaagaccg    660
gcattctgtt cagcgcgatg ctgcagatcg tcgccattgc ttccgcctcg tcgccgagca    720
cgcgagagac gctgcacgcc ttcgccctcg acttcggcca ggcgtttcaa ctgctggacg    780
atctgcgtga cgatcacccg gaaaccggta aagatcgcaa taaggacgcg ggaaaatcga    840
cgctggtcaa ccggctgggc gcagacgcgg cccggcaaaa gctgcgcgag catattgatt    900
ccgccgacaa acacctcact tttgcctgtc cgcagggcgg cgccatccga cagtttatgc    960
atctgtggtt tggccatcac cttgccgact ggtcaccggt catgaaaatc gcctgatacc   1020
gcccttttgg gttcaagcag tacataacga tggaaccaca ttacaggagt agtgatgaat   1080
gaaggacgag cgccttgttc agcgtaagaa cgatcatctg gatatcgttc tcgacccccg   1140
tcgcgccgta actcaggcta gcgcaggttt tgagcgctgg cgctttaccc actgcgccct   1200
gccagagctg aattttagcg acatcacgct ggaaaccacc ttcctgaatc ggcagctaca   1260
ggctccgctg ctgatcagct ccatgaccgg cggcgttgag cgctcgcgcc atatcaaccg   1320
ccacctcgcc gaggcggcgc aggtgctaaa aattgcgatg gggtgggct cccagcgcgt   1380
cgccattgag agcgacgcgg gcttagggct ggataaaacc ctgcggcagc tggctccgga   1440
cgtgccgctg ctggcgaacc tcggcgcggc gcagctgacc ggcagaaaag gtattgatta   1500
cgcccgacgg gccgtggaga tgatcgaggc ggatgcgctg attgtgcacc taaacccgct   1560
gcaggaggcg ctacagcccg gcggcgatcg cgactggcgc ggacggctgg cggctattga   1620
aactctggtc cgcgagctgc ccgttccgct ggtggtgaaa gaggtgggag ccggtatctc   1680
ccgaaccgtg gccgggcagc tgatcgatgc cggcgttacc gtgattgacg tcgcgggcgc   1740
gggcggcacc agctgggccg ccgttgaagg cgagcgggcg gccaccgagc agcagcgcag   1800
cgtggccaac gtctttgccg actgggggat ccccaccgct gaggcgctgg ttgacattgc   1860
cgaggcctgg ccgcagatgc cccttattgc ctcgggcggg attaaaaacg gcgtcgacgc   1920
ggcgaaagcg ctgcggctcg gcgcgtgcat ggtagggcag gccgccgccg tgctcggcag   1980
cgcaggcgtc tccacggaga aggtgatcga tcacttcaac gtgattattg agcagctgcg   2040
ggtggcctgc ttctgcaccg gcagccgcag cctgagcgat ctaaagcagg ctgatatccg   2100
ctatgttcgt gatacgccat aaggaggtac aaccatgaag aaaaccgttg tgattggcgc   2160
aggctttggt ggcctggcgc tggcgattcg cctgcaggcg gcagggatcc caaccgtact   2220
gctggagcag cgggacaagc ccggcggtcg ggcctacgtc tggcatgacc agggctttac   2280
ctttgacgcc gggccgacgg tgatcaccga tcctaccgcg cttgaggcgc tgttcaccct   2340
ggccggcagg cgcatggagg attacgtcag gctgctgccg gtaaaaccct tctaccgact   2400
ctgctgggag tccgggaaga ccctcgacta tgctaacgac agcgccgagc ttgaggcgca   2460
gattacccag ttcaaccccc gcgacgtcga gggctaccgg cgctttctgg cttactccca   2520
ggcggtattc caggagggat atttgcgcct cggcagcgtg ccgttcctct cttttcgcga   2580
catgctgcgc gccgggccgc agctgcttaa gctccaggcg tggcagagcg tctaccagtc   2640
ggtttcgcgc tttattgagg atgagcatct gcggcaggcc ttctcgttcc actccctgct   2700
```

```
ggtaggcggc aacccccttca ccacctcgtc catctacacc ctgatccacg cccttgagcg   2760

ggagtggggg gtctggttcc ctgagggcgg caccggggcg ctggtgaacg gcatggtgaa   2820

gctgtttacc gatctgggcg gggagatcga actcaacgcc cgggtcgaag agctggtggt   2880

ggccgataac cgcgtaagcc aggtccggct ggcggatggt cggatctttg acaccgacgc   2940

cgtagcctcg aacgctgacg tggtgaacac ctataaaaag ctgctcggcc accatccggt   3000

ggggcagaag cgggcggcag cgctggagcg caagagcatg agcaactcgc tgtttgtgct   3060

ctacttcggc ctgaaccagc ctcattccca gctggcgcac cataccatct gttttggtcc   3120

ccgctaccgg gagctgatcg acgagatctt taccggcagc gcgctggcgg atgacttctc   3180

gctctacctg cactcgccct gcgtgaccga tccctcgctc gcgcctcccg gctgcgccag   3240

cttctacgtg ctggccccgg tgccgcatct tggcaacgcg ccgctggact gggcgcagga   3300

ggggccgaag ctgcgcgacc gcatctttga ctaccttgaa gagcgctata tgcccggcct   3360

gcgtagccag ctggtgaccc agcggatctt taccccggca gacttccacg acacgctgga   3420

tgcgcatctg ggatcggcct tctccatcga gccgctgctg acccaaagcg cctggttccg   3480

cccgcacaac cgcgacagcg acattgccaa cctctacctg gtgggcgcag gtactcaccc   3540

tggggcgggc attcctggcg tagtggcctc ggcgaaagcc accgccagcc tgatgattga   3600

ggatctgcaa tgagccaacc gccgctgctt gaccacgcca cgcagaccat ggccaacggc   3660

tcgaaaagtt ttgccaccgc tgcgaagctg ttcgacccgg ccacccgccg tagcgtgctg   3720

atgctctaca cctggtgccg ccactgcgat gacgtcattg acgaccagac ccacggcttc   3780

gccagcgagg ccgcggcgga ggaggaggcc acccagcgcc tggcccggct gcgcacgctg   3840

accctggcgg cgtttgaagg ggccgagatg caggatccgg ccttcgctgc ctttcaggag   3900

gtggcgctga cccacggtat tacgccccgc atggcgctcg atcacctcga cggctttgcg   3960

atggacgtgg ctcagacccg ctatgtcacc tttgaggata cgctgcgcta ctgctatcac   4020

gtggcgggcg tggtgggtct gatgatggcc agggtgatgg gcgtgcggga tgagcgggtg   4080

ctggatcgcg cctgcgatct ggggctggcc ttccagctga cgaatatcgc ccgggatatt   4140

attgacgatg cggctattga ccgctgctat ctgcccgccg agtggctgca ggatgccggg   4200

ctgaccccgg agaactatgc cgcgcgggag aatcgggccg cgctggcgcg ggtggcggag   4260

cggcttattg atgccgcaga gccgtactac atctcctccc aggccgggct acacgatctg   4320

ccgccgcgct gcgcctgggc gatcgccacc gcccgcagcg tctaccggga gatcggtatt   4380

aaggtaaaag cggcgggagg cagcgcctgg gatcgccgcc agcacaccag caaaggtgaa   4440

aaaattgcca tgctgatggc ggcaccgggg caggttattc gggcgaagac gacgagggtg   4500

acgccgcgtc cggccggtct ttggcagcgt cccgtttaga ccgactccaa acgagtcggt   4560

ttttttgcgc ttgtttcggc gtgggtatgg tggcaggccc cgtggccggg ggactgttgg   4620

gcgccatctc cttggggtcg aatttgcttt cgaatttctg ccattcatcc gcttattatc   4680

acttattcag gcgtagcaac caggcgttta agggcaccaa taactgcctt aaaaaaatta   4740

cgccccgccc tgccactcat cgcagtactg ttgtaattca ttaagcattc tgccgacatg   4800

gaagccatca cagacggcat gatgaacctg aatcgccagc ggcatcagca ccttgtcgcc   4860

ttgcgtataa tatttgccca tggtgaaaac gggggcgaag aagttgtcca tattggccac   4920

gtttaaatca aaactggtga aactcaccca gggattggct gagacgaaaa acatattctc   4980

aataaaccct ttagggaaat aggccaggtt ttcaccgtaa cacgccacat cttgcgaata   5040
```

```
tatgtgtaga aactgccgga aatcgtcgtg gtattcactc cagagcgatg aaaacgtttc   5100

agtttgctca tggaaaacgg tgtaacaagg gtgaacacta tcccatatca ccagctcacc   5160

gtctttcatt gccatacgga attccggatg agcattcatc aggcgggcaa gaatgtgaat   5220

aaaggccgga taaaacttgt gcttattttt ctttacggtc tttaaaaagg ccgtaatatc   5280

cagctgaacg gtctggttat aggtacattg agcaactgac tgaaatgcct caaaatgttc   5340

tttacgatgc cattgggata tatcaacggt ggtatatcca gtgatttttt tctccatttt   5400

agcttcctta gctcctgaaa atctcgataa ctcaaaaaat acgcccggta gtgatcttat   5460

ttcattatgg tgaaagttgg aacctcttac gtgccgatca acgtctcatt ttcgccaaaa   5520

gttggcccag ggcttcccgg tatcaacagg gacaccagga tttatttatt ctgcgaagtg   5580

atcttccgtc acaggtattt attcggcgca aagtgcgtcg ggtgatgctg ccaacttact   5640

gatttagtgt atgatggtgt ttttgaggtg ctccagtggc ttctgtttct atcagctgtc   5700

cctcctgttc agctactgac ggggtggtgc gtaacggcaa aagcaccgcc ggacatcagc   5760

gctagcggag tgtatacact ccgctatcgc tacgtgactg ggtcatggct gcgccccgac   5820

acccgccaac acccgctgac gcgccctgac gggcttgtct gctcccggca tccgcttaca   5880

gacaagctgt gaccgtctcc gggagctgca tgtgtcagag gttttcaccg tcatcaccga   5940

aacgcgcgag gcagctggca cgacaggttt cccgactgga aagcgggcag tgagcgcaac   6000

gcaattaatg tgagttagct cactcattag gcaccccagg ctttacactt tatgcttccg   6060

gctcgtatgt tgtgtggaat tgtgagcgga taacaatttc acacaggaaa cagctatgac   6120

catgattacg ccaagctcta gctagaaata attttgttta actttaagaa ggagatatac   6180

ccatgacaca gagggcccac catcaccatc accattccat ggctagcggc ggcggaagtt   6240

ccggtagtga gagttgtgta gcggtgagag aagatttcgc tgacgaagaa gattttgtga   6300

aagctggtgg ttctgagatt ctatttgttc aaatgcagca gaacaaagat atggatgaac   6360

agtctaagct tgttgataag ttgcctccta tatcaattgg tgatggtgct ttggatctag   6420

tggttattgg ttgtggtcct gctggtttag ccttggctgc agaatcagct aagcttggat   6480

taaaagttgg actcattggt ccagatcttc cttttactaa caattacggt gtttgggaag   6540

atgaattcaa tgatcttggg ctgcaaaaat gtattgagca tgtttggaga gagactattg   6600

tgtatctgga tgatgacaag cctattacca ttggccgtgc ttatggaaga gttagtcgac   6660

gtttgctcca tgaggagctt ttgaggaggt gtgtcgagtc aggtgtctcg taccttagct   6720

cgaaagttga cagcataaca gaagcttctg atggccttag acttgttgct tgtgacgaca   6780

ataacgtcat tccctgcagg cttgccactg ttgcttctgg agcagcttcg ggaaagctct   6840

tgcaatacga agttggtgga cctagagtct gtgtgcaaac tgcatacggc gtggaggttg   6900

aggtggaaaa tagtccatat gatccagatc aaatggtttt catggattac agagattata   6960

ctaacgagaa agttcggagc ttagaagctg agtatccaac gtttctgtac gccatgccta   7020

tgacaaagtc aagactcttc ttcgaggaga catgtttggc ctcaaaagat gtcatgccct   7080

ttgatttgct aaaaacgaag ctcatgttaa gattagatac actcggaatt cgaattctaa   7140

agacttacga agaggagtgg tcctatatcc cagttggtgg ttccttgcca aacaccgaac   7200

aaaagaatct cgcctttggt gctgccgcta gcatggtaca tcccgcaaca ggctattcag   7260

ttgtgagatc tttgtctgaa gctccaaaat atgcatcagt catcgcagag atactaagag   7320

aagagactac caaacagatc aacagtaata tttcaagaca agcttgggat actttatggc   7380

caccagaaag gaaaagacag agagcattct ttctctttgg tcttnnnnnn atagttcaat   7440
```

```
tcgataccga aggcattaga agcttcttcc gtactttctt ccgccttcca aaatggatgt   7500

ggcaagggtt tctaggatca acattaacat caggagatct cgttctcttt nnnttataca   7560

tgttcgtcat ttcaccaaac aatttgagaa aaggtctcat caatcatctc atctctgatc   7620

caaccggagc aaccatgata aaaacctatc tcaaagtatg aggatccggc tgctaacaaa   7680

gcccgttctg tttaagaacg ggatttttg ctgaaaggag gaactatatc cggccggatt   7740

actggcttac tatgttggca ctgatgaggg tgtcagtgaa gtgcttcatg tggcaggaga   7800

aaaaaggctg caccggtgcg tcagcagaat atgtgataca ggatatattc cgcttcctcg   7860

ctcactgact cgctacgctc ggtcgttcga ctgcggcgag cggaaatggc ttacgaacgg   7920

ggcggagatt tcctggaaga tgccaggaag atacttaaca gggaagtgag agggccgcgg   7980

caaagccgtt tttccatagg ctccgccccc ctgacaagca tcacgaaatc tgacgctcaa   8040

atcagtggtg gcgaaacccg acaggactat aaagatacca ggcgtttccc cctggcggct   8100

ccctcgtgcg ctctcctgtt cctgcctttc ggtttaccgg tgtcattccg ctgttatggc   8160

cgcgtttgtc tcattccacg cctgacactc agttccgggt aggcagttcg ctccaagctg   8220

gactgtatgc acgaaccccc cgttcagtcc gaccgctgcg ccttatccgg taactatcgt   8280

cttgagtcca acccggaaag acatgcaaaa gcaccactgg cagcagccac tggtaattga   8340

tttagaggag ttagtcttga agtcatgcgc cggttaaggc taaactgaaa ggacaagttt   8400

tggtgactgc gctcctccaa gccagttacc tcggttcaaa gagttggtag ctcagagaac   8460

cttcgaaaaa ccgccctgca aggcggtttt ttcgttttca gagcaagaga ttacgcgcag   8520

accaaaacga tctcaagaag atcatcttat taatcagata aaatatttct agatttcagt   8580

gcaatttatc tcttcaaatg tagcacctga agtcagcccc atacgatata ag           8632
```

```
<210> SEQ ID NO 19
<211> LENGTH: 480
<212> TYPE: PRT
<213> ORGANISM: Artificial Sequence
<220> FEATURE:
<223> OTHER INFORMATION: Protein Variant AtEC-del

<400> SEQUENCE: 19

Met Ala Ser Gly Gly Gly Ser Ser Gly Ser Glu Ser Cys Val Ala Val
1               5                   10                  15

Arg Glu Asp Phe Ala Asp Glu Glu Asp Phe Val Lys Ala Gly Gly Ser
            20                  25                  30

Glu Ile Leu Phe Val Gln Met Gln Gln Asn Lys Asp Met Asp Glu Gln
        35                  40                  45

Ser Lys Leu Val Asp Lys Leu Pro Pro Ile Ser Ile Gly Asp Gly Ala
    50                  55                  60

Leu Asp Leu Val Val Ile Gly Cys Gly Pro Ala Gly Leu Ala Leu Ala
65                  70                  75                  80

Ala Glu Ser Ala Lys Leu Gly Leu Lys Val Gly Leu Ile Gly Pro Asp
                85                  90                  95

Leu Pro Phe Thr Asn Asn Tyr Gly Val Trp Glu Asp Glu Phe Asn Asp
            100                 105                 110

Leu Gly Leu Gln Lys Cys Ile Glu His Val Trp Arg Glu Thr Ile Val
        115                 120                 125

Tyr Leu Asp Asp Asp Lys Pro Ile Thr Ile Gly Arg Ala Tyr Gly Arg
    130                 135                 140

Val Ser Arg Arg Leu Leu His Glu Glu Leu Leu Arg Arg Cys Val Glu
```

```
145                 150                 155                 160

Ser Gly Val Ser Tyr Leu Ser Ser Lys Val Asp Ser Ile Thr Glu Ala
                165                 170                 175

Ser Asp Gly Leu Arg Leu Val Ala Cys Asp Asp Asn Asn Val Ile Pro
            180                 185                 190

Cys Arg Leu Ala Thr Val Ala Ser Gly Ala Ala Ser Gly Lys Leu Leu
        195                 200                 205

Gln Tyr Glu Val Gly Gly Pro Arg Val Cys Val Gln Thr Ala Tyr Gly
    210                 215                 220

Val Glu Val Glu Val Glu Asn Ser Pro Tyr Asp Pro Asp Gln Met Val
225                 230                 235                 240

Phe Met Asp Tyr Arg Asp Tyr Thr Asn Glu Lys Val Arg Ser Leu Glu
                245                 250                 255

Ala Glu Tyr Pro Thr Phe Leu Tyr Ala Met Pro Met Thr Lys Ser Arg
            260                 265                 270

Leu Phe Phe Glu Glu Thr Cys Leu Ala Ser Lys Asp Val Met Pro Phe
        275                 280                 285

Asp Leu Leu Lys Thr Lys Leu Met Leu Arg Leu Asp Thr Leu Gly Ile
    290                 295                 300

Arg Ile Leu Lys Thr Tyr Glu Glu Glu Trp Ser Tyr Ile Pro Val Gly
305                 310                 315                 320

Gly Ser Leu Pro Asn Thr Glu Gln Lys Asn Leu Ala Phe Gly Ala Ala
                325                 330                 335

Ala Ser Met Val His Pro Ala Thr Gly Tyr Ser Val Val Arg Ser Leu
            340                 345                 350

Ser Glu Ala Pro Lys Tyr Ala Ser Val Ile Ala Glu Ile Leu Arg Glu
        355                 360                 365

Glu Thr Thr Lys Gln Ile Asn Ser Asn Ile Ser Arg Gln Ala Trp Asp
    370                 375                 380

Thr Leu Trp Pro Pro Glu Arg Lys Arg Gln Arg Ala Phe Phe Leu Phe
385                 390                 395                 400

Gly Leu Ala Leu Ile Val Gln Phe Asp Thr Glu Gly Ile Arg Ser Phe
                405                 410                 415

Phe Arg Thr Phe Phe Arg Leu Pro Lys Trp Met Trp Gln Gly Phe Leu
            420                 425                 430

Gly Ser Thr Leu Thr Ser Gly Asp Leu Val Leu Phe Ala Leu Tyr Met
        435                 440                 445

Phe Val Ile Ser Pro Asn Asn Leu Arg Lys Gly Leu Ile Asn His Leu
    450                 455                 460

Ile Ser Asp Pro Thr Gly Ala Thr Met Ile Lys Thr Tyr Leu Lys Val
465                 470                 475                 480


<210> SEQ ID NO 20
<211> LENGTH: 480
<212> TYPE: PRT
<213> ORGANISM: Artificial Sequence
<220> FEATURE:
<223> OTHER INFORMATION: Protein Variant AtECmut3

<400> SEQUENCE: 20

Met Ala Ser Gly Gly Gly Ser Ser Gly Ser Glu Ser Cys Val Ala Val
1               5                   10                  15

Arg Glu Asp Phe Ala Asp Glu Glu Asp Phe Val Lys Ala Gly Gly Ser
            20                  25                  30

Glu Ile Leu Phe Val Gln Met Gln Gln Asn Lys Asp Met Asp Glu Gln
```

```
        35                  40                  45

Ser Lys Leu Val Asp Lys Leu Pro Pro Ile Ser Ile Gly Asp Gly Ala
    50                  55                  60

Leu Asp Leu Val Val Ile Gly Cys Gly Pro Ala Gly Leu Ala Leu Ala
65                  70                  75                  80

Ala Glu Ser Ala Lys Leu Gly Leu Lys Val Gly Leu Ile Gly Pro Asp
                85                  90                  95

Leu Pro Phe Thr Asn Asn Tyr Gly Val Trp Glu Asp Glu Phe Asn Asp
            100                 105                 110

Leu Gly Leu Gln Lys Cys Ile Glu His Val Trp Arg Glu Thr Ile Val
        115                 120                 125

Tyr Leu Asp Asp Asp Lys Pro Ile Thr Ile Gly Arg Ala Tyr Gly Arg
    130                 135                 140

Val Ser Arg Arg Leu Leu His Glu Glu Leu Leu Arg Arg Cys Val Glu
145                 150                 155                 160

Ser Gly Val Ser Tyr Leu Ser Ser Lys Val Asp Ser Ile Thr Glu Ala
                165                 170                 175

Ser Asp Gly Leu Arg Leu Val Ala Cys Asp Asp Asn Asn Val Ile Pro
            180                 185                 190

Cys Arg Leu Ala Thr Val Ala Ser Gly Ala Ala Ser Gly Lys Leu Leu
        195                 200                 205

Gln Tyr Glu Val Gly Gly Pro Arg Val Cys Val Gln Thr Ala Tyr Gly
    210                 215                 220

Val Glu Val Glu Val Glu Asn Ser Pro Tyr Asp Pro Asp Gln Met Val
225                 230                 235                 240

Phe Met Asp Tyr Arg Asp Tyr Thr Asn Glu Lys Val Arg Ser Leu Glu
                245                 250                 255

Ala Glu Tyr Pro Thr Phe Leu Tyr Ala Met Pro Met Thr Lys Ser Arg
            260                 265                 270

Leu Phe Phe Glu Glu Thr Cys Leu Ala Ser Lys Asp Val Met Pro Phe
        275                 280                 285

Asp Leu Leu Lys Thr Lys Leu Met Leu Arg Leu Asp Thr Leu Gly Ile
    290                 295                 300

Arg Ile Leu Lys Thr Tyr Glu Glu Glu Trp Ser Tyr Ile Pro Val Gly
305                 310                 315                 320

Gly Ser Leu Pro Asn Thr Glu Gln Lys Asn Leu Ala Phe Gly Ala Ala
                325                 330                 335

Ala Ser Met Val His Pro Ala Thr Gly Tyr Ser Val Val Arg Ser Leu
            340                 345                 350

Ser Glu Ala Pro Lys Tyr Ala Ser Val Ile Ala Glu Ile Leu Arg Glu
        355                 360                 365

Glu Thr Thr Lys Gln Ile Asn Ser Asn Ile Ser Arg Gln Ala Trp Asp
    370                 375                 380

Thr Leu Trp Pro Pro Glu Arg Lys Arg Gln Arg Ala Phe Phe Leu Phe
385                 390                 395                 400

Gly Leu Ala His Ile Val Gln Phe Asp Thr Glu Gly Ile Arg Ser Phe
                405                 410                 415

Phe Arg Thr Phe Phe Arg Leu Pro Lys Trp Met Trp Gln Gly Phe Leu
            420                 425                 430

Gly Ser Thr Leu Thr Ser Gly Asp Leu Val Leu Phe Ser Leu Tyr Met
        435                 440                 445

Phe Val Ile Ser Pro Asn Asn Leu Arg Lys Gly Leu Ile Asn His Leu
    450                 455                 460
```

```
Ile Ser Asp Pro Thr Gly Ala Thr Met Ile Lys Thr Tyr Leu Lys Val
465                 470                 475                 480


<210> SEQ ID NO 21
<211> LENGTH: 5717
<212> TYPE: DNA
<213> ORGANISM: Artificial Sequence
<220> FEATURE:
<223> OTHER INFORMATION: Nucleotide Sequence of pGT1069

<400> SEQUENCE: 21

aaaccaattg tccatattgc atcagacatt gccgtcactg cgtcttttac tggctcttct     60

cgctaaccaa accggtaacc ccgcttatta aaagcattct gtaacaaagc gggaccaaag    120

ccatgacaaa aacgcgtaac aaaagtgtct ataatcacgg cagaaaagtc cacattgatt    180

atttgcacgg cgtcacactt tgctatgcca tagcattttt atccataaga ttagctgatc    240

ctacctgacg ctttttatcg caactctcta ctgtttctcc atacccgttt aaataatttt    300

gtttaacttt aagaaggaga tatacccatg acacagaggg cccaccatca ccatcaccat    360

tccatggcgg agaaactcag tgatggcagc agcatcatct cagtccatcc tagaccctcc    420

aagggtttct cctcgaagct tctcgatctt ctcgagagac ttgttgtcaa gctcatgcac    480

gatgcttctc tccctctcca ctacctctca ggcaacttcg ctcccatccg tgatgaaact    540

cctcccgtca aggatctccc cgtccatgga tttcttcccg aatgcttgaa tggtgaattt    600

gtgagggttg gtccaaaccc caagtttgat gctgtcgctg gatatcactg gtttgatgga    660

gatgggatga ttcatggggt acgcatcaaa gatgggaaag ctacttatgt ttctcgatat    720

gttaagacat cacgtcttaa gcaggaagag ttcttcggag ctgccaaatt catgaagatt    780

ggtgacctta aggggttttt cggattgcta atggtcaatg tccaacagct gagaacgaag    840

ctcaaaatat tggacaacac ttatggaaat ggaactgcca atacagcact cgtatatcac    900

catggaaaac ttctagcatt acaggaggca gataagccgt acgtcatcaa agttttggaa    960

gatggagacc tgcaaactct tggtataata gattatgaca agagattgac ccactccttc   1020

actgctcacc caaaagttga cccggttacg ggtgaaatgt ttacattcgg ctattcgcat   1080

acgccacctt atctcacata cagagttatc tcgaaagatg gcattatgca tgacccagtc   1140

ccaattacta tatcagagcc tatcatgatg catgattttg ctattactga gacttatgca   1200

atcttcatgg atcttcctat gcacttcagg ccaaaggaaa tggtgaaaga gaagaaaatg   1260

atatactcat ttgatcccac aaaaaaggct cgttttggtg ttcttccacg ctatgccaag   1320

gatgaactta tgattagatg gtttgagctt cccaactgct ttattttcca caacgccaat   1380

gcttgggaag aagaggatga agtcgtcctc atcacttgtc gtcttgagaa tccagatctt   1440

gacatggtca gtgggaaagt gaaagaaaaa ctcgaaaatt ttggcaacga actgtacgaa   1500

atgagattca acatgaaaac gggctcagct tctcaaaaaa aactatccgc atctgcggtt   1560

gatttcccca gaatcaatga gtgctacacc ggaaagaaac agagatacgt atatggaaca   1620

attctggaca gtatcgcaaa ggttaccgga atcatcaagt ttgatctgca tgcagaagct   1680

gagacaggga aaagaatgct ggaagtagga ggtaatatca aaggaatata tgacctggga   1740

gaaggcagat atggttcaga ggctatctat gttccgcgtg agacagcaga agaagacgac   1800

ggttacttga tattctttgt tcatgatgaa aacacaggga aatcatgcgt gactgtgata   1860

gacgcaaaaa caatgtcggc tgaaccggtg gcagtggtgg agctgccgca cagggtccca   1920

tatggcttcc atgccttgtt tgttacagag gaacaactcc aggaacaaac tcttatataa   1980
```

```
ggatccggct gctaacaaag cccgaaagga agctgagttg gctgctgcca ccgctgagca   2040
ataactagca taaccccttg gggcctctaa acgggtcttg aggggttttt tgctgaaagg   2100
aggaactata tccggccgga tatccacagg acgggtgtgg tcgccatgat cgcgtagtcg   2160
atagtggctc caagtagcga agcgagcagg actgggcggc ggccaaagcg gtcggacagt   2220
gctccgagaa cgggtgcgca tagaaattgc atcaacgcat atagcgctag cagcacgcca   2280
tagtgactgg cgatgctgtc ggaatggacg atatcccgca agaggcccgg cagtaccggc   2340
ataaccaagc ctatgcctac agcatccagg gtgacggtgc cgaggatgac gatgagcgca   2400
ttgttagatt tcatacacgg tgcctgactg cgttagcaat ttaactgtga taaactaccg   2460
cattaaagct tatcgatgat aagctgtcaa acatgagaat tcttgaagac gaaagggcct   2520
cgtgatacgc ctatttttat aggttaatgt catgcatgag acaataaccc tgataaatgc   2580
ttcaataata ttgaaaaagg aagagtatga gtattcaaca tttccgtgtc gcccttattc   2640
ccttttttgc ggcattttgc cttcctgttt ttgctcaccc agaaacgctg gtgaaagtaa   2700
aagatgctga agatcagttg ggtgcacgag tgggttacat cgaactggat ctcaacagcg   2760
gtaagatcct tgagagtttt cgccccgaag aacgttttcc aatgatgagc acttttaaag   2820
ttctgctatg tggcgcggta ttatcccgtg ttgacgccgg gcaagagcaa ctcggtcgcc   2880
gcatacacta ttctcagaat gacttggttg acgcgtcacc agtcacagaa aagcatctta   2940
cggatggcat gacagtaaga gaattatgca gtgctgccat aaccatgagt gataacactg   3000
cggccaactt acttctgaca acgatcggag gaccgaagga gctaaccgct tttttgcaca   3060
acatggggga tcatgtaact cgccttgatc gttgggaacc ggagctgaat gaagccatac   3120
caaacgacga gcgtgacacc acgatgcctg cagcaatggc aacaacgttg cgcaaactat   3180
taactggcga actacttact ctagcttccc ggcaacaatt aatagactgg atggaggcgg   3240
ataaagttgc aggaccactt ctgcgctcgg cccttccggc tggctggttt attgctgata   3300
aatctggagc cggtgagcgt gggtctcgcg gtatcattgc agcactgggg ccagatggta   3360
agccctcccg tatcgtagtt atctacacga cggggagtca ggcaactatg gatgaacgaa   3420
atagacagat cgctgagata ggtgcctcac tgattaagca ttggtaactg tcagaccaag   3480
tttactcata tatactttag attgatttaa aacttcattt ttaatttaaa aggatctagg   3540
tgaagatcct ttttgataat ctcatgcatg accaaaatcc cttaacgtga gttttcgttc   3600
cactgagcgt cagaccccgt agaaaagatc aaaggatctt cttgagatcc tttttttctg   3660
cgcgtaatct gctgcttgca aacaaaaaaa ccaccgctac cagcggtggt ttgtttgccg   3720
gatcaagagc taccaactct ttttccgaag gtaactggct tcagcagagc gcagatacca   3780
aatactgtcc ttctagtgta gccgtagtta ggccaccact tcaagaactc tgtagcaccg   3840
cctacatacc tcgctctgct aatcctgtta ccagtggctg ctgccagtgg cgataagtcg   3900
tgtcttaccg ggttggactc aagacgatag ttaccggata aggcgcagcg gtcgggctga   3960
acggggggtt cgtgcacaca gcccagcttg gagcgaacga cctacaccga actgagatac   4020
ctacagcgtg agctatgaga aagcgccacg cttcccgaag ggagaaaggc ggacaggtat   4080
ccggtaagcg gcagggtcgg aacaggagag cgcacgaggg agcttccagg gggaaacgcc   4140
tggtatcttt atagtcctgt cgggtttcgc cacctctgac ttgagcgtcg atttttgtga   4200
tgctcgtcag gggggcggag cctatggaaa aacgccagca acgcggcctt tttacggttc   4260
ctggcctttt gctggccttt tgctcacatg ttctttcctg cgttatcccc tgattctgtg   4320
```

```
gataaccgta ttaccgcctt tgagtgagct gataccgctc gccgcagccg aacgaccgag   4380

cgcagcgagt cagtgagcga ggaagcggaa gagcgcctga tgcggtattt tctccttacg   4440

catctgtgcg gtatttcaca ccgcatatat ggtgcactct cagtacaatc tgctctgatg   4500

ccgcatagtt aagccagtat acactccgct atcgctacgt gactgggtca tggctgcgcc   4560

ccgacacccg ccaacacccg ctgacgcgcc ctgacgggct tgtctgctcc cggcatccgc   4620

ttacagacaa gctgtgaccg tctccgggag ctgcatgtgt cagaggtttt caccgtcatc   4680

accgaaacgc gcgaggcagc tggcacgaca ggtttcccga ctggaatgtg cctgtcaaat   4740

ggacgaagca gggattctgc aaaccctatg ctactccgtc aagccgtcaa ttgtctgatt   4800

cgttaccaat tatgacaact tgacggctac atcattcact ttttcttcac aaccggcacg   4860

gaactcgctc gggctggccc cggtgcattt tttaaatacc cgcgagaaat agagttgatc   4920

gtcaaaacca acattgcgac cgacggtggc gataggcatc cgggtggtgc tcaaaagcag   4980

cttcgcctgg ctgatacgtt ggtcctcgcg ccagcttaag acgctaatcc ctaactgctg   5040

gcggaaaaga tgtgacagac gcgacggcga caagcaaaca tgctgtgcga cgctggcgat   5100

atcaaaattg ctgtctgcca ggtgatcgct gatgtactga caagcctcgc gtacccgatt   5160

atccatcggt ggatggagcg actcgttaat cgcttccatg cgccgcagta acaattgctc   5220

aagcagattt atcgccagca gctccgaata gcgcccttcc ccttgcccgg cgttaatgat   5280

ttgcccaaac aggtcgctga aatgcggctg gtgcgcttca tccgggcgaa agaaccccgt   5340

attggcaaat attgacggcc agttaagcca ttcatgccag taggcgcgcg gacgaaagta   5400

aacccactgg tgataccatt cgcgagcctc cggatgacga ccgtagtgat gaatctctcc   5460

tggcgggaac agcaaaatat cacccggtcg gcaaacaaat tctcgtccct gatttttcac   5520

cacccccctga ccgcgaatgg tgagattgag aatataacct ttcattccca gcggtcggtc   5580

gataaaaaaa tcgagataac cgttggcctc aatcggcgtt aaacccgcca ccagatgggc   5640

attaaacgag tatcccggca gcaggggatc attttgcgct tcagccatac ttttcatact   5700

cccgccattc agagaag                                                  5717
```

<210> SEQ ID NO 22
<211> LENGTH: 11
<212> TYPE: PRT
<213> ORGANISM: Artificial Sequence
<220> FEATURE:
<223> OTHER INFORMATION: 6His

<400> SEQUENCE: 22

```
Met Thr Gln Arg Ala His His His His His His
1               5                   10
```

<210> SEQ ID NO 23
<211> LENGTH: 538
<212> TYPE: PRT
<213> ORGANISM: Arabidopsis thaliana

<400> SEQUENCE: 23

```
Met Ala Glu Lys Leu Ser Asp Gly Ser Ser Ile Ile Ser Val His Pro
1               5                   10                  15

Arg Pro Ser Lys Gly Phe Ser Ser Lys Leu Leu Asp Leu Leu Glu Arg
            20                  25                  30

Leu Val Val Lys Leu Met His Asp Ala Ser Leu Pro Leu His Tyr Leu
        35                  40                  45

Ser Gly Asn Phe Ala Pro Ile Arg Asp Glu Thr Pro Pro Val Lys Asp
```

```
    50                  55                  60

Leu Pro Val His Gly Phe Leu Pro Glu Cys Leu Asn Gly Glu Phe Val
65                  70                  75                  80

Arg Val Gly Pro Asn Pro Lys Phe Asp Ala Val Ala Gly Tyr His Trp
                85                  90                  95

Phe Asp Gly Asp Gly Met Ile His Gly Val Arg Ile Lys Asp Gly Lys
            100                 105                 110

Ala Thr Tyr Val Ser Arg Tyr Val Lys Thr Ser Arg Leu Lys Gln Glu
        115                 120                 125

Glu Phe Phe Gly Ala Ala Lys Phe Met Lys Ile Gly Asp Leu Lys Gly
    130                 135                 140

Phe Phe Gly Leu Leu Met Val Asn Val Gln Gln Leu Arg Thr Lys Leu
145                 150                 155                 160

Lys Ile Leu Asp Asn Thr Tyr Gly Asn Gly Thr Ala Asn Thr Ala Leu
                165                 170                 175

Val Tyr His His Gly Lys Leu Leu Ala Leu Gln Glu Ala Asp Lys Pro
            180                 185                 190

Tyr Val Ile Lys Val Leu Glu Asp Gly Asp Leu Gln Thr Leu Gly Ile
        195                 200                 205

Ile Asp Tyr Asp Lys Arg Leu Thr His Ser Phe Thr Ala His Pro Lys
    210                 215                 220

Val Asp Pro Val Thr Gly Glu Met Phe Thr Phe Gly Tyr Ser His Thr
225                 230                 235                 240

Pro Pro Tyr Leu Thr Tyr Arg Val Ile Ser Lys Asp Gly Ile Met His
                245                 250                 255

Asp Pro Val Pro Ile Thr Ile Ser Glu Pro Ile Met Met His Asp Phe
            260                 265                 270

Ala Ile Thr Glu Thr Tyr Ala Ile Phe Met Asp Leu Pro Met His Phe
        275                 280                 285

Arg Pro Lys Glu Met Val Lys Glu Lys Lys Met Ile Tyr Ser Phe Asp
    290                 295                 300

Pro Thr Lys Lys Ala Arg Phe Gly Val Leu Pro Arg Tyr Ala Lys Asp
305                 310                 315                 320

Glu Leu Met Ile Arg Trp Phe Glu Leu Pro Asn Cys Phe Ile Phe His
                325                 330                 335

Asn Ala Asn Ala Trp Glu Glu Glu Asp Glu Val Val Leu Ile Thr Cys
            340                 345                 350

Arg Leu Glu Asn Pro Asp Leu Asp Met Val Ser Gly Lys Val Lys Glu
        355                 360                 365

Lys Leu Glu Asn Phe Gly Asn Glu Leu Tyr Glu Met Arg Phe Asn Met
    370                 375                 380

Lys Thr Gly Ser Ala Ser Gln Lys Lys Leu Ser Ala Ser Ala Val Asp
385                 390                 395                 400

Phe Pro Arg Ile Asn Glu Cys Tyr Thr Gly Lys Lys Gln Arg Tyr Val
                405                 410                 415

Tyr Gly Thr Ile Leu Asp Ser Ile Ala Lys Val Thr Gly Ile Ile Lys
            420                 425                 430

Phe Asp Leu His Ala Glu Ala Glu Thr Gly Lys Arg Met Leu Glu Val
        435                 440                 445

Gly Gly Asn Ile Lys Gly Ile Tyr Asp Leu Gly Glu Gly Arg Tyr Gly
    450                 455                 460

Ser Glu Ala Ile Tyr Val Pro Arg Glu Thr Ala Glu Glu Asp Asp Gly
465                 470                 475                 480
```

```
Tyr Leu Ile Phe Phe Val His Asp Glu Asn Thr Gly Lys Ser Cys Val
                485                 490                 495

Thr Val Ile Asp Ala Lys Thr Met Ser Ala Glu Pro Val Ala Val Val
            500                 505                 510

Glu Leu Pro His Arg Val Pro Tyr Gly Phe His Ala Leu Phe Val Thr
        515                 520                 525

Glu Glu Gln Leu Gln Glu Gln Thr Leu Ile
    530                 535
```

<210> SEQ ID NO 24
<211> LENGTH: 5732
<212> TYPE: DNA
<213> ORGANISM: Artificial Sequence
<220> FEATURE:
<223> OTHER INFORMATION: Nucleotide Sequence of pGT1070

<400> SEQUENCE: 24

```
aaaccaattg tccatattgc atcagacatt gccgtcactg cgtcttttac tggctcttct     60
cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt    180
atttgcacgg cgtcacactt tgctatgcca tagcattttt atccataaga ttagctgatc    240
ctacctgacg ctttttatcg caactctcta ctgtttctcc atacccgttt aaataatttt    300
gtttaacttt aagaaggaga tatacccatg acacagaggg cccaccatca ccatcaccat    360
tccatgggta tgcagggtga agatgcacag cgtaccggta atattgttgc agttaaaccg    420
aaaccgagcc agggtctgac cagcaaagca attgattggc tggaatggct gtttgtgaaa    480
atgatgcatg atagcaaaca gccgctgcat tatctgagcg gtaattttgc accggttgat    540
gaaacccctc cgctgaaaga tctgccggtt accggtcatc tgccggaatg tctgaatggt    600
gaatttgttc gtgttggtcc gaatccgaaa tttgcaagca ttgcaggtta tcattggttt    660
gatggtgatg gtatgattca tggcatgcgc attaaagatg gtaaagcaac ctatgttagc    720
cgttatgttc agaccagccg tctgaaacaa gaggaattct ttggtcgtgc catgttcatg    780
aaaatcggtg atctgaaagg tatgtttggt ctgctgatgg ttaatatgca gatgctgcgt    840
gcaaaactga aagttctgga tattagctat ggtattggca ccgcaaatac cgcactggtt    900
tatcatcatg gtaaactgct ggcactgagc gaagcagata aaccgtatgc aattaaagtg    960
ctggaagatg gtgatctgca gaccattggc ctgctggatt atgataaacg tctggcacat   1020
agctttaccg cacatccgaa agttgatccg tttaccggtg agatgtttac ctttggttat   1080
agccataccc ctccgtatgt tacctatcgt gttattagca aagatggtgc aatgaatgat   1140
ccggttccga ttaccgttag cggtccgatc atgatgcacg attttgcaat taccgaaaac   1200
tacgccatct ttatggatct gccgctgtat ttcaaaccga aagaaatggt gaaagacaag   1260
aaattcatct ttagcttcga tgccacccag aaagcacgtt ttggtattct gcctcgttat   1320
gccaagaatg agctgctgat taaatggttt gaactgccga actgcttcat ctttcataat   1380
gcaaatgcat gggaagaggg tgatgaagtt gttctgatta cctgtcgtct ggaaaatccg   1440
gatctggata tggtgaatag caccgttaaa gaacgtctgg acaactttaa gaacgagctg   1500
tatgaaatgc gcttcaatct gcagaatggt ctggcaagcc agaaaaaact gagcgttagc   1560
gcagttgatt ttccgcgtgt taatgaaagc tataccaccc gtaaacagcg ttatgtttat   1620
ggcaccaccc tggataagat tgccaaagtt accggcatca tcaaattcga tctgcatgcc   1680
```

```
gaaccggaaa ccggtaaaga gaagctggaa ctgggtggta atgtgaaagg catttttgat   1740
ctgggtccgg gtcgttttgg ttcagaagca gtttttgttc cgcgtcatcc gggtattacc   1800
agcgaagagg atgatggtta tctgatcttc tttgtgcacg atgaaaacac cggcaaaagc   1860
gcagttaatg ttattgatgc aaaaaccatg agccctgatc cggtggcagt tgtggaactg   1920
cctaaacgtg ttccgtatgg ttttcatgca ttttttgtta ccgaagatca gctgcaagaa   1980
caggccaaag tttaaggatc cggctgctaa caaagcccga aaggaagctg agttggctgc   2040
tgccaccgct gagcaataac tagcataacc ccttggggcc tctaaacggg tcttgagggg   2100
ttttttgctg aaaggaggaa ctatatccgg ccggatatcc acaggacggg tgtggtcgcc   2160
atgatcgcgt agtcgatagt ggctccaagt agcgaagcga gcaggactgg gcggcggcca   2220
aagcggtcgg acagtgctcc gagaacgggt gcgcatagaa attgcatcaa cgcatatagc   2280
gctagcagca cgccatagtg actggcgatg ctgtcggaat ggacgatatc ccgcaagagg   2340
cccggcagta ccggcataac caagcctatg cctacagcat ccagggtgac ggtgccgagg   2400
atgacgatga gcgcattgtt agatttcata cacggtgcct gactgcgtta gcaatttaac   2460
tgtgataaac taccgcatta aagcttatcg atgataagct gtcaaacatg agaattcttg   2520
aagacgaaag ggcctcgtga tacgcctatt tttataggtt aatgtcatgc atgagacaat   2580
aaccctgata aatgcttcaa taatattgaa aaaggaagag tatgagtatt caacatttcc   2640
gtgtcgccct tattcccttt tttgcggcat tttgccttcc tgtttttgct cacccagaaa   2700
cgctggtgaa agtaaaagat gctgaagatc agttgggtgc acgagtgggt tacatcgaac   2760
tggatctcaa cagcggtaag atccttgaga gttttcgccc cgaagaacgt tttccaatga   2820
tgagcacttt taaagttctg ctatgtggcg cggtattatc ccgtgttgac gccgggcaag   2880
agcaactcgg tcgccgcata cactattctc agaatgactt ggttgacgcg tcaccagtca   2940
cagaaaagca tcttacggat ggcatgacag taagagaatt atgcagtgct gccataacca   3000
tgagtgataa cactgcggcc aacttacttc tgacaacgat cggaggaccg aaggagctaa   3060
ccgctttttt gcacaacatg ggggatcatg taactcgcct tgatcgttgg gaaccggagc   3120
tgaatgaagc cataccaaac gacgagcgtg acaccacgat gcctgcagca atggcaacaa   3180
cgttgcgcaa actattaact ggcgaactac ttactctagc ttcccggcaa caattaatag   3240
actggatgga ggcggataaa gttgcaggac cacttctgcg ctcggccctt ccggctggct   3300
ggtttattgc tgataaatct ggagccggtg agcgtgggtc tcgcggtatc attgcagcac   3360
tggggccaga tggtaagccc tcccgtatcg tagttatcta cacgacgggg agtcaggcaa   3420
ctatggatga acgaaataga cagatcgctg agataggtgc ctcactgatt aagcattggt   3480
aactgtcaga ccaagtttac tcatatatac tttagattga tttaaaactt catttttaat   3540
ttaaaaggat ctaggtgaag atcctttttg ataatctcat gcatgaccaa aatcccttaa   3600
cgtgagtttt cgttccactg agcgtcagac cccgtagaaa agatcaaagg atcttcttga   3660
gatccttttt ttctgcgcgt aatctgctgc ttgcaaacaa aaaaaccacc gctaccagcg   3720
gtggtttgtt tgccggatca agagctacca actctttttc cgaaggtaac tggcttcagc   3780
agagcgcaga taccaaatac tgtccttcta gtgtagccgt agttaggcca ccacttcaag   3840
aactctgtag caccgcctac atacctcgct ctgctaatcc tgttaccagt ggctgctgcc   3900
agtggcgata agtcgtgtct taccgggttg gactcaagac gatagttacc ggataaggcg   3960
cagcggtcgg gctgaacggg gggttcgtgc acacagccca gcttggagcg aacgacctac   4020
accgaactga gatacctaca gcgtgagcta tgagaaagcg ccacgcttcc cgaagggaga   4080
```

```
aaggcggaca ggtatccggt aagcggcagg gtcggaacag gagagcgcac gagggagctt   4140
ccagggggaa acgcctggta tctttatagt cctgtcgggt ttcgccacct ctgacttgag   4200
cgtcgatttt tgtgatgctc gtcagggggg cggagcctat ggaaaaacgc cagcaacgcg   4260
gcctttttac ggttcctggc cttttgctgg ccttttgctc acatgttctt tcctgcgtta   4320
tcccctgatt ctgtggataa ccgtattacc gcctttgagt gagctgatac cgctcgccgc   4380
agccgaacga ccgagcgcag cgagtcagtg agcgaggaag cggaagagcg cctgatgcgg   4440
tattttctcc ttacgcatct gtgcggtatt tcacaccgca tatatggtgc actctcagta   4500
caatctgctc tgatgccgca tagttaagcc agtatacact ccgctatcgc tacgtgactg   4560
ggtcatggct gcgccccgac acccgccaac acccgctgac gcgccctgac gggcttgtct   4620
gctcccggca tccgcttaca gacaagctgt gaccgtctcc gggagctgca tgtgtcagag   4680
gttttcaccg tcatcaccga aacgcgcgag gcagctggca cgacaggttt cccgactgga   4740
atgtgcctgt caaatggacg aagcagggat tctgcaaacc ctatgctact ccgtcaagcc   4800
gtcaattgtc tgattcgtta ccaattatga caacttgacg gctacatcat tcactttttc   4860
ttcacaaccg gcacggaact cgctcgggct ggccccggtg catttttttaa atacccgcga   4920
gaaatagagt tgatcgtcaa aaccaacatt gcgaccgacg gtggcgatag gcatccgggt   4980
ggtgctcaaa agcagcttcg cctggctgat acgttggtcc tcgcgccagc ttaagacgct   5040
aatccctaac tgctggcgga aaagatgtga cagacgcgac ggcgacaagc aaacatgctg   5100
tgcgacgctg gcgatatcaa aattgctgtc tgccaggtga tcgctgatgt actgacaagc   5160
ctcgcgtacc cgattatcca tcggtggatg gagcgactcg ttaatcgctt ccatgcgccg   5220
cagtaacaat tgctcaagca gatttatcgc cagcagctcc gaatagcgcc cttccccttg   5280
cccggcgtta atgatttgcc caaacaggtc gctgaaatgc ggctggtgcg cttcatccgg   5340
gcgaaagaac cccgtattgg caaatattga cggccagtta agccattcat gccagtaggc   5400
gcgcggacga aagtaaaccc actggtgata ccattcgcga gcctccggat gacgaccgta   5460
gtgatgaatc tctcctggcg ggaacagcaa aatatcaccc ggtcggcaaa caaattctcg   5520
tccctgattt ttcaccaccc cctgaccgcg aatggtgaga ttgagaatat aacctttcat   5580
tcccagcggt cggtcgataa aaaaatcgag ataaccgttg gcctcaatcg gcgttaaacc   5640
cgccaccaga tgggcattaa acgagtatcc cggcagcagg ggatcatttt gcgcttcagc   5700
catacttttc atactcccgc cattcagaga ag                                 5732
```

<210> SEQ ID NO 25
<211> LENGTH: 543
<212> TYPE: PRT
<213> ORGANISM: Osmanthus fragrans

<400> SEQUENCE: 25

```
Met Gly Met Gln Gly Glu Asp Ala Gln Arg Thr Gly Asn Ile Val Ala
1               5                   10                  15

Val Lys Pro Lys Pro Ser Gln Gly Leu Thr Ser Lys Ala Ile Asp Trp
            20                  25                  30

Leu Glu Trp Leu Phe Val Lys Met Met His Asp Ser Lys Gln Pro Leu
        35                  40                  45

His Tyr Leu Ser Gly Asn Phe Ala Pro Val Asp Glu Thr Pro Pro Leu
    50                  55                  60

Lys Asp Leu Pro Val Thr Gly His Leu Pro Glu Cys Leu Asn Gly Glu
65                  70                  75                  80
```

```
Phe Val Arg Val Gly Pro Asn Pro Lys Phe Ala Ser Ile Ala Gly Tyr
                85                  90                  95

His Trp Phe Asp Gly Asp Gly Met Ile His Gly Met Arg Ile Lys Asp
            100                 105                 110

Gly Lys Ala Thr Tyr Val Ser Arg Tyr Val Gln Thr Ser Arg Leu Lys
        115                 120                 125

Gln Glu Glu Phe Phe Gly Arg Ala Met Phe Met Lys Ile Gly Asp Leu
    130                 135                 140

Lys Gly Met Phe Gly Leu Leu Met Val Asn Met Gln Met Leu Arg Ala
145                 150                 155                 160

Lys Leu Lys Val Leu Asp Ile Ser Tyr Gly Ile Gly Thr Ala Asn Thr
                165                 170                 175

Ala Leu Val Tyr His His Gly Lys Leu Leu Ala Leu Ser Glu Ala Asp
            180                 185                 190

Lys Pro Tyr Ala Ile Lys Val Leu Glu Asp Gly Asp Leu Gln Thr Ile
        195                 200                 205

Gly Leu Leu Asp Tyr Asp Lys Arg Leu Ala His Ser Phe Thr Ala His
    210                 215                 220

Pro Lys Val Asp Pro Phe Thr Gly Glu Met Phe Thr Phe Gly Tyr Ser
225                 230                 235                 240

His Thr Pro Pro Tyr Val Thr Tyr Arg Val Ile Ser Lys Asp Gly Ala
                245                 250                 255

Met Asn Asp Pro Val Pro Ile Thr Val Ser Gly Pro Ile Met Met His
            260                 265                 270

Asp Phe Ala Ile Thr Glu Asn Tyr Ala Ile Phe Met Asp Leu Pro Leu
        275                 280                 285

Tyr Phe Lys Pro Lys Glu Met Val Lys Asp Lys Lys Phe Ile Phe Ser
    290                 295                 300

Phe Asp Ala Thr Gln Lys Ala Arg Phe Gly Ile Leu Pro Arg Tyr Ala
305                 310                 315                 320

Lys Asn Glu Leu Leu Ile Lys Trp Phe Glu Leu Pro Asn Cys Phe Ile
                325                 330                 335

Phe His Asn Ala Asn Ala Trp Glu Glu Gly Asp Glu Val Val Leu Ile
            340                 345                 350

Thr Cys Arg Leu Glu Asn Pro Asp Leu Asp Met Val Asn Ser Thr Val
        355                 360                 365

Lys Glu Arg Leu Asp Asn Phe Lys Asn Glu Leu Tyr Glu Met Arg Phe
    370                 375                 380

Asn Leu Gln Asn Gly Leu Ala Ser Gln Lys Lys Leu Ser Val Ser Ala
385                 390                 395                 400

Val Asp Phe Pro Arg Val Asn Glu Ser Tyr Thr Thr Arg Lys Gln Arg
                405                 410                 415

Tyr Val Tyr Gly Thr Thr Leu Asp Lys Ile Ala Lys Val Thr Gly Ile
            420                 425                 430

Ile Lys Phe Asp Leu His Ala Glu Pro Glu Thr Gly Lys Glu Lys Leu
        435                 440                 445

Glu Leu Gly Gly Asn Val Lys Gly Ile Phe Asp Leu Gly Pro Gly Arg
    450                 455                 460

Phe Gly Ser Glu Ala Val Phe Val Pro Arg His Pro Gly Ile Thr Ser
465                 470                 475                 480

Glu Glu Asp Asp Gly Tyr Leu Ile Phe Phe Val His Asp Glu Asn Thr
                485                 490                 495
```

```
Gly Lys Ser Ala Val Asn Val Ile Asp Ala Lys Thr Met Ser Pro Asp
            500                 505                 510

Pro Val Ala Val Val Glu Leu Pro Lys Arg Val Pro Tyr Gly Phe His
        515                 520                 525

Ala Phe Phe Val Thr Glu Asp Gln Leu Gln Glu Gln Ala Lys Val
    530                 535                 540


<210> SEQ ID NO 26
<211> LENGTH: 480
<212> TYPE: PRT
<213> ORGANISM: Artificial Sequence
<220> FEATURE:
<223> OTHER INFORMATION: AtECmut1

<400> SEQUENCE: 26

Met Ala Ser Gly Gly Gly Ser Ser Gly Ser Glu Ser Cys Val Ala Val
1               5                   10                  15

Arg Glu Asp Phe Ala Asp Glu Glu Asp Phe Val Lys Ala Gly Gly Ser
            20                  25                  30

Glu Ile Leu Phe Val Gln Met Gln Gln Asn Lys Asp Met Asp Glu Gln
        35                  40                  45

Ser Lys Leu Val Asp Lys Leu Pro Pro Ile Ser Ile Gly Asp Gly Ala
    50                  55                  60

Leu Asp Leu Val Val Ile Gly Cys Gly Pro Ala Gly Leu Ala Leu Ala
65                  70                  75                  80

Ala Glu Ser Ala Lys Leu Gly Leu Lys Val Gly Leu Ile Gly Pro Asp
                85                  90                  95

Leu Pro Phe Thr Asn Asn Tyr Gly Val Trp Glu Asp Glu Phe Asn Asp
            100                 105                 110

Leu Gly Leu Gln Lys Cys Ile Glu His Val Trp Arg Glu Thr Ile Val
        115                 120                 125

Tyr Leu Asp Asp Asp Lys Pro Ile Thr Ile Gly Arg Ala Tyr Gly Arg
    130                 135                 140

Val Ser Arg Arg Leu Leu His Glu Glu Leu Leu Arg Arg Cys Val Glu
145                 150                 155                 160

Ser Gly Val Ser Tyr Leu Ser Ser Lys Val Asp Ser Ile Thr Glu Ala
                165                 170                 175

Ser Asp Gly Leu Arg Leu Val Ala Cys Asp Asp Asn Asn Val Ile Pro
            180                 185                 190

Cys Arg Leu Ala Thr Val Ala Ser Gly Ala Ala Ser Gly Lys Leu Leu
        195                 200                 205

Gln Tyr Glu Val Gly Gly Pro Arg Val Cys Val Gln Thr Ala Tyr Gly
    210                 215                 220

Val Glu Val Glu Val Glu Asn Ser Pro Tyr Asp Pro Asp Gln Met Val
225                 230                 235                 240

Phe Met Asp Tyr Arg Asp Tyr Thr Asn Glu Lys Val Arg Ser Leu Glu
                245                 250                 255

Ala Glu Tyr Pro Thr Phe Leu Tyr Ala Met Pro Met Thr Lys Ser Arg
            260                 265                 270

Leu Phe Phe Glu Glu Thr Cys Leu Ala Ser Lys Asp Val Met Pro Phe
        275                 280                 285

Asp Leu Leu Lys Thr Lys Leu Met Leu Arg Leu Asp Thr Leu Gly Ile
    290                 295                 300

Arg Ile Leu Lys Thr Tyr Glu Glu Glu Trp Ser Tyr Ile Pro Val Gly
305                 310                 315                 320
```

```
Gly Ser Leu Pro Asn Thr Glu Gln Lys Asn Leu Ala Phe Gly Ala Ala
                325                 330                 335

Ala Ser Met Val His Pro Ala Thr Gly Tyr Ser Val Val Arg Ser Leu
            340                 345                 350

Ser Glu Ala Pro Lys Tyr Ala Ser Val Ile Ala Glu Ile Leu Arg Glu
        355                 360                 365

Glu Thr Thr Lys Gln Ile Asn Ser Asn Ile Ser Arg Gln Ala Trp Asp
    370                 375                 380

Thr Leu Trp Pro Pro Glu Arg Lys Arg Gln Arg Ala Phe Phe Leu Phe
385                 390                 395                 400

Gly Leu Ala His Ile Val Gln Phe Asp Thr Glu Gly Ile Arg Ser Phe
                405                 410                 415

Phe Arg Thr Phe Phe Arg Leu Pro Lys Trp Met Trp Gln Gly Phe Leu
            420                 425                 430

Gly Ser Thr Leu Thr Ser Gly Asp Leu Val Leu Phe Ala Leu Tyr Met
        435                 440                 445

Phe Val Ile Ser Pro Asn Asn Leu Arg Lys Gly Leu Ile Asn His Leu
    450                 455                 460

Ile Ser Asp Pro Thr Gly Ala Thr Met Ile Lys Thr Tyr Leu Lys Val
465                 470                 475                 480


<210> SEQ ID NO 27
<211> LENGTH: 9599
<212> TYPE: DNA
<213> ORGANISM: Artificial Sequence
<220> FEATURE:
<223> OTHER INFORMATION: pAC-BETAipi

<400> SEQUENCE: 27

gagtgtatac tggcttacta tgttggcact gatgagggtg tcagtgaagt gcttcatgtg      60

gcaggagaaa aaaggctgca ccggtgcgtc agcagaatat gtgatacagg atatattccg     120

cttcctcgct cactgactcg ctacgctcgg tcgttcgact gcggcgagcg gaaatggctt     180

acgaacgggg cggagatttc ctggaagatg ccaggaagat acttaacagg gaagtgagag     240

ggccgcggca aagccgtttt tccataggct ccgcccccct gacaagcatc acgaaatctg     300

acgctcaaat cagtggtggc gaaacccgac aggactataa agataccagg cgtttccccc     360

tggcggctcc ctcgtgcgct ctcctgttcc tgcctttcgg tttaccggtg tcattccgct     420

gttatggccg cgtttgtctc attccacgcc tgacactcag ttccgggtag gcagttcgct     480

ccaagctgga ctgtatgcac gaaccccccg ttcagtccga ccgctgcgcc ttatccggta     540

actatcgtct tgagtccaac ccggaaagac atgcaaaagc accactggca gcagccactg     600

gtaattgatt tagaggagtt agtcttgaag tcatgcgccg gttaaggcta aactgaaagg     660

acaagttttg gtgactgcgc tcctccaagc cagttacctc ggttcaaaga gttggtagct     720

cagagaacct tcgaaaaacc gccctgcaag gcggtttttt cgttttcaga gcaagagatt     780

acgcgcagac caaaacgatc tcaagaagat catcttatta atcagataaa atatttctag     840

atttcagtgc aatttatctc ttcaaatgta gcacctgaag tcagccccat acgatataag     900

ttgtaattct catgtttgac agcttatcat cgataagctt taatgcggta gtttatcaca     960

gttaaattgc taacgcagtc aggcaccgtg tatgaaatct aacaatgcgc tcatcgtcat    1020

cctcggcacc gtcaccctgg atgctgtagg cataggcttg gttatgccgg tactgccggg    1080

cctcttgcgg gatatcgtcc attccgacag catcgccagt cactatggcg tgctgctagc    1140

gctatatgcg ttgatgcaat ttctatgcgc acccgttctc ggagcactgt ccgaccgctt    1200
```

```
tggccgccgc ccagtcctgc tcgcttcgct acttggagcc actatcgact acgcgatcat   1260
ggcgaccaca cccgtcctgt ggatctaaag gcacagcgtc tcatgcttcg cacaatgtaa   1320
aactgcttca gaacctggcg agagctatcc gcgcggtcta cggttaactg atactaaaag   1380
acaattcagc gggtaacctt gcaatggtga gtggcagtaa agcgggcgtt tcgcctcatc   1440
gcgaaataga agtaatgaga caatccattg acgatcacct ggctggcctg ttacctgaaa   1500
ccgacagcca ggatatcgtc agccttgcga tgcgtgaagg cgtcatggca cccggtaaac   1560
ggatccgtcc gctgctgatg ctgctggccg cccgcgacct ccgctaccag ggcagtatgc   1620
ctacgctgct cgatctcgcc tgcgccgttg aactgaccca taccgcgtcg ctgatgctcg   1680
acgacatgcc ctgcatggac aacgccgagc tgcgccgcgg tcagcccact acccacaaaa   1740
aatttggtga gagcgtggcg atccttgcct ccgttgggct gctctctaaa gcctttggtc   1800
tgatcgccgc caccggcgat ctgccggggg agaggcgtgc ccaggcggtc aacgagctct   1860
ctaccgccgt gggcgtgcag ggcctggtac tggggcagtt tcgcgatctt aacgatgccg   1920
ccctcgaccg tacccctgac gctatcctca gcaccaacca cctcaagacc ggcattctgt   1980
tcagcgcgat gctgcagatc gtcgccattg cttccgcctc gtcgccgagc acgcgagaga   2040
cgctgcacgc cttcgccctc gacttcggcc aggcgtttca actgctggac gatctgcgtg   2100
acgatcaccc ggaaaccggt aaagatcgca ataaggacgc gggaaaatcg acgctggtca   2160
accggctggg cgcagacgcg gcccggcaaa agctgcgcga gcatattgat tccgccgaca   2220
aacacctcac ttttgcctgt ccgcagggcg gcgccatccg acagtttatg catctgtggt   2280
ttggccatca ccttgccgac tggtcaccgg tcatgaaaat cgcctgatac cgcccttttg   2340
ggttcaagca gtacataacg atggaaccac attacaggag tagtgatgaa tgaaggacga   2400
gcgccttgtt cagcgtaaga acgatcatct ggatatcgtt ctcgaccccc gtcgcgccgt   2460
aactcaggct agcgcaggtt ttgagcgctg gcgctttacc cactgcgccc tgccagagct   2520
gaattttagc gacatcacgc tggaaaccac cttcctgaat cggcagctac aggctccgct   2580
gctgatcagc tccatgaccg gcggcgttga gcgctcgcgc catatcaacc gccacctcgc   2640
cgaggcggcg caggtgctaa aaattgcgat gggggtgggc tcccagcgcg tcgccattga   2700
gagcgacgcg ggcttagggc tggataaaac cctgcggcag ctggctccgg acgtgccgct   2760
gctggcgaac ctcggcgcgg cgcagctgac cggcagaaaa ggtattgatt acgcccgacg   2820
ggccgtggag atgatcgagg cggatgcgct gattgtgcac ctaaacccgc tgcaggaggc   2880
gctacagccc ggcggcgatc gcgactggcg cggacggctg gcggctattg aaactctggt   2940
ccgcgagctg cccgttccgc tggtggtgaa agaggtggga gccggtatct cccgaaccgt   3000
ggccgggcag ctgatcgatg ccggcgttac cgtgattgac gtcgcgggcg cgggcggcac   3060
cagctgggcc gccgttgaag gcgagcgggc ggccaccgag cagcagcgca gcgtggccaa   3120
cgtctttgcc gactggggga tccccaccgc tgaggcgctg gttgacattg ccgaggcctg   3180
gccgcagatg ccccttattg cctcgggcgg gattaaaaac ggcgtcgacg cggcgaaagc   3240
gctgcggctc ggcgcgtgca tggtagggca ggccgccgcc gtgctcggca gcgcaggcgt   3300
ctccacggag aaggtgatcg atcacttcaa cgtgattatt gagcagctgc gggtggcctg   3360
cttctgcacc ggcagccgca gcctgagcga tctaaagcag gctgatatcc gctatgtgcg   3420
ggatacgcca tgagccattt tgccattgtg gcaccgccgc tctacagtca tgcggtggcg   3480
ctgcatgccc tggcgctgga gatggcccaa cgcggccacc ggtaattgat ttagaggagt   3540
```

-continued

```
tagtcttgaa gtcatgcgcc ggttaaggct aaactgaaag gacaagtttt ggtgactgcg   3600
ctcctccaag ccagttacct cggttcaaag agttggtagc tcagagaacc ttcgaaaaac   3660
cgccctgcaa ggcggttttt tcgttttcag agcaagagat tacgcgcaga ccaaaacgat   3720
ctcaagaaga tcatcttatt aatcagataa aatatttcta gatttcagtg caatttatct   3780
cttcaaatgt agcacctgaa gtcagcccca tacgatataa gttgtaattc tcatgtttga   3840
cagcttatca tcgataagct cgaccagccg cgctacgttg ccgaggctaa tctggtgatc   3900
acccacggcg gtctcaatac cgtactggat gcgctggctg ccgcgacgcc ggtgctggcg   3960
gtgccactct ctttcgacca gcccgccgtg gctgcccggc tggtctataa cgggctgggt   4020
cgccgggtat cgcgctttgc cagacagcag acgctggcgg atgagattgc ccaactgctg   4080
ggggatgaga cgctgcatca gcgtctggcg acggcccgcc agcagcttaa cgacgccggg   4140
ggcacgcccc gtgcggcgac cctgattgaa caggccatag cagggagtga gagcgtatcg   4200
tgagggatct gattttagtc ggcggcggcc tggccaacgg gctgatcgcc tggcgtctgc   4260
gccagcgcta cccgcagctt aacctgctgc tgatcgaggc cggggagcag cccggcggga   4320
accatacctg gtcattccat gaagacgatc tgactcccgg gcagcacgcc tggctggccc   4380
cgctggtggc ccacgcctgg ccgggctatg aggtgcagtt tcccgatctt cgccgtcgcc   4440
tcgcgcgcgg ctactactcc attacctcag agcgctttgc cgaggccctg catcaggcgc   4500
tgggggagaa catctggcta aactgttcgg tgagcgaggt gttacccaat agcgtgcgcc   4560
ttgccaacgg tgaggcgctg cttgccggag cggtgattga cggacgcggc gtgaccgcca   4620
gttcggcgat gcaaaccggc tatcagctct ttcttggtca gcagtggcgg ctgacacagc   4680
cccacggcct gaccgtaccg atcctgatgg atgccacggt ggcgcagcag cagggctatc   4740
gctttgtcta cacgctgccg ctctccgccg acacgctgct gatcgaggat acgcgctacg   4800
ccaatgtccc gcagcgtgat gataatgccc tacgccagac ggttaccgac tatgctcaca   4860
gcaaagggtg gcagctggcc cagcttgaac gcgaggagac cggctgtctg ccgattaccc   4920
tggcgggtga catccaggct ctgtgggccg atgcgccggg cgtgccgcgc tcgggaatgc   4980
gggctgggct atttcaccct accactggct attcgctgcc gctggcggtg gcccttgccg   5040
acgcgattgc cgacagcccg cggctgggca gcgttccgct ctatcagctc acccggcagt   5100
ttgccgaacg ccactggcgc aggcagggat tcttccgcct gctgaaccgg atgcttttcc   5160
tggccgggcg cgaggagaac cgctggcggg tgatgcagcg cttttatggg ctgccggagc   5220
ccaccgtaga gcgcttttac gccggtcggc tctctctctt tgataaggcc cgcattttga   5280
cgggcaagcc accggttccg ctgggcgaag cctggcgggc ggcgctgaac cattttcctg   5340
acagacgaga taaaggatga aaaaaaccgt tgtgattggc gcaggctttg gtggcctggc   5400
gctggcgatt cgcctgcagg cggcagggat cccaaccgta ctgctggagc agcgggacaa   5460
gcccggcggt cgggcctacg tctggcatga ccagggcttt acctttgacg ccgggccgac   5520
ggtgatcacc gatcctaccg cgcttgaggc gctgttcacc ctggccggca ggcgcatgga   5580
ggattacgtc aggctgctgc cggtaaaacc cttctaccga ctctgctggg agtccgggaa   5640
gaccctcgac tatgctaacg acagcgccga gcttgaggcg cagattaccc agttcaaccc   5700
ccgcgacgtc gagggctacc ggcgctttct ggcttactcc caggcggtat tccaggaggg   5760
atatttgcgc ctcggcagcg tgccgttcct ctcttttcgc gacatgctgc gcgccgggcc   5820
gcagctgctt aagctccagg cgtggcagag cgtctaccag tcggtttcgc gctttattga   5880
ggatgagcat ctgcggcagg ccttctcgtt ccactccctg ctggtaggcg gcaacccctt   5940
```

```
caccacctcg tccatctaca ccctgatcca cgcccttgag cgggagtggg gggtctggtt   6000
ccctgagggc ggcaccgggg cgctggtgaa cggcatggtg aagctgttta ccgatctggg   6060
cggggagatc gaactcaacg cccgggtcga agagctggtg gtggccgata accgcgtaag   6120
ccaggtccgg ctggcggatg gtcggatctt tgacaccgac gccgtagcct cgaacgctga   6180
cgtggtgaac acctataaaa agctgctcgg ccaccatccg gtggggcaga agcgggcggc   6240
agcgctggag cgcaagagca tgagcaactc gctgtttgtg ctctacttcg gcctgaacca   6300
gcctcattcc cagctggcgc accataccat ctgttttggt ccccgctacc gggagctgat   6360
cgacgagatc tttaccggca gcgcgctggc ggatgacttc tcgctctacc tgcactcgcc   6420
ctgcgtgacc gatccctcgc tcgcgcctcc cggctgcgcc agcttctacg tgctggcccc   6480
ggtgccgcat cttggcaacg cgccgctgga ctgggcgcag gaggggccga agctgcgcga   6540
ccgcatcttt gactaccttg aagagcgcta tatgcccggc ctgcgtagcc agctggtgac   6600
ccagcggatc tttaccccgg cagacttcca cgacacgctg gatgcgcatc tgggatcggc   6660
cttctccatc gagccgctgc tgacccaaag cgcctggttc cgcccgcaca accgcgacag   6720
cgacattgcc aacctctacc tggtgggcgc aggtactcac cctggggcgg gcattcctgg   6780
cgtagtggcc tcggcgaaag ccaccgccag cctgatgatt gaggatctgc aatgagccaa   6840
ccgccgctgc ttgaccacgc cacgcagacc atggccaacg gctcgaaaag ttttgccacc   6900
gctgcgaagc tgttcgaccc ggccacccgc cgtagcgtgc tgatgctcta cacctggtgc   6960
cgccactgcg atgacgtcat tgacgaccag acccacggct tcgccagcga ggccgcggcg   7020
gaggaggagg ccacccagcg cctggcccgg ctgcgcacgc tgaccctggc ggcgtttgaa   7080
ggggccgaga tgcaggatcc ggccttcgct gcctttcagg aggtggcgct gacccacggt   7140
attacgcccc gcatggcgct cgatcacctc gacggctttg cgatggacgt ggctcagacc   7200
cgctatgtca cctttgagga tacgctgcgc tactgctatc acgtggcggg cgtggtgggt   7260
ctgatgatgg ccagggtgat gggcgtgcgg gatgagcggg tgctggatcg cgcctgcgat   7320
ctggggctgg ccttccagct gacgaatatc gcccgggata ttattgacga tgcggctatt   7380
gaccgctgct atctgcccgc cgagtggctg caggatgccg ggctgacccc ggagaactat   7440
gccgcgcggg agaatcgggc cgcgctggcg cgggtggcgg agcggcttat tgatgccgca   7500
gagccgtact acatctcctc ccaggccggg ctacacgatc tgccgccgcg ctgcgcctgg   7560
gcgatcgcca ccgcccgcag cgtctaccgg gagatcggta ttaaggtaaa agcggcggga   7620
ggcagcgcct gggatcgccg ccagcacacc agcaaaggtg aaaaaattgc catgctgatg   7680
gcggcaccgg ggcaggttat tcgggcgaag acgacgaggg tgacgccgcg tccggccggt   7740
ctttggcagc gtcccgttta ggcgggcggc catgacgttc acgcaggatc gcctgtaggt   7800
cggcaggctt gcgggcgtaa ataaaaccga aggagacgca gccctcccgg ccgcgcaccg   7860
cgtggtgcag gcggtgggcg acgtagagcc gcttcaggta gccccggcgc gggatcccgc   7920
ctcgccgtgc tgtccggtct caacctgatc cgccagaatc gagccaacgg gatcggccag   7980
cacgaattcg gtatgcggag agtgtttggc aaaccatgcc tgcaagccac ccagcgtgcc   8040
gccggagcca acgcctacta ccacggcatc aaccctgcct gccagctggt cgaacagctc   8100
cggtgcggtg gtggtggcgt gcgccagcgg gttggccggg ttagagaact gatcaatata   8160
gtaagcaccc ggcgtctcct ctgccaggcg gcgggcgtag tcctgatagt actccgggtg   8220
gccctttgtc acgtcggagc gggtcaggcg cacatcaaca cccagcgcac gcaggtggta   8280
```

```
gatcctctac gccggacgca tcgtggccgg catcaccggc gccacaggtg cggttgctgg   8340
cgcctatatc gccgacatca ccgatgggga agatcgggct cgccacttcg ggctcatgag   8400
cgcttgtttc ggcgtgggta tggtggcagg ccccgtggcc gggggactgt tgggcgccat   8460
ctccttgggg tcgaatttgc tttcgaattt ctgccattca tccgcttatt atcacttatt   8520
caggcgtagc accaggcgtt taagggcacc aataactgcc ttaaaaaaat tacgccccgc   8580
cctgccactc atcgcagtac tgttgtaatt cattaagcat tctgccgaca tggaagccat   8640
cacagacggc atgatgaacc tgaatcgcca gcggcatcag caccttgtcg ccttgcgtat   8700
aatatttgcc catggtgaaa acgggggcga agaagttgtc catattggcc acgtttaaat   8760
caaaactggt gaaactcacc cagggattgg ctgagacgaa aaacatattc tcaataaacc   8820
ctttagggaa ataggccagg ttttcaccgt aacacgccac atcttgcgaa tatatgtgta   8880
gaaactgccg gaaatcgtcg tggtattcac tccagagcga tgaaaacgtt tcagtttgct   8940
catggaaaac ggtgtaacaa gggtgaacac tatcccatat caccagctca ccgtctttca   9000
ttgccatacg gaattccgga tgagcattca tcaggcgggc aagaatgtga ataaaggccg   9060
gataaaactt gtgcttattt ttctttacgg tctttaaaaa ggccgtaata tccagctgaa   9120
cggtctggtt ataggtacat tgagcaactg actgaaatgc ctcaaaatgt tctttacgat   9180
gccattggga tatatcaacg gtggtatatc cagtgatttt tttctccatt ttagcttcct   9240
tagctcctga aaatctcgat aactcaaaaa atacgcccgg tagtgatctt atttcattat   9300
ggtgaaagtt ggaacctctt acgtgccgat caacgtctca ttttcgccaa aagttggccc   9360
agggcttccc ggtatcaaca gggacaccag gatttattta ttctgcgaag tgatcttccg   9420
tcacaggtat ttattcggcg caaagtgcgt cgggtgatgc tgccaactta ctgatttagt   9480
gtatgatggt gtttttgagg tgctccagtg gcttctgttt ctatcagctg tccctcctgt   9540
tcagctactg acggggtggt gcgtaacggc aaaagcaccg ccggacatca gcgctagcg    9599
```

<210> SEQ ID NO 28
<211> LENGTH: 8442
<212> TYPE: DNA
<213> ORGANISM: Artificial Sequence
<220> FEATURE:
<223> OTHER INFORMATION: pAC-BETAipi-del-crtY

<400> SEQUENCE: 28

```
gagtgtatac tggcttacta tgttggcact gatgagggtg tcagtgaagt gcttcatgtg     60
gcaggagaaa aaaggctgca ccggtgcgtc agcagaatat gtgatacagg atatattccg    120
cttcctcgct cactgactcg ctacgctcgg tcgttcgact gcggcgagcg gaaatggctt    180
acgaacgggg cggagatttc ctggaagatg ccaggaagat acttaacagg gaagtgagag    240
ggccgcggca aagccgtttt tccataggct ccgcccccct gacaagcatc acgaaatctg    300
acgctcaaat cagtggtggc gaaacccgac aggactataa agataccagg cgtttccccc    360
tggcggctcc ctcgtgcgct ctcctgttcc tgcctttcgg tttaccggtg tcattccgct    420
gttatggccg cgtttgtctc attccacgcc tgacactcag ttccgggtag gcagttcgct    480
ccaagctgga ctgtatgcac gaaccccccg ttcagtccga ccgctgcgcc ttatccggta    540
actatcgtct tgagtccaac ccggaaagac atgcaaaagc accactggca gcagccactg    600
gtaattgatt tagaggagtt agtcttgaag tcatgcgccg gttaaggcta aactgaaagg    660
acaagttttg gtgactgcgc tcctccaagc cagttacctc ggttcaaaga gttggtagct    720
cagagaacct tcgaaaaacc gccctgcaag gcggtttttt cgttttcaga gcaagagatt    780
```

```
acgcgcagac caaaacgatc tcaagaagat catcttatta atcagataaa atatttctag    840
atttcagtgc aatttatctc ttcaaatgta gcacctgaag tcagccccat acgatataag    900
ttgtaattct catgtttgac agcttatcat cgataagctt taatgcggta gtttatcaca    960
gttaaattgc taacgcagtc aggcaccgtg tatgaaatct aacaatgcgc tcatcgtcat   1020
cctcggcacc gtcaccctgg atgctgtagg cataggcttg gttatgccgg tactgccggg   1080
cctcttgcgg gatatcgtcc attccgacag catcgccagt cactatggcg tgctgctagc   1140
gctatatgcg ttgatgcaat ttctatgcgc acccgttctc ggagcactgt ccgaccgctt   1200
tggccgccgc ccagtcctgc tcgcttcgct acttggagcc actatcgact acgcgatcat   1260
ggcgaccaca cccgtcctgt ggatctaaag gcacagcgtc tcatgcttcg cacaatgtaa   1320
aactgcttca gaacctggcg agagctatcc gcgcggtcta cggttaactg atactaaaag   1380
acaattcagc gggtaacctt gcaatggtga gtggcagtaa agcgggcgtt tcgcctcatc   1440
gcgaaataga agtaatgaga caatccattg acgatcacct ggctggcctg ttacctgaaa   1500
ccgacagcca ggatatcgtc agccttgcga tgcgtgaagg cgtcatggca cccggtaaac   1560
ggatccgtcc gctgctgatg ctgctggccg cccgcgacct ccgctaccag ggcagtatgc   1620
ctacgctgct cgatctcgcc tgcgccgttg aactgaccca taccgcgtcg ctgatgctcg   1680
acgacatgcc ctgcatggac aacgccgagc tgcgccgcgg tcagcccact acccacaaaa   1740
aatttggtga gagcgtggcg atccttgcct ccgttgggct gctctctaaa gcctttggtc   1800
tgatcgccgc caccggcgat ctgccggggg agaggcgtgc ccaggcggtc aacgagctct   1860
ctaccgccgt gggcgtgcag ggcctggtac tggggcagtt tcgcgatctt aacgatgccg   1920
ccctcgaccg taccccctgac gctatcctca gcaccaacca cctcaagacc ggcattctgt   1980
tcagcgcgat gctgcagatc gtcgccattg cttccgcctc gtcgccgagc acgcgagaga   2040
cgctgcacgc cttcgccctc gacttcggcc aggcgtttca actgctggac gatctgcgtg   2100
acgatcaccc ggaaaccggt aaagatcgca ataaggacgc gggaaaatcg acgctggtca   2160
accggctggg cgcagacgcg gcccggcaaa agctgcgcga gcatattgat tccgccgaca   2220
aacacctcac ttttgcctgt ccgcagggcg gcgccatccg acagtttatg catctgtggt   2280
ttggccatca ccttgccgac tggtcaccgg tcatgaaaat cgcctgatac cgcccttttg   2340
ggttcaagca gtacataacg atggaaccac attacaggag tagtgatgaa tgaaggacga   2400
gcgccttgtt cagcgtaaga acgatcatct ggatatcgtt ctcgaccccc gtcgcgccgt   2460
aactcaggct agcgcaggtt ttgagcgctg gcgctttacc cactgcgccc tgccagagct   2520
gaattttagc gacatcacgc tggaaaccac cttcctgaat cggcagctac aggctccgct   2580
gctgatcagc tccatgaccg gcggcgttga gcgctcgcgc catatcaacc gccacctcgc   2640
cgaggcggcg caggtgctaa aaattgcgat gggggtgggc tcccagcgcg tcgccattga   2700
gagcgacgcg ggcttagggc tggataaaac cctgcggcag ctggctccgg acgtgccgct   2760
gctggcgaac ctcggcgcgg cgcagctgac cggcagaaaa ggtattgatt acgcccgacg   2820
ggccgtggag atgatcgagg cggatgcgct gattgtgcac ctaaacccgc tgcaggaggc   2880
gctacagccc ggcggcgatc gcgactggcg cggacggctg gcggctattg aaactctggt   2940
ccgcgagctg cccgttccgc tggtggtgaa agaggtggga gccggtatct cccgaaccgt   3000
ggccgggcag ctgatcgatg ccggcgttac cgtgattgac gtcgcgggcg cgggcggcac   3060
cagctgggcc gccgttgaag gcgagcgggc ggccaccgag cagcagcgca gcgtggccaa   3120
```

-continued

```
cgtctttgcc gactgggggga tccccaccgc tgaggcgctg gttgacattg ccgaggcctg   3180
gccgcagatg cccctattg cctcgggcgg gattaaaaac ggcgtcgacg cggcgaaagc   3240
gctgcggctc ggcgcgtgca tggtagggca ggccgccgcc gtgctcggca gcgcaggcgt   3300
ctccacggag aaggtgatcg atcacttcaa cgtgattatt gagcagctgc gggtggcctg   3360
cttctgcacc ggcagccgca gcctgagcga tctaaagcag gctgatatcc gctatgtgcg   3420
ggatacgcca tgagccattt tgccattgtg gcaccgccgc tctacagtca tgcggtggcg   3480
ctgcatgccc tggcgctgga gatggcccaa cgcggccacc ggtaattgat ttagaggagt   3540
tagtcttgaa gtcatgcgcc ggttaaggct aaactgaaag gacaagtttt ggtgactgcg   3600
ctcctccaag ccagttacct cggttcaaag agttggtagc tcagagaacc ttcgaaaaac   3660
cgccctgcaa ggcggttttt tcgttttcag agcaagagat tacgcgcaga ccaaaacgat   3720
ctcaagaaga tcatcttatt aatcagataa aatatttcta gatttcagtg caatttatct   3780
cttcaaatgt agcacctgaa gtcagcccca tacgatataa gttgtaattc tcatgtttga   3840
cagcttatca tcgataagct cgaccagccg cgctacgttg ccgaggctaa tctggtgatc   3900
acccacggcg gtctcaatac cgtactggat gcgctggctg ccgcgacgcc ggtgctggcg   3960
gtgccactct ctttcgacca gcccgccgtg gctgcccggc tggtctataa cgggctgggt   4020
cgccgggtat cgcgctttgc cagacagcag acgctggcgg atgagattgc ccaactgctg   4080
ggggatgaga cgctgcatca gcgtctggcg acggcccgcc agcagcttaa cgacgccggg   4140
ggcacgcccc gtgcggcgac cctgattgaa caggccatag cagggagtga gagcgtatca   4200
tgaaaaaaac cgttgtgatt ggcgcaggct ttggtggcct ggcgctggcg attcgcctgc   4260
aggcggcagg gatcccaacc gtactgctgg agcagcggga caagcccggc ggtcgggcct   4320
acgtctggca tgaccagggc tttacctttg acgccgggcc gacggtgatc accgatccta   4380
ccgcgcttga ggcgctgttc accctggccg gcaggcgcat ggaggattac gtcaggctgc   4440
tgccggtaaa acccttctac cgactctgct gggagtccgg gaagaccctc gactatgcta   4500
acgacagcgc cgagcttgag gcgcagatta cccagttcaa cccccgcgac gtcgagggct   4560
accggcgctt tctggcttac tcccaggcgg tattccagga gggatatttg cgcctcggca   4620
gcgtgccgtt cctctctttt cgcgacatgc tgcgcgccgg gccgcagctg cttaagctcc   4680
aggcgtggca gagcgtctac cagtcggttt cgcgctttat tgaggatgag catctgcggc   4740
aggccttctc gttccactcc ctgctggtag gcggcaaccc cttcaccacc tcgtccatct   4800
acaccctgat ccacgccctt gagcgggagt ggggggtctg gttccctgag ggcggcaccg   4860
gggcgctggt gaacggcatg gtgaagctgt ttaccgatct gggcggggag atcgaactca   4920
acgcccgggt cgaagagctg gtggtggccg ataaccgcgt aagccaggtc cggctggcgg   4980
atggtcggat ctttgacacc gacgccgtag cctcgaacgc tgacgtggtg aacacctata   5040
aaaagctgct cggccaccat ccggtggggc agaagcgggc ggcagcgctg gagcgcaaga   5100
gcatgagcaa ctcgctgttt gtgctctact tcggcctgaa ccagcctcat tcccagctgg   5160
cgcaccatac catctgtttt ggtccccgct accgggagct gatcgacgag atctttaccg   5220
gcagcgcgct ggcggatgac ttctcgctct acctgcactc gccctgcgtg accgatccct   5280
cgctcgcgcc tcccggctgc gccagcttct acgtgctggc cccggtgccg catcttggca   5340
acgcgccgct ggactgggcg caggaggggc cgaagctgcg cgaccgcatc tttgactacc   5400
ttgaagagcg ctatatgccc ggcctgcgta gccagctggt gacccagcgg atctttaccc   5460
cggcagactt ccacgacacg ctggatgcgc atctgggatc ggccttctcc atcgagccgc   5520
```

```
tgctgaccca aagcgcctgg ttccgcccgc acaaccgcga cagcgacatt gccaacctct   5580
acctggtggg cgcaggtact caccctgggg cgggcattcc tggcgtagtg gcctcggcga   5640
aagccaccgc cagcctgatg attgaggatc tgcaatgagc caaccgccgc tgcttgacca   5700
cgccacgcag accatggcca acggctcgaa aagttttgcc accgctgcga agctgttcga   5760
cccggccacc cgccgtagcg tgctgatgct ctacacctgg tgccgccact gcgatgacgt   5820
cattgacgac cagacccacg gcttcgccag cgaggccgcg gcggaggagg aggccaccca   5880
gcgcctggcc cggctgcgca cgctgaccct ggcggcgttt gaaggggccg agatgcagga   5940
tccggccttc gctgcctttc aggaggtggc gctgacccac ggtattacgc cccgcatggc   6000
gctcgatcac ctcgacggct ttgcgatgga cgtggctcag acccgctatg tcacctttga   6060
ggatacgctg cgctactgct atcacgtggc gggcgtggtg ggtctgatga tggccagggt   6120
gatgggcgtg cgggatgagc gggtgctgga tcgcgcctgc gatctggggc tggccttcca   6180
gctgacgaat atcgcccggg atattattga cgatgcggct attgaccgct gctatctgcc   6240
cgccgagtgg ctgcaggatg ccgggctgac cccggagaac tatgccgcgc gggagaatcg   6300
ggccgcgctg gcgcgggtgg cggagcggct tattgatgcc gcagagccgt actacatctc   6360
ctcccaggcc gggctacacg atctgccgcc gcgctgcgcc tgggcgatcg ccaccgcccg   6420
cagcgtctac cgggagatcg gtattaaggt aaaagcggcg ggaggcagcg cctgggatcg   6480
ccgccagcac accagcaaag gtgaaaaaat tgccatgctg atggcggcac cggggcaggt   6540
tattcgggcg aagacgacga gggtgacgcc gcgtccggcc ggtctttggc agcgtcccgt   6600
ttaggcgggc ggccatgacg ttcacgcagg atcgcctgta ggtcggcagg cttgcgggcg   6660
taaataaaac cgaaggagac gcagccctcc cggccgcgca ccgcgtggtg caggcggtgg   6720
gcgacgtaga gccgcttcag gtagccccgg cgcgggatcc cgcctcgccg tgctgtccgg   6780
tctcaacctg atccgccaga atcgagccaa cgggatcggc cagcacgaat tcggtatgcg   6840
gagagtgttt ggcaaaccat gcctgcaagc cacccagcgt gccgccggag ccaacgccta   6900
ctaccacggc atcaaccctg cctgccagct ggtcgaacag ctccggtgcg gtggtggtgg   6960
cgtgcgccag cgggttggcc gggttagaga actgatcaat atagtaagca cccggcgtct   7020
cctctgccag gcggcgggcg tagtcctgat agtactccgg gtggcccttt gtcacgtcgg   7080
agcgggtcag gcgcacatca acacccagcg cacgcaggtg gtagatcctc tacgccggac   7140
gcatcgtggc cggcatcacc ggcgccacag gtgcggttgc tggcgcctat atcgccgaca   7200
tcaccgatgg ggaagatcgg gctcgccact tcgggctcat gagcgcttgt ttcggcgtgg   7260
gtatggtggc aggccccgtg gccgggggac tgttgggcgc catctccttg gggtcgaatt   7320
tgctttcgaa tttctgccat tcatccgctt attatcactt attcaggcgt agcaccaggc   7380
gtttaagggc accaataact gccttaaaaa aattacgccc cgccctgcca ctcatcgcag   7440
tactgttgta attcattaag cattctgccg acatggaagc catcacagac ggcatgatga   7500
acctgaatcg ccagcggcat cagcaccttg tcgccttgcg tataatattt gcccatggtg   7560
aaaacggggg cgaagaagtt gtccatattg gccacgttta aatcaaaact ggtgaaactc   7620
acccagggat tggctgagac gaaaaacata ttctcaataa accctttagg gaaataggcc   7680
aggttttcac cgtaacacgc cacatcttgc gaatatatgt gtagaaactg ccggaaatcg   7740
tcgtggtatt cactccagag cgatgaaaac gtttcagttt gctcatggaa aacggtgtaa   7800
caagggtgaa cactatccca tatcaccagc tcaccgtctt tcattgccat acggaattcc   7860
```

```
ggatgagcat tcatcaggcg ggcaagaatg tgaataaagg ccggataaaa cttgtgctta   7920

tttttcttta cggtctttaa aaaggccgta atatccagct gaacggtctg gttataggta   7980

cattgagcaa ctgactgaaa tgcctcaaaa tgttctttac gatgccattg ggatatatca   8040

acggtggtat atccagtgat ttttttctcc attttagctt ccttagctcc tgaaaatctc   8100

gataactcaa aaaatacgcc cggtagtgat cttatttcat tatggtgaaa gttggaacct   8160

cttacgtgcc gatcaacgtc tcattttcgc caaaagttgg cccagggctt cccggtatca   8220

acagggacac caggatttat ttattctgcg aagtgatctt ccgtcacagg tatttattcg   8280

gcgcaaagtg cgtcgggtga tgctgccaac ttactgattt agtgtatgat ggtgtttttg   8340

aggtgctcca gtggcttctg tttctatcag ctgtccctcc tgttcagcta ctgacggggt   8400

ggtgcgtaac ggcaaaagca ccgccggaca tcagcgctag cg                       8442
```

<210> SEQ ID NO 29
<211> LENGTH: 8632
<212> TYPE: DNA
<213> ORGANISM: Artificial Sequence
<220> FEATURE:
<223> OTHER INFORMATION: pGT1066-AtEC-del

<400> SEQUENCE: 29

```
ttgtaattct catgtttgac agcttatcat cgataagctt taatgcggta gtttatcaca     60

gttaaattgc taacgcagtc aggaaccttg caatggtgag tggcagtaaa gcgggcgttt    120

cgcctcatcg cgaaatagaa gtaatgagac aatccattga cgatcacctg gctggcctgt    180

tacctgaaac cgacagccag gatatcgtca gccttgcgat gcgtgaaggc gtcatggcac    240

ccggtaaacg gatccgtccg ctgctgatgc tgctggccgc ccgcgacctc cgctaccagg    300

gcagtatgcc tacgctgctc gatctcgcct gcgccgttga actgacccat accgcgtcgc    360

tgatgctcga cgacatgccc tgcatggaca acgccgagct gcgccgcggt cagcccacta    420

cccacaaaaa atttggtgag agcgtggcga tccttgcctc cgttgggctg ctctctaaag    480

cctttggtct gatcgccgcc accggcgatc tgccggggga gaggcgtgcc caggcggtca    540

acgagctctc taccgccgtg ggcgtgcagg gcctggtact ggggcagttt cgcgatctta    600

acgatgccgc cctcgaccgt acccctgacg ctatcctcag caccaaccac ctcaagaccg    660

gcattctgtt cagcgcgatg ctgcagatcg tcgccattgc ttccgcctcg tcgccgagca    720

cgcgagagac gctgcacgcc ttcgccctcg acttcggcca ggcgtttcaa ctgctggacg    780

atctgcgtga cgatcacccg gaaaccggta aagatcgcaa taaggacgcg ggaaaatcga    840

cgctggtcaa ccggctgggc gcagacgcgg cccggcaaaa gctgcgcgag catattgatt    900

ccgccgacaa acacctcact tttgcctgtc cgcagggcgg cgccatccga cagtttatgc    960

atctgtggtt tggccatcac cttgccgact ggtcaccggt catgaaaatc gcctgatacc   1020

gcccttttgg gttcaagcag tacataacga tggaaccaca ttacaggagt agtgatgaat   1080

gaaggacgag cgccttgttc agcgtaagaa cgatcatctg gatatcgttc tcgacccccg   1140

tcgcgccgta actcaggcta gcgcaggttt tgagcgctgg cgctttaccc actgcgccct   1200

gccagagctg aattttagcg acatcacgct ggaaaccacc ttcctgaatc ggcagctaca   1260

ggctccgctg ctgatcagct ccatgaccgg cggcgttgag cgctcgcgcc atatcaaccg   1320

ccacctcgcc gaggcggcgc aggtgctaaa aattgcgatg ggggtgggct cccagcgcgt   1380

cgccattgag agcgacgcgg gcttagggct ggataaaacc ctgcggcagc tggctccgga   1440

cgtgccgctg ctggcgaacc tcggcgcggc gcagctgacc ggcagaaaag gtattgatta   1500
```

```
cgcccgacgg gccgtggaga tgatcgaggc ggatgcgctg attgtgcacc taaacccgct   1560
gcaggaggcg ctacagcccg gcggcgatcg cgactggcgc ggacggctgg cggctattga   1620
aactctggtc cgcgagctgc ccgttccgct ggtggtgaaa gaggtgggag ccggtatctc   1680
ccgaaccgtg gccgggcagc tgatcgatgc cggcgttacc gtgattgacg tcgcgggcgc   1740
gggcggcacc agctgggccg ccgttgaagg cgagcgggcg gccaccgagc agcagcgcag   1800
cgtggccaac gtctttgccg actgggggat ccccaccgct gaggcgctgg ttgacattgc   1860
cgaggcctgg ccgcagatgc cccttattgc ctcgggcggg attaaaaacg gcgtcgacgc   1920
ggcgaaagcg ctgcggctcg gcgcgtgcat ggtagggcag gccgccgccg tgctcggcag   1980
cgcaggcgtc tccacggaga aggtgatcga tcacttcaac gtgattattg agcagctgcg   2040
ggtggcctgc ttctgcaccg gcagccgcag cctgagcgat ctaaagcagg ctgatatccg   2100
ctatgttcgt gatacgccat aaggaggtac aaccatgaag aaaaccgttg tgattggcgc   2160
aggctttggt ggcctggcgc tggcgattcg cctgcaggcg gcagggatcc caaccgtact   2220
gctggagcag cgggacaagc ccggcggtcg ggcctacgtc tggcatgacc agggctttac   2280
ctttgacgcc gggccgacgg tgatcaccga tcctaccgcg cttgaggcgc tgttcaccct   2340
ggccggcagg cgcatggagg attacgtcag gctgctgccg gtaaaaccct tctaccgact   2400
ctgctgggag tccgggaaga ccctcgacta tgctaacgac agcgccgagc ttgaggcgca   2460
gattacccag ttcaaccccc gcgacgtcga gggctaccgg cgctttctgg cttactccca   2520
ggcggtattc caggagggat atttgcgcct cggcagcgtg ccgttcctct cttttcgcga   2580
catgctgcgc gccgggccgc agctgcttaa gctccaggcg tggcagagcg tctaccagtc   2640
ggtttcgcgc tttattgagg atgagcatct gcggcaggcc ttctcgttcc actccctgct   2700
ggtaggcggc aacccettca ccacctcgtc catctacacc ctgatccacg cccttgagcg   2760
ggagtggggg gtctggttcc ctgagggcgg caccggggcg ctggtgaacg gcatggtgaa   2820
gctgtttacc gatctgggcg gggagatcga actcaacgcc cgggtcgaag agctggtggt   2880
ggccgataac cgcgtaagcc aggtccggct ggcggatggt cggatctttg acaccgacgc   2940
cgtagcctcg aacgctgacg tggtgaacac ctataaaaag ctgctcggcc accatccggt   3000
ggggcagaag cgggcggcag cgctggagcg caagagcatg agcaactcgc tgtttgtgct   3060
ctacttcggc ctgaaccagc ctcattccca gctggcgcac cataccatct gttttggtcc   3120
ccgctaccgg gagctgatcg acgagatctt taccggcagc gcgctggcgg atgacttctc   3180
gctctacctg cactcgccct gcgtgaccga tccctcgctc gcgcctcccg gctgcgccag   3240
cttctacgtg ctggccccgg tgccgcatct tggcaacgcg ccgctggact gggcgcagga   3300
ggggccgaag ctgcgcgacc gcatctttga ctaccttgaa gagcgctata tgcccggcct   3360
gcgtagccag ctggtgaccc agcggatctt taccccggca gacttccacg acacgctgga   3420
tgcgcatctg ggatcggcct tctccatcga gccgctgctg acccaaagcg cctggttccg   3480
cccgcacaac cgcgacagcg acattgccaa cctctacctg gtgggcgcag gtactcaccc   3540
tggggcgggc attcctggcg tagtggcctc ggcgaaagcc accgccagcc tgatgattga   3600
ggatctgcaa tgagccaacc gccgctgctt gaccacgcca cgcagaccat ggccaacggc   3660
tcgaaaagtt ttgccaccgc tgcgaagctg ttcgacccgg ccacccgccg tagcgtgctg   3720
atgctctaca cctggtgccg ccactgcgat gacgtcattg acgaccagac ccacggcttc   3780
gccagcgagg ccgcggcgga ggaggaggcc acccagcgcc tggcccggct gcgcacgctg   3840
```

```
accctggcgg cgtttgaagg ggccgagatg caggatccgg ccttcgctgc ctttcaggag   3900
gtggcgctga cccacggtat tacgccccgc atggcgctcg atcacctcga cggctttgcg   3960
atggacgtgg ctcagacccg ctatgtcacc tttgaggata cgctgcgcta ctgctatcac   4020
gtggcgggcg tggtgggtct gatgatggcc agggtgatgg gcgtgcggga tgagcgggtg   4080
ctggatcgcg cctgcgatct ggggctggcc ttccagctga cgaatatcgc ccgggatatt   4140
attgacgatg cggctattga ccgctgctat ctgcccgccg agtggctgca ggatgccggg   4200
ctgaccccgg agaactatgc cgcgcgggag aatcgggccg cgctggcgcg ggtggcggag   4260
cggcttattg atgccgcaga gccgtactac atctcctccc aggccgggct acacgatctg   4320
ccgccgcgct gcgcctgggc gatcgccacc gcccgcagcg tctaccggga gatcggtatt   4380
aaggtaaaag cggcgggagg cagcgcctgg gatcgccgcc agcacaccag caaaggtgaa   4440
aaaattgcca tgctgatggc ggcaccgggg caggttattc gggcgaagac gacgagggtg   4500
acgccgcgtc cggccggtct ttggcagcgt cccgtttaga ccgactccaa acgagtcggt   4560
ttttttgcgc ttgtttcggc gtgggtatgg tggcaggccc cgtggccggg ggactgttgg   4620
gcgccatctc cttggggtcg aatttgcttt cgaatttctg ccattcatcc gcttattatc   4680
acttattcag gcgtagcaac caggcgttta agggcaccaa taactgcctt aaaaaaatta   4740
cgccccgccc tgccactcat cgcagtactg ttgtaattca ttaagcattc tgccgacatg   4800
gaagccatca cagacggcat gatgaacctg aatcgccagc ggcatcagca ccttgtcgcc   4860
ttgcgtataa tatttgccca tggtgaaaac gggggcgaag aagttgtcca tattggccac   4920
gtttaaatca aaactggtga aactcaccca gggattggct gagacgaaaa acatattctc   4980
aataaaccct ttagggaaat aggccaggtt ttcaccgtaa cacgccacat cttgcgaata   5040
tatgtgtaga aactgccgga aatcgtcgtg gtattcactc cagagcgatg aaaacgtttc   5100
agtttgctca tggaaaacgg tgtaacaagg gtgaacacta tcccatatca ccagctcacc   5160
gtctttcatt gccatacgga attccggatg agcattcatc aggcgggcaa gaatgtgaat   5220
aaaggccgga taaaacttgt gcttattttt ctttacggtc tttaaaaagg ccgtaatatc   5280
cagctgaacg gtctggttat aggtacattg agcaactgac tgaaatgcct caaaatgttc   5340
tttacgatgc cattgggata tatcaacggt ggtatatcca gtgatttttt tctccatttt   5400
agcttcctta gctcctgaaa atctcgataa ctcaaaaaat acgcccggta gtgatcttat   5460
ttcattatgg tgaaagttgg aacctcttac gtgccgatca acgtctcatt ttcgccaaaa   5520
gttggcccag ggcttcccgg tatcaacagg gacaccagga tttatttatt ctgcgaagtg   5580
atcttccgtc acaggtattt attcggcgca aagtgcgtcg ggtgatgctg ccaacttact   5640
gatttagtgt atgatggtgt ttttgaggtg ctccagtggc ttctgtttct atcagctgtc   5700
cctcctgttc agctactgac ggggtggtgc gtaacggcaa aagcaccgcc ggacatcagc   5760
gctagcggag tgtatacact ccgctatcgc tacgtgactg ggtcatggct gcgccccgac   5820
acccgccaac acccgctgac gcgccctgac gggcttgtct gctcccggca tccgcttaca   5880
gacaagctgt gaccgtctcc gggagctgca tgtgtcagag gttttcaccg tcatcaccga   5940
aacgcgcgag gcagctggca cgacaggttt cccgactgga aagcgggcag tgagcgcaac   6000
gcaattaatg tgagttagct cactcattag gcaccccagg ctttacactt tatgcttccg   6060
gctcgtatgt tgtgtggaat tgtgagcgga taacaatttc acacaggaaa cagctatgac   6120
catgattacg ccaagctcta gctagaaata attttgttta actttaagaa ggagatatac   6180
ccatgacaca gagggcccac catcaccatc accattccat ggctagcggc ggcggaagtt   6240
```

```
ccggtagtga gagttgtgta gcggtgagag aagatttcgc tgacgaagaa gattttgtga   6300
aagctggtgg ttctgagatt ctatttgttc aaatgcagca gaacaaagat atggatgaac   6360
agtctaagct tgttgataag ttgcctccta tatcaattgg tgatggtgct ttggatctag   6420
tggttattgg ttgtggtcct gctggtttag ccttggctgc agaatcagct aagcttggat   6480
taaaagttgg actcattggt ccagatcttc cttttactaa caattacggt gtttgggaag   6540
atgaattcaa tgatcttggg ctgcaaaaat gtattgagca tgtttggaga gagactattg   6600
tgtatctgga tgatgacaag cctattacca ttggccgtgc ttatggaaga gttagtcgac   6660
gtttgctcca tgaggagctt ttgaggaggt gtgtcgagtc aggtgtctcg taccttagct   6720
cgaaagttga cagcataaca gaagcttctg atggccttag acttgttgct tgtgacgaca   6780
ataacgtcat tccctgcagg cttgccactg ttgcttctgg agcagcttcg ggaaagctct   6840
tgcaatacga agttggtgga cctagagtct gtgtgcaaac tgcatacggc gtggaggttg   6900
aggtggaaaa tagtccatat gatccagatc aaatggtttt catggattac agagattata   6960
ctaacgagaa agttcggagc ttagaagctg agtatccaac gtttctgtac gccatgccta   7020
tgacaaagtc aagactcttc ttcgaggaga catgtttggc ctcaaaagat gtcatgccct   7080
ttgatttgct aaaaacgaag ctcatgttaa gattagatac actcggaatt cgaattctaa   7140
agacttacga agaggagtgg tcctatatcc cagttggtgg ttccttgcca aacaccgaac   7200
aaaagaatct cgcctttggt gctgccgcta gcatggtaca tcccgcaaca ggctattcag   7260
ttgtgagatc tttgtctgaa gctccaaaat atgcatcagt catcgcagag atactaagag   7320
aagagactac caaacagatc aacagtaata tttcaagaca agcttgggat actttatggc   7380
caccagaaag gaaaagacag agagcattct ttctctttgg tcttgcactc atagttcaat   7440
tcgataccga aggcattaga agcttcttcc gtactttctt ccgccttcca aaatggatgt   7500
ggcaagggtt tctaggatca acattaacat caggagatct cgttctcttt gctttataca   7560
tgttcgtcat ttcaccaaac aatttgagaa aaggtctcat caatcatctc atctctgatc   7620
caaccggagc aaccatgata aaaacctatc tcaaagtatg aggatccggc tgctaacaaa   7680
gcccgttctg tttaagaacg ggatttttttg ctgaaaggag gaactatatc cggccggatt   7740
actggcttac tatgttggca ctgatgaggg tgtcagtgaa gtgcttcatg tggcaggaga   7800
aaaaaggctg caccggtgcg tcagcagaat atgtgataca ggatatattc cgcttcctcg   7860
ctcactgact cgctacgctc ggtcgttcga ctgcggcgag cggaaatggc ttacgaacgg   7920
ggcggagatt tcctggaaga tgccaggaag atacttaaca gggaagtgag agggccgcgg   7980
caaagccgtt tttccatagg ctccgccccc ctgacaagca tcacgaaatc tgacgctcaa   8040
atcagtggtg gcgaaacccg acaggactat aaagatacca ggcgtttccc cctggcggct   8100
ccctcgtgcg ctctcctgtt cctgcctttc ggtttaccgg tgtcattccg ctgttatggc   8160
cgcgtttgtc tcattccacg cctgacactc agttccgggt aggcagttcg ctccaagctg   8220
gactgtatgc acgaaccccc cgttcagtcc gaccgctgcg ccttatccgg taactatcgt   8280
cttgagtcca acccggaaag acatgcaaaa gcaccactgg cagcagccac tggtaattga   8340
tttagaggag ttagtcttga agtcatgcgc cggttaaggc taaactgaaa ggacaagttt   8400
tggtgactgc gctcctccaa gccagttacc tcggttcaaa gagttggtag ctcagagaac   8460
cttcgaaaaa ccgccctgca aggcggtttt ttcgttttca gagcaagaga ttacgcgcag   8520
accaaaacga tctcaagaag atcatcttat taatcagata aaatatttct agatttcagt   8580
```

```
gcaatttatc tcttcaaatg tagcacctga agtcagcccc atacgatata ag          8632


<210> SEQ ID NO 30
<211> LENGTH: 8632
<212> TYPE: DNA
<213> ORGANISM: Artificial Sequence
<220> FEATURE:
<223> OTHER INFORMATION: Plasmid pGT1182

<400> SEQUENCE: 30

ttgtaattct catgtttgac agcttatcat cgataagctt taatgcggta gtttatcaca     60

gttaaattgc taacgcagtc aggaaccttg caatggtgag tggcagtaaa gcgggcgttt    120

cgcctcatcg cgaaatagaa gtaatgagac aatccattga cgatcacctg gctggcctgt    180

tacctgaaac cgacagccag gatatcgtca gccttgcgat gcgtgaaggc gtcatggcac    240

ccggtaaacg gatccgtccg ctgctgatgc tgctggccgc ccgcgacctc cgctaccagg    300

gcagtatgcc tacgctgctc gatctcgcct gcgccgttga actgacccat accgcgtcgc    360

tgatgctcga cgacatgccc tgcatggaca acgccgagct gcgccgcggt cagcccacta    420

cccacaaaaa atttggtgag agcgtggcga tccttgcctc cgttgggctg ctctctaaag    480

cctttggtct gatcgccgcc accggcgatc tgccggggga gaggcgtgcc caggcggtca    540

acgagctctc taccgccgtg ggcgtgcagg gcctggtact ggggcagttt cgcgatctta    600

acgatgccgc cctcgaccgt acccctgacg ctatcctcag caccaaccac ctcaagaccg    660

gcattctgtt cagcgcgatg ctgcagatcg tcgccattgc ttccgcctcg tcgccgagca    720

cgcgagagac gctgcacgcc ttcgccctcg acttcggcca ggcgtttcaa ctgctggacg    780

atctgcgtga cgatcacccg gaaaccggta aagatcgcaa taaggacgcg ggaaaatcga    840

cgctggtcaa ccggctgggc gcagacgcgg cccggcaaaa gctgcgcgag catattgatt    900

ccgccgacaa acacctcact tttgcctgtc cgcagggcgg cgccatccga cagtttatgc    960

atctgtggtt tggccatcac cttgccgact ggtcaccggt catgaaaatc gcctgatacc   1020

gcccttttgg gttcaagcag tacataacga tggaaccaca ttacaggagt agtgatgaat   1080

gaaggacgag cgccttgttc agcgtaagaa cgatcatctg gatatcgttc tcgacccccg   1140

tcgcgccgta actcaggcta gcgcaggttt tgagcgctgg cgctttaccc actgcgccct   1200

gccagagctg aattttagcg acatcacgct ggaaaccacc ttcctgaatc ggcagctaca   1260

ggctccgctg ctgatcagct ccatgaccgg cggcgttgag cgctcgcgcc atatcaaccg   1320

ccacctcgcc gaggcggcgc aggtgctaaa aattgcgatg gggtgggct cccagcgcgt    1380

cgccattgag agcgacgcgg gcttagggct ggataaaacc ctgcggcagc tggctccgga   1440

cgtgccgctg ctggcgaacc tcggcgcggc gcagctgacc ggcagaaaag gtattgatta   1500

cgcccgacgg gccgtggaga tgatcgaggc ggatgcgctg attgtgcacc taaacccgct   1560

gcaggaggcg ctacagcccg gcggcgatcg cgactggcgc ggacggctgg cggctattga   1620

aactctggtc cgcgagctgc ccgttccgct ggtggtgaaa gaggtgggag ccggtatctc   1680

ccgaaccgtg gccgggcagc tgatcgatgc cggcgttacc gtgattgacg tcgcgggcgc   1740

gggcggcacc agctgggccg ccgttgaagg cgagcgggcg gccaccgagc agcagcgcag   1800

cgtggccaac gtctttgccg actgggggat ccccaccgct gaggcgctgg ttgacattgc   1860

cgaggcctgg ccgcagatgc cccttattgc ctcgggcggg attaaaaacg gcgtcgacgc   1920

ggcgaaagcg ctgcggctcg gcgcgtgcat ggtagggcag gccgccgccg tgctcggcag   1980

cgcaggcgtc tccacggaga aggtgatcga tcacttcaac gtgattattg agcagctgcg   2040
```

```
ggtggcctgc ttctgcaccg gcagccgcag cctgagcgat ctaaagcagg ctgatatccg   2100

ctatgttcgt gatacgccat aaggaggtac aaccatgaag aaaaccgttg tgattggcgc   2160

aggctttggt ggcctggcgc tggcgattcg cctgcaggcg gcagggatcc caaccgtact   2220

gctggagcag cgggacaagc ccggcggtcg ggcctacgtc tggcatgacc agggctttac   2280

ctttgacgcc gggccgacgg tgatcaccga tcctaccgcg cttgaggcgc tgttcaccct   2340

ggccggcagg cgcatggagg attacgtcag gctgctgccg gtaaaaccct tctaccgact   2400

ctgctgggag tccgggaaga ccctcgacta tgctaacgac agcgccgagc ttgaggcgca   2460

gattacccag ttcaaccccc gcgacgtcga gggctaccgg cgctttctgg cttactccca   2520

ggcggtattc caggagggat atttgcgcct cggcagcgtg ccgttcctct cttttcgcga   2580

catgctgcgc gccgggccgc agctgcttaa gctccaggcg tggcagagcg tctaccagtc   2640

ggtttcgcgc tttattgagg atgagcatct gcggcaggcc ttctcgttcc actccctgct   2700

ggtaggcggc aacccccttca ccacctcgtc catctacacc ctgatccacg cccttgagcg   2760

ggagtggggg gtctggttcc ctgagggcgg caccggggcg ctggtgaacg gcatggtgaa   2820

gctgtttacc gatctgggcg gggagatcga actcaacgcc cgggtcgaag agctggtggt   2880

ggccgataac cgcgtaagcc aggtccggct ggcggatggt cggatctttg acaccgacgc   2940

cgtagcctcg aacgctgacg tggtgaacac ctataaaaag ctgctcggcc accatccggt   3000

ggggcagaag cgggcggcag cgctggagcg caagagcatg agcaactcgc tgtttgtgct   3060

ctacttcggc ctgaaccagc ctcattccca gctggcgcac cataccatct gttttggtcc   3120

ccgctaccgg gagctgatcg acgagatctt taccggcagc gcgctggcgg atgacttctc   3180

gctctacctg cactcgccct gcgtgaccga tccctcgctc gcgcctcccg gctgcgccag   3240

cttctacgtg ctggccccgg tgccgcatct tggcaacgcg ccgctggact gggcgcagga   3300

ggggccgaag ctgcgcgacc gcatctttga ctaccttgaa gagcgctata tgcccggcct   3360

gcgtagccag ctggtgaccc agcggatctt taccccggca gacttccacg acacgctgga   3420

tgcgcatctg ggatcggcct tctccatcga gccgctgctg acccaaagcg cctggttccg   3480

cccgcacaac cgcgacagcg acattgccaa cctctacctg gtgggcgcag gtactcaccc   3540

tggggcgggc attcctggcg tagtggcctc ggcgaaagcc accgccagcc tgatgattga   3600

ggatctgcaa tgagccaacc gccgctgctt gaccacgcca cgcagaccat ggccaacggc   3660

tcgaaaagtt ttgccaccgc tgcgaagctg ttcgacccgg ccacccgccg tagcgtgctg   3720

atgctctaca cctggtgccg ccactgcgat gacgtcattg acgaccagac ccacggcttc   3780

gccagcgagg ccgcggcgga ggaggaggcc acccagcgcc tggcccggct gcgcacgctg   3840

accctggcgg cgtttgaagg ggccgagatg caggatccgg ccttcgctgc ctttcaggag   3900

gtggcgctga cccacggtat tacgccccgc atggcgctcg atcacctcga cggctttgcg   3960

atggacgtgg ctcagacccg ctatgtcacc tttgaggata cgctgcgcta ctgctatcac   4020

gtggcgggcg tggtgggtct gatgatggcc agggtgatgg gcgtgcggga tgagcgggtg   4080

ctggatcgcg cctgcgatct ggggctggcc ttccagctga cgaatatcgc ccgggatatt   4140

attgacgatg cggctattga ccgctgctat ctgcccgccg agtggctgca ggatgccggg   4200

ctgaccccgg agaactatgc cgcgcgggag aatcgggccg cgctggcgcg ggtggcggag   4260

cggcttattg atgccgcaga gccgtactac atctcctccc aggccgggct acacgatctg   4320

ccgccgcgct gcgcctgggc gatcgccacc gcccgcagcg tctaccggga gatcggtatt   4380
```

```
aaggtaaaag cggcgggagg cagcgcctgg gatcgccgcc agcacaccag caaaggtgaa   4440
aaaattgcca tgctgatggc ggcaccgggg caggttattc gggcgaagac gacgagggtg   4500
acgccgcgtc cggccggtct ttggcagcgt cccgtttaga ccgactccaa acgagtcggt   4560
tttttgcgc ttgtttcggc gtgggtatgg tggcaggccc cgtggccggg ggactgttgg   4620
gcgccatctc cttggggtcg aatttgcttt cgaatttctg ccattcatcc gcttattatc   4680
acttattcag gcgtagcaac caggcgttta agggcaccaa taactgcctt aaaaaaatta   4740
cgccccgccc tgccactcat cgcagtactg ttgtaattca ttaagcattc tgccgacatg   4800
gaagccatca cagacggcat gatgaacctg aatcgccagc ggcatcagca ccttgtcgcc   4860
ttgcgtataa tatttgccca tggtgaaaac gggggcgaag aagttgtcca tattggccac   4920
gtttaaatca aaactggtga aactcaccca gggattggct gagacgaaaa acatattctc   4980
aataaaccct ttagggaaat aggccaggtt ttcaccgtaa cacgccacat cttgcgaata   5040
tatgtgtaga aactgccgga aatcgtcgtg gtattcactc cagagcgatg aaaacgtttc   5100
agtttgctca tggaaaacgg tgtaacaagg gtgaacacta tcccatatca ccagctcacc   5160
gtctttcatt gccatacgga attccggatg agcattcatc aggcgggcaa gaatgtgaat   5220
aaaggccgga taaaacttgt gcttattttt ctttacggtc tttaaaaagg ccgtaatatc   5280
cagctgaacg gtctggttat aggtacattg agcaactgac tgaaatgcct caaaatgttc   5340
tttacgatgc cattgggata tatcaacggt ggtatatcca gtgatttttt tctccatttt   5400
agcttcctta gctcctgaaa atctcgataa ctcaaaaaat acgcccggta gtgatcttat   5460
ttcattatgg tgaaagttgg aacctcttac gtgccgatca acgtctcatt ttcgccaaaa   5520
gttggcccag ggcttcccgg tatcaacagg gacaccagga tttatttatt ctgcgaagtg   5580
atcttccgtc acaggtattt attcggcgca aagtgcgtcg ggtgatgctg ccaacttact   5640
gatttagtgt atgatggtgt ttttgaggtg ctccagtggc ttctgtttct atcagctgtc   5700
cctcctgttc agctactgac ggggtggtgc gtaacggcaa aagcaccgcc ggacatcagc   5760
gctagcggag tgtatacact ccgctatcgc tacgtgactg ggtcatggct gcgccccgac   5820
acccgccaac acccgctgac gcgccctgac gggcttgtct gctcccggca tccgcttaca   5880
gacaagctgt gaccgtctcc gggagctgca tgtgtcagag gttttcaccg tcatcaccga   5940
aacgcgcgag gcagctggca cgacaggttt cccgactgga aagcgggcag tgagcgcaac   6000
gcaattaatg tgagttagct cactcattag gcaccccagg ctttacactt tatgcttccg   6060
gctcgtatgt tgtgtggaat tgtgagcgga taacaatttc acacaggaaa cagctatgac   6120
catgattacg ccaagctcta gctagaaata attttgttta actttaagaa ggagatatac   6180
ccatgacaca gagggcccac catcaccatc accattccat ggctagcggc ggcggaagtt   6240
ccggtagtga gagttgtgta gcggtgagag aagatttcgc tgacgaagaa gattttgtga   6300
aagctggtgg ttctgagatt ctatttgttc aaatgcagca gaacaaagat atggatgaac   6360
agtctaagct tgttgataag ttgcctccta tatcaattgg tgatggtgct ttggatctag   6420
tggttattgg ttgtggtcct gctggtttag ccttggctgc agaatcagct aagcttggat   6480
taaaagttgg actcattggt ccagatcttc cttttactaa caattacggt gtttgggaag   6540
atgaattcaa tgatcttggg ctgcaaaaat gtattgagca tgtttggaga gagactattg   6600
tgtatctgga tgatgacaag cctattacca ttggccgtgc ttatggaaga gttagtcgac   6660
gtttgctcca tgaggagctt ttgaggaggt gtgtcgagtc aggtgtctcg taccttagct   6720
cgaaagttga cagcataaca gaagcttctg atggccttag acttgttgct tgtgacgaca   6780
```

```
ataacgtcat tccctgcagg cttgccactg ttgcttctgg agcagcttcg ggaaagctct   6840
tgcaatacga agttggtgga cctagagtct gtgtgcaaac tgcatacggc gtggaggttg   6900
aggtggaaaa tagtccatat gatccagatc aaatggtttt catggattac agagattata   6960
ctaacgagaa agttcggagc ttagaagctg agtatccaac gtttctgtac gccatgccta   7020
tgacaaagtc aagactcttc ttcgaggaga catgtttggc ctcaaaagat gtcatgccct   7080
ttgatttgct aaaaacgaag ctcatgttaa gattagatac actcggaatt cgaattctaa   7140
agacttacga agaggagtgg tcctatatcc cagttggtgg ttccttgcca aacaccgaac   7200
aaaagaatct cgcctttggt gctgccgcta gcatggtaca tcccgcaaca ggctattcag   7260
ttgtgagatc tttgtctgaa gctccaaaat atgcatcagt catcgcagag atactaagag   7320
aagagactac caaacagatc aacagtaata tttcaagaca agcttgggat actttatggc   7380
caccagaaag gaaaagacag agagcattct ttctctttgg tcttgaggct atagttcaat   7440
tcgataccga aggcattaga agcttcttcc gtactttctt ccgccttcca aaatggatgt   7500
ggcaagggtt tctaggatca acattaacat caggagatct cgttctcttt tctttataca   7560
tgttcgtcat ttcaccaaac aatttgagaa aaggtctcat caatcatctc atctctgatc   7620
caaccggagc aaccatgata aaaacctatc tcaaagtatg aggatccggc tgctaacaaa   7680
gcccgttctg tttaagaacg ggattttttg ctgaaaggag gaactatatc cggccggatt   7740
actggcttac tatgttggca ctgatgaggg tgtcagtgaa gtgcttcatg tggcaggaga   7800
aaaaaggctg caccggtgcg tcagcagaat atgtgataca ggatatattc cgcttcctcg   7860
ctcactgact cgctacgctc ggtcgttcga ctgcggcgag cggaaatggc ttacgaacgg   7920
ggcggagatt tcctggaaga tgccaggaag atacttaaca gggaagtgag agggccgcgg   7980
caaagccgtt tttccatagg ctccgccccc ctgacaagca tcacgaaatc tgacgctcaa   8040
atcagtggtg gcgaaacccg acaggactat aaagatacca ggcgtttccc cctggcggct   8100
ccctcgtgcg ctctcctgtt cctgcctttc ggtttaccgg tgtcattccg ctgttatggc   8160
cgcgtttgtc tcattccacg cctgacactc agttccgggt aggcagttcg ctccaagctg   8220
gactgtatgc acgaaccccc cgttcagtcc gaccgctgcg ccttatccgg taactatcgt   8280
cttgagtcca acccggaaag acatgcaaaa gcaccactgg cagcagccac tggtaattga   8340
tttagaggag ttagtcttga agtcatgcgc cggttaaggc taaactgaaa ggacaagttt   8400
tggtgactgc gctcctccaa gccagttacc tcggttcaaa gagttggtag ctcagagaac   8460
cttcgaaaaa ccgccctgca aggcggtttt ttcgttttca gagcaagaga ttacgcgcag   8520
accaaaacga tctcaagaag atcatcttat taatcagata aaatatttct agatttcagt   8580
gcaatttatc tcttcaaatg tagcacctga agtcagcccc atacgatata ag           8632
```

<210> SEQ ID NO 31
<211> LENGTH: 8492
<212> TYPE: DNA
<213> ORGANISM: Artificial Sequence
<220> FEATURE:
<223> OTHER INFORMATION: Plasmid pGT1464

<400> SEQUENCE: 31

```
ttgtaattct catgtttgac agcttatcat cgataagctt taatgcggta gtttatcaca     60
gttaaattgc taacgcagtc aggaaccttg caatggtgag tggcagtaaa gcgggcgttt    120
cgcctcatcg cgaaatagaa gtaatgagac aatccattga cgatcacctg gctggcctgt    180
```

-continued

```
tacctgaaac cgacagccag gatatcgtca gccttgcgat gcgtgaaggc gtcatggcac    240
ccggtaaacg gatccgtccg ctgctgatgc tgctggccgc ccgcgacctc cgctaccagg    300
gcagtatgcc tacgctgctc gatctcgcct gcgccgttga actgacccat accgcgtcgc    360
tgatgctcga cgacatgccc tgcatggaca acgccgagct gcgccgcggt cagcccacta    420
cccacaaaaa atttggtgag agcgtggcga tccttgcctc cgttgggctg ctctctaaag    480
cctttggtct gatcgccgcc accggcgatc tgccggggga gaggcgtgcc caggcggtca    540
acgagctctc taccgccgtg ggcgtgcagg gcctggtact ggggcagttt cgcgatctta    600
acgatgccgc cctcgaccgt accccctgacg ctatcctcag caccaaccac ctcaagaccg    660
gcattctgtt cagcgcgatg ctgcagatcg tcgccattgc ttccgcctcg tcgccgagca    720
cgcgagagac gctgcacgcc ttcgccctcg acttcggcca ggcgtttcaa ctgctggacg    780
atctgcgtga cgatcacccg gaaaccggta aagatcgcaa taaggacgcg ggaaaatcga    840
cgctggtcaa ccggctgggc gcagacgcgg cccggcaaaa gctgcgcgag catattgatt    900
ccgccgacaa acacctcact tttgcctgtc cgcagggcgg cgccatccga cagtttatgc    960
atctgtggtt tggccatcac cttgccgact ggtcaccggt catgaaaatc gcctgatacc   1020
gcccttttgg gttcaagcag tacataacga tggaaccaca ttacaggagt agtgatgaat   1080
gaaggacgag cgccttgttc agcgtaagaa cgatcatctg gatatcgttc tcgacccccg   1140
tcgcgccgta actcaggcta gcgcaggttt tgagcgctgg cgctttaccc actgcgccct   1200
gccagagctg aattttagcg acatcacgct ggaaaccacc ttcctgaatc ggcagctaca   1260
ggctccgctg ctgatcagct ccatgaccgg cggcgttgag cgctcgcgcc atatcaaccg   1320
ccacctcgcc gaggcggcgc aggtgctaaa aattgcgatg gggtgggct cccagcgcgt   1380
cgccattgag agcgacgcgg gcttagggct ggataaaacc ctgcggcagc tggctccgga   1440
cgtgccgctg ctggcgaacc tcggcgcggc gcagctgacc ggcagaaaag gtattgatta   1500
cgcccgacgg gccgtggaga tgatcgaggc ggatgcgctg attgtgcacc taaacccgct   1560
gcaggaggcg ctacagcccg gcggcgatcg cgactggcgc ggacggctgg cggctattga   1620
aactctggtc cgcgagctgc ccgttccgct ggtggtgaaa gaggtgggag ccggtatctc   1680
ccgaaccgtg gccgggcagc tgatcgatgc cggcgttacc gtgattgacg tcgcgggcgc   1740
gggcggcacc agctgggccg ccgttgaagg cgagcgggcg gccaccgagc agcagcgcag   1800
cgtggccaac gtctttgccg actgggggat ccccaccgct gaggcgctgg ttgacattgc   1860
cgaggcctgg ccgcagatgc cccttattgc ctcgggcggg attaaaaacg gcgtcgacgc   1920
ggcgaaagcg ctgcggctcg gcgcgtgcat ggtagggcag gccgccgccg tgctcggcag   1980
cgcaggcgtc tccacggaga aggtgatcga tcacttcaac gtgattattg agcagctgcg   2040
ggtggcctgc ttctgcaccg gcagccgcag cctgagcgat ctaaagcagg ctgatatccg   2100
ctatgttcgt gatacgccat aaggaggtac aaccatgaag aaaaccgttg tgattggcgc   2160
aggctttggt ggcctggcgc tggcgattcg cctgcaggcg gcagggatcc caaccgtact   2220
gctggagcag cgggacaagc ccggcggtcg ggcctacgtc tggcatgacc agggctttac   2280
ctttgacgcc gggccgacgg tgatcaccga tcctaccgcg cttgaggcgc tgttcaccct   2340
ggccggcagg cgcatggagg attacgtcag gctgctgccg gtaaaaccct tctaccgact   2400
ctgctgggag tccgggaaga ccctcgacta tgctaacgac agcgccgagc ttgaggcgca   2460
gattacccag ttcaaccccc gcgacgtcga gggctaccgg cgctttctgg cttactccca   2520
ggcggtattc caggagggat atttgcgcct cggcagcgtg ccgttcctct cttttcgcga   2580
```

```
catgctgcgc gccgggccgc agctgcttaa gctccaggcg tggcagagcg tctaccagtc   2640
ggtttcgcgc tttattgagg atgagcatct gcggcaggcc ttctcgttcc actccctgct   2700
ggtaggcggc aacccccttca ccacctcgtc catctacacc ctgatccacg cccttgagcg   2760
ggagtggggg gtctggttcc ctgagggcgg caccggggcg ctggtgaacg gcatggtgaa   2820
gctgtttacc gatctgggcg gggagatcga actcaacgcc cgggtcgaag agctggtggt   2880
ggccgataac cgcgtaagcc aggtccggct ggcggatggt cggatctttg acaccgacgc   2940
cgtagcctcg aacgctgacg tggtgaacac ctataaaaag ctgctcggcc accatccggt   3000
ggggcagaag cgggcggcag cgctggagcg caagagcatg agcaactcgc tgtttgtgct   3060
ctacttcggc ctgaaccagc ctcattccca gctggcgcac cataccatct gttttggtcc   3120
ccgctaccgg gagctgatcg acgagatctt taccggcagc gcgctggcgg atgacttctc   3180
gctctacctg cactcgccct gcgtgaccga tccctcgctc gcgcctcccg gctgcgccag   3240
cttctacgtg ctggccccgg tgccgcatct tggcaacgcg ccgctggact gggcgcagga   3300
ggggccgaag ctgcgcgacc gcatctttga ctaccttgaa gagcgctata tgcccggcct   3360
gcgtagccag ctggtgaccc agcggatctt taccccggca gacttccacg acacgctgga   3420
tgcgcatctg ggatcggcct tctccatcga gccgctgctg acccaaagcg cctggttccg   3480
cccgcacaac cgcgacagcg acattgccaa cctctacctg gtgggcgcag gtactcaccc   3540
tggggcgggc attcctggcg tagtggcctc ggcgaaagcc accgccagcc tgatgattga   3600
ggatctgcaa tgagccaacc gccgctgctt gaccacgcca cgcagaccat ggccaacggc   3660
tcgaaaagtt ttgccaccgc tgcgaagctg ttcgacccgg ccacccgccg tagcgtgctg   3720
atgctctaca cctggtgccg ccactgcgat gacgtcattg acgaccagac ccacggcttc   3780
gccagcgagg ccgcggcgga ggaggaggcc acccagcgcc tggcccggct gcgcacgctg   3840
accctggcgg cgtttgaagg ggccgagatg caggatccgg ccttcgctgc ctttcaggag   3900
gtggcgctga cccacggtat tacgccccgc atggcgctcg atcacctcga cggctttgcg   3960
atggacgtgg ctcagacccg ctatgtcacc tttgaggata cgctgcgcta ctgctatcac   4020
gtggcgggcg tggtgggtct gatgatggcc agggtgatgg gcgtgcggga tgagcgggtg   4080
ctggatcgcg cctgcgatct ggggctggcc ttccagctga cgaatatcgc ccgggatatt   4140
attgacgatg cggctattga ccgctgctat ctgcccgccg agtggctgca ggatgccggg   4200
ctgaccccgg agaactatgc cgcgcgggag aatcgggccg cgctggcgcg ggtggcggag   4260
cggcttattg atgccgcaga gccgtactac atctcctccc aggccgggct acacgatctg   4320
ccgccgcgct gcgcctgggc gatcgccacc gcccgcagcg tctaccggga gatcggtatt   4380
aaggtaaaag cggcgggagg cagcgcctgg gatcgccgcc agcacaccag caaaggtgaa   4440
aaaattgcca tgctgatggc ggcaccgggg caggttattc gggcgaagac gacgagggtg   4500
acgccgcgtc cggccggtct ttggcagcgt cccgtttaga ccgactccaa acgagtcggt   4560
ttttttgcgc ttgtttcggc gtgggtatgg tggcaggccc cgtggccggg ggactgttgg   4620
gcgccatctc cttggggtcg aatttgcttt cgaatttctg ccattcatcc gcttattatc   4680
acttattcag gcgtagcaac caggcgttta agggcaccaa taactgcctt aaaaaaatta   4740
cgccccgccc tgccactcat cgcagtactg ttgtaattca ttaagcattc tgccgacatg   4800
gaagccatca cagacggcat gatgaacctg aatcgccagc ggcatcagca ccttgtcgcc   4860
ttgcgtataa tatttgccca tggtgaaaac gggggcgaag aagttgtcca tattggccac   4920
```

-continued

```
gtttaaatca aaactggtga aactcaccca gggattggct gagacgaaaa acatattctc   4980
aataaaccct ttagggaaat aggccaggtt ttcaccgtaa cacgccacat cttgcgaata   5040
tatgtgtaga aactgccgga aatcgtcgtg gtattcactc cagagcgatg aaaacgtttc   5100
agtttgctca tggaaaacgg tgtaacaagg gtgaacacta tcccatatca ccagctcacc   5160
gtctttcatt gccatacgga attccggatg agcattcatc aggcgggcaa gaatgtgaat   5220
aaaggccgga taaaacttgt gcttattttt ctttacggtc tttaaaaagg ccgtaatatc   5280
cagctgaacg gtctggttat aggtacattg agcaactgac tgaaatgcct caaaatgttc   5340
tttacgatgc cattgggata tatcaacggt ggtatatcca gtgatttttt tctccatttt   5400
agcttcctta gctcctgaaa atctcgataa ctcaaaaaat acgcccggta gtgatcttat   5460
ttcattatgg tgaaagttgg aacctcttac gtgccgatca acgtctcatt ttcgccaaaa   5520
gttggcccag ggcttcccgg tatcaacagg gacaccagga tttatttatt ctgcgaagtg   5580
atcttccgtc acaggtattt attcggcgca aagtgcgtcg ggtgatgctg ccaacttact   5640
gatttagtgt atgatggtgt ttttgaggtg ctccagtggc ttctgtttct atcagctgtc   5700
cctcctgttc agctactgac ggggtggtgc gtaacggcaa aagcaccgcc ggacatcagc   5760
gctagcggag tgtatacact ccgctatcgc tacgtgactg ggtcatggct gcgccccgac   5820
acccgccaac acccgctgac gcgccctgac gggcttgtct gctcccggca tccgcttaca   5880
gacaagctgt gaccgtctcc gggagctgca tgtgtcagag gttttcaccg tcatcaccga   5940
aacgcgcgag gcagctggca cgacaggttt cccgactgga aagcgaatt ggtataatgc   6000
cctcgtaata attttgttta actttaagaa ggagatatac ccatgacaca gagggcccac   6060
catcaccatc accattccat ggctagcggc ggcggaagtt ccggtagtga gagttgtgta   6120
gcggtgagag aagatttcgc tgacgaagaa gattttgtga aagctggtgg ttctgagatt   6180
ctatttgttc aaatgcagca gaacaaagat atggatgaac agtctaagct tgttgataag   6240
ttgcctccta tatcaattgg tgatggtgct ttggatctag tggttattgg ttgtggtcct   6300
gctggtttag ccttggctgc agaatcagct aagcttggat taaaagttgg actcattggt   6360
ccagatcttc cttttactaa caattacggt gtttgggaag atgaattcaa tgatcttggg   6420
ctgcaaaaat gtattgagca tgtttggaga gagactattg tgtatctgga tgatgacaag   6480
cctattacca ttggccgtgc ttatggaaga gttagtcgac gtttgctcca tgaggagctt   6540
ttgaggaggt gtgtcgagtc aggtgtctcg taccttagct cgaaagttga cagcataaca   6600
gaagcttctg atggccttag acttgttgct tgtgacgaca ataacgtcat tccctgcagg   6660
cttgccactg ttgcttctgg agcagcttcg ggaaagctct tgcaatacga agttggtgga   6720
cctagagtct gtgtgcaaac tgcatacggc gtggaggttg aggtggaaaa tagtccatat   6780
gatccagatc aaatggtttt catggattac agagattata ctaacgagaa agttcggagc   6840
ttagaagctg agtatccaac gtttctgtac gccatgccta tgacaaagtc aagactcttc   6900
ttcgaggaga catgtttggc ctcaaaagat gtcatgccct ttgatttgct aaaaacgaag   6960
ctcatgttaa gattagatac actcggaatt cgaattctaa agacttacga agaggagtgg   7020
tcctatatcc cagttggtgg ttccttgcca aacaccgaac aaaagaatct cgcctttggt   7080
gctgccgcta gcatggtaca tcccgcaaca ggctattcag ttgtgagatc tttgtctgaa   7140
gctccaaaat atgcatcagt catcgcagag atactaagag aagagactac caaacagatc   7200
aacagtaata tttcaagaca agcttgggat actttatggc caccagaaag gaaaagacag   7260
agagcattct ttctctttgg tcttgaggct atagttcaat tcgataccga aggcattaga   7320
```

```
agcttcttcc gtactttctt ccgccttcca aaatggatgt ggcaagggtt tctaggatca   7380

acattaacat caggagatct cgttctcttt tctttataca tgttcgtcat ttcaccaaac   7440

aatttgagaa aggtctcat  caatcatctc atctctgatc caaccggagc aaccatgata   7500

aaaacctatc tcaaagtatg aggatccggc tgctaacaaa gcccgttctg tttaagaacg   7560

ggattttttg ctgaaaggag gaactatatc cggccggatt actggcttac tatgttggca   7620

ctgatgaggg tgtcagtgaa gtgcttcatg tggcaggaga aaaaaggctg caccggtgcg   7680

tcagcagaat atgtgataca ggatatattc cgcttcctcg ctcactgact cgctacgctc   7740

ggtcgttcga ctgcggcgag cggaaatggc ttacgaacgg ggcggagatt tcctggaaga   7800

tgccaggaag atacttaaca gggaagtgag agggccgcgg caaagccgtt tttccatagg   7860

ctccgccccc ctgacaagca tcacgaaatc tgacgctcaa atcagtggtg gcgaaacccg   7920

acaggactat aaagatacca ggcgtttccc cctggcggct ccctcgtgcg ctctcctgtt   7980

cctgcctttc ggtttaccgg tgtcattccg ctgttatggc cgcgtttgtc tcattccacg   8040

cctgacactc agttccgggt aggcagttcg ctccaagctg gactgtatgc acgaaccccc   8100

cgttcagtcc gaccgctgcg ccttatccgg taactatcgt cttgagtcca acccggaaag   8160

acatgcaaaa gcaccactgg cagcagccac tggtaattga tttagaggag ttagtcttga   8220

agtcatgcgc cggttaaggc taaactgaaa ggacaagttt tggtgactgc gctcctccaa   8280

gccagttacc tcggttcaaa gagttggtag ctcagagaac cttcgaaaaa ccgccctgca   8340

aggcggtttt ttcgttttca gagcaagaga ttacgcgcag accaaaacga tctcaagaag   8400

atcatcttat taatcagata aaatatttct agatttcagt gcaatttatc tcttcaaatg   8460

tagcacctga agtcagcccc atacgatata ag                                  8492
```

```
<210> SEQ ID NO 32
<211> LENGTH: 8669
<212> TYPE: DNA
<213> ORGANISM: Artificial Sequence
<220> FEATURE:
<223> OTHER INFORMATION: Plasmid pGT1484

<400> SEQUENCE: 32

atatttctag atttcagtgc aatttatctc ttcaaatgta gcacctgaag tcagccccat     60

acgatataag ttgtaattct catgtttgac agcttatcat cgataagctt taatgcggta    120

gtttatcaca gttaaattgc taacgcagtc aggaaccttg caatgagcag tttcgatgcc    180

catgaccttg acctcgacaa atttccggag gtcgtgcgag atcgtttgac gcagttcctc    240

gatgctcaag agctaacaat tgctgatatc ggcgctcctg tcacagatgc tgtggcccat    300

cttcgcagtt tcgtgctcaa tggaggaaag cgaatccgtc ctctttatgc gtgggctggt    360

ttcctggcgg cgcaaggcca taagaattct tctgaaaaac ttgagtccgt ccttgacgcc    420

gcagcgagtc tcgaattcat ccaggcttgt gccttgattc atgacgatat tatcgattct    480

tctgataccc ggcgcggagc ccctacagtt caccgggctg tggaagctga tcaccgcgcc    540

aataatttcg aaggcgatcc tgagcacttt ggcgtttcag tctcgatttt ggctggcgat    600

atggcattgg tgtgggcaga agacatgctg caggattccg gtttgagtgc agaggcattg    660

gcccgcacga gggatgcttg gcgtggcatg cgtactgagg ttattggcgg ccagctgctt    720

gatatttatc ttgagtcgca cgccaacgag tcggtggagc ttgcggattc tgtcaaccgc    780

ttcaaaacgg ccgcttacac gattgcgcgc ccattgcacc tgggcgcctc cattgctggc    840
```

-continued

```
ggttcgccgc agcttatcga cgcgctcctc cactacggcc acgacatcgg cattgcattc    900
cagttgaggg atgatctgct tggtgtgttt ggtgatcctg ctatcaccgg caaaccagct    960
ggagacgata tccgtgaagg caagcgcact gttcttcttg cgctcgctct acaacgcgct   1020
gataagcaat ctcctgaagc tgcaacggcc attcgcgcag gtgttggaaa ggtgacttca   1080
ccagaagata ttgctgtcat tacagagcat attcgagcta ctggtgctga agaagaagtt   1140
gagcagcgaa tttcccagct gactgaatcc ggtttggctc acctcgatga tgtagacatc   1200
cctgatgagg tgcgcgcaca gttgcgggca ctggctatcc gctcaaccga acgtcggatg   1260
taataccgcc cttttgggtt caagcagtac ataacgatgg aaccacatta caggagtagt   1320
gatgaatgaa ggacgagcgc cttgttcagc gtaagaacga tcatctggat atcgttctcg   1380
acccccgtcg cgccgtaact caggctagcg caggttttga gcgctggcgc tttacccact   1440
gcgccctgcc agagctgaat tttagcgaca tcacgctgga aaccaccttc ctgaatcggc   1500
agctacaggc tccgctgctg atcagctcca tgaccggcgg cgttgagcgc tcgcgccata   1560
tcaaccgcca cctcgccgag gcggcgcagg tgctaaaaat tgcgatgggg gtgggctccc   1620
agcgcgtcgc cattgagagc gacgcgggct tagggctgga taaaaccctg cggcagctgg   1680
ctccggacgt gccgctgctg gcgaacctcg gcgcggcgca gctgaccggc agaaaaggta   1740
ttgattacgc ccgacgggcc gtggagatga tcgaggcgga tgcgctgatt gtgcacctaa   1800
acccgctgca ggaggcgcta cagcccggcg gcgatcgcga ctggcgcgga cggctggcgg   1860
ctattgaaac tctggtccgc gagctgcccg ttccgctggt ggtgaaagag gtgggagccg   1920
gtatctcccg aaccgtggcc gggcagctga tcgatgccgg cgttaccgtg attgacgtcg   1980
cgggcgcggg cggcaccagc tgggccgccg ttgaaggcga gcgggcggcc accgagcagc   2040
agcgcagcgt ggccaacgtc tttgccgact gggggatccc caccgctgag gcgctggttg   2100
acattgccga ggcctggccg cagatgcccc ttattgcctc gggcgggatt aaaaacggcg   2160
tcgacgcggc gaaagcgctg cggctcggcg cgtgcatggt agggcaggcc gccgccgtgc   2220
tcggcagcgc aggcgtctcc acggagaagg tgatcgatca cttcaacgtg attattgagc   2280
agctgcgggt ggcctgcttc tgcaccggca gccgcagcct gagcgatcta aagcaggctg   2340
atatccgcta tgttcgtgat acgccataag gaggtacaac catgaagaaa accgttgtga   2400
ttggcgcagg ctttggtggc ctggcgctgg cgattcgcct gcaggcggca gggatcccaa   2460
ccgtactgct ggagcagcgg gacaagcccg gcggtcgggc ctacgtctgg catgaccagg   2520
gctttacctt tgacgccggg ccgacggtga tcaccgatcc taccgcgctt gaggcgctgt   2580
tcaccctggc cggcaggcgc atggaggatt acgtcaggct gctgccggta aaacccttct   2640
accgactctg ctgggagtcc gggaagaccc tcgactatgc taacgacagc gccgagcttg   2700
aggcgcagat tacccagttc aacccccgcg acgtcgaggg ctaccggcgc tttctggctt   2760
actcccaggc ggtattccag gagggatatt tgcgcctcgg cagcgtgccg ttcctctctt   2820
ttcgcgacat gctgcgcgcc gggccgcagc tgcttaagct ccaggcgtgg cagagcgtct   2880
accagtcggt ttcgcgcttt attgaggatg agcatctgcg gcaggccttc tcgttccact   2940
ccctgctggt aggcggcaac cccttcacca cctcgtccat ctacaccctg atccacgccc   3000
ttgagcggga gtggggggtc tggttccctg agggcggcac cggggcgctg gtgaacggca   3060
tggtgaagct gtttaccgat ctgggcgggg agatcgaact caacgcccgg gtcgaagagc   3120
tggtggtggc cgataaccgc gtaagccagg tccggctggc ggatggtcgg atctttgaca   3180
ccgacgccgt agcctcgaac gctgacgtgg tgaacaccta taaaaagctg ctcggccacc   3240
```

```
atccggtggg gcagaagcgg gcggcagcgc tggagcgcaa gagcatgagc aactcgctgt   3300

ttgtgctcta cttcggcctg aaccagcctc attcccagct ggcgcaccat accatctgtt   3360

ttggtccccg ctaccgggag ctgatcgacg agatctttac cggcagcgcg ctggcggatg   3420

acttctcgct ctacctgcac tcgccctgcg tgaccgatcc ctcgctcgcg cctcccggct   3480

gcgccagctt ctacgtgctg gccccggtgc cgcatcttgg caacgcgccg ctggactggg   3540

cgcaggaggg gccgaagctg cgcgaccgca tctttgacta ccttgaagag cgctatatgc   3600

ccggcctgcg tagccagctg gtgacccagc ggatctttac cccggcagac ttccacgaca   3660

cgctggatgc gcatctggga tcggccttct ccatcgagcc gctgctgacc caaagcgcct   3720

ggttccgccc gcacaaccgc gacagcgaca ttgccaacct ctacctggtg ggcgcaggta   3780

ctcaccctgg ggcgggcatt cctggcgtag tggcctcggc gaaagccacc gccagcctga   3840

tgattgagga tctgcaatga gccaaccgcc gctgcttgac cacgccacgc agaccatggc   3900

caacggctcg aaaagttttg ccaccgctgc gaagctgttc gacccggcca cccgccgtag   3960

cgtgctgatg ctctacacct ggtgccgcca ctgcgatgac gtcattgacg accagaccca   4020

cggcttcgcc agcgaggccg cggcggagga ggaggccacc cagcgcctgg cccggctgcg   4080

cacgctgacc ctggcggcgt ttgaagggcc cgagatgcag gatccggcct tcgctgcctt   4140

tcaggaggtg gcgctgaccc acggtattac gccccgcatg gcgctcgatc acctcgacgg   4200

ctttgcgatg gacgtggctc agacccgcta tgtcaccttt gaggatacgc tgcgctactg   4260

ctatcacgtg gcgggcgtgg tgggtctgat gatggccagg gtgatgggcg tgcgggatga   4320

gcgggtgctg gatcgcgcct gcgatctggg gctggccttc cagctgacga atatcgcccg   4380

ggatattatt gacgatgcgg ctattgaccg ctgctatctg cccgccgagt ggctgcagga   4440

tgccgggctg accccggaga actatgccgc gcgggagaat cgggccgcgc tggcgcgggt   4500

ggcggagcgg cttattgatg ccgcagagcc gtactacatc tcctcccagg ccgggctaca   4560

cgatctgccg ccgcgctgcg cctgggcgat cgccaccgcc cgcagcgtct accgggagat   4620

cggtattaag gtaaaagcgg cgggaggcag cgcctgggat cgccgccagc acaccagcaa   4680

aggtgaaaaa attgccatgc tgatggcggc accggggcag gttattcggg cgaagacgac   4740

gagggtgacg ccgcgtccgg ccggtctttg gcagcgtccc gtttagaccg actccaaacg   4800

agtcggtttt tttgcgcttg tttcggcgtg ggtatggtgg caggccccgt ggccggggga   4860

ctgttgggcg ccatctcctt ggggtcgaat ttgctttcga atttctgcca ttcatccgct   4920

tattatcact tattcaggcg tagcaaccag gcgtttaagg gcaccaataa ctgccttaaa   4980

aaaattacgc cccgccctgc cactcatcgc agtactgttg taattcatta agcattctgc   5040

cgacatggaa gccatcacag acggcatgat gaacctgaat cgccagcggc atcagcacct   5100

tgtcgccttg cgtataatat ttgcccatgg tgaaaacggg ggcgaagaag ttgtccatat   5160

tggccacgtt taaatcaaaa ctggtgaaac tcacccaggg attggctgag acgaaaaaca   5220

tattctcaat aaacccttta gggaaatagg ccaggttttc accgtaacac gccacatctt   5280

gcgaatatat gtgtagaaac tgccggaaat cgtcgtggta ttcactccag agcgatgaaa   5340

acgtttcagt ttgctcatgg aaaacggtgt aacaagggtg aacactatcc catatcacca   5400

gctcaccgtc tttcattgcc atacggaatt ccggatgagc attcatcagg cgggcaagaa   5460

tgtgaataaa ggccggataa aacttgtgct tatttttctt tacggtcttt aaaaaggccg   5520

taatatccag ctgaacggtc tggttatagg tacattgagc aactgactga aatgcctcaa   5580
```

```
aatgttcttt acgatgccat tgggatatat caacggtggt atatccagtg attttttttct   5640
ccattttagc ttccttagct cctgaaaatc tcgataactc aaaaaatacg cccggtagtg   5700
atcttatttc attatggtga aagttggaac ctcttacgtg ccgatcaacg tctcattttc   5760
gccaaaagtt ggcccagggc ttcccggtat caacagggac accaggattt atttattctg   5820
cgaagtgatc ttccgtcaca ggtatttatt cggcgcaaag tgcgtcgggt gatgctgcca   5880
acttactgat ttagtgtatg atggtgtttt tgaggtgctc cagtggcttc tgtttctatc   5940
agctgtccct cctgttcagc tactgacggg gtggtgcgta acggcaaaag caccgccgga   6000
catcagcgct agcggagtgt atacactccg ctatcgctac gtgactgggt catggctgcg   6060
ccccgacacc cgccaacacc cgctgacgcg ccctgacggg cttgtctgct cccggcatcc   6120
gcttacagac aagctgtgac cgtctccggg agctgcatgt gtcagaggtt ttcaccgtca   6180
tcaccgaaac gcgcgaggca gctggcacga caggtttccc gactggaaaa gcgaattggt   6240
ataatgccct cgtaataatt ttgtttaact ttaagaagga gatataccca tgacacagag   6300
ggcccaccat caccatcacc attccatggc tagcggcggc ggaagttccg gtagtgagag   6360
ttgtgtagcg gtgagagaag atttcgctga cgaagaagat tttgtgaaag ctggtggttc   6420
tgagattcta tttgttcaaa tgcagcagaa caaagatatg gatgaacagt ctaagcttgt   6480
tgataagttg cctcctatat caattggtga tggtgctttg gatctagtgg ttattggttg   6540
tggtcctgct ggtttagcct tggctgcaga atcagctaag cttggattaa aagttggact   6600
cattggtcca gatcttcctt ttactaacaa ttacggtgtt tgggaagatg aattcaatga   6660
tcttgggctg caaaaatgta ttgagcatgt ttggagagag actattgtgt atctggatga   6720
tgacaagcct attaccattg gccgtgctta tggaagagtt agtcgacgtt tgctccatga   6780
ggagcttttg aggaggtgtg tcgagtcagg tgtctcgtac cttagctcga aagttgacag   6840
cataacagaa gcttctgatg gccttagact tgttgcttgt gacgacaata acgtcattcc   6900
ctgcaggctt gccactgttg cttctggagc agcttcggga aagctcttgc aatacgaagt   6960
tggtggacct agagtctgtg tgcaaactgc atacggcgtg gaggttgagg tggaaaatag   7020
tccatatgat ccagatcaaa tggttttcat ggattacaga gattatacta acgagaaagt   7080
tcggagctta gaagctgagt atccaacgtt tctgtacgcc atgcctatga caaagtcaag   7140
actcttcttc gaggagacat gtttggcctc aaaagatgtc atgccctttg atttgctaaa   7200
aacgaagctc atgttaagat tagatacact cggaattcga attctaaaga cttacgaaga   7260
ggagtggtcc tatatcccag ttggtggttc cttgccaaac accgaacaaa agaatctcgc   7320
ctttggtgct gccgctagca tggtacatcc cgcaacaggc tattcagttg tgagatcttt   7380
gtctgaagct ccaaaatatg catcagtcat cgcagagata ctaagagaag agactaccaa   7440
acagatcaac agtaatattt caagacaagc ttgggatact ttatggccac cagaaaggaa   7500
aagacagaga gcattctttc tctttggtct tgaggctata gttcaattcg ataccgaagg   7560
cattagaagc ttcttccgta ctttcttccg ccttccaaaa tggatgtggc aagggtttct   7620
aggatcaaca ttaacatcag gagatctcgt tctcttttct ttatacatgt tcgtcatttc   7680
accaaacaat ttgagaaaag gtctcatcaa tcatctcatc tctgatccaa ccggagcaac   7740
catgataaaa acctatctca aagtatgagg atccggctgc taacaaagcc cgttctgttt   7800
aagaacggga ttttttgctg aaaggaggaa ctatatccgg ccggattact ggcttactat   7860
gttggcactg atgagggtgt cagtgaagtg cttcatgtgg caggagaaaa aaggctgcac   7920
cggtgcgtca gcagaatatg tgatacagga tatattccgc ttcctcgctc actgactcgc   7980
```

```
tacgctcggt cgttcgactg cggcgagcgg aaatggctta cgaacggggc ggagatttcc   8040

tggaagatgc caggaagata cttaacaggg aagtgagagg gccgcggcaa agccgttttt   8100

ccataggctc cgcccccctg acaagcatca cgaaatctga cgctcaaatc agtggtggcg   8160

aaacccgaca ggactataaa gataccaggc gtttccccct ggcggctccc tcgtgcgctc   8220

tcctgttcct gcctttcggt ttaccggtgt cattccgctg ttatggccgc gtttgtctca   8280

ttccacgcct gacactcagt tccgggtagg cagttcgctc caagctggac tgtatgcacg   8340

aaccccccgt tcagtccgac cgctgcgcct tatccggtaa ctatcgtctt gagtccaacc   8400

cggaaagaca tgcaaaagca ccactggcag cagccactgg taattgattt agaggagtta   8460

gtcttgaagt catgcgccgg ttaaggctaa actgaaagga caagttttgg tgactgcgct   8520

cctccaagcc agttacctcg gttcaaagag ttggtagctc agagaacctt cgaaaaaccg   8580

ccctgcaagg cggttttttc gttttcagag caagagatta cgcgcagacc aaaacgatct   8640

caagaagatc atcttattaa tcagataaa                                     8669
```

```
<210> SEQ ID NO 33
<211> LENGTH: 8651
<212> TYPE: DNA
<213> ORGANISM: Artificial Sequence
<220> FEATURE:
<223> OTHER INFORMATION: Plasmid pGT1518

<400> SEQUENCE: 33

ttgtaattct catgtttgac agcttatcat cgataagctt taatgcggta gttaacgcag     60

tcaggaacct tgcaatgagc agtttcgatg cccatgacct tgacctcgac aaatttccgg    120

aggtcgtgcg agatcgtttg acgcagttcc tcgatgctca agagctaaca attgctgata    180

tcggcgctcc tgtcacagat gctgtggccc atcttcgcag tttcgtgctc aatggaggaa    240

agcgaatccg tcctctttat gcgtgggctg gtttcctggc ggcgcaaggc cataagaatt    300

cttctgaaaa acttgagtcc gtccttgacg ccgcagcgag tctcgaattc atccaggctt    360

gtgccttgat tcatgacgat attatcgatt cttctgatac ccggcgcgga gcccctacag    420

ttcaccgggc tgtggaagct gatcaccgcg ccaataattt cgaaggcgat cctgagcact    480

ttggcgtttc agtctcgatt ttggctggcg atatggcatt ggtgtgggca gaagacatgc    540

tgcaggattc cggtttgagt gcagaggcat tggcccgcac gagggatgct tggcgtggca    600

tgcgtactga ggttattggc ggccagctgc ttgatattta tcttgagtcg cacgccaacg    660

agtcggtgga gcttgcggat tctgtcaacc gcttcaaaac ggccgcttac acgattgcgc    720

gcccattgca cctgggcgcc tccattgctg gcggttcgcc gcagcttatc gacgcgctcc    780

tccactacgg ccacgacatc ggcattgcat tccagttgag ggatgatctg cttggtgtgt    840

ttggtgatcc tgctatcacc ggcaaaccag ctggagacga tatccgtgaa ggcaagcgca    900

ctgttcttct tgcgctcgct ctacaacgcg ctgataagca atctcctgaa gctgcaacgg    960

ccattcgcgc aggtgttgga aaggtgactt caccagaaga tattgctgtc attacagagc   1020

atattcgagc tactggtgct gaagaagaag ttgagcagcg aatttcccag ctgactgaat   1080

ccggtttggc tcacctcgat gatgtagaca tccctgatga ggtgcgcgca cagttgcggg   1140

cactggctat ccgctcaacc gaacgtcgga tgtaataccg cccttttggg ttcaagcagt   1200

acataacgat ggaaccacat tacaggagta gtgatgaatg aaggacgagc gccttgttca   1260

gcgtaagaac gatcatctgg atatcgttct cgaccccgt cgcgccgtaa ctcaggctag    1320
```

```
cgcaggtttt gagcgctggc gctttaccca ctgcgccctg ccagagctga attttagcga   1380

catcacgctg gaaaccacct tcctgaatcg gcagctacag gctccgctgc tgatcagctc   1440

catgaccggc ggcgttgagc gctcgcgcca tatcaaccgc cacctcgccg aggcggcgca   1500

ggtgctaaaa attgcgatgg gggtgggctc ccagcgcgtc gccattgaga gcgacgcggg   1560

cttagggctg gataaaaccc tgcggcagct ggctccggac gtgccgctgc tggcgaacct   1620

cggcgcggcg cagctgaccg gcagaaaagg tattgattac gcccgacggg ccgtggagat   1680

gatcgaggcg gatgcgctga ttgtgcacct aaacccgctg caggaggcgc tacagcccgg   1740

cggcgatcgc gactggcgcg gacggctggc ggctattgaa actctggtcc gcgagctgcc   1800

cgttccgctg gtggtgaaag aggtgggagc cggtatctcc cgaaccgtgg ccgggcagct   1860

gatcgatgcc ggcgttaccg tgattgacgt cgcgggcgcg ggcggcacca gctgggccgc   1920

cgttgaaggc gagcgggcgg ccaccgagca gcagcgcagc gtggccaacg tctttgccga   1980

ctgggggatc cccaccgctg aggcgctggt tgacattgcc gaggcctggc cgcagatgcc   2040

ccttattgcc tcgggcggga ttaaaaacgg cgtcgacgcg gcgaaagcgc tgcggctcgg   2100

cgcgtgcatg gtagggcagg ccgccgccgt gctcggcagc gcaggcgtct ccacggagaa   2160

ggtgatcgat cacttcaacg tgattattga gcagctgcgg gtggcctgct tctgcaccgg   2220

cagccgcagc ctgagcgatc taaagcaggc tgatatccgc tatgttcgtg atacgccata   2280

aggaggtaca accatgaaga aaaccgttgt gattggcgca ggctttggtg gcctggcgct   2340

ggcgattcgc ctgcaggcgg cagggatccc aaccgtactg ctggagcagc gggacaagcc   2400

cggcggtcgg gcctacgtct ggcatgacca gggctttacc tttgacgccg ggccgacggt   2460

gatcaccgat cctaccgcgc ttgaggcgct gttcaccctg gccggcaggc gcatggagga   2520

ttacgtcagg ctgctgccgg taaaaccctt ctaccgactc tgctgggagt ccgggaagac   2580

cctcgactat gctaacgaca gcgccgagct tgaggcgcag attacccagt tcaacccccg   2640

cgacgtcgag ggctaccggc gctttctggc ttactcccag gcggtattcc aggagggata   2700

tttgcgcctc ggcagcgtgc cgttcctctc ttttcgcgac atgctgcgcg ccgggccgca   2760

gctgcttaag ctccaggcgt ggcagagcgt ctaccagtcg gtttcgcgct ttattgagga   2820

tgagcatctg cggcaggcct tctcgttcca ctccctgctg gtaggcggca accccttcac   2880

cacctcgtcc atctacaccc tgatccacgc ccttgagcgg gagtgggggg tctggttccc   2940

tgagggcggc accggggcgc tggtgaacgg catggtgaag ctgtttaccg atctgggcgg   3000

ggagatcgaa ctcaacgccc gggtcgaaga gctggtggtg gccgataacc gcgtaagcca   3060

ggtccggctg gcggatggtc ggatctttga caccgacgcc gtagcctcga acgctgacgt   3120

ggtgaacacc tataaaaagc tgctcggcca ccatccggtg gggcagaagc gggcggcagc   3180

gctggagcgc aagagcatga gcaactcgct gtttgtgctc tacttcggcc tgaaccagcc   3240

tcattcccag ctggcgcacc ataccatctg ttttggtccc cgctaccggg agctgatcga   3300

cgagatcttt accggcagcg cgctggcgga tgacttctcg ctctacctgc actcgccctg   3360

cgtgaccgat ccctcgctcg cgcctcccgg ctgcgccagc ttctacgtgc tggccccggt   3420

gccgcatctt ggcaacgcgc cgctggactg ggcgcaggag gggccgaagc tgcgcgaccg   3480

catctttgac taccttgaag agcgctatat gcccggcctg cgtagccagc tggtgaccca   3540

gcggatcttt accccggcag acttccacga cacgctggat gcgcatctgg gatcggcctt   3600

ctccatcgag ccgctgctga cccaaagcgc ctggttccgc ccgcacaacc gcgacagcga   3660

cattgccaac ctctacctgg tgggcgcagg tactcaccct ggggcgggca ttcctggcgt   3720
```

```
agtggcctcg gcgaaagcca ccgccagcct gatgattgag gatctgcaat gagccaaccg   3780
ccgctgcttg accacgccac gcagaccatg gccaacggct cgaaaagttt tgccaccgct   3840
gcgaagctgt tcgacccggc cacccgccgt agcgtgctga tgctctacac ctggtgccgc   3900
cactgcgatg acgtcattga cgaccagacc cacggcttcg ccagcgaggc cgcggcggag   3960
gaggaggcca cccagcgcct ggcccggctg cgcacgctga ccctggcggc gtttgaaggg   4020
gccgagatgc aggatccggc cttcgctgcc tttcaggagg tggcgctgac ccacggtatt   4080
acgccccgca tggcgctcga tcacctcgac ggctttgcga tggacgtggc tcagacccgc   4140
tatgtcacct ttgaggatac gctgcgctac tgctatcacg tggcgggcgt ggtgggtctg   4200
atgatggcca gggtgatggg cgtgcgggat gagcgggtgc tggatcgcgc ctgcgatctg   4260
gggctggcct tccagctgac gaatatcgcc cgggatatta ttgacgatgc ggctattgac   4320
cgctgctatc tgcccgccga gtggctgcag gatgccgggc tgaccccgga gaactatgcc   4380
gcgcgggaga atcgggccgc gctggcgcgg gtggcggagc ggcttattga tgccgcagag   4440
ccgtactaca tctcctccca ggccgggcta cacgatctgc cgccgcgctg cgcctgggcg   4500
atcgccaccg cccgcagcgt ctaccgggag atcggtatta aggtaaaagc ggcgggaggc   4560
agcgcctggg atcgccgcca gcacaccagc aaaggtgaaa aaattgccat gctgatggcg   4620
gcaccggggc aggttattcg ggcgaagacg acgagggtga cgccgcgtcc ggccggtctt   4680
tggcagcgtc ccgtttagac cgactccaaa cgagtcggtt tttttgcgct tgtttcggcg   4740
tgggtatggt ggcaggcccc gtggccgggg gactgttggg cgccatctcc ttggggtcga   4800
atttgctttc gaatttctgc cattcatccg cttattatca cttattcagg cgtagcaacc   4860
aggcgtttaa gggcaccaat aactgcctta aaaaaattac gccccgccct gccactcatc   4920
gcagtactgt tgtaattcat taagcattct gccgacatgg aagccatcac agacggcatg   4980
atgaacctga atcgccagcg gcatcagcac cttgtcgcct tgcgtataat atttgcccat   5040
ggtgaaaacg ggggcgaaga agttgtccat attggccacg tttaaatcaa aactggtgaa   5100
actcacccag ggattggctg agacgaaaaa catattctca ataaaccctt tagggaaata   5160
ggccaggttt tcaccgtaac acgccacatc ttgcgaatat atgtgtagaa actgccggaa   5220
atcgtcgtgg tattcactcc agagcgatga aaacgtttca gtttgctcat ggaaaacggt   5280
gtaacaaggg tgaacactat cccatatcac cagctcaccg tctttcattg ccatacggaa   5340
ttccggatga gcattcatca ggcgggcaag aatgtgaata aaggccggat aaaacttgtg   5400
cttatttttc tttacggtct ttaaaaaggc cgtaatatcc agctgaacgg tctggttata   5460
ggtacattga gcaactgact gaaatgcctc aaaatgttct ttacgatgcc attgggatat   5520
atcaacggtg gtatatccag tgattttttt ctccatttta gcttccttag ctcctgaaaa   5580
tctcgataac tcaaaaaata cgcccggtag tgatcttatt tcattatggt gaaagttgga   5640
acctcttacg tgccgatcaa cgtctcattt tcgccaaaag ttggcccagg gcttcccggt   5700
atcaacaggg acaccaggat ttatttattc tgcgaagtga tcttccgtca caggtattta   5760
ttcggcgcaa agtgcgtcgg gtgatgctgc caacttactg atttagtgta tgatggtgtt   5820
tttgaggtgc tccagtggct tctgtttcta tcagctgtcc ctcctgttca gctactgacg   5880
gggtggtgcg taacggcaaa agcaccgccg gacatcagcg ctagcggagt gtatacactc   5940
cgctatcgct acgtgactgg gtcatggctg cgccccgaca cccgccaaca cccgctgacg   6000
cgccctgacg ggcttgtctg ctcccggcat ccgcttacag acaagctgtg accgtctccg   6060
```

```
ggagctgcat gtgtcagagg ttttcaccgt catcaccgaa acgcgcgagg cagctggcac   6120
gacaggtttc ccgactggaa aagcgaattg gtataatgcc ctcgtaataa ttttgtttaa   6180
ctttaagaag gagatatacc catgacacag agggcccacc atcaccatca ccattccatg   6240
gctagcggcg gcggaagttc cggtagtgag agttgtgtag cggtgagaga agatttcgct   6300
gacgaagaag attttgtgaa agctggtggt tctgagattc tatttgttca aatgcagcag   6360
aacaaagata tggatgaaca gtctaagctt gttgataagt tgcctcctat atcaattggt   6420
gatggtgctt tggatctagt ggttattggt tgtggtcctg ctggtttagc cttggctgca   6480
gaatcagcta agcttggatt aaaagttgga ctcattggtc cagatcttcc ttttactaac   6540
aattacggtg tttgggaaga tgaattcaat gatcttgggc tgcaaaaatg tattgagcat   6600
gtttggagag agactattgt gtatctggat gatgacaagc ctattaccat tggccgtgct   6660
tatggaagag ttagtcgacg tttgctccat gaggagcttt tgaggaggtg tgtcgagtca   6720
ggtgtctcgt accttagctc gaaagttgac agcataacag aagcttctga tggccttaga   6780
cttgttgctt gtgacgacaa taacgtcatt ccctgcaggc ttgccactgt tgcttctgga   6840
gcagcttcgg gaaagctctt gcaatacgaa gttggtggac ctagagtctg tgtgcaaact   6900
gcatacggcg tggaggttga ggtggaaaat agtccatatg atccagatca aatggttttc   6960
atggattaca gagattatac taacgagaaa gttcggagct tagaagctga gtatccaacg   7020
tttctgtacg ccatgcctat gacaaagtca agactcttct tcgaggagac atgtttggcc   7080
tcaaaagatg tcatgccctt tgatttgcta aaaacgaagc tcatgttaag attagataca   7140
ctcggaattc gaattctaaa gacttacgaa gaggagtggt cctatatccc agttggtggt   7200
tccttgccaa acaccgaaca aaagaatctc gcctttggtg ctgccgctag catggtacat   7260
cccgcaacag gctattcagt tgtgagatct ttgtctgaag ctccaaaata tgcatcagtc   7320
atcgcagaga tactaagaga agagactacc aaacagatca acagtaatat ttcaagacaa   7380
gcttgggata ctttatggcc accagaaagg aaaagacaga gagcattctt tctctttggt   7440
cttgaggcta tagttcaatt cgataccgaa ggcattagaa gcttcttccg tactttcttc   7500
cgccttccaa aatggatgtg gcaagggttt ctaggatcaa cattaacatc aggagatctc   7560
gttctctttt ctttatacat gttcgtcatt tcaccaaaca atttgagaaa aggtctcatc   7620
aatcatctca tctctgatcc aaccggagca accatgataa aaacctatct caaagtatga   7680
ggatccggct gctaacaaag cccgttctgt ttaagaacgg gatttttttgc tgaaaggagg   7740
aactatatcc ggccggatta ctggcttact atgttggcac tgatgagggt gtcagtgaag   7800
tgcttcatgt ggcaggagaa aaaaggctgc accggtgcgt cagcagaata tgtgatacag   7860
gatatattcc gcttcctcgc tcactgactc gctacgctcg gtcgttcgac tgcggcgagc   7920
ggaaatggct tacgaacggg gcggagattt cctggaagat gccaggaaga tacttaacag   7980
ggaagtgaga gggccgcggc aaagccgttt ttccataggc tccgcccccc tgacaagcat   8040
cacgaaatct gacgctcaaa tcagtggtgg cgaaacccga caggactata aagataccag   8100
gcgtttcccc ctggcggctc cctcgtgcgc tctcctgttc ctgcctttcg gtttaccggt   8160
gtcattccgc tgttatggcc gcgtttgtct cattccacgc ctgacactca gttccgggta   8220
ggcagttcgc tccaagctgg actgtatgca cgaacccccc gttcagtccg accgctgcgc   8280
cttatccggt aactatcgtc ttgagtccaa cccggaaaga catgcaaaag caccactggc   8340
agcagccact ggtaattgat ttagaggagt tagtcttgaa gtcatgcgcc ggttaaggct   8400
aaactgaaag gacaagtttt ggtgactgcg ctcctccaag ccagttacct cggttcaaag   8460
```

```
agttggtagc tcagagaacc ttcgaaaaac cgccctgcaa ggcggttttt tcgttttcag   8520

agcaagagat tacgcgcaga ccaaaacgat ctcaagaaga tcatcttatt aatcagataa   8580

aatatttcta gatttcagtg caatttatct cttcaaatgt agcacctgaa gtcagcccca   8640

tacgatataa g                                                        8651
```

<210> SEQ ID NO 34
<211> LENGTH: 8399
<212> TYPE: DNA
<213> ORGANISM: Artificial Sequence
<220> FEATURE:
<223> OTHER INFORMATION: Plasmid pGT1543

<400> SEQUENCE: 34

```
gctggcacga caggtttccc gactggaaag cgaattgtga tttagcttat taaattcttg     60

acagggggc ttgtggtata atgtatgcgt aataattttg taacgcagtg aggaaccttg    120

caatgagcag tttcgatgcc catgaccttg acctcgacaa atttccggag gtcgtgcgag    180

atcgtttgac gcagttcctc gatgctcaag agctaacaat tgctgatatc ggcgctcctg    240

tcacagatgc tgtggcccat cttcgcagtt tcgtgctcaa tggaggaaag cgaatccgtc    300

ctctttatgc gtgggctggt ttcctggcgg cgcaaggcca taagaattct tctgaaaaac    360

ttgagtccgt ccttgacgcc gcagcgagtc tcgaattcat ccaggcttgt gccttgattc    420

atgacgatat tatcgattct tctgataccc ggcgcggagc ccctacagtt caccgggctg    480

tggaagctga tcaccgcgcc aataatttcg aaggcgatcc tgagcacttt ggcgtttcag    540

tctcgatttt ggctggcgat atggcattgg tgtgggcaga agacatgctg caggattccg    600

gtttgagtgc agaggcattg gcccgcacga gggatgcttg gcgtggcatg cgtactgagg    660

ttattggcgg ccagctgctt gatatttatc ttgagtcgca cgccaacgag tcggtggagc    720

ttgcggattc tgtcaaccgc ttcaaaacgg ccgcttacac gattgcgcgc ccattgcacc    780

tgggcgcctc cattgctggc ggttcgccgc agcttatcga cgcgctcctc cactacggcc    840

acgacatcgg cattgcattc cagttgaggg atgatctgct tggtgtgttt ggtgatcctg    900

ctatcaccgg caaaccagct ggagacgata tccgtgaagg caagcgcact gttcttcttg    960

cgctcgctct acaacgcgct gataagcaat ctcctgaagc tgcaacggcc attcgcgcag   1020

gtgttggaaa ggtgacttca ccagaagata ttgctgtcat tacagagcat attcgagcta   1080

ctggtgctga agaagaagtt gagcagcgaa tttcccagct gactgaatcc ggtttggctc   1140

acctcgatga tgtagacatc cctgatgagg tgcgcgcaca gttgcgggca ctggctatcc   1200

gctcaaccga acgtcggatg taataccgcc cttttgggtt caagcagtac ataacgatgg   1260

aaccacatta caggagtagt gatgaatgaa ggacgagcgc cttgttcagc gtaagaacga   1320

tcatctggat atcgttctcg acccccgtcg cgccgtaact caggctagcg caggttttga   1380

gcgctggcgc tttacccact gcgccctgcc agagctgaat tttagcgaca tcacgctgga   1440

aaccaccttc ctgaatcggc agctacaggc tccgctgctg atcagctcca tgaccggcgg   1500

cgttgagcgc tcgcgccata tcaaccgcca cctcgccgag gcggcgcagg tgctaaaaat   1560

tgcgatgggg gtgggctccc agcgcgtcgc cattgagagc gacgcgggct tagggctgga   1620

taaaaccctg cggcagctgg ctccggacgt gccgctgctg gcgaacctcg gcgcggcgca   1680

gctgaccggc agaaaaggta ttgattacgc ccgacgggcc gtggagatga tcgaggcgga   1740

tgcgctgatt gtgcacctaa acccgctgca ggaggcgcta cagcccggcg gcgatcgcga   1800
```

```
ctggcgcgga cggctggcgg ctattgaaac tctggtccgc gagctgcccg ttccgctggt   1860
ggtgaaagag gtgggagccg gtatctcccg aaccgtggcc gggcagctga tcgatgccgg   1920
cgttaccgtg attgacgtcg cgggcgcggg cggcaccagc tgggccgccg ttgaaggcga   1980
gcgggcggcc accgagcagc agcgcagcgt ggccaacgtc tttgccgact gggggatccc   2040
caccgctgag gcgctggttg acattgccga ggcctggccg cagatgcccc ttattgcctc   2100
gggcgggatt aaaaacggcg tcgacgcggc gaaagcgctg cggctcggcg cgtgcatggt   2160
agggcaggcc gccgccgtgc tcggcagcgc aggcgtctcc acggagaagg tgatcgatca   2220
cttcaacgtg attattgagc agctgcgggt ggcctgcttc tgcaccggca gccgcagcct   2280
gagcgatcta aagcaggctg atatccgcta tgttcgtgat acgccataag gaggtacaac   2340
catgaagaaa accgttgtga ttggcgcagg ctttggtggc ctggcgctgg cgattcgcct   2400
gcaggcggca gggatcccaa ccgtactgct ggagcagcgg gacaagcccg gcggtcgggc   2460
ctacgtctgg catgaccagg gctttacctt tgacgccggg ccgacggtga tcaccgatcc   2520
taccgcgctt gaggcgctgt tcaccctggc cggcaggcgc atggaggatt acgtcaggct   2580
gctgccggta aaacccttct accgactctg ctgggagtcc gggaagaccc tcgactatgc   2640
taacgacagc gccgagcttg aggcgcagat tacccagttc aacccccgcg acgtcgaggg   2700
ctaccggcgc tttctggctt actcccaggc ggtattccag gagggatatt tgcgcctcgg   2760
cagcgtgccg ttcctctctt ttcgcgacat gctgcgcgcc gggccgcagc tgcttaagct   2820
ccaggcgtgg cagagcgtct accagtcggt ttcgcgcttt attgaggatg agcatctgcg   2880
gcaggccttc tcgttccact ccctgctggt aggcggcaac cccttcacca cctcgtccat   2940
ctacaccctg atccacgccc ttgagcggga gtgggggtc tggttccctg agggcggcac   3000
cggggcgctg gtgaacggca tggtgaagct gtttaccgat ctgggcgggg agatcgaact   3060
caacgcccgg gtcgaagagc tggtggtggc cgataaccgc gtaagccagg tccggctggc   3120
ggatggtcgg atctttgaca ccgacgccgt agcctcgaac gctgacgtgg tgaacaccta   3180
taaaaagctg ctcggccacc atccggtggg gcagaagcgg gcggcagcgc tggagcgcaa   3240
gagcatgagc aactcgctgt ttgtgctcta cttcggcctg aaccagcctc attcccagct   3300
ggcgcaccat accatctgtt ttggtccccg ctaccgggag ctgatcgacg agatctttac   3360
cggcagcgcg ctggcggatg acttctcgct ctacctgcac tcgccctgcg tgaccgatcc   3420
ctcgctcgcg cctcccggct gcgccagctt ctacgtgctg gccccggtgc cgcatcttgg   3480
caacgcgccg ctggactggg cgcaggaggg gccgaagctg cgcgaccgca tctttgacta   3540
ccttgaagag cgctatatgc ccggcctgcg tagccagctg gtgacccagc ggatctttac   3600
cccggcagac ttccacgaca cgctggatgc gcatctggga tcggccttct ccatcgagcc   3660
gctgctgacc caaagcgcct ggttccgccc gcacaaccgc gacagcgaca ttgccaacct   3720
ctacctggtg ggcgcaggta ctcaccctgg ggcgggcatt cctggcgtag tggcctcggc   3780
gaaagccacc gccagcctga tgattgagga tctgcaatga gccaaccgcc gctgcttgac   3840
cacgccacgc agaccatggc caacggctcg aaaagttttg ccaccgctgc gaagctgttc   3900
gacccggcca cccgccgtag cgtgctgatg ctctacacct ggtgccgcca ctgcgatgac   3960
gtcattgacg accagaccca cggcttcgcc agcgaggccg cggcggagga ggaggccacc   4020
cagcgcctgg cccggctgcg cacgctgacc ctggcggcgt ttgaaggggc cgagatgcag   4080
gatccggcct tcgctgcctt tcaggaggtg gcgctgaccc acggtattac gccccgcatg   4140
gcgctcgatc acctcgacgg ctttgcgatg gacgtggctc agacccgcta tgtcaccttt   4200
```

```
gaggatacgc tgcgctactg ctatcacgtg gcgggcgtgg tgggtctgat gatggccagg   4260
gtgatgggcg tgcgggatga gcgggtgctg gatcgcgcct gcgatctggg gctggccttc   4320
cagctgacga atatcgcccg ggatattatt gacgatgcgg ctattgaccg ctgctatctg   4380
cccgccgagt ggctgcagga tgccgggctg accccggaga actatgccgc gcgggagaat   4440
cgggccgcgc tggcgcgggt ggcggagcgg cttattgatg ccgcagagcc gtactacatc   4500
tcctcccagg ccgggctaca cgatctgccg ccgcgctgcg cctgggcgat cgccaccgcc   4560
cgcagcgtct accgggagat cggtattaag gtaaaagcgg cgggaggcag cgcctgggat   4620
cgccgccagc acaccagcaa aggtgaaaaa attgccatgc tgatggcggc accggggcag   4680
gttattcggg cgaagacgac gagggtgacg ccgcgtccgg ccggtctttg gcagcgtccc   4740
gtttagaccg actccaaacg agtcggtttt tttgcgcttg tttcggcgtg ggtatggtgg   4800
caggccccgt ggccggggga ctgttgggcg ccatctcctt ggggtcgaat ttgctttcga   4860
atttctgcca ttcatccgct tattatcact tattcaggcg tagcaaccag gcgtttaagg   4920
gcaccaataa ctgccttaaa aaaattacgc cccgccctgc cactcatcgc agtactgttg   4980
taattcatta agcattctgc cgacatggaa gccatcacag acggcatgat gaacctgaat   5040
cgccagcggc atcagcacct tgtcgccttg cgtataatat ttgcccatgg tgaaaacggg   5100
ggcgaagaag ttgtccatat tggccacgtt taaatcaaaa ctggtgaaac tcacccaggg   5160
attggctgag acgaaaaaca tattctcaat aaacccttta gggaaatagg ccaggttttc   5220
accgtaacac gccacatctt gcgaatatat gtgtagaaac tgccggaaat cgtcgtggta   5280
ttcactccag agcgatgaaa acgtttcagt ttgctcatgg aaaacggtgt aacaagggtg   5340
aacactatcc catatcacca gctcaccgtc tttcattgcc atacggaatt ccggatgagc   5400
attcatcagg cgggcaagaa tgtgaataaa ggccggataa aacttgtgct tatttttctt   5460
tacggtcttt aaaaaggccg taatatccag ctgaacggtc tggttatagg tacattgagc   5520
aactgactga aatgcctcaa aatgttcttt acgatgccat tgggatatat caacggtggt   5580
atatccagtg attttttct ccattttagc ttccttagct cctgaaaatc tcgataactc   5640
aaaaaatacg cccggtagtg atcttatttc attatggtga aagttggaac ctcttacgtg   5700
ccgatcaacg tctcattttc gccaaaagtt ggcccagggc ttcccggtat caacagggac   5760
accaggattt atttattctg cgaagtgatc ttccgtcaca ggtttcccga ctggaaaagc   5820
gaattggtat aatgccctcg taataatttt gtttaacttt aagaaggaga tatacccatg   5880
acacagaggg cccaccatca ccatcaccat tccatggcta gcggcggcgg aagttccggt   5940
agtgagagtt gtgtagcggt gagagaagat ttcgctgacg aagaagattt tgtgaaagct   6000
ggtggttctg agattctatt tgttcaaatg cagcagaaca aagatatgga tgaacagtct   6060
aagcttgttg ataagttgcc tcctatatca attggtgatg gtgctttgga tctagtggtt   6120
attggttgtg gtcctgctgg tttagccttg gctgcagaat cagctaagct tggattaaaa   6180
gttggactca ttggtccaga tcttcctttt actaacaatt acggtgtttg ggaagatgaa   6240
ttcaatgatc ttgggctgca aaaatgtatt gagcatgttt ggagagagac tattgtgtat   6300
ctggatgatg acaagcctat taccattggc cgtgcttatg gaagagttag tcgacgtttg   6360
ctccatgagg agcttttgag gaggtgtgtc gagtcaggtg tctcgtacct tagctcgaaa   6420
gttgacagca taacagaagc ttctgatggc cttagacttg ttgcttgtga cgacaataac   6480
gtcattccct gcaggcttgc cactgttgct tctggagcag cttcgggaaa gctcttgcaa   6540
```

```
tacgaagttg gtggacctag agtctgtgtg caaactgcat acggcgtgga ggttgaggtg   6600

gaaaatagtc catatgatcc agatcaaatg gttttcatgg attacagaga ttatactaac   6660

gagaaagttc ggagcttaga agctgagtat ccaacgtttc tgtacgccat gcctatgaca   6720

aagtcaagac tcttcttcga ggagacatgt ttggcctcaa aagatgtcat gccctttgat   6780

ttgctaaaaa cgaagctcat gttaagatta gatacactcg gaattcgaat tctaaagact   6840

tacgaagagg agtggtccta tatcccagtt ggtggttcct tgccaaacac cgaacaaaag   6900

aatctcgcct ttggtgctgc cgctagcatg gtacatcccg caacaggcta ttcagttgtg   6960

agatctttgt ctgaagctcc aaaatatgca tcagtcatcg cagagatact aagagaagag   7020

actaccaaac agatcaacag taatatttca agacaagctt gggatacttt atggccacca   7080

gaaaggaaaa gacagagagc attctttctc tttggtcttg aggctatagt tcaattcgat   7140

accgaaggca ttagaagctt cttccgtact ttcttccgcc ttccaaaatg gatgtggcaa   7200

gggtttctag gatcaacatt aacatcagga gatctcgttc tcttttcttt atacatgttc   7260

gtcatttcac caaacaattt gagaaaaggt ctcatcaatc atctcatctc tgatccaacc   7320

ggagcaacca tgataaaaac ctatctcaaa gtatgaggat ccggctgcta acaaagcccg   7380

ttctgtttaa gaacgggatt ttttgctgaa aggaggaact atatccggcc ggcttcatgt   7440

ggcaggagaa aaaaggctgc accggtgcgt cagcagaata tgtgatacag gatatattcc   7500

gcttcctcgc tcactgactc gctacgctcg gtcgttcgac tgcggcgagc ggaaatggct   7560

tacgaacggg gcggagattt cctggaagat gccaggaaga tacttaacag ggaagtgaga   7620

gggccgcggc aaagccgttt ttccataggc tccgcccccc tgacaagcaa tcacgaatct   7680

gacgctcaaa tcagtggtgg cgaaacccga caggactata aagataccag gcgtttcccc   7740

tggcggctcc ctcgtgcgct ctcctgttcc tgcctttcgg tttaccggtg tcattccgct   7800

gttatggccg cgtttgtctc attccacgcc tgacactcag ttccgggtag gcagttcgct   7860

ccaagctgga ctgtatgcac gaaccccccg ttcagtccga ccgctgcgcc ttatccggta   7920

actatcgtct tgagtccaac ccggaaagac atgcaaaagc accactggca gcagccactg   7980

gtaattgatt tagaggagtt agtcttgaag tcatgcgccg gttaaggcta aactgaaagg   8040

acaagttttg gtgactgcgc tcctccaagc cagttacctc ggttcaaaga gttggtagct   8100

cagagaacct tcgaaaaacc gccctgcaag gcggtttttt cgttttcaga gcaagagatt   8160

acgcgcagac caaaacgatc tcaagaagat catcttatta atcagataaa atatttctag   8220

tacactccgc tatcgctacg tgactgggtc atggctgcgc cccgacaccc gccaacaccc   8280

gctgacgcgc cctgacgggc ttgtctgctc ccggcatccg cttacagaca agctgtgacc   8340

gtctccggga gctgcatgtg tcagaggttt tcaccgtcat caccgaaacg cgcgaggca    8399
```

<210> SEQ ID NO 35
<211> LENGTH: 8397
<212> TYPE: DNA
<213> ORGANISM: Artificial Sequence
<220> FEATURE:
<223> OTHER INFORMATION: Plasmid pGT1544

<400> SEQUENCE: 35

```
gctggcacga caggtttccc gactggaaag cgaattgtga tagaaaacaa ataattcttg     60

acatcttcat atggtataat tggaaggtaa taattttgta acgcagtcag gaaccttgca    120

atgagcagtt tcgatgccca tgaccttgac ctcgacaaat ttccggaggt cgtgcgagat    180

cgtttgacgc agttcctcga tgctcaagag ctaacaattg ctgatatcgg cgctcctgtc    240
```

```
acagatgctg tggcccatct tcgcagtttc gtgctcaatg gaggaaagcg aatccgtcct    300
ctttatgcgt gggctggttt cctggcggcg caaggccata agaattcttc tgaaaaactt    360
gagtccgtcc ttgacgccgc agcgagtctc gaattcatcc aggcttgtgc cttgattcat    420
gacgatatta tcgattcttc tgatacccgg cgcggagccc ctacagttca ccgggctgtg    480
gaagctgatc accgcgccaa taatttcgaa ggcgatcctg agcactttgg cgtttcagtc    540
tcgattttgg ctggcgatat ggcattggtg tgggcagaag acatgctgca ggattccggt    600
ttgagtgcag aggcattggc ccgcacgagg gatgcttggc gtggcatgcg tactgaggtt    660
attggcggcc agctgcttga tatttatctt gagtcgcacg ccaacgagtc ggtggagctt    720
gcggattctg tcaaccgctt caaaacggcc gcttacacga ttgcgcgccc attgcacctg    780
ggcgcctcca ttgctggcgg ttcgccgcag cttatcgacg cgctcctcca ctacggccac    840
gacatcggca ttgcattcca gttgagggat gatctgcttg gtgtgtttgg tgatcctgct    900
atcaccggca aaccagctgg agacgatatc cgtgaaggca agcgcactgt tcttcttgcg    960
ctcgctctac aacgcgctga taagcaatct cctgaagctg caacggccat tcgcgcaggt   1020
gttggaaagg tgacttcacc agaagatatt gctgtcatta cagagcatat tcgagctact   1080
ggtgctgaag aagaagttga gcagcgaatt tcccagctga ctgaatccgg tttggctcac   1140
ctcgatgatg tagacatccc tgatgaggtg cgcgcacagt tgcgggcact ggctatccgc   1200
tcaaccgaac gtcggatgta ataccgccct tttgggttca agcagtacat aacgatggaa   1260
ccacattaca ggagtagtga tgaatgaagg acgagcgcct tgttcagcgt aagaacgatc   1320
atctggatat cgttctcgac ccccgtcgcg ccgtaactca ggctagcgca ggttttgagc   1380
gctggcgctt tacccactgc gccctgccag agctgaattt tagcgacatc acgctggaaa   1440
ccaccttcct gaatcggcag ctacaggctc cgctgctgat cagctccatg accggcggcg   1500
ttgagcgctc gcgccatatc aaccgccacc tcgccgaggc ggcgcaggtg ctaaaaattg   1560
cgatgggggt gggctcccag cgcgtcgcca ttgagagcga cgcgggctta gggctggata   1620
aaaccctgcg gcagctggct ccggacgtgc cgctgctggc gaacctcggc gcggcgcagc   1680
tgaccggcag aaaaggtatt gattacgccc gacgggccgt ggagatgatc gaggcggatg   1740
cgctgattgt gcacctaaac ccgctgcagg aggcgctaca gcccggcggc gatcgcgact   1800
ggcgcggacg gctggcggct attgaaactc tggtccgcga gctgcccgtt ccgctggtgg   1860
tgaaagaggt gggagccggt atctcccgaa ccgtggccgg gcagctgatc gatgccggcg   1920
ttaccgtgat tgacgtcgcg ggcgcgggcg gcaccagctg ggccgccgtt gaaggcgagc   1980
gggcggccac cgagcagcag cgcagcgtgg ccaacgtctt tgccgactgg gggatcccca   2040
ccgctgaggc gctggttgac attgccgagg cctggccgca gatgcccctt attgcctcgg   2100
gcgggattaa aaacggcgtc gacgcggcga aagcgctgcg gctcggcgcg tgcatggtag   2160
ggcaggccgc cgccgtgctc ggcagcgcag gcgtctccac ggagaaggtg atcgatcact   2220
tcaacgtgat tattgagcag ctgcgggtgg cctgcttctg caccggcagc cgcagcctga   2280
gcgatctaaa gcaggctgat atccgctatg ttcgtgatac gccataagga ggtacaacca   2340
tgaagaaaac cgttgtgatt ggcgcaggct ttggtggcct ggcgctggcg attcgcctgc   2400
aggcggcagg gatcccaacc gtactgctgg agcagcggga caagcccggc ggtcgggcct   2460
acgtctggca tgaccagggc tttacctttg acgccgggcc gacggtgatc accgatccta   2520
ccgcgcttga ggcgctgttc accctggccg gcaggcgcat ggaggattac gtcaggctgc   2580
```

-continued

```
tgccggtaaa acccttctac cgactctgct gggagtccgg gaagaccctc gactatgcta   2640
acgacagcgc cgagcttgag gcgcagatta cccagttcaa cccccgcgac gtcgagggct   2700
accggcgctt tctggcttac tcccaggcgg tattccagga gggatatttg cgcctcggca   2760
gcgtgccgtt cctctctttt cgcgacatgc tgcgcgccgg gccgcagctg cttaagctcc   2820
aggcgtggca gagcgtctac cagtcggttt cgcgctttat tgaggatgag catctgcggc   2880
aggccttctc gttccactcc ctgctggtag gcggcaaccc cttcaccacc tcgtccatct   2940
acaccctgat ccacgccctt gagcgggagt ggggggtctg gttccctgag ggcggcaccg   3000
gggcgctggt gaacggcatg gtgaagctgt ttaccgatct gggcggggag atcgaactca   3060
acgcccgggt cgaagagctg gtggtggccg ataaccgcgt aagccaggtc cggctggcgg   3120
atggtcggat ctttgacacc gacgccgtag cctcgaacgc tgacgtggtg aacacctata   3180
aaaagctgct cggccaccat ccggtggggc agaagcgggc ggcagcgctg gagcgcaaga   3240
gcatgagcaa ctcgctgttt gtgctctact tcggcctgaa ccagcctcat tcccagctgg   3300
cgcaccatac catctgtttt ggtccccgct accgggagct gatcgacgag atctttaccg   3360
gcagcgcgct ggcggatgac ttctcgctct acctgcactc gccctgcgtg accgatccct   3420
cgctcgcgcc tcccggctgc gccagcttct acgtgctggc cccggtgccg catcttggca   3480
acgcgccgct ggactgggcg caggaggggc cgaagctgcg cgaccgcatc tttgactacc   3540
ttgaagagcg ctatatgccc ggcctgcgta gccagctggt gacccagcgg atctttaccc   3600
cggcagactt ccacgacacg ctggatgcgc atctgggatc ggccttctcc atcgagccgc   3660
tgctgaccca aagcgcctgg ttccgcccgc acaaccgcga cagcgacatt gccaacctct   3720
acctggtggg cgcaggtact caccctgggg cgggcattcc tggcgtagtg gcctcggcga   3780
aagccaccgc cagcctgatg attgaggatc tgcaatgagc caaccgccgc tgcttgacca   3840
cgccacgcag accatggcca acggctcgaa aagttttgcc accgctgcga agctgttcga   3900
cccggccacc cgccgtagcg tgctgatgct ctacacctgg tgccgccact gcgatgacgt   3960
cattgacgac cagacccacg gcttcgccag cgaggccgcg gcggaggagg aggccaccca   4020
gcgcctggcc cggctgcgca cgctgaccct ggcggcgttt gaaggggccg agatgcagga   4080
tccggccttc gctgcctttc aggaggtggc gctgacccac ggtattacgc cccgcatggc   4140
gctcgatcac ctcgacggct ttgcgatgga cgtggctcag acccgctatg tcacctttga   4200
ggatacgctg cgctactgct atcacgtggc gggcgtggtg ggtctgatga tggccagggt   4260
gatgggcgtg cgggatgagc gggtgctgga tcgcgcctgc gatctggggc tggccttcca   4320
gctgacgaat atcgcccggg atattattga cgatgcggct attgaccgct gctatctgcc   4380
cgccgagtgg ctgcaggatg ccgggctgac ccccggagaac tatgccgcgc gggagaatcg   4440
ggccgcgctg gcgcgggtgg cggagcggct tattgatgcc gcagagccgt actacatctc   4500
ctcccaggcc gggctacacg atctgccgcc gcgctgcgcc tgggcgatcg ccaccgcccg   4560
cagcgtctac cgggagatcg gtattaaggt aaaagcggcg ggaggcagcg cctgggatcg   4620
ccgccagcac accagcaaag gtgaaaaaat tgccatgctg atggcggcac cggggcaggt   4680
tattcgggcg aagacgacga gggtgacgcc gcgtccggcc ggtctttggc agcgtcccgt   4740
ttagaccgac tccaaacgag tcggtttttt tgcgcttgtt tcggcgtggg tatggtggca   4800
ggccccgtgg ccgggggact gttgggcgcc atctccttgg ggtcgaattt gctttcgaat   4860
ttctgccatt catccgctta ttatcactta ttcaggcgta gcaaccaggc gtttaagggc   4920
accaataact gccttaaaaa aattacgccc cgccctgcca ctcatcgcag tactgttgta   4980
```

```
attcattaag cattctgccg acatggaagc catcacagac ggcatgatga acctgaatcg   5040
ccagcggcat cagcaccttg tcgccttgcg tataatattt gcccatggtg aaaacggggg   5100
cgaagaagtt gtccatattg gccacgttta aatcaaaact ggtgaaactc acccagggat   5160
tggctgagac gaaaaacata ttctcaataa accctttagg gaaataggcc aggttttcac   5220
cgtaacacgc cacatcttgc gaatatatgt gtagaaactg ccggaaatcg tcgtggtatt   5280
cactccagag cgatgaaaac gtttcagttt gctcatggaa aacggtgtaa caagggtgaa   5340
cactatccca tatcaccagc tcaccgtctt tcattgccat acggaattcc ggatgagcat   5400
tcatcaggcg ggcaagaatg tgaataaagg ccggataaaa cttgtgctta tttttcttta   5460
cggtctttaa aaaggccgta atatccagct gaacggtctg gttataggta cattgagcaa   5520
ctgactgaaa tgcctcaaaa tgttctttac gatgccattg ggatatatca acggtggtat   5580
atccagtgat ttttttctcc attttagctt ccttagctcc tgaaaatctc gataactcaa   5640
aaaatacgcc cggtagtgat cttatttcat tatggtgaaa gttggaacct cttacgtgcc   5700
gatcaacgtc tcattttcgc caaaagttgg cccagggctt cccggtatca acagggacac   5760
caggatttat ttattctgcg aagtgatctt ccgtcacagg tttcccgact ggaaaagcga   5820
attggtataa tgccctcgta ataattttgt ttaactttaa gaaggagata tacccatgac   5880
acagagggcc caccatcacc atcaccattc catggctagc ggcggcggaa gttccggtag   5940
tgagagttgt gtagcggtga gagaagattt cgctgacgaa gaagattttg tgaaagctgg   6000
tggttctgag attctatttg ttcaaatgca gcagaacaaa gatatggatg aacagtctaa   6060
gcttgttgat aagttgcctc ctatatcaat tggtgatggt gctttggatc tagtggttat   6120
tggttgtggt cctgctggtt tagccttggc tgcagaatca gctaagcttg gattaaaagt   6180
tggactcatt ggtccagatc ttccttttac taacaattac ggtgtttggg aagatgaatt   6240
caatgatctt gggctgcaaa aatgtattga gcatgtttgg agagagacta ttgtgtatct   6300
ggatgatgac aagcctatta ccattggccg tgcttatgga agagttagtc gacgtttgct   6360
ccatgaggag cttttgagga ggtgtgtcga gtcaggtgtc tcgtacctta gctcgaaagt   6420
tgacagcata acagaagctt ctgatggcct tagacttgtt gcttgtgacg acaataacgt   6480
cattccctgc aggcttgcca ctgttgcttc tggagcagct tcgggaaagc tcttgcaata   6540
cgaagttggt ggacctagag tctgtgtgca aactgcatac ggcgtggagg ttgaggtgga   6600
aaatagtcca tatgatccag atcaaatggt tttcatggat tacagagatt atactaacga   6660
gaaagttcgg agcttagaag ctgagtatcc aacgtttctg tacgccatgc ctatgacaaa   6720
gtcaagactc ttcttcgagg agacatgttt ggcctcaaaa gatgtcatgc cctttgattt   6780
gctaaaaacg aagctcatgt taagattaga tacactcgga attcgaattc taaagactta   6840
cgaagaggag tggtcctata tcccagttgg tggttccttg ccaaacaccg aacaaaagaa   6900
tctcgccttt ggtgctgccg ctagcatggt acatcccgca acaggctatt cagttgtgag   6960
atctttgtct gaagctccaa aatatgcatc agtcatcgca gagatactaa gagaagagac   7020
taccaaacag atcaacagta atatttcaag acaagcttgg gatactttat ggccaccaga   7080
aaggaaaaga cagagagcat tctttctctt tggtcttgag gctatagttc aattcgatac   7140
cgaaggcatt agaagcttct tccgtacttt cttccgcctt ccaaaatgga tgtggcaagg   7200
gtttctagga tcaacattaa catcaggaga tctcgttctc ttttctttat acatgttcgt   7260
catttcacca aacaatttga gaaaaggtct catcaatcat ctcatctctg atccaaccgg   7320
```

-continued agcaaccatg ataaaaacct atctcaaagt atgaggatcc ggctgctaac aaagcccgtt 7380
ctgtttaaga acgggatttt ttgctgaaag gaggaactat atccggccgg cttcatgtgg 7440
caggagaaaa aaggctgcac cggtgcgtca gcagaatatg tgatacagga tatattccgc 7500
ttcctcgctc actgactcgc tacgctcggt cgttcgactg cggcgagcgg aaatggctta 7560
cgaacggggc ggagatttcc tggaagatgc caggaagata cttaacaggg aagtgagagg 7620
gccgcggcaa agccgttttt ccataggctc cgcccccctg acaagcaatc acgaatctga 7680
cgctcaaatc agtggtggcg aaacccgaca ggactataaa gataccaggc gtttcccctg 7740
gcggctccct cgtgcgctct cctgttcctg cctttcggtt taccggtgtc attccgctgt 7800
tatggccgcg tttgtctcat tccacgcctg acactcagtt ccgggtaggc agttcgctcc 7860
aagctggact gtatgcacga accccccgtt cagtccgacc gctgcgcctt atccggtaac 7920
tatcgtcttg agtccaaccc ggaaagacat gcaaaagcac cactggcagc agccactggt 7980
aattgattta gaggagttag tcttgaagtc atgcgccggt taaggctaaa ctgaaaggac 8040
aagttttggt gactgcgctc ctccaagcca gttacctcgg ttcaaagagt tggtagctca 8100
gagaaccttc gaaaaaccgc cctgcaaggc ggtttttttcg ttttcagagc aagagattac 8160
gcgcagacca aaacgatctc aagaagatca tcttattaat cagataaaat atttctagta 8220
cactccgcta tcgctacgtg actgggtcat ggctgcgccc cgacacccgc caacacccgc 8280
tgacgcgccc tgacgggctt gtctgctccc ggcatccgct tacagacaag ctgtgaccgt 8340
ctccgggagc tgcatgtgtc agaggttttc accgtcatca ccgaaacgcg cgaggca 8397

<210> SEQ ID NO 36
<211> LENGTH: 8402
<212> TYPE: DNA
<213> ORGANISM: Artificial Sequence
<220> FEATURE:
<223> OTHER INFORMATION: Plasmid pGT1546

<400> SEQUENCE: 36
gctggcacga caggtttccc gactggaaag cgaattgtga ttaaacggaa ttctttcttg 60
acatgttttg tcgttatggt ataatttttt agtaataatt ttgtaacgca gtcaggaacc 120
ttgcaatgag cagtttcgat gcccatgacc ttgacctcga caaatttccg gaggtcgtgc 180
gagatcgttt gacgcagttc ctcgatgctc aagagctaac aattgctgat atcggcgctc 240
ctgtcacaga tgctgtggcc catcttcgca gtttcgtgct caatggagga aagcgaatcc 300
gtcctcttta tgcgtgggct ggtttcctgg cggcgcaagg ccataagaat tcttctgaaa 360
aacttgagtc cgtccttgac gccgcagcga gtctcgaatt catccaggct tgtgccttga 420
ttcatgacga tattatcgat tcttctgata cccggcgcgg agcccctaca gttcaccggg 480
ctgtggaagc tgatcaccgc gccaataatt tcgaaggcga tcctgagcac tttggcgttt 540
cagtctcgat tttggctggc gatatggcat tggtgtgggc agaagacatg ctgcaggatt 600
ccggtttgag tgcagaggca ttggcccgca cgagggatgc ttggcgtggc atgcgtactg 660
aggttattgg cggccagctg cttgatattt atcttgagtc gcacgccaac gagtcggtgg 720
agcttgcgga ttctgtcaac cgcttcaaaa cggccgctta cacgattgcg cgcccattgc 780
acctgggcgc ctccattgct ggcggttcgc cgcagcttat cgacgcgctc ctccactacg 840
gccacgacat cggcattgca ttccagttga gggatgatct gcttggtgtg tttggtgatc 900
ctgctatcac cggcaaacca gctggagacg atatccgtga aggcaagcgc actgttcttc 960
ttgcgctcgc tctacaacgc gctgataagc aatctcctga agctgcaacg gccattcgcg 1020

```
caggtgttgg aaaggtgact tcaccagaag atattgctgt cattacagag catattcgag   1080
ctactggtgc tgaagaagaa gttgagcagc gaatttccca gctgactgaa tccggtttgg   1140
ctcacctcga tgatgtagac atccctgatg aggtgcgcgc acagttgcgg gcactggcta   1200
tccgctcaac cgaacgtcgg atgtaatacc gccctttttgg gttcaagcag tacataacga   1260
tggaaccaca ttacaggagt agtgatgaat gaaggacgag cgccttgttc agcgtaagaa   1320
cgatcatctg gatatcgttc tcgacccccg tcgcgccgta actcaggcta gcgcaggttt   1380
tgagcgctgg cgctttaccc actgcgccct gccagagctg aattttagcg acatcacgct   1440
ggaaaccacc ttcctgaatc ggcagctaca ggctccgctg ctgatcagct ccatgaccgg   1500
cggcgttgag cgctcgcgcc atatcaaccg ccacctcgcc gaggcggcgc aggtgctaaa   1560
aattgcgatg gggggtgggct cccagcgcgt cgccattgag agcgacgcgg gcttagggct   1620
ggataaaacc ctgcggcagc tggctccgga cgtgccgctg ctggcgaacc tcggcgcggc   1680
gcagctgacc ggcagaaaag gtattgatta cgcccgacgg gccgtggaga tgatcgaggc   1740
ggatgcgctg attgtgcacc taaacccgct gcaggaggcg ctacagcccg gcggcgatcg   1800
cgactggcgc ggacggctgg cggctattga aactctggtc cgcgagctgc ccgttccgct   1860
ggtggtgaaa gaggtgggag ccggtatctc ccgaaccgtg gccgggcagc tgatcgatgc   1920
cggcgttacc gtgattgacg tcgcgggcgc gggcggcacc agctgggccg ccgttgaagg   1980
cgagcgggcg gccaccgagc agcagcgcag cgtggccaac gtctttgccg actgggggat   2040
ccccaccgct gaggcgctgg ttgacattgc cgaggcctgg ccgcagatgc cccttattgc   2100
ctcgggcggg attaaaaacg gcgtcgacgc ggcgaaagcg ctgcggctcg gcgcgtgcat   2160
ggtagggcag gccgccgccg tgctcggcag cgcaggcgtc tccacggaga aggtgatcga   2220
tcacttcaac gtgattattg agcagctgcg ggtggcctgc ttctgcaccg gcagccgcag   2280
cctgagcgat ctaaagcagg ctgatatccg ctatgttcgt gatacgccat aaggaggtac   2340
aaccatgaag aaaaccgttg tgattggcgc aggctttggt ggcctggcgc tggcgattcg   2400
cctgcaggcg gcagggatcc caaccgtact gctggagcag cgggacaagc ccggcggtcg   2460
ggcctacgtc tggcatgacc agggctttac ctttgacgcc gggccgacgg tgatcaccga   2520
tcctaccgcg cttgaggcgc tgttcaccct ggccggcagg cgcatggagg attacgtcag   2580
gctgctgccg gtaaaaccct tctaccgact ctgctgggag tccgggaaga ccctcgacta   2640
tgctaacgac agcgccgagc ttgaggcgca gattacccag ttcaaccccc gcgacgtcga   2700
gggctaccgg cgctttctgg cttactccca ggcggtattc caggagggat atttgcgcct   2760
cggcagcgtg ccgttcctct cttttcgcga catgctgcgc gccgggccgc agctgcttaa   2820
gctccaggcg tggcagagcg tctaccagtc ggtttcgcgc tttattgagg atgagcatct   2880
gcggcaggcc ttctcgttcc actccctgct ggtaggcggc aacccccttca ccacctcgtc   2940
catctacacc ctgatccacg cccttgagcg ggagtggggg gtctggttcc ctgagggcgg   3000
caccggggcg ctggtgaacg gcatggtgaa gctgtttacc gatctgggcg gggagatcga   3060
actcaacgcc cgggtcgaag agctggtggt ggccgataac cgcgtaagcc aggtccggct   3120
ggcggatggt cggatctttg acaccgacgc cgtagcctcg aacgctgacg tggtgaacac   3180
ctataaaaag ctgctcggcc accatccggt ggggcagaag cgggcggcag cgctggagcg   3240
caagagcatg agcaactcgc tgtttgtgct ctacttcggc ctgaaccagc ctcattccca   3300
gctggcgcac cataccatct gttttggtcc ccgctaccgg gagctgatcg acgagatctt   3360
```

```
taccggcagc gcgctggcgg atgacttctc gctctacctg cactcgccct gcgtgaccga   3420

tccctcgctc gcgcctcccg gctgcgccag cttctacgtg ctggccccgg tgccgcatct   3480

tggcaacgcg ccgctggact gggcgcagga ggggccgaag ctgcgcgacc gcatctttga   3540

ctaccttgaa gagcgctata tgcccggcct gcgtagccag ctggtgaccc agcggatctt   3600

taccccggca gacttccacg acacgctgga tgcgcatctg ggatcggcct tctccatcga   3660

gccgctgctg acccaaagcg cctggttccg cccgcacaac cgcgacagcg acattgccaa   3720

cctctacctg gtgggcgcag gtactcaccc tggggcgggc attcctggcg tagtggcctc   3780

ggcgaaagcc accgccagcc tgatgattga ggatctgcaa tgagccaacc gccgctgctt   3840

gaccacgcca cgcagaccat ggccaacggc tcgaaaagtt ttgccaccgc tgcgaagctg   3900

ttcgacccgg ccacccgccg tagcgtgctg atgctctaca cctggtgccg ccactgcgat   3960

gacgtcattg acgaccagac ccacggcttc gccagcgagg ccgcggcgga ggaggaggcc   4020

acccagcgcc tggcccggct gcgcacgctg accctggcgg cgtttgaagg ggccgagatg   4080

caggatccgg ccttcgctgc ctttcaggag gtggcgctga cccacggtat tacgccccgc   4140

atggcgctcg atcacctcga cggctttgcg atggacgtgg ctcagacccg ctatgtcacc   4200

tttgaggata cgctgcgcta ctgctatcac gtggcgggcg tggtgggtct gatgatggcc   4260

agggtgatgg gcgtgcggga tgagcgggtg ctggatcgcg cctgcgatct ggggctggcc   4320

ttccagctga cgaatatcgc ccgggatatt attgacgatg cggctattga ccgctgctat   4380

ctgcccgccg agtggctgca ggatgccggg ctgaccccgg agaactatgc cgcgcgggag   4440

aatcgggccg cgctggcgcg ggtggcggag cggcttattg atgccgcaga gccgtactac   4500

atctcctccc aggccgggct acacgatctg ccgccgcgct gcgcctgggc gatcgccacc   4560

gcccgcagcg tctaccggga gatcggtatt aaggtaaaag cggcgggagg cagcgcctgg   4620

gatcgccgcc agcacaccag caaaggtgaa aaaattgcca tgctgatggc ggcaccgggg   4680

caggttattc gggcgaagac gacgagggtg acgccgcgtc cggccggtct ttggcagcgt   4740

cccgtttaga ccgactccaa acgagtcggt ttttttgcgc ttgtttcggc gtgggtatgg   4800

tggcaggccc cgtggccggg ggactgttgg gcgccatctc cttggggtcg aatttgcttt   4860

cgaatttctg ccattcatcc gcttattatc acttattcag gcgtagcaac caggcgttta   4920

agggcaccaa taactgcctt aaaaaaatta cgccccgccc tgccactcat cgcagtactg   4980

ttgtaattca ttaagcattc tgccgacatg gaagccatca cagacggcat gatgaacctg   5040

aatcgccagc ggcatcagca ccttgtcgcc ttgcgtataa tatttgccca tggtgaaaac   5100

gggggcgaag aagttgtcca tattggccac gtttaaatca aaactggtga aactcaccca   5160

gggattggct gagacgaaaa acatattctc aataaaccct ttagggaaat aggccaggtt   5220

ttcaccgtaa cacgccacat cttgcgaata tatgtgtaga aactgccgga aatcgtcgtg   5280

gtattcactc cagagcgatg aaaacgtttc agtttgctca tggaaaacgg tgtaacaagg   5340

gtgaacacta tcccatatca ccagctcacc gtctttcatt gccatacgga attccggatg   5400

agcattcatc aggcgggcaa gaatgtgaat aaaggccgga taaaacttgt gcttattttt   5460

ctttacggtc tttaaaaagg ccgtaatatc cagctgaacg gtctggttat aggtacattg   5520

agcaactgac tgaaatgcct caaaatgttc tttacgatgc cattgggata tatcaacggt   5580

ggtatatcca gtgatttttt tctccatttt agcttcctta gctcctgaaa atctcgataa   5640

ctcaaaaaat acgcccggta gtgatcttat ttcattatgg tgaaagttgg aacctcttac   5700

gtgccgatca acgtctcatt ttcgccaaaa gttggcccag ggcttcccgg tatcaacagg   5760
```

```
gacaccagga tttatttatt ctgcgaagtg atcttccgtc acaggtttcc cgactggaaa   5820
agcgaattgg tataatgccc tcgtaataat tttgtttaac tttaagaagg agatataccc   5880
atgacacaga gggcccacca tcaccatcac cattccatgg ctagcggcgg cggaagttcc   5940
ggtagtgaga gttgtgtagc ggtgagagaa gatttcgctg acgaagaaga ttttgtgaaa   6000
gctggtggtt ctgagattct atttgttcaa atgcagcaga acaaagatat ggatgaacag   6060
tctaagcttg ttgataagtt gcctcctata tcaattggtg atggtgcttt ggatctagtg   6120
gttattggtt gtggtcctgc tggtttagcc ttggctgcag aatcagctaa gcttggatta   6180
aaagttggac tcattggtcc agatcttcct tttactaaca attacggtgt ttgggaagat   6240
gaattcaatg atcttgggct gcaaaaatgt attgagcatg tttggagaga gactattgtg   6300
tatctggatg atgacaagcc tattaccatt ggccgtgctt atggaagagt tagtcgacgt   6360
ttgctccatg aggagctttt gaggaggtgt gtcgagtcag gtgtctcgta ccttagctcg   6420
aaagttgaca gcataacaga agcttctgat ggccttagac ttgttgcttg tgacgacaat   6480
aacgtcattc cctgcaggct tgccactgtt gcttctggag cagcttcggg aaagctcttg   6540
caatacgaag ttggtggacc tagagtctgt gtgcaaactg catacggcgt ggaggttgag   6600
gtggaaaata gtccatatga tccagatcaa atggttttca tggattacag agattatact   6660
aacgagaaag ttcggagctt agaagctgag tatccaacgt ttctgtacgc catgcctatg   6720
acaaagtcaa gactcttctt cgaggagaca tgtttggcct caaaagatgt catgcccttt   6780
gatttgctaa aaacgaagct catgttaaga ttagatacac tcggaattcg aattctaaag   6840
acttacgaag aggagtggtc ctatatccca gttggtggtt ccttgccaaa caccgaacaa   6900
aagaatctcg cctttggtgc tgccgctagc atggtacatc ccgcaacagg ctattcagtt   6960
gtgagatctt tgtctgaagc tccaaaatat gcatcagtca tcgcagagat actaagagaa   7020
gagactacca aacagatcaa cagtaatatt tcaagacaag cttgggatac tttatggcca   7080
ccagaaagga aaagacagag agcattcttt ctctttggtc ttgaggctat agttcaattc   7140
gataccgaag gcattagaag cttcttccgt actttcttcc gccttccaaa atggatgtgg   7200
caagggtttc taggatcaac attaacatca ggagatctcg ttctcttttc tttatacatg   7260
ttcgtcattt caccaaacaa tttgagaaaa ggtctcatca atcatctcat ctctgatcca   7320
accggagcaa ccatgataaa aacctatctc aaagtatgag gatccggctg ctaacaaagc   7380
ccgttctgtt taagaacggg attttttgct gaaaggagga actatatccg gccggcttca   7440
tgtggcagga gaaaaaaggc tgcaccggtg cgtcagcaga atatgtgata caggatatat   7500
tccgcttcct cgctcactga ctcgctacgc tcggtcgttc gactgcggcg agcggaaatg   7560
gcttacgaac ggggcggaga tttcctggaa gatgccagga agatacttaa cagggaagtg   7620
agagggccgc ggcaaagccg tttttccata ggctccgccc ccctgacaag caatcacgaa   7680
tctgacgctc aaatcagtgg tggcgaaacc cgacaggact ataaagatac caggcgtttc   7740
ccctggcggc tccctcgtgc gctctcctgt tcctgccttt cggtttaccg gtgtcattcc   7800
gctgttatgg ccgcgtttgt ctcattccac gcctgacact cagttccggg taggcagttc   7860
gctccaagct ggactgtatg cacgaacccc ccgttcagtc cgaccgctgc gccttatccg   7920
gtaactatcg tcttgagtcc aacccggaaa gacatgcaaa agcaccactg gcagcagcca   7980
ctggtaattg atttagagga gttagtcttg aagtcatgcg ccggttaagg ctaaactgaa   8040
aggacaagtt ttggtgactg cgctcctcca agccagttac ctcggttcaa agagttggta   8100
```

gctcagagaa ccttcgaaaa accgccctgc aaggcggttt tttcgttttc agagcaagag 8160
attacgcgca gaccaaaacg atctcaagaa gatcatctta ttaatcagat aaaatatttc 8220
tagtacactc cgctatcgct acgtgactgg gtcatggctg cgccccgaca cccgccaaca 8280
cccgctgacg cgccctgacg ggcttgtctg ctcccggcat ccgcttacag acaagctgtg 8340
accgtctccg ggagctgcat gtgtcagagg ttttcaccgt catcaccgaa acgcgcgagg 8400
ca 8402

<210> SEQ ID NO 37
<211> LENGTH: 6022
<212> TYPE: DNA
<213> ORGANISM: Artificial Sequence
<220> FEATURE:
<223> OTHER INFORMATION: Plasmid pGT1454

<400> SEQUENCE: 37
acccagtttc atcattccat tttattttgc gagcgagcgc acacttgtga attatctcaa 60
tagcagtgtg aaataacata attgagcaac tgaaagggag tgcccaatat tacgacatca 120
tccatcacgc ggagttacct gattatgaca cagagggccc accatcacca tcaccattcc 180
atggcggaga aactcagtga tggcagcagc atcatctcag tccatcctag accctccaag 240
ggtttctcct cgaagcttct cgatcttctc gagagacttg ttgtcaagct catgcacgat 300
gcttctctcc ctctccacta cctctcaggc aacttcgctc ccatccgtga tgaaactcct 360
cccgtcaagg atctccccgt ccatggattt cttcccgaat gcttgaatgg tgaatttgtg 420
agggttggtc caaaccccaa gtttgatgct gtcgctggat atcactggtt tgatggagat 480
gggatgattc atggggtacg catcaaagat gggaaagcta cttatgtttc tcgatatgtt 540
aagacatcac gtcttaagca ggaagagttc ttcggagctg ccaaattcat gaagattggt 600
gaccttaagg ggtttttcgg attgctaatg gtcaatgtcc aacagctgag aacgaagctc 660
aaaatattgg acaacactta tggaaatgga actgccaata cagcactcgt atatcaccat 720
ggaaaacttc tagcattaca ggaggcagat aagccgtacg tcatcaaagt tttggaagat 780
ggagacctgc aaactcttgg tataatagat tatgacaaga gattgaccca ctccttcact 840
gctcacccaa aagttgaccc ggttacgggt gaaatgttta cattcggcta ttcgcatacg 900
ccaccttatc tcacatacag agttatctcg aaagatggca ttatgcatga cccagtccca 960
attactatat cagagcctat catgatgcat gattttgcta ttactgagac ttatgcaatc 1020
ttcatggatc ttcctatgca cttcaggcca aaggaaatgg tgaaagagaa gaaaatgata 1080
tactcatttg atcccacaaa aaaggctcgt tttggtgttc ttccacgcta tgccaaggat 1140
gaacttatga ttagatggtt tgagcttccc aactgcttta ttttccacaa cgccaatgct 1200
tgggaagaag aggatgaagt cgtcctcatc acttgtcgtc ttgagaatcc agatcttgac 1260
atggtcagtg ggaaagtgaa agaaaaactc gaaaattttg gcaacgaact gtacgaaatg 1320
agattcaaca tgaaaacggg ctcagcttct caaaaaaaac tatccgcatc tgcggttgat 1380
ttccccagaa tcaatgagtg ctacaccgga aagaaacaga gatacgtata tggaacaatt 1440
ctggacagta tcgcaaaggt taccggaatc atcaagtttg atctgcatgc agaagctgag 1500
acagggaaaa gaatgctgga agtaggaggt aatatcaaag gaatatatga cctgggagaa 1560
ggcagatatg gttcagaggc tatctatgtt ccgcgtgaga cagcagaaga agacgacggt 1620
tacttgatat tctttgttca tgatgaaaac acagggaaat catgcgtgac tgtgatagac 1680
gcaaaaacaa tgtcggctga accggtggca gtggtggagc tgccgcacag ggtcccatat 1740

```
ggcttccatg ccttgtttgt tacagaggaa caactccagg aacaaactct tatataagga   1800
tccggctgct aacaaagccc gaaaggaagc tgagttggct gctgccaccg ctgagcaata   1860
actagcataa ccccttgggg cctctaaacg ggtcttgagg ggttttttgc tgaaaggagg   1920
aactatatcc ggccggatat ccacaggacg ggtgtggtcg ccatgatcgc gtagtcgata   1980
gtggctccaa gtagcgaagc gagcaggact gggcggcggc caaagcggtc ggacagtgct   2040
ccgagaacgg gtgcgcatag aaattgcatc aacgcatata gcgctagcag cacgccatag   2100
tgactggcga tgctgtcgga atggacgata tcccgcaaga ggcccggcag taccggcata   2160
accaagccta tgcctacagc atccagggtg acggtgccga ggatgacgat gagcgcattg   2220
ttagatttca tacacggtgc ctgactgcgt tagcaattta actgtgataa actaccgcat   2280
taaagcttat cgatgataag ctgtcaaaca tgagaattct tgaagacgaa agggcctcgt   2340
gatacgccta tttttatagg ttaatgtcat gcatgagaca ataaccctga taaatgcttc   2400
aataatattg aaaaaggaag agtatgagta ttcaacattt ccgtgtcgcc cttattccct   2460
tttttgcggc attttgcctt cctgtttttg ctcacccaga aacgctggtg aaagtaaaag   2520
atgctgaaga tcagttgggt gcacgagtgg gttacatcga actggatctc aacagcggta   2580
agatccttga gagttttcgc cccgaagaac gttttccaat gatgagcact tttaaagttc   2640
tgctatgtgg cgcggtatta tcccgtgttg acgccgggca agagcaactc ggtcgccgca   2700
tacactattc tcagaatgac ttggttgacg cgtcaccagt cacagaaaag catcttacgg   2760
atggcatgac agtaagagaa ttatgcagtg ctgccataac catgagtgat aacactgcgg   2820
ccaacttact tctgacaacg atcggaggac cgaaggagct aaccgctttt ttgcacaaca   2880
tgggggatca tgtaactcgc cttgatcgtt gggaaccgga gctgaatgaa gccataccaa   2940
acgacgagcg tgacaccacg atgcctgcag caatggcaac aacgttgcgc aaactattaa   3000
ctggcgaact acttactcta gcttcccggc aacaattaat agactggatg gaggcggata   3060
aagttgcagg accacttctg cgctcggccc ttccggctgg ctggtttatt gctgataaat   3120
ctggagccgg tgagcgtggg tctcgcggta tcattgcagc actggggcca gatggtaagc   3180
cctcccgtat cgtagttatc tacacgacgg ggagtcaggc aactatggat gaacgaaata   3240
gacagatcgc tgagataggt gcctcactga ttaagcattg gtaactgtca gaccaagttt   3300
actcatatat actttagatt gatttaaaac ttcattttta atttaaaagg atctaggtga   3360
agatcctttt tgataatctc atgcatgacc aaaatccctt aacgtgagtt ttcgttccac   3420
tgagcgtcag accccgtaga aaagatcaaa ggatcttctt gagatccttt ttttctgcgc   3480
gtaatctgct gcttgcaaac aaaaaaacca ccgctaccag cggtggtttg tttgccggat   3540
caagagctac caactctttt tccgaaggta actggcttca gcagagcgca gataccaaat   3600
actgtccttc tagtgtagcc gtagttaggc caccacttca agaactctgt agcaccgcct   3660
acatacctcg ctctgctaat cctgttacca gtggctgctg ccagtggcga taagtcgtgt   3720
cttaccgggt tggactcaag acgatagtta ccggataagg cgcagcggtc gggctgaacg   3780
gggggttcgt gcacacagcc cagcttggag cgaacgacct acaccgaact gagataccta   3840
cagcgtgagc tatgagaaag cgccacgctt cccgaaggga gaaaggcgga caggtatccg   3900
gtaagcggca gggtcggaac aggagagcgc acgagggagc ttccaggggg aaacgcctgg   3960
tatctttata gtcctgtcgg gtttcgccac ctctgacttg agcgtcgatt tttgtgatgc   4020
tcgtcagggg ggcggagcct atggaaaaac gccagcaacg cggccttttt acggttcctg   4080
```

```
gccttttgct ggccttttgc tcacatgttc tttcctgcgt tatcccctga ttctgtggat   4140

aaccgtatta ccgcctttga gtgagctgat accgctcgcc gcagccgaac gaccgagcgc   4200

agcgagtcag tgagcgagga agcggaagag cgcctgatgc ggtattttct ccttacgcat   4260

ctgtgcggta tttcacaccg catatatggt gcactctcag tacaatctgc tctgatgccg   4320

catagttaag ccagtataca ctccgctatc gctacgtgac tgggtcatgg ctgcgccccg   4380

acacccgcca acacccgctg acgcgccctg acgggcttgt ctgctcccgg catccgctta   4440

cagacaagct gtgaccgtct ccgggagctg catgtgtcag aggttttcac cgtcatcacc   4500

gaaacgcgcg aggcagctgg cacgacaggt ttcccgactg ggttggtgcg ttttatcatg   4560

cctggcgggt aggtcggata aggcgttcac gccgcatccg acaaccacgc agcgttacct   4620

gatgtgacgc cgacaattct catcatcgct acaacatgac ctcgctattt acatcgcgat   4680

actcttttgg cgtcgtgtca tatgcttttt taaaaacaga gtagaaatat tgcagcgatg   4740

gataaccgca catttgcgat atctcattga tcgacaaggt ggttgaaatc agcagactgc   4800

gcgctttctc cagcttctcg gcatgaatca tggcatggat ggtttcaccc acctcttctt   4860

taaaacgctt ctcaagattg gagcgcgaga tcccgaccgc atccagtacc tgatccactt   4920

taatcccttt acaggcgtga ttacgaatgt aatgcatggc ctgaataacg gcgggatcgg   4980

tcagcgagcg ataatctgtt gagcgccgtt caatgacgcg aactggtggg accaaaattc   5040

gctgtagcgg catttcttct ttatctaata atcgatgcaa cagttttgcc gcctgatagc   5100

ccatttgccg cgcgccctga gcgaccgaag aaagggcgac acgcgacaga tagcgggtca   5160

gttcttcgtt atcgatgcca atcacgcata atttttccgg tacgggaata tgtagatgtt   5220

cacatacttg cagaatatgc cgcgctcggg cgtcagtaac ggcaataatc ccggtttgcg   5280

gtggtagcgt ttgtagccag tctgccagcc gattttgcgc gtgttgccag ttctctggcg   5340

cggtttctaa cccctgataa accactccgc gatacttttc ttcggcgaca agctgacgaa   5400

atgcatattc gcgctcagtg gcccaacgtt tgccgcttga ttccggaaga ccataaaaag   5460

caaagcggtt aacgcctttc tcttttaaat gcaaaaatgc gctttcaacc agcgcatagt   5520

tatcggtggc aatgtaatga acgggtgggt aactttctgc aaggtgatac gagccgccaa   5580

ccccaacaat ggggacgtcg acatcagcca gcgcttgctc gatctgtttg tcgtcgaagt   5640

cggcaatgac gccatctcct aaccagtcct tgattttatc aatgcgggcg cggaaatctt   5700

cttcaatgaa aatatcccat tccgattgtg acgcctgtaa atattcccct acgccttcta   5760

ctacctgccg gtcataggct ttattggcat tgaacagtaa tgtgatgcgg tgacgtttag   5820

taaacatggt tcttttcctg ctgaatcatg ctaagtaaca atcaccgcga taaacgtaac   5880

caatttttag caactaaaca ggggaaaaca attacagatt tttatctttc gattacgatt   5940

tttggtttat ttcttgattt atgaccgaga tcttactttt gttgcgcaat tgtacttatt   6000

gcatttttct cttcgaggaa tt                                            6022
```

```
<210> SEQ ID NO 38
<211> LENGTH: 6022
<212> TYPE: DNA
<213> ORGANISM: Artificial Sequence
<220> FEATURE:
<223> OTHER INFORMATION: Plasmid pGT1455

<400> SEQUENCE: 38

acccagtttc atcattccat tttattttgc gagcgagcgc acacttgtga attatctcaa     60

tagcagtgtg aaataacata attgagcaac tgaaagggag tgccctatat tacgacatca    120
```

```
tccatcacgc ggagttacct gattatgaca cagagggccc accatcacca tcaccattcc    180
atggcggaga aactcagtga tggcagcagc atcatctcag tccatcctag accctccaag    240
ggtttctcct cgaagcttct cgatcttctc gagagacttg ttgtcaagct catgcacgat    300
gcttctctcc ctctccacta cctctcaggc aacttcgctc ccatccgtga tgaaactcct    360
cccgtcaagg atctccccgt ccatggattt cttcccgaat gcttgaatgg tgaatttgtg    420
agggttggtc caaaccccaa gtttgatgct gtcgctggat atcactggtt tgatggagat    480
gggatgattc atggggtacg catcaaagat gggaaagcta cttatgtttc tcgatatgtt    540
aagacatcac gtcttaagca ggaagagttc ttcggagctg ccaaattcat gaagattggt    600
gaccttaagg ggtttttcgg attgctaatg gtcaatgtcc aacagctgag aacgaagctc    660
aaaatattgg acaacactta tggaaatgga actgccaata cagcactcgt atatcaccat    720
ggaaaacttc tagcattaca ggaggcagat aagccgtacg tcatcaaagt tttggaagat    780
ggagacctgc aaactcttgg tataatagat tatgacaaga gattgaccca ctccttcact    840
gctcacccaa aagttgaccc ggttacgggt gaaatgttta cattcggcta ttcgcatacg    900
ccaccttatc tcacatacag agttatctcg aaagatggca ttatgcatga cccagtccca    960
attactatat cagagcctat catgatgcat gattttgcta ttactgagac ttatgcaatc   1020
ttcatggatc ttcctatgca cttcaggcca aaggaaatgg tgaaagagaa gaaaatgata   1080
tactcatttg atcccacaaa aaaggctcgt tttggtgttc ttccacgcta tgccaaggat   1140
gaacttatga ttagatggtt tgagcttccc aactgcttta ttttccacaa cgccaatgct   1200
tgggaagaag aggatgaagt cgtcctcatc acttgtcgtc ttgagaatcc agatcttgac   1260
atggtcagtg ggaaagtgaa agaaaaactc gaaaattttg gcaacgaact gtacgaaatg   1320
agattcaaca tgaaaacggg ctcagcttct caaaaaaaac tatccgcatc tgcggttgat   1380
ttccccagaa tcaatgagtg ctacaccgga aagaaacaga gatacgtata tggaacaatt   1440
ctggacagta tcgcaaaggt taccggaatc atcaagtttg atctgcatgc agaagctgag   1500
acagggaaaa gaatgctgga agtaggaggt aatatcaaag gaatatatga cctgggagaa   1560
ggcagatatg gttcagaggc tatctatgtt ccgcgtgaga cagcagaaga agacgacggt   1620
tacttgatat tctttgttca tgatgaaaac acagggaaat catgcgtgac tgtgatagac   1680
gcaaaaacaa tgtcggctga accggtggca gtggtggagc tgccgcacag ggtcccatat   1740
ggcttccatg ccttgtttgt tacagaggaa caactccagg aacaaactct tatataagga   1800
tccggctgct aacaaagccc gaaaggaagc tgagttggct gctgccaccg ctgagcaata   1860
actagcataa ccccttgggg cctctaaacg ggtcttgagg ggttttttgc tgaaaggagg   1920
aactatatcc ggccggatat ccacaggacg ggtgtggtcg ccatgatcgc gtagtcgata   1980
gtggctccaa gtagcgaagc gagcaggact gggcggcggc caaagcggtc ggacagtgct   2040
ccgagaacgg gtgcgcatag aaattgcatc aacgcatata gcgctagcag cacgccatag   2100
tgactggcga tgctgtcgga atggacgata tcccgcaaga ggcccggcag taccggcata   2160
accaagccta tgcctacagc atccagggtg acggtgccga ggatgacgat gagcgcattg   2220
ttagatttca tacacggtgc ctgactgcgt tagcaattta actgtgataa actaccgcat   2280
taaagcttat cgatgataag ctgtcaaaca tgagaattct tgaagacgaa agggcctcgt   2340
gatacgccta tttttatagg ttaatgtcat gcatgagaca ataaccctga taaatgcttc   2400
aataatattg aaaaaggaag agtatgagta ttcaacattt ccgtgtcgcc cttattccct   2460
```

```
tttttgcggc attttgcctt cctgtttttg ctcacccaga aacgctggtg aaagtaaaag   2520
atgctgaaga tcagttgggt gcacgagtgg gttacatcga actggatctc aacagcggta   2580
agatccttga gagttttcgc cccgaagaac gttttccaat gatgagcact tttaaagttc   2640
tgctatgtgg cgcggtatta tcccgtgttg acgccgggca agagcaactc ggtcgccgca   2700
tacactattc tcagaatgac ttggttgacg cgtcaccagt cacagaaaag catcttacgg   2760
atggcatgac agtaagagaa ttatgcagtg ctgccataac catgagtgat aacactgcgg   2820
ccaacttact tctgacaacg atcggaggac cgaaggagct aaccgctttt ttgcacaaca   2880
tgggggatca tgtaactcgc cttgatcgtt gggaaccgga gctgaatgaa gccataccaa   2940
acgacgagcg tgacaccacg atgcctgcag caatggcaac aacgttgcgc aaactattaa   3000
ctggcgaact acttactcta gcttcccggc aacaattaat agactggatg gaggcggata   3060
aagttgcagg accacttctg cgctcggccc ttccggctgg ctggtttatt gctgataaat   3120
ctggagccgg tgagcgtggg tctcgcggta tcattgcagc actggggcca gatggtaagc   3180
cctcccgtat cgtagttatc tacacgacgg ggagtcaggc aactatggat gaacgaaata   3240
gacagatcgc tgagataggt gcctcactga ttaagcattg gtaactgtca gaccaagttt   3300
actcatatat actttagatt gatttaaaac ttcattttta atttaaaagg atctaggtga   3360
agatcctttt tgataatctc atgcatgacc aaaatccctt aacgtgagtt ttcgttccac   3420
tgagcgtcag accccgtaga aaagatcaaa ggatcttctt gagatccttt ttttctgcgc   3480
gtaatctgct gcttgcaaac aaaaaaacca ccgctaccag cggtggtttg tttgccggat   3540
caagagctac caactctttt tccgaaggta actggcttca gcagagcgca gataccaaat   3600
actgtccttc tagtgtagcc gtagttaggc caccacttca agaactctgt agcaccgcct   3660
acatacctcg ctctgctaat cctgttacca gtggctgctg ccagtggcga taagtcgtgt   3720
cttaccgggt tggactcaag acgatagtta ccggataagg cgcagcggtc gggctgaacg   3780
gggggttcgt gcacacagcc cagcttggag cgaacgacct acaccgaact gagataccta   3840
cagcgtgagc tatgagaaag cgccacgctt cccgaaggga gaaaggcgga caggtatccg   3900
gtaagcggca gggtcggaac aggagagcgc acgagggagc ttccaggggg aaacgcctgg   3960
tatctttata gtcctgtcgg gtttcgccac ctctgacttg agcgtcgatt tttgtgatgc   4020
tcgtcagggg ggcggagcct atggaaaaac gccagcaacg cggccttttt acggttcctg   4080
gccttttgct ggccttttgc tcacatgttc tttcctgcgt tatcccctga ttctgtggat   4140
aaccgtatta ccgcctttga gtgagctgat accgctcgcc gcagccgaac gaccgagcgc   4200
agcgagtcag tgagcgagga agcggaagag cgcctgatgc ggtattttct ccttacgcat   4260
ctgtgcggta tttcacaccg catatatggt gcactctcag tacaatctgc tctgatgccg   4320
catagttaag ccagtataca ctccgctatc gctacgtgac tgggtcatgg ctgcgccccg   4380
acacccgcca acacccgctg acgcgccctg acgggcttgt ctgctcccgg catccgctta   4440
cagacaagct gtgaccgtct ccgggagctg catgtgtcag aggttttcac cgtcatcacc   4500
gaaacgcgcg aggcagctgg cacgacaggt ttcccgactg ggttggtgcg ttttatcatg   4560
cctggcgggt aggtcggata aggcgttcac gccgcatccg acaaccacgc agcgttacct   4620
gatgtgacgc cgacaattct catcatcgct acaacatgac ctcgctattt acatcgcgat   4680
actcttttgg cgtcgtgtca tatgcttttt taaaaacaga gtagaaatat tgcagcgatg   4740
gataaccgca catttgcgat atctcattga tcgacaaggt ggttgaaatc agcagactgc   4800
gcgctttctc cagcttctcg gcatgaatca tggcatggat ggtttcaccc acctcttctt   4860
```

```
taaaacgctt ctcaagattg gagcgcgaga tcccgaccgc atccagtacc tgatccactt   4920

taatcccttt acaggcgtga ttacgaatgt aatgcatggc ctgaataacg gcgggatcgg   4980

tcagcgagcg ataatctgtt gagcgccgtt caatgacgcg aactggtggg accaaaattc   5040

gctgtagcgg catttcttct ttatctaata atcgatgcaa cagttttgcc gcctgatagc   5100

ccatttgccg cgcgccctga gcgaccgaag aaagggcgac acgcgacaga tagcgggtca   5160

gttcttcgtt atcgatgcca atcacgcata atttttccgg tacgggaata tgtagatgtt   5220

cacatacttg cagaatatgc cgcgctcggg cgtcagtaac ggcaataatc ccggtttgcg   5280

gtggtagcgt ttgtagccag tctgccagcc gattttgcgc gtgttgccag ttctctggcg   5340

cggtttctaa cccctgataa accactccgc gatacttttc ttcggcgaca agctgacgaa   5400

atgcatattc gcgctcagtg gcccaacgtt tgccgcttga ttccggaaga ccataaaaag   5460

caaagcggtt aacgcctttc tcttttaaat gcaaaaatgc gctttcaacc agcgcatagt   5520

tatcggtggc aatgtaatga acgggtgggt aactttctgc aaggtgatac gagccgccaa   5580

ccccaacaat ggggacgtcg acatcagcca gcgcttgctc gatctgtttg tcgtcgaagt   5640

cggcaatgac gccatctcct aaccagtcct tgattttatc aatgcgggcg cggaaatctt   5700

cttcaatgaa aatatcccat tccgattgtg acgcctgtaa atattcccct acgccttcta   5760

ctacctgccg gtcataggct ttattggcat tgaacagtaa tgtgatgcgg tgacgtttag   5820

taaacatggt tcttttcctg ctgaatcatg ctaagtaaca atcaccgcga taaacgtaac   5880

caatttttag caactaaaca ggggaaaaca attacagatt tttatctttc gattacgatt   5940

tttggtttat ttcttgattt atgaccgaga tcttactttt gttgcgcaat tgtacttatt   6000

gcatttttct cttcgaggaa tt                                            6022
```

<210> SEQ ID NO 39
<211> LENGTH: 4506
<212> TYPE: DNA
<213> ORGANISM: Artificial Sequence
<220> FEATURE:
<223> OTHER INFORMATION: Plasmid pGT1557

<400> SEQUENCE: 39

```
aaagcgaatt gtgattctag aaaaaaactt cttgacatgt ttggtataat aagagggtaa     60

taattttgtt taactttaag aaggagatat acccatgaca cagagggccc accatcacca    120

tcaccattcc atgggtatgc agggtgaaga tgcacagcgt accggtaata ttgttgcagt    180

taaaccgaaa ccgagccagg gtctgaccag caaagcaatt gattggctgg aatggctgtt    240

tgtgaaaatg atgcatgata gcaaacagcc gctgcattat ctgagcggta attttgcacc    300

ggttgatgaa acccctccgc tgaaagatct gccggttacc ggtcatctgc cggaatgtct    360

gaatggtgaa tttgttcgtg ttggtccgaa tccgaaattt gcaagcattg caggttatca    420

ttggtttgat ggtgatggta tgattcatgg catgcgcatt aaagatggta aagcaaccta    480

tgttagccgt tatgttcaga ccagccgtct gaaacaagag gaattctttg gtcgtgccat    540

gttcatgaaa atcggtgatc tgaaaggtat gtttggtctg ctgatggtta atatgcagat    600

gctgcgtgca aaactgaaag ttctggatat tagctatggt attggcaccg caaataccgc    660

actggtttat catcatggta aactgctggc actgagcgaa gcagataaac cgtatgcaat    720

taaagtgctg gaagatggtg atctgcagac cattggcctg ctggattatg ataaacgtct    780

ggcacatagc tttaccgcac atccgaaagt tgatccgttt accggtgaga tgtttacctt    840
```

```
tggttatagc catacccctc cgtatgttac ctatcgtgtt attagcaaag atggtgcaat    900
gaatgatccg gttccgatta ccgttagcgg tccgatcatg atgcacgatt ttgcaattac    960
cgaaaactac gccatcttta tggatctgcc gctgtatttc aaaccgaaag aaatggtgaa   1020
agacaagaaa ttcatcttta gcttcgatgc cacccagaaa gcacgttttg gtattctgcc   1080
tcgttatgcc aagaatgagc tgctgattaa atggtttgaa ctgccgaact gcttcatctt   1140
tcataatgca aatgcatggg aagagggtga tgaagttgtt ctgattacct gtcgtctgga   1200
aaatccggat ctggatatgg tgaatagcac cgttaaagaa cgtctggaca actttaagaa   1260
cgagctgtat gaaatgcgct tcaatctgca gaatggtctg gcaagccaga aaaaactgag   1320
cgttagcgca gttgattttc cgcgtgttaa tgaaagctat accacccgta aacagcgtta   1380
tgtttatggc accaccctgg ataagattgc caaagttacc ggcatcatca aattcgatct   1440
gcatgccgaa ccggaaaccg gtaaagagaa gctggaactg ggtggtaatg tgaaaggcat   1500
ttttgatctg ggtccgggtc gttttggttc agaagcagtt tttgttccgc gtcatccggg   1560
tattaccagc gaagaggatg atggttatct gatcttcttt gtgcacgatg aaaacaccgg   1620
caaaagcgca gttaatgtta ttgatgcaaa aaccatgagc cctgatccgg tggcagttgt   1680
ggaactgcct aaacgtgttc cgtatggttt tcatgcattt tttgttaccg aagatcagct   1740
gcaagaacag gccaaagttt aaggatccgg ctgctaacaa agcccgaaag gaagctgagt   1800
tggctgctgc caccgctgag caataactag cataacccct tggggcctct aaacgggtct   1860
tgaggggttt tttgctgaaa ggaggaacta tatccggccg gatatccaca ggacgggtgt   1920
ggtcgccatg atcgcgtagt cgatagtggc tccaagtagc gaagcgagca ggactgggcg   1980
gcggccaaag cggtcggaca gtgctccgag aacgggtgcg catagaaatt gcatcaacgc   2040
atatagcgct agcagcacgc catagtgact ggcgatgctg tcggaatgga cgatatcccg   2100
caagaggccc ggcagtaccg gcataaccaa gcctatgcct acagcatcca gggtgacggt   2160
gccgaggatg acgatgagcg cattgttaga tttcatacac ggtgcctgac tgcgttagca   2220
atttaactgt gataaactac cgcattaaag cttatcgatg ataagctgtc aaacatgaga   2280
attcttgaag acgaaagggc ctcgtgatac gcctattttt ataggttaat gtcatgcatg   2340
agacaataac cctgataaat gcttcaataa tattgaaaaa ggaagagtat gagtattcaa   2400
catttccgtg tcgcccttat tccctttttt gcggcatttt gccttcctgt ttttgctcac   2460
ccagaaacgc tggtgaaagt aaaagatgct gaagatcagt tgggtgcacg agtgggttac   2520
atcgaactgg atctcaacag cggtaagatc cttgagagtt ttcgccccga agaacgtttt   2580
ccaatgatga gcacttttaa agttctgcta tgtggcgcgg tattatcccg tgttgacgcc   2640
gggcaagagc aactcggtcg ccgcatacac tattctcaga atgacttggt tgacgcgtca   2700
ccagtcacag aaaagcatct tacggatggc atgacagtaa gagaattatg cagtgctgcc   2760
ataaccatga gtgataacac tgcggccaac ttacttctga caacgatcgg aggaccgaag   2820
gagctaaccg cttttttgca caacatgggg gatcatgtaa ctcgccttga tcgttgggaa   2880
ccggagctga atgaagccat accaaacgac gagcgtgaca ccacgatgcc tgcagcaatg   2940
gcaacaacgt tgcgcaaact attaactggc gaactactta ctctagcttc ccggcaacaa   3000
ttaatagact ggatggaggc ggataaagtt gcaggaccac ttctgcgctc ggcccttccg   3060
gctggctggt ttattgctga taaatctgga gccggtgagc gtgggtctcg cggtatcatt   3120
gcagcactgg ggccagatgg taagccctcc cgtatcgtag ttatctacac gacggggagt   3180
caggcaacta tggatgaacg aaatagacag atcgctgaga taggtgcctc actgattaag   3240
```

```
cattggtaac tgtcagacca agtttactca tatatacttt agattgattt aaaacttcat   3300
ttttaattta aaaggatcta ggtgaagatc ctttttgata atctcatgca tgaccaaaat   3360
cccttaacgt gagttttcgt tccactgagc gtcagacccc gtagaaaaga tcaaaggatc   3420
ttcttgagat cctttttttc tgcgcgtaat ctgctgcttg caaacaaaaa aaccaccgct   3480
accagcggtg gtttgtttgc cggatcaaga gctaccaact ctttttccga aggtaactgg   3540
cttcagcaga gcgcagatac caaatactgt ccttctagtg tagccgtagt taggccacca   3600
cttcaagaac tctgtagcac cgcctacata cctcgctctg ctaatcctgt taccagtggc   3660
tgctgccagt ggcgataagt cgtgtcttac cgggttggac tcaagacgat agttaccgga   3720
taaggcgcag cggtcgggct gaacgggggg ttcgtgcaca cagcccagct tggagcgaac   3780
gacctacacc gaactgagat acctacagcg tgagctatga gaaagcgcca cgcttcccga   3840
agggagaaag gcggacaggt atccggtaag cggcagggtc ggaacaggag agcgcacgag   3900
ggagcttcca gggggaaacg cctggtatct ttatagtcct gtcgggtttc gccacctctg   3960
acttgagcgt cgatttttgt gatgctcgtc aggggggcgg agcctatgga aaaacgccag   4020
caacgcggcc tttttacggt tcctggcctt ttgctggcct tttgctcaca tgttctttcc   4080
tgcgttatcc cctgattctg tggataaccg tattaccgcc tttgagtgag ctgataccgc   4140
tcgccgcagc cgaacgaccg agcgcagcga gtcagtgagc gaggaagcgg aagagcgcct   4200
gatgcggtat tttctcctta cgcatctgtg cggtatttca caccgcatat atggtgcact   4260
ctcagtacaa tctgctctga tgccgcatag ttaagccagt atacactccg ctatcgctac   4320
gtgactgggt catggctgcg ccccgacacc cgccaacacc cgctgacgcg ccctgacggg   4380
cttgtctgct cccggcatcc gcttacagac aagctgtgac cgtctccggg agctgcatgt   4440
gtcagaggtt ttcaccgtca tcaccgaaac gcgcgaggca gctggcacga caggtttccc   4500
gactgg                                                              4506
```

```
<210> SEQ ID NO 40
<211> LENGTH: 4507
<212> TYPE: DNA
<213> ORGANISM: Artificial Sequence
<220> FEATURE:
<223> OTHER INFORMATION: Plasmid pGT1560

<400> SEQUENCE: 40
```

```
aaagcgaatt gtgattgaaa tcaaaatttt cttgactaat tatggtataa tttactggta     60
ataattttgt ttaactttaa gaaggagata tacccatgac acagagggcc caccatcacc    120
atcaccattc catgggtatg cagggtgaag atgcacagcg taccggtaat attgttgcag    180
ttaaaccgaa accgagccag ggtctgacca gcaaagcaat tgattggctg gaatggctgt    240
ttgtgaaaat gatgcatgat agcaaacagc cgctgcatta tctgagcggt aattttgcac    300
cggttgatga aacccctccg ctgaaagatc tgccggttac cggtcatctg ccggaatgtc    360
tgaatggtga atttgttcgt gttggtccga atccgaaatt tgcaagcatt gcaggttatc    420
attggtttga tggtgatggt atgattcatg gcatgcgcat taaagatggt aaagcaacct    480
atgttagccg ttatgttcag accagccgtc tgaaacaaga ggaattcttt ggtcgtgcca    540
tgttcatgaa aatcggtgat ctgaaaggta tgtttggtct gctgatggtt aatatgcaga    600
tgctgcgtgc aaaactgaaa gttctggata ttagctatgg tattggcacc gcaaataccg    660
cactggttta tcatcatggt aaactgctgg cactgagcga agcagataaa ccgtatgcaa    720
```

-continued

```
ttaaagtgct ggaagatggt gatctgcaga ccattggcct gctggattat gataaacgtc    780
tggcacatag ctttaccgca catccgaaag ttgatccgtt taccggtgag atgtttacct    840
ttggttatag ccatacccct ccgtatgtta cctatcgtgt tattagcaaa gatggtgcaa    900
tgaatgatcc ggttccgatt accgttagcg gtccgatcat gatgcacgat tttgcaatta    960
ccgaaaacta cgccatcttt atggatctgc cgctgtattt caaaccgaaa gaaatggtga   1020
aagacaagaa attcatcttt agcttcgatg ccacccagaa agcacgtttt ggtattctgc   1080
ctcgttatgc caagaatgag ctgctgatta aatggtttga actgccgaac tgcttcatct   1140
ttcataatgc aaatgcatgg gaagagggtg atgaagttgt tctgattacc tgtcgtctgg   1200
aaaatccgga tctggatatg gtgaatagca ccgttaaaga acgtctggac aactttaaga   1260
acgagctgta tgaaatgcgc ttcaatctgc agaatggtct ggcaagccag aaaaaactga   1320
gcgttagcgc agttgatttt ccgcgtgtta atgaaagcta taccacccgt aaacagcgtt   1380
atgtttatgg caccaccctg gataagattg ccaaagttac cggcatcatc aaattcgatc   1440
tgcatgccga accggaaacc ggtaaagaga agctggaact gggtggtaat gtgaaaggca   1500
tttttgatct gggtccgggt cgttttggtt cagaagcagt tttgttccg cgtcatccgg   1560
gtattaccag cgaagaggat gatggttatc tgatcttctt tgtgcacgat gaaaacaccg   1620
gcaaaagcgc agttaatgtt attgatgcaa aaaccatgag ccctgatccg gtggcagttg   1680
tggaactgcc taaacgtgtt ccgtatggtt ttcatgcatt ttttgttacc gaagatcagc   1740
tgcaagaaca ggccaaagtt taaggatccg gctgctaaca aagcccgaaa ggaagctgag   1800
ttggctgctg ccaccgctga gcaataacta gcataacccc ttggggcctc taaacgggtc   1860
ttgaggggtt ttttgctgaa aggaggaact atatccggcc ggatatccac aggacgggtg   1920
tggtcgccat gatcgcgtag tcgatagtgg ctccaagtag cgaagcgagc aggactgggc   1980
ggcggccaaa gcggtcggac agtgctccga gaacgggtgc gcatagaaat tgcatcaacg   2040
catatagcgc tagcagcacg ccatagtgac tggcgatgct gtcggaatgg acgatatccc   2100
gcaagaggcc cggcagtacc ggcataacca agcctatgcc tacagcatcc agggtgacgg   2160
tgccgaggat gacgatgagc gcattgttag atttcataca cggtgcctga ctgcgttagc   2220
aatttaactg tgataaacta ccgcattaaa gcttatcgat gataagctgt caaacatgag   2280
aattcttgaa gacgaaaggg cctcgtgata cgcctatttt tataggttaa tgtcatgcat   2340
gagacaataa ccctgataaa tgcttcaata atattgaaaa aggaagagta tgagtattca   2400
acatttccgt gtcgccctta ttcccttttt tgcggcattt tgccttcctg tttttgctca   2460
cccagaaacg ctggtgaaag taaaagatgc tgaagatcag ttgggtgcac gagtgggtta   2520
catcgaactg gatctcaaca gcggtaagat ccttgagagt tttcgccccg aagaacgttt   2580
tccaatgatg agcactttta aagttctgct atgtggcgcg gtattatccc gtgttgacgc   2640
cgggcaagag caactcggtc gccgcataca ctattctcag aatgacttgg ttgacgcgtc   2700
accagtcaca gaaaagcatc ttacggatgg catgacagta agagaattat gcagtgctgc   2760
cataaccatg agtgataaca ctgcggccaa cttacttctg acaacgatcg gaggaccgaa   2820
ggagctaacc gcttttttgc acaacatggg ggatcatgta actcgccttg atcgttggga   2880
accggagctg aatgaagcca taccaaacga cgagcgtgac accacgatgc ctgcagcaat   2940
ggcaacaacg ttgcgcaaac tattaactgg cgaactactt actctagctt cccggcaaca   3000
attaatagac tggatggagg cggataaagt tgcaggacca cttctgcgct cggcccttcc   3060
ggctggctgg tttattgctg ataaatctgg agccggtgag cgtgggtctc gcggtatcat   3120
```

tgcagcactg gggccagatg gtaagccctc ccgtatcgta gttatctaca cgacggggag 3180
tcaggcaact atggatgaac gaaatagaca gatcgctgag ataggtgcct cactgattaa 3240
gcattggtaa ctgtcagacc aagtttactc atatatactt tagattgatt taaaacttca 3300
tttttaattt aaaaggatct aggtgaagat cctttttgat aatctcatgc atgaccaaaa 3360
tcccttaacg tgagttttcg ttccactgag cgtcagaccc cgtagaaaag atcaaaggat 3420
cttcttgaga tccttttttt ctgcgcgtaa tctgctgctt gcaaacaaaa aaaccaccgc 3480
taccagcggt ggtttgtttg ccggatcaag agctaccaac tctttttccg aaggtaactg 3540
gcttcagcag agcgcagata ccaaatactg tccttctagt gtagccgtag ttaggccacc 3600
acttcaagaa ctctgtagca ccgcctacat acctcgctct gctaatcctg ttaccagtgg 3660
ctgctgccag tggcgataag tcgtgtctta ccgggttgga ctcaagacga tagttaccgg 3720
ataaggcgca gcggtcgggc tgaacggggg gttcgtgcac acagcccagc ttggagcgaa 3780
cgacctacac cgaactgaga tacctacagc gtgagctatg agaaagcgcc acgcttcccg 3840
aagggagaaa ggcggacagg tatccggtaa gcggcagggt cggaacagga gagcgcacga 3900
gggagcttcc agggggaaac gcctggtatc tttatagtcc tgtcgggttt cgccacctct 3960
gacttgagcg tcgatttttg tgatgctcgt caggggggcg gagcctatgg aaaaacgcca 4020
gcaacgcggc ctttttacgg ttcctggcct tttgctggcc ttttgctcac atgttctttc 4080
ctgcgttatc ccctgattct gtggataacc gtattaccgc ctttgagtga gctgataccg 4140
ctcgccgcag ccgaacgacc gagcgcagcg agtcagtgag cgaggaagcg gaagagcgcc 4200
tgatgcggta ttttctcctt acgcatctgt gcggtatttc acaccgcata tatggtgcac 4260
tctcagtaca atctgctctg atgccgcata gttaagccag tatacactcc gctatcgcta 4320
cgtgactggg tcatggctgc gccccgacac ccgccaacac ccgctgacgc gccctgacgg 4380
gcttgtctgc tcccggcatc cgcttacaga caagctgtga ccgtctccgg gagctgcatg 4440
tgtcagaggt tttcaccgtc atcaccgaaa cgcgcgaggc agctggcacg acaggtttcc 4500
cgactgg 4507

<210> SEQ ID NO 41
<211> LENGTH: 6037
<212> TYPE: DNA
<213> ORGANISM: Artificial Sequence
<220> FEATURE:
<223> OTHER INFORMATION: Plasmid pGT1584

<400> SEQUENCE: 41
acccagtttc atcattccat tttattttgc gagcgagcgc acacttgtga attatctcaa 60
tagcagtgtg aaataacata attgagcaac tgaaagggag tgcccaatat tacgacatca 120
tccatcacgc ggagttacct gattatgaca cagagggccc accatcacca tcaccattcc 180
atgggtatgc agggtgaaga tgcacagcgt accggtaata ttgttgcagt taaaccgaaa 240
ccgagccagg gtctgaccag caaagcaatt gattggctgg aatggctgtt tgtgaaaatg 300
atgcatgata gcaaacagcc gctgcattat ctgagcggta attttgcacc ggttgatgaa 360
acccctccgc tgaaagatct gccggttacc ggtcatctgc cggaatgtct gaatggtgaa 420
tttgttcgtg ttggtccgaa tccgaaattt gcaagcattg caggttatca ttggtttgat 480
ggtgatggta tgattcatgg catgcgcatt aaagatggta aagcaaccta tgttagccgt 540
tatgttcaga ccagccgtct gaaacaagag gaattctttg gtcgtgccat gttcatgaaa 600

```
atcggtgatc tgaaaggtat gtttggtctg ctgatggtta atatgcagat gctgcgtgca    660
aaactgaaag ttctggatat tagctatggt attggcaccg caaataccgc actggtttat    720
catcatggta aactgctggc actgagcgaa gcagataaac cgtatgcaat taaagtgctg    780
gaagatggtg atctgcagac cattggcctg ctggattatg ataaacgtct ggcacatagc    840
tttaccgcac atccgaaagt tgatccgttt accggtgaga tgtttacctt tggttatagc    900
catacccctc cgtatgttac ctatcgtgtt attagcaaag atggtgcaat gaatgatccg    960
gttccgatta ccgttagcgg tccgatcatg atgcacgatt ttgcaattac cgaaaactac   1020
gccatcttta tggatctgcc gctgtatttc aaaccgaaag aaatggtgaa agacaagaaa   1080
ttcatcttta gcttcgatgc cacccagaaa gcacgttttg gtattctgcc tcgttatgcc   1140
aagaatgagc tgctgattaa atggtttgaa ctgccgaact gcttcatctt tcataatgca   1200
aatgcatggg aagagggtga tgaagttgtt ctgattacct gtcgtctgga aaatccggat   1260
ctggatatgg tgaatagcac cgttaaagaa cgtctggaca actttaagaa cgagctgtat   1320
gaaatgcgct tcaatctgca gaatggtctg gcaagccaga aaaaactgag cgttagcgca   1380
gttgattttc cgcgtgttaa tgaaagctat accacccgta aacagcgtta tgtttatggc   1440
accaccctgg ataagattgc caaagttacc ggcatcatca aattcgatct gcatgccgaa   1500
ccggaaaccg gtaaagagaa gctggaactg ggtggtaatg tgaaaggcat ttttgatctg   1560
ggtccgggtc gttttggttc agaagcagtt tttgttccgc gtcatccggg tattaccagc   1620
gaagaggatg atggttatct gatcttcttt gtgcacgatg aaaacaccgg caaaagcgca   1680
gttaatgtta ttgatgcaaa aaccatgagc cctgatccgg tggcagttgt ggaactgcct   1740
aaacgtgttc cgtatggttt tcatgcattt tttgttaccg aagatcagct gcaagaacag   1800
gccaaagttt aaggatccgg ctgctaacaa agcccgaaag gaagctgagt tggctgctgc   1860
caccgctgag caataactag cataacccct tggggcctct aaacgggtct tgaggggttt   1920
tttgctgaaa ggaggaacta tatccggccg gatatccaca ggacgggtgt ggtcgccatg   1980
atcgcgtagt cgatagtggc tccaagtagc gaagcgagca ggactgggcg gcggccaaag   2040
cggtcggaca gtgctccgag aacgggtgcg catagaaatt gcatcaacgc atatagcgct   2100
agcagcacgc catagtgact ggcgatgctg tcggaatgga cgatatcccg caagaggccc   2160
ggcagtaccg gcataaccaa gcctatgcct acagcatcca gggtgacggt gccgaggatg   2220
acgatgagcg cattgttaga tttcatacac ggtgcctgac tgcgttagca atttaactgt   2280
gataaactac cgcattaaag cttatcgatg ataagctgtc aaacatgaga attcttgaag   2340
acgaaagggc ctcgtgatac gcctattttt ataggttaat gtcatgcatg agacaataac   2400
cctgataaat gcttcaataa tattgaaaaa ggaagagtat gagtattcaa catttccgtg   2460
tcgcccttat tccctttttt gcggcatttt gccttcctgt ttttgctcac ccagaaacgc   2520
tggtgaaagt aaaagatgct gaagatcagt tgggtgcacg agtgggttac atcgaactgg   2580
atctcaacag cggtaagatc cttgagagtt ttcgccccga agaacgtttt ccaatgatga   2640
gcacttttaa agttctgcta tgtggcgcgg tattatcccg tgttgacgcc gggcaagagc   2700
aactcggtcg ccgcatacac tattctcaga atgacttggt tgacgcgtca ccagtcacag   2760
aaaagcatct tacggatggc atgacagtaa gagaattatg cagtgctgcc ataaccatga   2820
gtgataacac tgcggccaac ttacttctga caacgatcgg aggaccgaag gagctaaccg   2880
ctttttttgca caacatgggg gatcatgtaa ctcgccttga tcgttgggaa ccggagctga   2940
atgaagccat accaaacgac gagcgtgaca ccacgatgcc tgcagcaatg gcaacaacgt   3000
```

```
tgcgcaaact attaactggc gaactactta ctctagcttc ccggcaacaa ttaatagact   3060
ggatggaggc ggataaagtt gcaggaccac ttctgcgctc ggcccttccg gctggctggt   3120
ttattgctga taaatctgga gccggtgagc gtgggtctcg cggtatcatt gcagcactgg   3180
ggccagatgg taagccctcc cgtatcgtag ttatctacac gacggggagt caggcaacta   3240
tggatgaacg aaatagacag atcgctgaga taggtgcctc actgattaag cattggtaac   3300
tgtcagacca agtttactca tatatacttt agattgattt aaaacttcat ttttaattta   3360
aaaggatcta ggtgaagatc ctttttgata atctcatgca tgaccaaaat cccttaacgt   3420
gagttttcgt tccactgagc gtcagacccc gtagaaaaga tcaaaggatc ttcttgagat   3480
cctttttttc tgcgcgtaat ctgctgcttg caaacaaaaa aaccaccgct accagcggtg   3540
gtttgtttgc cggatcaaga gctaccaact ctttttccga aggtaactgg cttcagcaga   3600
gcgcagatac caaatactgt ccttctagtg tagccgtagt taggccacca cttcaagaac   3660
tctgtagcac cgcctacata cctcgctctg ctaatcctgt taccagtggc tgctgccagt   3720
ggcgataagt cgtgtcttac cgggttggac tcaagacgat agttaccgga taaggcgcag   3780
cggtcgggct gaacgggggg ttcgtgcaca cagcccagct tggagcgaac gacctacacc   3840
gaactgagat acctacagcg tgagctatga gaaagcgcca cgcttcccga agggagaaag   3900
gcggacaggt atccggtaag cggcagggtc ggaacaggag agcgcacgag ggagcttcca   3960
gggggaaacg cctggtatct ttatagtcct gtcgggtttc gccacctctg acttgagcgt   4020
cgatttttgt gatgctcgtc aggggggcgg agcctatgga aaaacgccag caacgcggcc   4080
tttttacggt tcctggcctt ttgctggcct tttgctcaca tgttctttcc tgcgttatcc   4140
cctgattctg tggataaccg tattaccgcc tttgagtgag ctgataccgc tcgccgcagc   4200
cgaacgaccg agcgcagcga gtcagtgagc gaggaagcgg aagagcgcct gatgcggtat   4260
tttctcctta cgcatctgtg cggtatttca caccgcatat atggtgcact ctcagtacaa   4320
tctgctctga tgccgcatag ttaagccagt atacactccg ctatcgctac gtgactgggt   4380
catggctgcg ccccgacacc cgccaacacc cgctgacgcg ccctgacggg cttgtctgct   4440
cccggcatcc gcttacagac aagctgtgac cgtctccggg agctgcatgt gtcagaggtt   4500
ttcaccgtca tcaccgaaac gcgcgaggca gctggcacga caggtttccc gactgggttg   4560
gtgcgtttta tcatgcctgg cgggtaggtc ggataaggcg ttcacgccgc atccgacaac   4620
cacgcagcgt tacctgatgt gacgccgaca attctcatca tcgctacaac atgacctcgc   4680
tatttacatc gcgatactct tttggcgtcg tgtcatatgc ttttttaaaa acagagtaga   4740
aatattgcag cgatggataa ccgcacattt gcgatatctc attgatcgac aaggtggttg   4800
aaatcagcag actgcgcgct ttctccagct tctcggcatg aatcatggca tggatggttt   4860
cacccacctc ttctttaaaa cgcttctcaa gattggagcg cgagatcccg accgcatcca   4920
gtacctgatc cactttaatc cctttacagg cgtgattacg aatgtaatgc atggcctgaa   4980
taacggcggg atcggtcagc gagcgataat ctgttgagcg ccgttcaatg acgcgaactg   5040
gtgggaccaa aattcgctgt agcggcattt cttctttatc taataatcga tgcaacagtt   5100
ttgccgcctg atagcccatt tgccgcgcgc cctgagcgac cgaagaaagg gcgacacgcg   5160
acagatagcg ggtcagttct tcgttatcga tgccaatcac gcataatttt tccggtacgg   5220
gaatatgtag atgttcacat acttgcagaa tatgccgcgc tcgggcgtca gtaacggcaa   5280
taatcccggt ttgcggtggt agcgtttgta gccagtctgc cagccgattt tgcgcgtgtt   5340
```

```
gccagttctc tggcgcggtt tctaacccct gataaaccac tccgcgatac ttttcttcgg   5400

cgacaagctg acgaaatgca tattcgcgct cagtggccca acgtttgccg cttgattccg   5460

gaagaccata aaaagcaaag cggttaacgc ctttctcttt taaatgcaaa aatgcgcttt   5520

caaccagcgc atagttatcg gtggcaatgt aatgaacggg tgggtaactt tctgcaaggt   5580

gatacgagcc gccaacccca acaatgggga cgtcgacatc agccagcgct tgctcgatct   5640

gtttgtcgtc gaagtcggca atgacgccat ctcctaacca gtccttgatt ttatcaatgc   5700

gggcgcggaa atcttcttca atgaaaatat cccattccga ttgtgacgcc tgtaaatatt   5760

cccctacgcc ttctactacc tgccggtcat aggctttatt ggcattgaac agtaatgtga   5820

tgcggtgacg tttagtaaac atggttcttt tcctgctgaa tcatgctaag taacaatcac   5880

cgcgataaac gtaaccaatt tttagcaact aaacagggga aaacaattac agatttttat   5940

ctttcgatta cgatttttgg tttatttctt gatttatgac cgagatctta cttttgttgc   6000

gcaattgtac ttattgcatt tttctcttcg aggaatt                            6037
```

```
<210> SEQ ID NO 42
<211> LENGTH: 6037
<212> TYPE: DNA
<213> ORGANISM: Artificial Sequence
<220> FEATURE:
<223> OTHER INFORMATION: Plasmid pGT1586

<400> SEQUENCE: 42

acccagtttc atcattccat tttattttgc gagcgagcgc acacttgtga attatctcaa     60

tagcagtgtg aaataacata attgagcaac tgaaagggag tgccctatat tacgacatca    120

tccatcacgc ggagttacct gattatgaca cagagggccc accatcacca tcaccattcc    180

atgggtatgc agggtgaaga tgcacagcgt accggtaata ttgttgcagt taaaccgaaa    240

ccgagccagg gtctgaccag caaagcaatt gattggctgg aatggctgtt tgtgaaaatg    300

atgcatgata gcaaacagcc gctgcattat ctgagcggta attttgcacc ggttgatgaa    360

acccctccgc tgaaagatct gccggttacc ggtcatctgc cggaatgtct gaatggtgaa    420

tttgttcgtg ttggtccgaa tccgaaattt gcaagcattg caggttatca ttggtttgat    480

ggtgatggta tgattcatgg catgcgcatt aaagatggta aagcaaccta tgttagccgt    540

tatgttcaga ccagccgtct gaaacaagag gaattctttg gtcgtgccat gttcatgaaa    600

atcggtgatc tgaaaggtat gtttggtctg ctgatggtta atatgcagat gctgcgtgca    660

aaactgaaag ttctggatat tagctatggt attggcaccg caaataccgc actggtttat    720

catcatggta aactgctggc actgagcgaa gcagataaac cgtatgcaat taaagtgctg    780

gaagatggtg atctgcagac cattggcctg ctggattatg ataaacgtct ggcacatagc    840

tttaccgcac atccgaaagt tgatccgttt accggtgaga tgtttacctt tggttatagc    900

catacccctc cgtatgttac ctatcgtgtt attagcaaag atggtgcaat gaatgatccg    960

gttccgatta ccgttagcgg tccgatcatg atgcacgatt ttgcaattac cgaaaactac   1020

gccatcttta tggatctgcc gctgtatttc aaaccgaaag aaatggtgaa agacaagaaa   1080

ttcatcttta gcttcgatgc cacccagaaa gcacgttttg gtattctgcc tcgttatgcc   1140

aagaatgagc tgctgattaa atggtttgaa ctgccgaact gcttcatctt tcataatgca   1200

aatgcatggg aagagggtga tgaagttgtt ctgattacct gtcgtctgga aaatccggat   1260

ctggatatgg tgaatagcac cgttaaagaa cgtctggaca actttaagaa cgagctgtat   1320

gaaatgcgct tcaatctgca gaatggtctg gcaagccaga aaaaactgag cgttagcgca   1380
```

```
gttgattttc cgcgtgttaa tgaaagctat accacccgta aacagcgtta tgtttatggc   1440
accaccctgg ataagattgc caaagttacc ggcatcatca aattcgatct gcatgccgaa   1500
ccggaaaccg gtaaagagaa gctggaactg ggtggtaatg tgaaaggcat tttgatctg    1560
ggtccgggtc gttttggttc agaagcagtt tttgttccgc gtcatccggg tattaccagc   1620
gaagaggatg atggttatct gatcttcttt gtgcacgatg aaaacaccgg caaaagcgca   1680
gttaatgtta ttgatgcaaa aaccatgagc cctgatccgg tggcagttgt ggaactgcct   1740
aaacgtgttc cgtatggttt tcatgcattt tttgttaccg aagatcagct gcaagaacag   1800
gccaaagttt aaggatccgg ctgctaacaa agcccgaaag gaagctgagt tggctgctgc   1860
caccgctgag caataactag cataacccct tggggcctct aaacgggtct tgaggggttt   1920
tttgctgaaa ggaggaacta tatccggccg gatatccaca ggacgggtgt ggtcgccatg   1980
atcgcgtagt cgatagtggc tccaagtagc gaagcgagca ggactgggcg gcggccaaag   2040
cggtcggaca gtgctccgag aacgggtgcg catagaaatt gcatcaacgc atatagcgct   2100
agcagcacgc catagtgact ggcgatgctg tcggaatgga cgatatcccg caagaggccc   2160
ggcagtaccg gcataaccaa gcctatgcct acagcatcca gggtgacggt gccgaggatg   2220
acgatgagcg cattgttaga tttcatacac ggtgcctgac tgcgttagca atttaactgt   2280
gataaactac cgcattaaag cttatcgatg ataagctgtc aaacatgaga attcttgaag   2340
acgaaagggc ctcgtgatac gcctattttt ataggttaat gtcatgcatg agacaataac   2400
cctgataaat gcttcaataa tattgaaaaa ggaagagtat gagtattcaa catttccgtg   2460
tcgcccttat tccctttttt gcggcatttt gccttcctgt ttttgctcac ccagaaacgc   2520
tggtgaaagt aaaagatgct gaagatcagt tgggtgcacg agtgggttac atcgaactgg   2580
atctcaacag cggtaagatc cttgagagtt ttcgccccga agaacgtttt ccaatgatga   2640
gcacttttaa agttctgcta tgtggcgcgg tattatcccg tgttgacgcc gggcaagagc   2700
aactcggtcg ccgcatacac tattctcaga atgacttggt tgacgcgtca ccagtcacag   2760
aaaagcatct tacggatggc atgacagtaa gagaattatg cagtgctgcc ataaccatga   2820
gtgataacac tgcggccaac ttacttctga caacgatcgg aggaccgaag gagctaaccg   2880
ctttttttgca caacatgggg gatcatgtaa ctcgccttga tcgttgggaa ccggagctga  2940
atgaagccat accaaacgac gagcgtgaca ccacgatgcc tgcagcaatg gcaacaacgt   3000
tgcgcaaact attaactggc gaactactta ctctagcttc ccggcaacaa ttaatagact   3060
ggatggaggc ggataaagtt gcaggaccac ttctgcgctc ggcccttccg gctggctggt   3120
ttattgctga taaatctgga gccggtgagc gtgggtctcg cggtatcatt gcagcactgg   3180
ggccagatgg taagccctcc cgtatcgtag ttatctacac gacggggagt caggcaacta   3240
tggatgaacg aaatagacag atcgctgaga taggtgcctc actgattaag cattggtaac   3300
tgtcagacca agtttactca tatatacttt agattgattt aaaacttcat ttttaattta   3360
aaaggatcta ggtgaagatc ctttttgata atctcatgca tgaccaaaat cccttaacgt   3420
gagttttcgt tccactgagc gtcagacccc gtagaaaaga tcaaaggatc ttcttgagat   3480
cctttttttc tgcgcgtaat ctgctgcttg caaacaaaaa aaccaccgct accagcggtg   3540
gtttgtttgc cggatcaaga gctaccaact ctttttccga aggtaactgg cttcagcaga   3600
gcgcagatac caaatactgt ccttctagtg tagccgtagt taggccacca cttcaagaac   3660
tctgtagcac cgcctacata cctcgctctg ctaatcctgt taccagtggc tgctgccagt   3720
```

```
ggcgataagt cgtgtcttac cgggttggac tcaagacgat agttaccgga taaggcgcag   3780
cggtcgggct gaacgggggg ttcgtgcaca cagcccagct tggagcgaac gacctacacc   3840
gaactgagat acctacagcg tgagctatga gaaagcgcca cgcttcccga agggagaaag   3900
gcggacaggt atccggtaag cggcagggtc ggaacaggag agcgcacgag ggagcttcca   3960
gggggaaacg cctggtatct ttatagtcct gtcgggtttc gccacctctg acttgagcgt   4020
cgatttttgt gatgctcgtc aggggggcgg agcctatgga aaaacgccag caacgcggcc   4080
tttttacggt tcctggcctt ttgctggcct tttgctcaca tgttctttcc tgcgttatcc   4140
cctgattctg tggataaccg tattaccgcc tttgagtgag ctgataccgc tcgccgcagc   4200
cgaacgaccg agcgcagcga gtcagtgagc gaggaagcgg aagagcgcct gatgcggtat   4260
tttctcctta cgcatctgtg cggtatttca caccgcatat atggtgcact ctcagtacaa   4320
tctgctctga tgccgcatag ttaagccagt atacactccg ctatcgctac gtgactgggt   4380
catggctgcg ccccgacacc cgccaacacc cgctgacgcg ccctgacggg cttgtctgct   4440
cccggcatcc gcttacagac aagctgtgac cgtctccggg agctgcatgt gtcagaggtt   4500
ttcaccgtca tcaccgaaac gcgcgaggca gctggcacga caggtttccc gactgggttg   4560
gtgcgtttta tcatgcctgg cgggtaggtc ggataaggcg ttcacgccgc atccgacaac   4620
cacgcagcgt tacctgatgt gacgccgaca attctcatca tcgctacaac atgacctcgc   4680
tatttacatc gcgatactct tttggcgtcg tgtcatatgc ttttttaaaa acagagtaga   4740
aatattgcag cgatggataa ccgcacattt gcgatatctc attgatcgac aaggtggttg   4800
aaatcagcag actgcgcgct ttctccagct tctcggcatg aatcatggca tggatggttt   4860
cacccacctc ttctttaaaa cgcttctcaa gattggagcg cgagatcccg accgcatcca   4920
gtacctgatc cactttaatc cctttacagg cgtgattacg aatgtaatgc atggcctgaa   4980
taacggcggg atcggtcagc gagcgataat ctgttgagcg ccgttcaatg acgcgaactg   5040
gtgggaccaa aattcgctgt agcggcattt cttctttatc taataatcga tgcaacagtt   5100
ttgccgcctg atagcccatt tgccgcgcgc cctgagcgac cgaagaaagg gcgacacgcg   5160
acagatagcg ggtcagttct tcgttatcga tgccaatcac gcataatttt tccggtacgg   5220
gaatatgtag atgttcacat acttgcagaa tatgccgcgc tcgggcgtca gtaacggcaa   5280
taatcccggt ttgcggtggt agcgtttgta gccagtctgc cagccgattt tgcgcgtgtt   5340
gccagttctc tggcgcggtt tctaacccct gataaaccac tccgcgatac ttttcttcgg   5400
cgacaagctg acgaaatgca tattcgcgct cagtggccca acgtttgccg cttgattccg   5460
gaagaccata aaaagcaaag cggttaacgc ctttctcttt taaatgcaaa aatgcgcttt   5520
caaccagcgc atagttatcg gtggcaatgt aatgaacggg tgggtaactt tctgcaaggt   5580
gatacgagcc gccaacccca acaatgggga cgtcgacatc agccagcgct tgctcgatct   5640
gtttgtcgtc gaagtcggca atgacgccat ctcctaacca gtccttgatt ttatcaatgc   5700
gggcgcggaa atcttcttca atgaaaatat cccattccga ttgtgacgcc tgtaaatatt   5760
cccctacgcc ttctactacc tgccggtcat aggctttatt ggcattgaac agtaatgtga   5820
tgcggtgacg tttagtaaac atggttcttt tcctgctgaa tcatgctaag taacaatcac   5880
cgcgataaac gtaaccaatt tttagcaact aaacagggga aaacaattac agatttttat   5940
ctttcgatta cgatttttgg tttatttctt gatttatgac cgagatctta cttttgttgc   6000
gcaattgtac ttattgcatt tttctcttcg aggaatt                            6037
```

<210> SEQ ID NO 43
<211> LENGTH: 10307
<212> TYPE: DNA
<213> ORGANISM: Artificial Sequence
<220> FEATURE:
<223> OTHER INFORMATION: Plasmid pGT1574

<400> SEQUENCE: 43

```
ttgtaattct catgtttgac agcttatcat cgataagctt taatgcggta gttaacgcag     60

tcaggaacct tgcaatgagc agtttcgatg cccatgacct tgacctcgac aaatttccgg    120

aggtcgtgcg agatcgtttg acgcagttcc tcgatgctca agagctaaca attgctgata    180

tcggcgctcc tgtcacagat gctgtggccc atcttcgcag tttcgtgctc aatggaggaa    240

agcgaatccg tcctctttat gcgtgggctg gtttcctggc ggcgcaaggc cataagaatt    300

cttctgaaaa acttgagtcc gtccttgacg ccgcagcgag tctcgaattc atccaggctt    360

gtgccttgat tcatgacgat attatcgatt cttctgatac ccggcgcgga gcccctacag    420

ttcaccgggc tgtggaagct gatcaccgcg ccaataattt cgaaggcgat cctgagcact    480

ttggcgtttc agtctcgatt ttggctggcg atatggcatt ggtgtgggca gaagacatgc    540

tgcaggattc cggtttgagt gcagaggcat tggcccgcac gagggatgct tggcgtggca    600

tgcgtactga ggttattggc ggccagctgc ttgatattta tcttgagtcg cacgccaacg    660

agtcggtgga gcttgcggat tctgtcaacc gcttcaaaac ggccgcttac acgattgcgc    720

gcccattgca cctgggcgcc tccattgctg gcggttcgcc gcagcttatc gacgcgctcc    780

tccactacgg ccacgacatc ggcattgcat tccagttgag ggatgatctg cttggtgtgt    840

ttggtgatcc tgctatcacc ggcaaaccag ctggagacga tatccgtgaa ggcaagcgca    900

ctgttcttct tgcgctcgct ctacaacgcg ctgataagca atctcctgaa gctgcaacgg    960

ccattcgcgc aggtgttgga aaggtgactt caccagaaga tattgctgtc attacagagc   1020

atattcgagc tactggtgct gaagaagaag ttgagcagcg aatttcccag ctgactgaat   1080

ccggtttggc tcacctcgat gatgtagaca tccctgatga ggtgcgcgca cagttgcggg   1140

cactggctat ccgctcaacc gaacgtcgga tgtaataccg cccttttggg ttcaagcagt   1200

acataacgat ggaaccacat tacaggagta gtgatgaatg aaggacgagc gccttgttca   1260

gcgtaagaac gatcatctgg atatcgttct cgaccccccgt cgcgccgtaa ctcaggctag   1320

cgcaggtttt gagcgctggc gctttaccca ctgcgccctg ccagagctga attttagcga   1380

catcacgctg gaaaccacct tcctgaatcg gcagctacag gctccgctgc tgatcagctc   1440

catgaccggc ggcgttgagc gctcgcgcca tatcaaccgc cacctcgccg aggcggcgca   1500

ggtgctaaaa attgcgatgg gggtgggctc ccagcgcgtc gccattgaga gcgacgcggg   1560

cttagggctg gataaaaccc tgcggcagct ggctccggac gtgccgctgc tggcgaacct   1620

cggcgcggcg cagctgaccg gcagaaaagg tattgattac gcccgacggg ccgtggagat   1680

gatcgaggcg gatgcgctga ttgtgcacct aaacccgctg caggaggcgc tacagcccgg   1740

cggcgatcgc gactggcgcg gacggctggc ggctattgaa actctggtcc gcgagctgcc   1800

cgttccgctg gtggtgaaag aggtgggagc cggtatctcc cgaaccgtgg ccgggcagct   1860

gatcgatgcc ggcgttaccg tgattgacgt cgcgggcgcg ggcggcacca gctgggccgc   1920

cgttgaaggc gagcgggcgg ccaccgagca gcagcgcagc gtggccaacg tctttgccga   1980

ctgggggatc cccaccgctg aggcgctggt tgacattgcc gaggcctggc cgcagatgcc   2040

ccttattgcc tcgggcggga ttaaaaacgg cgtcgacgcg gcgaaagcgc tgcggctcgg   2100
```

```
cgcgtgcatg gtagggcagg ccgccgccgt gctcggcagc gcaggcgtct ccacggagaa 2160
ggtgatcgat cacttcaacg tgattattga gcagctgcgg gtggcctgct tctgcaccgg 2220
cagccgcagc ctgagcgatc taaagcaggc tgatatccgc tatgttcgtg atacgccata 2280
aggaggtaca accatgaaga aaaccgttgt gattggcgca ggctttggtg gcctggcgct 2340
ggcgattcgc ctgcaggcgg cagggatccc aaccgtactg ctggagcagc gggacaagcc 2400
cggcggtcgg gcctacgtct ggcatgacca gggctttacc tttgacgccg ggccgacggt 2460
gatcaccgat cctaccgcgc ttgaggcgct gttcaccctg gccggcaggc gcatggagga 2520
ttacgtcagg ctgctgccgg taaaaccctt ctaccgactc tgctgggagt ccgggaagac 2580
cctcgactat gctaacgaca gcgccgagct tgaggcgcag attacccagt tcaacccccg 2640
cgacgtcgag ggctaccggc gctttctggc ttactcccag gcggtattcc aggagggata 2700
tttgcgcctc ggcagcgtgc cgttcctctc ttttcgcgac atgctgcgcg ccgggccgca 2760
gctgcttaag ctccaggcgt ggcagagcgt ctaccagtcg gtttcgcgct ttattgagga 2820
tgagcatctg cggcaggcct tctcgttcca ctccctgctg gtaggcggca accccttcac 2880
cacctcgtcc atctacaccc tgatccacgc ccttgagcgg gagtgggggg tctggttccc 2940
tgagggcggc accggggcgc tggtgaacgg catggtgaag ctgtttaccg atctgggcgg 3000
ggagatcgaa ctcaacgccc gggtcgaaga gctggtggtg gccgataacc gcgtaagcca 3060
ggtccggctg gcggatggtc ggatctttga caccgacgcc gtagcctcga acgctgacgt 3120
ggtgaacacc tataaaaagc tgctcggcca ccatccggtg gggcagaagc gggcggcagc 3180
gctggagcgc aagagcatga gcaactcgct gtttgtgctc tacttcggcc tgaaccagcc 3240
tcattcccag ctggcgcacc ataccatctg ttttggtccc cgctaccggg agctgatcga 3300
cgagatcttt accggcagcg cgctggcgga tgacttctcg ctctacctgc actcgccctg 3360
cgtgaccgat ccctcgctcg cgcctcccgg ctgcgccagc ttctacgtgc tggccccggt 3420
gccgcatctt ggcaacgcgc cgctggactg ggcgcaggag gggccgaagc tgcgcgaccg 3480
catctttgac taccttgaag agcgctatat gcccggcctg cgtagccagc tggtgaccca 3540
gcggatcttt accccggcag acttccacga cacgctggat gcgcatctgg gatcggcctt 3600
ctccatcgag ccgctgctga cccaaagcgc ctggttccgc ccgcacaacc gcgacagcga 3660
cattgccaac ctctacctgg tgggcgcagg tactcaccct ggggcgggca ttcctggcgt 3720
agtggcctcg gcgaaagcca ccgccagcct gatgattgag gatctgcaat gagccaaccg 3780
ccgctgcttg accacgccac gcagaccatg gccaacggct cgaaaagttt tgccaccgct 3840
gcgaagctgt tcgacccggc cacccgccgt agcgtgctga tgctctacac ctggtgccgc 3900
cactgcgatg acgtcattga cgaccagacc cacggcttcg ccagcgaggc cgcggcggag 3960
gaggaggcca cccagcgcct ggcccggctg cgcacgctga ccctggcggc gtttgaaggg 4020
gccgagatgc aggatccggc cttcgctgcc tttcaggagg tggcgctgac ccacggtatt 4080
acgccccgca tggcgctcga tcacctcgac ggctttgcga tggacgtggc tcagacccgc 4140
tatgtcacct ttgaggatac gctgcgctac tgctatcacg tggcgggcgt ggtgggtctg 4200
atgatggcca gggtgatggg cgtgcgggat gagcgggtgc tggatcgcgc ctgcgatctg 4260
gggctggcct tccagctgac gaatatcgcc cgggatatta ttgacgatgc ggctattgac 4320
cgctgctatc tgcccgccga gtggctgcag gatgccgggc tgaccccgga gaactatgcc 4380
gcgcgggaga atcgggccgc gctggcgcgg gtggcggagc ggcttattga tgccgcagag 4440
ccgtactaca tctcctccca ggccgggcta cacgatctgc cgccgcgctg cgcctgggcg 4500
```

```
atcgccaccg cccgcagcgt ctaccgggag atcggtatta aggtaaaagc ggcgggaggc   4560
agcgcctggg atcgccgcca gcacaccagc aaaggtgaaa aaattgccat gctgatggcg   4620
gcaccggggc aggttattcg ggcgaagacg acgagggtga cgccgcgtcc ggccggtctt   4680
tggcagcgtc ccgtttagac cgactccaaa cgagtcggtt tttttgcgct tgtttcggcg   4740
tgggtatggt ggcaggcccc gtggccgggg gactgttggg cgccatctcc ttggggtcga   4800
atttgctttc gaatttctgc cattcatccg cttattatca cttattcagg cgtagcaacc   4860
aggcgtttaa gggcaccaat aactgcctta aaaaaattac gccccgccct gccactcatc   4920
gcagtactgt tgtaattcat taagcattct gccgacatgg aagccatcac agacggcatg   4980
atgaacctga atcgccagcg gcatcagcac cttgtcgcct tgcgtataat atttgcccat   5040
ggtgaaaacg ggggcgaaga agttgtccat attggccacg tttaaatcaa aactggtgaa   5100
actcacccag ggattggctg agacgaaaaa catattctca ataaaccctt tagggaaata   5160
ggccaggttt tcaccgtaac acgccacatc ttgcgaatat atgtgtagaa actgccggaa   5220
atcgtcgtgg tattcactcc agagcgatga aaacgtttca gtttgctcat ggaaaacggt   5280
gtaacaaggg tgaacactat cccatatcac cagctcaccg tctttcattg ccatacggaa   5340
ttccggatga gcattcatca ggcgggcaag aatgtgaata aaggccggat aaaacttgtg   5400
cttatttttc tttacggtct ttaaaaaggc cgtaatatcc agctgaacgg tctggttata   5460
ggtacattga gcaactgact gaaatgcctc aaaatgttct ttacgatgcc attgggatat   5520
atcaacggtg gtatatccag tgattttttt ctccatttta gcttccttag ctcctgaaaa   5580
tctcgataac tcaaaaaata cgcccggtag tgatcttatt tcattatggt gaaagttgga   5640
acctcttacg tgccgatcaa cgtctcattt tcgccaaaag ttggcccagg gcttcccggt   5700
atcaacaggg acaccaggat ttatttattc tgcgaagtga tcttccgtca caggtattta   5760
ttcggcgcaa agtgcgtcgg gtgatgctgc caacttactg atttagtgta tgatggtgtt   5820
tttgaggtgc tccagtggct tctgtttcta tcagctgtcc ctcctgttca gctactgacg   5880
gggtggtgcg taacggcaaa agcaccgccg gacatcagcg ctagcggagt gtatacactc   5940
cgctatcgct acgtgactgg gtcatggctg cgccccgaca cccgccaaca cccgctgacg   6000
cgccctgacg ggcttgtctg ctcccggcat ccgcttacag acaagctgtg accgtctccg   6060
ggagctgcat gtgtcagagg ttttcaccgt catcaccgaa acgcgcgagg cagctggcac   6120
gacaggtttc ccgactggaa aagcgaattg gtataatgcc ctcgtaataa ttttgtttaa   6180
ctttaagaag gagatatacc catgacacag agggcccacc atcaccatca ccattccatg   6240
gctagcggcg gcggaagttc cggtagtgag agttgtgtag cggtgagaga agatttcgct   6300
gacgaagaag attttgtgaa agctggtggt tctgagattc tatttgttca aatgcagcag   6360
aacaaagata tggatgaaca gtctaagctt gttgataagt tgcctcctat atcaattggt   6420
gatggtgctt tggatctagt ggttattggt tgtggtcctg ctggtttagc cttggctgca   6480
gaatcagcta agcttggatt aaaagttgga ctcattggtc cagatcttcc ttttactaac   6540
aattacggtg tttgggaaga tgaattcaat gatcttgggc tgcaaaaatg tattgagcat   6600
gtttggagag agactattgt gtatctggat gatgacaagc ctattaccat tggccgtgct   6660
tatggaagag ttagtcgacg tttgctccat gaggagcttt tgaggaggtg tgtcgagtca   6720
ggtgtctcgt accttagctc gaaagttgac agcataacag aagcttctga tggccttaga   6780
cttgttgctt gtgacgacaa taacgtcatt ccctgcaggc ttgccactgt tgcttctgga   6840
```

-continued

```
gcagcttcgg gaaagctctt gcaatacgaa gttggtggac ctagagtctg tgtgcaaact   6900
gcatacggcg tggaggttga ggtggaaaat agtccatatg atccagatca aatggttttc   6960
atggattaca gagattatac taacgagaaa gttcggagct tagaagctga gtatccaacg   7020
tttctgtacg ccatgcctat gacaaagtca agactcttct tcgaggagac atgtttggcc   7080
tcaaaagatg tcatgccctt tgatttgcta aaaacgaagc tcatgttaag attagataca   7140
ctcggaattc gaattctaaa gacttacgaa gaggagtggt cctatatccc agttggtggt   7200
tccttgccaa acaccgaaca aaagaatctc gcctttggtg ctgccgctag catggtacat   7260
cccgcaacag gctattcagt tgtgagatct ttgtctgaag ctccaaaata tgcatcagtc   7320
atcgcagaga tactaagaga agagactacc aaacagatca acagtaatat ttcaagacaa   7380
gcttgggata ctttatggcc accagaaagg aaaagacaga gagcattctt tctctttggt   7440
cttgaggcta tagttcaatt cgataccgaa ggcattagaa gcttcttccg tactttcttc   7500
cgccttccaa aatggatgtg gcaagggttt ctaggatcaa cattaacatc aggagatctc   7560
gttctctttt ctttatacat gttcgtcatt tcaccaaaca atttgagaaa aggtctcatc   7620
aatcatctca tctctgatcc aaccggagca accatgataa aaacctatct caaagtataa   7680
ggaggatctt actccatggc ccaccatcac catcaccatt ccgcggagaa actcagtgat   7740
ggcagcagca tcatctcagt ccatcctaga ccctccaagg gtttctcctc gaagcttctc   7800
gatcttctcg agagacttgt tgtcaagctc atgcacgatg cttctctccc tctccactac   7860
ctctcaggca acttcgctcc catccgtgat gaaactcctc ccgtcaagga tctccccgtc   7920
catggatttc ttcccgaatg cttgaatggt gaatttgtga gggttggtcc aaaccccaag   7980
tttgatgctg tcgctggata tcactggttt gatggagatg ggatgattca tggggtacgc   8040
atcaaagatg ggaaagctac ttatgtttct cgatatgtta agacatcacg tcttaagcag   8100
gaagagttct tcggagctgc caaattcatg aagattggtg accttaaggg gtttttcgga   8160
ttgctaatgg tcaatgtcca acagctgaga acgaagctca aaatattgga caacacttat   8220
ggaaatggaa ctgccaatac agcactcgta tatcaccatg gaaaacttct agcattacag   8280
gaggcagata agccgtacgt catcaaagtt ttggaagatg gagacctgca aactcttggt   8340
ataatagatt atgacaagag attgacccac tccttcactg ctcacccaaa agttgacccg   8400
gttacgggtg aaatgtttac attcggctat tcgcatacgc caccttatct cacatacaga   8460
gttatctcga aagatggcat tatgcatgac ccagtcccaa ttactatatc agagcctatc   8520
atgatgcatg attttgctat tactgagact tatgcaatct tcatggatct tcctatgcac   8580
ttcaggccaa aggaaatggt gaaagagaag aaaatgatat actcatttga tcccacaaaa   8640
aaggctcgtt ttggtgttct tccacgctat gccaaggatg aacttatgat tagatggttt   8700
gagcttccca actgctttat tttccacaac gccaatgctt gggaagaaga ggatgaagtc   8760
gtcctcatca cttgtcgtct tgagaatcca gatcttgaca tggtcagtgg gaaagtgaaa   8820
gaaaaactcg aaaattttgg caacgaactg tacgaaatga gattcaacat gaaaacgggc   8880
tcagcttctc aaaaaaaact atccgcatct gcggttgatt tccccagaat caatgagtgc   8940
tacaccggaa agaaacagag atacgtatat ggaacaattc tggacagtat cgcaaaggtt   9000
accggaatca tcaagtttga tctgcatgca gaagctgaga cagggaaaag aatgctggaa   9060
gtaggaggta atatcaaagg aatatatgac ctgggagaag gcagatatgg ttcagaggct   9120
atctatgttc cgcgtgagac agcagaagaa gacgacggtt acttgatatt ctttgttcat   9180
gatgaaaaca cagggaaatc atgcgtgact gtgatagacg caaaaacaat gtcggctgaa   9240
```

```
ccggtggcag tggtggagct gccgcacagg gtcccatatg gcttccatgc cttgtttgtt   9300

acagaggaac aactccagga acaaactctt atataaggat ccggctgcta acaaagcccg   9360

ttctgtttaa gaacgggatt ttttgctgaa aggaggaact atatccggcc ggattactgg   9420

cttactatgt tggcactgat gagggtgtca gtgaagtgct tcatgtggca ggagaaaaaa   9480

ggctgcaccg gtgcgtcagc agaatatgtg atacaggata tattccgctt cctcgctcac   9540

tgactcgcta cgctcggtcg ttcgactgcg gcgagcggaa atggcttacg aacggggcgg   9600

agatttcctg gaagatgcca ggaagatact taacagggaa gtgagagggc cgcggcaaag   9660

ccgtttttcc ataggctccg cccccctgac aagcatcacg aaatctgacg ctcaaatcag   9720

tggtggcgaa acccgacagg actataaaga taccaggcgt ttccccctgg cggctccctc   9780

gtgcgctctc ctgttcctgc ctttcggttt accggtgtca ttccgctgtt atggccgcgt   9840

ttgtctcatt ccacgcctga cactcagttc cgggtaggca gttcgctcca agctggactg   9900

tatgcacgaa ccccccgttc agtccgaccg ctgcgcctta tccggtaact atcgtcttga   9960

gtccaacccg gaaagacatg caaaagcacc actggcagca gccactggta attgatttag  10020

aggagttagt cttgaagtca tgcgccggtt aaggctaaac tgaaaggaca agttttggtg  10080

actgcgctcc tccaagccag ttacctcggt tcaaagagtt ggtagctcag agaaccttcg  10140

aaaaaccgcc ctgcaaggcg gttttttcgt tttcagagca agagattacg cgcagaccaa  10200

aacgatctca agaagatcat cttattaatc agataaaata tttctagatt tcagtgcaat  10260

ttatctcttc aaatgtagca cctgaagtca gccccatacg atataag               10307
```

<210> SEQ ID NO 44
<211> LENGTH: 10325
<212> TYPE: DNA
<213> ORGANISM: Artificial Sequence
<220> FEATURE:
<223> OTHER INFORMATION: Plasmid pGT1575

<400> SEQUENCE: 44

```
ttgtaattct catgtttgac agcttatcat cgataagctt taatgcggta gttaacgcag     60

tcaggaacct tgcaatgagc agtttcgatg cccatgacct tgacctcgac aaatttccgg    120

aggtcgtgcg agatcgtttg acgcagttcc tcgatgctca agagctaaca attgctgata    180

tcggcgctcc tgtcacagat gctgtggccc atcttcgcag tttcgtgctc aatggaggaa    240

agcgaatccg tcctctttat gcgtgggctg gtttcctggc ggcgcaaggc cataagaatt    300

cttctgaaaa acttgagtcc gtccttgacg ccgcagcgag tctcgaattc atccaggctt    360

gtgccttgat tcatgacgat attatcgatt cttctgatac ccggcgcgga gcccctacag    420

ttcaccgggc tgtggaagct gatcaccgcg ccaataattt cgaaggcgat cctgagcact    480

ttggcgtttc agtctcgatt ttggctggcg atatggcatt ggtgtgggca gaagacatgc    540

tgcaggattc cggtttgagt gcagaggcat tggcccgcac gagggatgct tggcgtggca    600

tgcgtactga ggttattggc ggccagctgc ttgatattta tcttgagtcg cacgccaacg    660

agtcggtgga gcttgcggat tctgtcaacc gcttcaaaac ggccgcttac acgattgcgc    720

gcccattgca cctgggcgcc tccattgctg gcggttcgcc gcagcttatc gacgcgctcc    780

tccactacgg ccacgacatc ggcattgcat tccagttgag ggatgatctg cttggtgtgt    840

ttggtgatcc tgctatcacc ggcaaaccag ctggagacga tatccgtgaa ggcaagcgca    900

ctgttcttct tgcgctcgct ctacaacgcg ctgataagca atctcctgaa gctgcaacgg    960
```

-continued

```
ccattcgcgc aggtgttgga aaggtgactt caccagaaga tattgctgtc attacagagc   1020
atattcgagc tactggtgct gaagaagaag ttgagcagcg aatttcccag ctgactgaat   1080
ccggtttggc tcacctcgat gatgtagaca tccctgatga ggtgcgcgca cagttgcggg   1140
cactggctat ccgctcaacc gaacgtcgga tgtaataccg cccttttggg ttcaagcagt   1200
acataacgat ggaaccacat tacaggagta gtgatgaatg aaggacgagc gccttgttca   1260
gcgtaagaac gatcatctgg atatcgttct cgacccccgt cgcgccgtaa ctcaggctag   1320
cgcaggtttt gagcgctggc gctttaccca ctgcgccctg ccagagctga attttagcga   1380
catcacgctg gaaaccacct tcctgaatcg gcagctacag gctccgctgc tgatcagctc   1440
catgaccggc ggcgttgagc gctcgcgcca tatcaaccgc cacctcgccg aggcggcgca   1500
ggtgctaaaa attgcgatgg gggtgggctc ccagcgcgtc gccattgaga gcgacgcggg   1560
cttagggctg gataaaaccc tgcggcagct ggctccggac gtgccgctgc tggcgaacct   1620
cggcgcggcg cagctgaccg gcagaaaagg tattgattac gcccgacggg ccgtggagat   1680
gatcgaggcg gatgcgctga ttgtgcacct aaacccgctg caggaggcgc tacagcccgg   1740
cggcgatcgc gactggcgcg gacggctggc ggctattgaa actctggtcc gcgagctgcc   1800
cgttccgctg gtggtgaaag aggtgggagc cggtatctcc cgaaccgtgg ccgggcagct   1860
gatcgatgcc ggcgttaccg tgattgacgt cgcgggcgcg ggcggcacca gctgggccgc   1920
cgttgaaggc gagcgggcgg ccaccgagca gcagcgcagc gtggccaacg tctttgccga   1980
ctgggggatc cccaccgctg aggcgctggt tgacattgcc gaggcctggc cgcagatgcc   2040
ccttattgcc tcgggcggga ttaaaaacgg cgtcgacgcg gcgaaagcgc tgcggctcgg   2100
cgcgtgcatg gtagggcagg ccgccgccgt gctcggcagc gcaggcgtct ccacggagaa   2160
ggtgatcgat cacttcaacg tgattattga gcagctgcgg gtggcctgct tctgcaccgg   2220
cagccgcagc ctgagcgatc taaagcaggc tgatatccgc tatgttcgtg atacgccata   2280
aggaggtaca accatgaaga aaaccgttgt gattggcgca ggctttggtg gcctggcgct   2340
ggcgattcgc ctgcaggcgg cagggatccc aaccgtactg ctggagcagc gggacaagcc   2400
cggcggtcgg gcctacgtct ggcatgacca gggctttacc tttgacgccg ggccgacggt   2460
gatcaccgat cctaccgcgc ttgaggcgct gttcaccctg gccggcaggc gcatggagga   2520
ttacgtcagg ctgctgccgg taaaaccctt ctaccgactc tgctgggagt ccgggaagac   2580
cctcgactat gctaacgaca gcgccgagct tgaggcgcag attacccagt tcaacccccg   2640
cgacgtcgag ggctaccggc gctttctggc ttactcccag gcggtattcc aggagggata   2700
tttgcgcctc ggcagcgtgc cgttcctctc ttttcgcgac atgctgcgcg ccgggccgca   2760
gctgcttaag ctccaggcgt ggcagagcgt ctaccagtcg gtttcgcgct ttattgagga   2820
tgagcatctg cggcaggcct tctcgttcca ctccctgctg gtaggcggca accccttcac   2880
cacctcgtcc atctacaccc tgatccacgc ccttgagcgg gagtgggggg tctggttccc   2940
tgagggcggc accggggcgc tggtgaacgg catggtgaag ctgtttaccg atctgggcgg   3000
ggagatcgaa ctcaacgccc gggtcgaaga gctggtggtg gccgataacc gcgtaagcca   3060
ggtccggctg gcggatggtc ggatctttga caccgacgcc gtagcctcga acgctgacgt   3120
ggtgaacacc tataaaaagc tgctcggcca ccatccggtg gggcagaagc gggcggcagc   3180
gctggagcgc aagagcatga gcaactcgct gtttgtgctc tacttcggcc tgaaccagcc   3240
tcattcccag ctggcgcacc ataccatctg ttttggtccc cgctaccggg agctgatcga   3300
cgagatcttt accggcagcg cgctggcgga tgacttctcg ctctacctgc actcgccctg   3360
```

```
cgtgaccgat ccctcgctcg cgcctcccgg ctgcgccagc ttctacgtgc tggccccggt   3420
gccgcatctt ggcaacgcgc cgctggactg ggcgcaggag gggccgaagc tgcgcgaccg   3480
catctttgac taccttgaag agcgctatat gcccggcctg cgtagccagc tggtgaccca   3540
gcggatcttt accccggcag acttccacga cacgctggat gcgcatctgg gatcggcctt   3600
ctccatcgag ccgctgctga cccaaagcgc ctggttccgc ccgcacaacc gcgacagcga   3660
cattgccaac ctctacctgg tgggcgcagg tactcaccct ggggcgggca ttcctggcgt   3720
agtggcctcg gcgaaagcca ccgccagcct gatgattgag gatctgcaat gagccaaccg   3780
ccgctgcttg accacgccac gcagaccatg gccaacggct cgaaaagttt tgccaccgct   3840
gcgaagctgt tcgacccggc cacccgccgt agcgtgctga tgctctacac ctggtgccgc   3900
cactgcgatg acgtcattga cgaccagacc cacggcttcg ccagcgaggc cgcggcggag   3960
gaggaggcca cccagcgcct ggcccggctg cgcacgctga ccctggcggc gtttgaaggg   4020
gccgagatgc aggatccggc cttcgctgcc tttcaggagg tggcgctgac ccacggtatt   4080
acgccccgca tggcgctcga tcacctcgac ggctttgcga tggacgtggc tcagacccgc   4140
tatgtcacct ttgaggatac gctgcgctac tgctatcacg tggcgggcgt ggtgggtctg   4200
atgatggcca gggtgatggg cgtgcgggat gagcgggtgc tggatcgcgc ctgcgatctg   4260
gggctggcct tccagctgac gaatatcgcc cgggatatta ttgacgatgc ggctattgac   4320
cgctgctatc tgcccgccga gtggctgcag gatgccgggc tgaccccgga gaactatgcc   4380
gcgcgggaga atcgggccgc gctggcgcgg gtggcggagc ggcttattga tgccgcagag   4440
ccgtactaca tctcctccca ggccgggcta cacgatctgc cgccgcgctg cgcctgggcg   4500
atcgccaccg cccgcagcgt ctaccgggag atcggtatta aggtaaaagc ggcgggaggc   4560
agcgcctggg atcgccgcca gcacaccagc aaaggtgaaa aaattgccat gctgatggcg   4620
gcaccggggc aggttattcg ggcgaagacg acgagggtga cgccgcgtcc ggccggtctt   4680
tggcagcgtc ccgtttagac cgactccaaa cgagtcggtt tttttgcgct tgtttcggcg   4740
tgggtatggt ggcaggcccc gtggccgggg gactgttggg cgccatctcc ttggggtcga   4800
atttgctttc gaatttctgc cattcatccg cttattatca cttattcagg cgtagcaacc   4860
aggcgtttaa gggcaccaat aactgcctta aaaaaattac gccccgccct gccactcatc   4920
gcagtactgt tgtaattcat taagcattct gccgacatgg aagccatcac agacggcatg   4980
atgaacctga atcgccagcg gcatcagcac cttgtcgcct tgcgtataat atttgcccat   5040
ggtgaaaacg ggggcgaaga agttgtccat attggccacg tttaaatcaa aactggtgaa   5100
actcacccag ggattggctg agacgaaaaa catattctca ataaaccctt tagggaaata   5160
ggccaggttt tcaccgtaac acgccacatc ttgcgaatat atgtgtagaa actgccggaa   5220
atcgtcgtgg tattcactcc agagcgatga aaacgtttca gtttgctcat ggaaaacggt   5280
gtaacaaggg tgaacactat cccatatcac cagctcaccg tctttcattg ccatacggaa   5340
ttccggatga gcattcatca ggcgggcaag aatgtgaata aaggccggat aaaacttgtg   5400
cttatttttc tttacggtct ttaaaaaggc cgtaatatcc agctgaacgg tctggttata   5460
ggtacattga gcaactgact gaaatgcctc aaaatgttct ttacgatgcc attgggatat   5520
atcaacggtg gtatatccag tgattttttt ctccatttta gcttccttag ctcctgaaaa   5580
tctcgataac tcaaaaaata cgcccggtag tgatcttatt tcattatggt gaaagttgga   5640
acctcttacg tgccgatcaa cgtctcattt tcgccaaaag ttggcccagg gcttcccggt   5700
```

-continued

```
atcaacaggg acaccaggat ttatttattc tgcgaagtga tcttccgtca caggtattta   5760
ttcggcgcaa agtgcgtcgg gtgatgctgc caacttactg atttagtgta tgatggtgtt   5820
tttgaggtgc tccagtggct tctgtttcta tcagctgtcc ctcctgttca gctactgacg   5880
gggtggtgcg taacggcaaa agcaccgccg gacatcagcg ctagcggagt gtatacactc   5940
cgctatcgct acgtgactgg gtcatggctg cgccccgaca cccgccaaca cccgctgacg   6000
cgccctgacg ggcttgtctg ctcccggcat ccgcttacag acaagctgtg accgtctccg   6060
ggagctgcat gtgtcagagg ttttcaccgt catcaccgaa acgcgcgagg cagctggcac   6120
gacaggtttc ccgactggaa aagcgaattg gtataatgcc ctcgtaataa ttttgtttaa   6180
ctttaagaag gagatatacc catgacacag agggcccacc atcaccatca ccattccatg   6240
gctagcggcg gcggaagttc cggtagtgag agttgtgtag cggtgagaga agatttcgct   6300
gacgaagaag attttgtgaa agctggtggt tctgagattc tatttgttca aatgcagcag   6360
aacaaagata tggatgaaca gtctaagctt gttgataagt tgcctcctat atcaattggt   6420
gatggtgctt tggatctagt ggttattggt tgtggtcctg ctggtttagc cttggctgca   6480
gaatcagcta agcttggatt aaaagttgga ctcattggtc cagatcttcc ttttactaac   6540
aattacggtg tttgggaaga tgaattcaat gatcttgggc tgcaaaaatg tattgagcat   6600
gtttggagag agactattgt gtatctggat gatgacaagc ctattaccat tggccgtgct   6660
tatggaagag ttagtcgacg tttgctccat gaggagcttt tgaggaggtg tgtcgagtca   6720
ggtgtctcgt accttagctc gaaagttgac agcataacag aagcttctga tggccttaga   6780
cttgttgctt gtgacgacaa taacgtcatt ccctgcaggc ttgccactgt tgcttctgga   6840
gcagcttcgg gaaagctctt gcaatacgaa gttggtggac ctagagtctg tgtgcaaact   6900
gcatacggcg tggaggttga ggtggaaaat agtccatatg atccagatca aatggttttc   6960
atggattaca gagattatac taacgagaaa gttcggagct tagaagctga gtatccaacg   7020
tttctgtacg ccatgcctat gacaaagtca agactcttct tcgaggagac atgtttggcc   7080
tcaaaagatg tcatgccctt tgatttgcta aaaacgaagc tcatgttaag attagataca   7140
ctcggaattc gaattctaaa gacttacgaa gaggagtggt cctatatccc agttggtggt   7200
tccttgccaa acaccgaaca aaagaatctc gcctttggtg ctgccgctag catggtacat   7260
cccgcaacag gctattcagt tgtgagatct ttgtctgaag ctccaaaata tgcatcagtc   7320
atcgcagaga tactaagaga agagactacc aaacagatca acagtaatat ttcaagacaa   7380
gcttgggata ctttatggcc accagaaagg aaaagacaga gagcattctt tctctttggt   7440
cttgaggcta tagttcaatt cgataccgaa ggcattagaa gcttcttccg tactttcttc   7500
cgccttccaa aatggatgtg gcaagggttt ctaggatcaa cattaacatc aggagatctc   7560
gttctctttt ctttatacat gttcgtcatt tcaccaaaca atttgagaaa aggtctcatc   7620
aatcatctca tctctgatcc aaccggagca accatgataa aaacctatct caaagtataa   7680
ggaggatctt actccatggc ccaccatcac catcaccatt ccatgggtat gcagggtgaa   7740
gatgcacagc gtaccggtaa tattgttgca gttaaaccga aaccgagcca gggtctgacc   7800
agcaaagcaa ttgattggct ggaatggctg tttgtgaaaa tgatgcatga tagcaaacag   7860
ccgctgcatt atctgagcgg taattttgca ccggttgatg aaacccctcc gctgaaagat   7920
ctgccggtta ccggtcatct gccggaatgt ctgaatggtg aatttgttcg tgttggtccg   7980
aatccgaaat ttgcaagcat tgcaggttat cattggtttg atggtgatgg tatgattcat   8040
ggcatgcgca ttaaagatgg taaagcaacc tatgttagcc gttatgttca gaccagccgt   8100
```

```
ctgaaacaag aggaattctt tggtcgtgcc atgttcatga aaatcggtga tctgaaaggt   8160
atgtttggtc tgctgatggt taatatgcag atgctgcgtg caaaactgaa agttctggat   8220
attagctatg gtattggcac cgcaaatacc gcactggttt atcatcatgg taaactgctg   8280
gcactgagcg aagcagataa accgtatgca attaaagtgc tggaagatgg tgatctgcag   8340
accattggcc tgctggatta tgataaacgt ctggcacata gctttaccgc acatccgaaa   8400
gttgatccgt ttaccggtga gatgtttacc tttggttata gccatacccc tccgtatgtt   8460
acctatcgtg ttattagcaa agatggtgca atgaatgatc cggttccgat taccgttagc   8520
ggtccgatca tgatgcacga ttttgcaatt accgaaaact acgccatctt tatggatctg   8580
ccgctgtatt tcaaaccgaa agaaatggtg aaagacaaga aattcatctt tagcttcgat   8640
gccacccaga aagcacgttt tggtattctg cctcgttatg ccaagaatga gctgctgatt   8700
aaatggtttg aactgccgaa ctgcttcatc tttcataatg caaatgcatg ggaagagggt   8760
gatgaagttg ttctgattac ctgtcgtctg gaaaatccgg atctggatat ggtgaatagc   8820
accgttaaag aacgtctgga caactttaag aacgagctgt atgaaatgcg cttcaatctg   8880
cagaatggtc tggcaagcca gaaaaaactg agcgttagcg cagttgattt tccgcgtgtt   8940
aatgaaagct ataccacccg taaacagcgt tatgtttatg gcaccaccct ggataagatt   9000
gccaaagtta ccggcatcat caaattcgat ctgcatgccg aaccggaaac cggtaaagag   9060
aagctggaac tgggtggtaa tgtgaaaggc atttttgatc tgggtccggg tcgttttggt   9120
tcagaagcag tttttgttcc gcgtcatccg ggtattacca gcgaagagga tgatggttat   9180
ctgatcttct ttgtgcacga tgaaaacacc ggcaaaagcg cagttaatgt tattgatgca   9240
aaaaccatga gccctgatcc ggtggcagtt gtggaactgc ctaaacgtgt tccgtatggt   9300
tttcatgcat tttttgttac cgaagatcag ctgcaagaac aggccaaagt ttaaggatcc   9360
ggctgctaac aaagcccgtt ctgtttaaga acgggatttt ttgctgaaag gaggaactat   9420
atccggccgg attactggct tactatgttg gcactgatga gggtgtcagt gaagtgcttc   9480
atgtggcagg agaaaaaagg ctgcaccggt gcgtcagcag aatatgtgat acaggatata   9540
ttccgcttcc tcgctcactg actcgctacg ctcggtcgtt cgactgcggc gagcggaaat   9600
ggcttacgaa cggggcggag atttcctgga agatgccagg aagatactta acagggaagt   9660
gagagggccg cggcaaagcc gtttttccat aggctccgcc cccctgacaa gcatcacgaa   9720
atctgacgct caaatcagtg gtggcgaaac ccgacaggac tataaagata ccaggcgttt   9780
cccccctggcg gctccctcgt gcgctctcct gttcctgcct ttcggtttac cggtgtcatt   9840
ccgctgttat ggccgcgttt gtctcattcc acgcctgaca ctcagttccg ggtaggcagt   9900
tcgctccaag ctggactgta tgcacgaacc ccccgttcag tccgaccgct gcgccttatc   9960
cggtaactat cgtcttgagt ccaacccgga aagacatgca aaagcaccac tggcagcagc  10020
cactggtaat tgatttagag gagttagtct tgaagtcatg cgccggttaa ggctaaactg  10080
aaaggacaag ttttggtgac tgcgctcctc caagccagtt acctcggttc aaagagttgg  10140
tagctcagag aaccttcgaa aaaccgccct gcaaggcggt tttttcgttt tcagagcaag  10200
agattacgcg cagaccaaaa cgatctcaag aagatcatct tattaatcag ataaaatatt  10260
tctagatttc agtgcaattt atctcttcaa atgtagcacc tgaagtcagc cccatacgat  10320
ataag                                                              10325
```

<210> SEQ ID NO 45

```
<211> LENGTH: 5183
<212> TYPE: DNA
<213> ORGANISM: Artificial Sequence
<220> FEATURE:
<223> OTHER INFORMATION: Plasmid pGT1534

<400> SEQUENCE: 45

aaagcgaatt gtgattgaaa tcaaaatttt cttgactaat tatggtataa tttactggta     60
ataattttgt ttaactttaa gaaggagata taccatgggc gatcttttat caatacagga    120
cccgtcgttt ttaaaaaaca tgtccattga tgaattagag aaattaagtg atgaaatccg    180
tcagttttta attacaagtt tatccgcttc cggcggccac atcggcccaa acttaggtgt    240
cgtagagctt actgttgccc tgcataagga atttaacagc ccgaaagaca aatttttatg    300
ggatgtaggc catcagtcgt atgtccataa gctgctgaca ggacgcggaa aagaatttgc    360
gacgcttcgc cagtacaaag ggctttgcgg atttccaaag cggagtgaaa gcgagcacga    420
tgtttgggaa accgggcaca gctcgacttc tctgtcaggc gcgatgggaa tggcagctgc    480
ccgtgatatt aaaggaacgg atgaatatat tattccgatc attggtgacg gcgcgctgac    540
cggcggtatg gcgctcgaag cccttaacca catcggcgac gagaaaaaag acatgattgt    600
catccttaat gataatgaaa tgagtattgc gccaaacgtc ggtgccattc actctatgct    660
cggacggctc cgcactgcgg ggaaatacca gtgggtcaaa gatgagcttg aatacttatt    720
taaaaagatt ccggcagttg gggcaagct tgccgccacg gcggaacggg tcaaagacag    780
cctgaaatac atgctcgtct ccggaatgtt tttcgaggag ctcggtttta cgtatttggg    840
cccagtggac ggacattctt atcatgagct gattgagaat cttcaatacg ccaaaaaaac    900
gaaaggccct gttcttctgc acgtcattac gaaaaaaggg aaggggtaca aaccggctga    960
gaccgatacg attgggacat ggcatggtac cggaccatat aaaattaata ccggtgactt   1020
tgtaaagccg aaagccgcag ctccttcgtg gagcggtctt gtcagcggaa ctgtgcagcg   1080
aatggcgcgc gaggacggac gcattgtagc cattacgccg gctatgcctg tcggttcaaa   1140
gcttgaaggc ttcgcaaagg aattccctga ccggatgttc gacgtaggaa tcgcagaaca   1200
gcatgccgca acaatggctg cagctatggc aatgcagggt atgaagccgt ttttggcgat   1260
ttactcaacc ttcctgcaaa gggcatatga ccaagttgtt catgacatct gccgccaaaa   1320
cgctaatgtg tttattggaa ttgaccgtgc tggactcgtt ggcgctgatg gagagacaca   1380
tcaaggcgtg tttgatattg cgtttatgcg ccacattcca aacatggtct taatgatgcc   1440
gaaagacgaa aatgaaggcc agcacatggt tcatacagca cttagctatg acgaaggccc   1500
gatagcaatg cgttttccgc gcggaaacgg actcggcgta aaaatggatg aacagttgaa   1560
aacgattccg atcggtacgt gggaggtgct gcgtccaggg aacgatgctg tcatcttaac   1620
attcggcaca acaatcgaaa tggcgattga agcagccgaa gagctgcaga aagaaggcct   1680
ttccgtgcgc gttgtgaatg cgcgttttat taagccgatt gatgaaaaga tgatgaagag   1740
tatcctaaaa gaaggcttgc caattttaac aattgaagaa gcggtcttag aaggcggttt   1800
cggaagctcg attttagaat tcgctcatga tcaaggtgaa tatcatactc cgattgacag   1860
aatgggtata cctgatcggt ttattgaaca cggaagtgta acagcgcttc ttgaggaaat   1920
tggactgaca aaacagcagg tggcaaatcg tattagatta ctgatgccac caaagacaca   1980
caaaggaatt ggatcataag gatccggctg ctaacaaagc ccgaaaggaa gctgagttgg   2040
ctgctgccac cgctgagcaa taactagcat aaccccttgg ggcctctaaa cgggtcttga   2100
ggggtttttt gctgaaagga ggaactatat ccggccggat atccacagga cgggtgtggt   2160
```

```
cgccatgatc gcgtagtcga tattattaga ccagcttatg gattgtttcc atatcggctg   2220
cctccagcag ggtaccctgt tccacacgcg cccaccattc catcagaaag ttgtccacga   2280
ccaagcggaa ccaaggtgac agtttcacac cttcctctcc ggcatccgcc ttgcgcagca   2340
gctctttcag ctgatcacga ttgacatact ttacatccgc cacttcatcc ggattcggca   2400
gcagtttcac atcgcgcacg ataaacagca aataatctac ctcatgctcg ccccatttac   2460
cgtcggatgg cgccttgtac agcatacggc ccagcgggat aaactcatcc actggaatgt   2520
cctccgcagg aatgcccagt tcatccagga gtttacgctg cgcggcattg cgcacaccca   2580
ggtagttttc ttgaattaac tcagactcgc ggtacaaggg gtggctgcag caggtgtttg   2640
tccagaccag gggaaggtc accttggttt cactgcgttg ctgtaaaagt aattcatatt   2700
tgctattaaa cagaaacact gaaaacgcac ggtgcaagag gttcaacgac tcaatctttt   2760
cgacaagatg gcaattatat ttcgactcat gtccaatcac aacgtcgttt tcgtcaacga   2820
gaatacattc atcttcaaac ataagacggc gctgaacagc atccatgctg gcatcgtcgg   2880
ctacggctgc catgaattta acctcctgat aaactaccgc attaaagctt atcgatgata   2940
agctgtcaaa catgagaatt cttgaagacg aaagggcctc gtgatacgcc tatttttata   3000
ggttaatgtc atgcatgaga caataaccct gataaatgct tcaataatat tgaaaaagga   3060
agagtatgag tattcaacat ttccgtgtcg cccttattcc cttttttgcg gcattttgcc   3120
ttcctgtttt tgctcaccca gaaacgctgg tgaaagtaaa agatgctgaa gatcagttgg   3180
gtgcacgagt gggttacatc gaactggatc tcaacagcgg taagatcctt gagagttttc   3240
gccccgaaga acgttttcca atgatgagca cttttaaagt tctgctatgt ggcgcggtat   3300
tatcccgtgt tgacgccggg caagagcaac tcggtcgccg catacactat tctcagaatg   3360
acttggttga cgcgtcacca gtcacagaaa agcatcttac ggatggcatg acagtaagag   3420
aattatgcag tgctgccata accatgagtg ataacactgc ggccaactta cttctgacaa   3480
cgatcggagg accgaaggag ctaaccgctt ttttgcacaa catgggggat catgtaactc   3540
gccttgatcg ttgggaaccg gagctgaatg aagccatacc aaacgacgag cgtgacacca   3600
cgatgcctgc agcaatggca acaacgttgc gcaaactatt aactggcgaa ctacttactc   3660
tagcttcccg gcaacaatta atagactgga tggaggcgga taaagttgca ggaccacttc   3720
tgcgctcggc ccttccggct ggctggttta ttgctgataa atctggagcc ggtgagcgtg   3780
ggtctcgcgg tatcattgca gcactggggc cagatggtaa gccctcccgt atcgtagtta   3840
tctacacgac ggggagtcag gcaactatgg atgaacgaaa tagacagatc gctgagatag   3900
gtgcctcact gattaagcat tggtaactgt cagaccaagt ttactcatat atactttaga   3960
ttgatttaaa acttcatttt taatttaaaa ggatctaggt gaagatcctt tttgataatc   4020
tcatgcatga ccaaaatccc ttaacgtgag ttttcgttcc actgagcgtc agaccccgta   4080
gaaaagatca aaggatcttc ttgagatcct ttttttctgc gcgtaatctg ctgcttgcaa   4140
acaaaaaaac caccgctacc agcggtggtt tgtttgccgg atcaagagct accaactctt   4200
tttccgaagg taactggctt cagcagagcg cagataccaa atactgtcct tctagtgtag   4260
ccgtagttag gccaccactt caagaactct gtagcaccgc ctacatacct cgctctgcta   4320
atcctgttac cagtggctgc tgccagtggc gataagtcgt gtcttaccgg gttggactca   4380
agacgatagt taccggataa ggcgcagcgg tcgggctgaa cggggggttc gtgcacacag   4440
cccagcttgg agcgaacgac ctacaccgaa ctgagatacc tacagcgtga gctatgagaa   4500
```

```
agcgccacgc ttcccgaagg gagaaaggcg gacaggtatc cggtaagcgg cagggtcgga   4560

acaggagagc gcacgaggga gcttccaggg ggaaacgcct ggtatcttta tagtcctgtc   4620

gggtttcgcc acctctgact tgagcgtcga tttttgtgat gctcgtcagg ggggcggagc   4680

ctatggaaaa acgccagcaa cgcggccttt ttacggttcc tggccttttg ctggcctttt   4740

gctcacatgt tctttcctgc gttatcccct gattctgtgg ataaccgtat taccgccttt   4800

gagtgagctg ataccgctcg ccgcagccga acgaccgagc gcagcgagtc agtgagcgag   4860

gaagcggaag agcgcctgat gcggtatttt ctccttacgc atctgtgcgg tatttcacac   4920

cgcatatatg gtgcactctc agtacaatct gctctgatgc cgcatagtta agccagtata   4980

cactccgcta tcgctacgtg actgggtcat ggctgcgccc cgacacccgc caacacccgc   5040

tgacgcgccc tgacgggctt gtctgctccc ggcatccgct tacagacaag ctgtgaccgt   5100

ctccgggagc tgcatgtgtc agaggttttc accgtcatca ccgaaacgcg cgaggcagct   5160

ggcacgacag gtttcccgac tgg                                            5183
```

<210> SEQ ID NO 46
<211> LENGTH: 6337
<212> TYPE: DNA
<213> ORGANISM: Artificial Sequence
<220> FEATURE:
<223> OTHER INFORMATION: Plasmid pGT1579

<400> SEQUENCE: 46

```
aaagcgaatt gtgattgaaa tcaaaatttt cttgactaat tatggtataa tttactggta     60

ataattttgt ttaactttaa gaaggagata taccatgggc gatcttttat caatacagga    120

cccgtcgttt ttaaaaaaca tgtccattga tgaattagag aaattaagtg atgaaatccg    180

tcagttttta attacaagtt tatccgcttc cggcggccac atcggcccaa acttaggtgt    240

cgtagagctt actgttgccc tgcataagga atttaacagc ccgaaagaca aatttttatg    300

ggatgtaggc catcagtcgt atgtccataa gctgctgaca ggacgcggaa aagaatttgc    360

gacgcttcgc cagtacaaag ggctttgcgg atttccaaag cggagtgaaa gcgagcacga    420

tgtttgggaa accgggcaca gctcgacttc tctgtcaggc gcgatgggaa tggcagctgc    480

ccgtgatatt aaaggaacgg atgaatatat tattccgatc attggtgacg gcgcgctgac    540

cggcggtatg gcgctcgaag cccttaacca catcggcgac gagaaaaaag acatgattgt    600

catccttaat gataatgaaa tgagtattgc gccaaacgtc ggtgccattc actctatgct    660

cggacggctc cgcactgcgg ggaaatacca gtgggtcaaa gatgagcttg aatacttatt    720

taaaaagatt ccggcagttg gggcaagct tgccgccacg gcggaacggg tcaaagacag     780

cctgaaatac atgctcgtct ccggaatgtt tttcgaggag ctcggtttta cgtatttggg    840

cccagtggac ggacattctt atcatgagct gattgagaat cttcaatacg ccaaaaaaac    900

gaaaggccct gttcttctgc acgtcattac gaaaaaaggg aaggggtaca aaccggctga    960

gaccgatacg attgggacat ggcatggtac cggaccatat aaaattaata ccggtgactt   1020

tgtaaagccg aaagccgcag ctccttcgtg gagcggtctt gtcagcggaa ctgtgcagcg   1080

aatggcgcgc gaggacggac gcattgtagc cattacgccg gctatgcctg tcggttcaaa   1140

gcttgaaggc ttcgcaaagg aattccctga ccggatgttc gacgtaggaa tcgcagaaca   1200

gcatgccgca acaatggctg cagctatggc aatgcagggt atgaagccgt tttggcgat    1260

ttactcaacc ttcctgcaaa gggcatatga ccaagttgtt catgacatct gccgccaaaa   1320

cgctaatgtg tttattggaa ttgaccgtgc tggactcgtt ggcgctgatg gagagacaca   1380
```

```
tcaaggcgtg tttgatattg cgtttatgcg ccacattcca aacatggtct taatgatgcc   1440
gaaagacgaa aatgaaggcc agcacatggt tcatacagca cttagctatg acgaaggccc   1500
gatagcaatg cgttttccgc gcggaaacgg actcggcgta aaaatggatg aacagttgaa   1560
aacgattccg atcggtacgt gggaggtgct gcgtccaggg aacgatgctg tcatcttaac   1620
attcggcaca acaatcgaaa tggcgattga agcagccgaa gagctgcaga aagaaggcct   1680
ttccgtgcgc gttgtgaatg cgcgttttat taagccgatt gatgaaaaga tgatgaagag   1740
tatcctaaaa gaaggcttgc caattttaac aattgaagaa gcggtcttag aaggcggttt   1800
cggaagctcg attttagaat tcgctcatga tcaaggtgaa tatcatactc cgattgacag   1860
aatgggtata cctgatcggt ttattgaaca cggaagtgta acagcgcttc ttgaggaaat   1920
tggactgaca aaacagcagg tggcaaatcg tattagatta ctgatgccac caaagacaca   1980
caaaggaatt ggatcataag gatccggctg ctaacaaagc ccgaaaggaa gctgagttgg   2040
ctgctgccac cgctgagcaa taactagcat aaccccttgg ggcctctaaa cgggtcttga   2100
ggggtttttt gctgaaagga ggaactatat ccggccggat atccacagga cgggtgtggt   2160
cgccatgatc gcgtagtcga aaaaacccgc cagaatagcg ggtagattat tatttttcaa   2220
cctgctgaac gtcaattcga cgcgcttcgt ccagctgact ggctttcgca cgaatgcgtg   2280
cttccagctg gtcgatcata tcgttgttgt ccagacggtc tttgcgcacg ccatcttcat   2340
agaggccgct tttcttgttg ccgccggtga cgccgagtgt agaaaccagc gcctcacctg   2400
ggccattcac cacgcagccg ataatcgaaa cgtccatcgg agtgatgata tcttccaggc   2460
gttgctccag cgcgttaacc gtaccgataa catcaaattc ctgacgcgaa caggtcgggc   2520
aggcgatgaa gttgatccct cgcgaacgga tacgcagcga tttcaaaata tcgaaaccga   2580
ctttgatctc ttcgaccgga tcggccgcca gcgatacgcg cagcgtgtcg ccgatgcctt   2640
cagacagcag cagacctaaa ccaatggcgg attttactgc cccgctgcgc gcaccaccgg   2700
cttcggtgat ccccagatgc aacggctgat cgatctgttt tgccagcaaa cgataagact   2760
caacagcgag gaagacgtca gacgctttca cgctgacttt gaactgatcg aagttcaggc   2820
gatcgagatg atcaacatga cgcatggcag attccagcaa cgcctgcggc gtcggttcgc   2880
catacttttc ttgcagatct tttccagcg atccggcgtt aacgccaata cggatcggaa   2940
tgtttttatc gcgcgcacag tcaaccacca tgcgaatacg ctcttcatta ccgatattgc   3000
cagggttaat acgcagacaa tcgacgccgt attccgctac tttcagcgca atgcgatagt   3060
cgaagtggat gtcagccacc agcggcacgt taacctgctg tttgatgagt ttgaacgctt   3120
ctgccgcgtc catcgtcggt acggatacac ggacgatatc agcgccaacg cgttccagcg   3180
ccttgatttg attgaccgtt gcttcgacgt ctgtcgtacg cgtattggtc atggactgta   3240
cggcgatggg agcaccatcg ccaatcggca cattcccaac gtaaatacgt gttgattttc   3300
tacgttgaat tggagcctgg ttatgcatta gtaatctcct tagaccagct tatggattgt   3360
ttccatatcg gctgcctcca gcagggtacc ctgttccaca cgcgcccacc attccatcag   3420
aaagttgtcc acgaccaagc ggaaccaagg tgacagtttc acaccttcct ctccggcatc   3480
cgccttgcgc agcagctctt tcagctgatc acgattgaca tactttacat ccgccacttc   3540
atccggattc ggcagcagtt tcacatcgcg cacgataaac agcaaataat ctacctcatg   3600
ctcgccccat ttaccgtcgg atggcgcctt gtacagcata cggcccagcg ggataaactc   3660
atccactgga atgtcctccg caggaatgcc cagttcatcc aggagtttac gctgcgcggc   3720
```

```
attgcgcaca cccaggtagt tttcttgaat taactcagac tcgcggtaca aggggtggct   3780
gcagcaggtg tttgtccaga ccagggggaa ggtcaccttg gtttcactgc gttgctgtaa   3840
aagtaattca tatttgctat taaacagaaa cactgaaaac gcacggtgca agaggttcaa   3900
cgactcaatc ttttcgacaa gatggcaatt atatttcgac tcatgtccaa tcacaacgtc   3960
gttttcgtca acgagaatac attcatcttc aaacataaga cggcgctgaa cagcatccat   4020
gctggcatcg tcggctacgg ctgccatgaa tttaacctcc tgataaacta ccgcattaaa   4080
gcttatcgat gataagctgt caaacatgag aattcttgaa gacgaaaggg cctcgtgata   4140
cgcctatttt tataggttaa tgtcatgcat gagacaataa ccctgataaa tgcttcaata   4200
atattgaaaa aggaagagta tgagtattca acatttccgt gtcgccctta ttcccttttt   4260
tgcggcattt tgccttcctg tttttgctca cccagaaacg ctggtgaaag taaaagatgc   4320
tgaagatcag ttgggtgcac gagtgggtta catcgaactg gatctcaaca gcggtaagat   4380
ccttgagagt tttcgccccg aagaacgttt tccaatgatg agcactttta aagttctgct   4440
atgtggcgcg gtattatccc gtgttgacgc cgggcaagag caactcggtc gccgcataca   4500
ctattctcag aatgacttgg ttgacgcgtc accagtcaca gaaaagcatc ttacggatgg   4560
catgacagta agagaattat gcagtgctgc cataaccatg agtgataaca ctgcggccaa   4620
cttacttctg acaacgatcg gaggaccgaa ggagctaacc gcttttttgc acaacatggg   4680
ggatcatgta actcgccttg atcgttggga accggagctg aatgaagcca taccaaacga   4740
cgagcgtgac accacgatgc ctgcagcaat ggcaacaacg ttgcgcaaac tattaactgg   4800
cgaactactt actctagctt cccggcaaca attaatagac tggatggagg cggataaagt   4860
tgcaggacca cttctgcgct cggcccttcc ggctggctgg tttattgctg ataaatctgg   4920
agccggtgag cgtgggtctc gcggtatcat tgcagcactg gggccagatg gtaagccctc   4980
ccgtatcgta gttatctaca cgacggggag tcaggcaact atggatgaac gaaatagaca   5040
gatcgctgag ataggtgcct cactgattaa gcattggtaa ctgtcagacc aagtttactc   5100
atatatactt tagattgatt taaaacttca tttttaattt aaaaggatct aggtgaagat   5160
cctttttgat aatctcatgc atgaccaaaa tcccttaacg tgagttttcg ttccactgag   5220
cgtcagaccc cgtagaaaag atcaaaggat cttcttgaga tccttttttt ctgcgcgtaa   5280
tctgctgctt gcaaacaaaa aaaccaccgc taccagcggt ggtttgtttg ccggatcaag   5340
agctaccaac tctttttccg aaggtaactg gcttcagcag agcgcagata ccaaatactg   5400
tccttctagt gtagccgtag ttaggccacc acttcaagaa ctctgtagca ccgcctacat   5460
acctcgctct gctaatcctg ttaccagtgg ctgctgccag tggcgataag tcgtgtctta   5520
ccgggttgga ctcaagacga tagttaccgg ataaggcgca gcggtcgggc tgaacggggg   5580
gttcgtgcac acagcccagc ttggagcgaa cgacctacac cgaactgaga tacctacagc   5640
gtgagctatg agaaagcgcc acgcttcccg aagggagaaa ggcggacagg tatccggtaa   5700
gcggcagggt cggaacagga gagcgcacga gggagcttcc agggggaaac gcctggtatc   5760
tttatagtcc tgtcgggttt cgccacctct gacttgagcg tcgatttttg tgatgctcgt   5820
caggggggcg gagcctatgg aaaaacgcca gcaacgcggc ctttttacgg ttcctggcct   5880
tttgctggcc ttttgctcac atgttctttc ctgcgttatc ccctgattct gtggataacc   5940
gtattaccgc ctttgagtga gctgataccg ctcgccgcag ccgaacgacc gagcgcagcg   6000
agtcagtgag cgaggaagcg gaagagcgcc tgatgcggta ttttctcctt acgcatctgt   6060
gcggtatttc acaccgcata tatggtgcac tctcagtaca atctgctctg atgccgcata   6120
```

```
gttaagccag tatacactcc gctatcgcta cgtgactggg tcatggctgc gccccgacac   6180

ccgccaacac ccgctgacgc gccctgacgg gcttgtctgc tcccggcatc cgcttacaga   6240

caagctgtga ccgtctccgg gagctgcatg tgtcagaggt tttcaccgtc atcaccgaaa   6300

cgcgcgaggc agctggcacg acaggtttcc cgactgg                            6337


<210> SEQ ID NO 47
<211> LENGTH: 6378
<212> TYPE: DNA
<213> ORGANISM: Artificial Sequence
<220> FEATURE:
<223> OTHER INFORMATION: Plasmid pGT1582

<400> SEQUENCE: 47

aaagcgaatt gtgattgaaa tcaaaatttt cttgactaat tatggtataa tttactggta     60

atacgataaa tcagcccggg aattaacatg gcaaccactc atttggatgt ttgcgccgtg    120

gttccggcgg ccggatttgg ccgtcgaatg caaacggaat gtcctaagca atatctctca    180

atcggtaatc aaaccattct tgaacactcg gtgcatgcgc tgctggcgca tccccgggtg    240

aaacgtgtcg tcattgccat aagtcctggc gatagccgtt ttgcacaact tcctctggcg    300

aatcatccgc aaatcaccgt tgtagatggc ggtgatgagc gtgccgattc cgtgctggca    360

ggtctgaaag ccgctggcga cgcgcagtgg gtattggtgc atgacgccgc tcgtccttgt    420

ttgcatcagg atgacctcgc gcgattgttg gcgttgagcg aaaccagccg cacggggggg    480

atcctcgccg caccagtgcg cgatactatg aaacgtgccg aaccgggcaa aaatgccatt    540

gctcataccg ttgatcgcaa cggcttatgg cacgcgctga cgccgcaatt tttccctcgt    600

gagctgttac atgactgtct gacgcgcgct ctaaatgaag gcgcgactat taccgacgaa    660

gcctcggcgc tggaatattg cggattccat cctcagttgg tcgaaggccg tgcggataac    720

attaaagtca cgcgcccgga agatttggca ctggccgagt tttacctcac ccgaaccatc    780

catcaggaga atacataatg cgaattggac acggttttga cgtacatgcc tttggcggtg    840

aaggcccaat tatcattggt ggcgtacgca ttccttacga aaaaggattg ctggcgcatt    900

ctgatggcga cgtggcgctc catgcgttga ccgatgcatt gcttggcgcg gcggcgctgg    960

gggatatcgg caagctgttc ccggataccg atccggcatt taaaggtgcc gatagccgcg   1020

agctgctacg cgaagcctgg cgtcgtattc aggcgaaggg ttataccctt ggcaacgtcg   1080

atgtcactat catcgctcag gcaccgaaga tgttgccgca cattccacaa atgcgcgtgt   1140

ttattgccga agatctcggc tgccatatgg atgatgttaa cgtgaaagcc actactacgg   1200

aaaaactggg atttaccgga cgtggggaag ggattgcctg tgaagcggtg gcgctactca   1260

ttaaggcaac aaaataagga ggatatacca tgggcgatct tttatcaata caggacccgt   1320

cgtttttaaa aaacatgtcc attgatgaat tagagaaatt aagtgatgaa atccgtcagt   1380

ttttaattac aagtttatcc gcttccggcg gccacatcgg cccaaactta ggtgtcgtag   1440

agcttactgt tgccctgcat aaggaattta acagcccgaa agacaaattt ttatgggatg   1500

taggccatca gtcgtatgtc cataagctgc tgacaggacg cggaaaagaa tttgcgacgc   1560

ttcgccagta caaagggctt tgcggatttc caaagcggag tgaaagcgag cacgatgttt   1620

gggaaaccgg gcacagctcg acttctctgt caggcgcgat gggaatggca gctgcccgtg   1680

atattaaagg aacggatgaa tatattattc cgatcattgg tgacggcgcg ctgaccggcg   1740

gtatggcgct cgaagccctt aaccacatcg gcgacgagaa aaaagacatg attgtcatcc   1800
```

```
ttaatgataa tgaaatgagt attgcgccaa acgtcggtgc cattcactct atgctcggac   1860
ggctccgcac tgcggggaaa taccagtggg tcaaagatga gcttgaatac ttatttaaaa   1920
agattccggc agttgggggc aagcttgccg ccacggcgga acgggtcaaa gacagcctga   1980
aatacatgct cgtctccgga atgtttttcg aggagctcgg ttttacgtat ttgggcccag   2040
tggacggaca ttcttatcat gagctgattg agaatcttca atacgccaaa aaaacgaaag   2100
gccctgttct tctgcacgtc attacgaaaa aagggaaggg gtacaaaccg gctgagaccg   2160
atacgattgg gacatggcat ggtaccggac catataaaat taataccggt gactttgtaa   2220
agccgaaagc cgcagctcct tcgtggagcg gtcttgtcag cggaactgtg cagcgaatgg   2280
cgcgcgagga cggacgcatt gtagccatta cgccggctat gcctgtcggt tcaaagcttg   2340
aaggcttcgc aaaggaattc cctgaccgga tgttcgacgt aggaatcgca gaacagcatg   2400
ccgcaacaat ggctgcagct atggcaatgc agggtatgaa gccgtttttg gcgatttact   2460
caaccttcct gcaaagggca tatgaccaag ttgttcatga catctgccgc caaaacgcta   2520
atgtgtttat tggaattgac cgtgctggac tcgttggcgc tgatggagag acacatcaag   2580
gcgtgtttga tattgcgttt atgcgccaca ttccaaacat ggtcttaatg atgccgaaag   2640
acgaaaatga aggccagcac atggttcata cagcacttag ctatgacgaa ggcccgatag   2700
caatgcgttt tccgcgcgga aacggactcg gcgtaaaaat ggatgaacag ttgaaaacga   2760
ttccgatcgg tacgtgggag gtgctgcgtc cagggaacga tgctgtcatc ttaacattcg   2820
gcacaacaat cgaaatggcg attgaagcag ccgaagagct gcagaaagaa ggcctttccg   2880
tgcgcgttgt gaatgcgcgt tttattaagc cgattgatga aaagatgatg aagagtatcc   2940
taaaagaagg cttgccaatt ttaacaattg aagaagcggt cttagaaggc ggtttcggaa   3000
gctcgatttt agaattcgct catgatcaag gtgaatatca tactccgatt gacagaatgg   3060
gtatacctga tcggtttatt gaacacggaa gtgtaacagc gcttcttgag gaaattggac   3120
tgacaaaaca gcaggtggca aatcgtatta gattactgat gccaccaaag acacacaaag   3180
gaattggatc ataaggatcc ggctgctaac aaagcccgaa aggaagctga gttggctgct   3240
gccaccgctg agcaataact agcataaccc cttggggcct ctaaacgggt cttgaggggt   3300
tttttgctga aaggaggaac tatatccggc cggatatcca caggacgggt gtggtcgcca   3360
tgatcgcgta gtcgatatta ttagaccagc ttatggattg tttccatatc ggctgcctcc   3420
agcagggtac cctgttccac acgcgcccac cattccatca gaaagttgtc cacgaccaag   3480
cggaaccaag gtgacagttt cacaccttcc tctccggcat ccgccttgcg cagcagctct   3540
ttcagctgat cacgattgac atactttaca tccgccactt catccggatt cggcagcagt   3600
ttcacatcgc gcacgataaa cagcaaataa tctacctcat gctcgcccca tttaccgtcg   3660
gatggcgcct tgtacagcat acggcccagc gggataaact catccactgg aatgtcctcc   3720
gcaggaatgc ccagttcatc caggagttta cgctgcgcgg cattgcgcac acccaggtag   3780
ttttcttgaa ttaactcaga ctcgcggtac aaggggtggc tgcagcaggt gtttgtccag   3840
accaggggga aggtcacctt ggtttcactg cgttgctgta aaagtaattc atatttgcta   3900
ttaaacagaa acactgaaaa cgcacggtgc aagaggttca acgactcaat cttttcgaca   3960
agatggcaat tatatttcga ctcatgtcca atcacaacgt cgttttcgtc aacgagaata   4020
cattcatctt caaacataag acggcgctga acagcatcca tgctggcatc gtcggctacg   4080
gctgccatga atttaacctc ctgataaact accgcattaa agcttatcga tgataagctg   4140
tcaaacatga gaattcttga agacgaaagg gcctcgtgat acgcctattt ttataggtta   4200
```

-continued

```
atgtcatgca tgagacaata accctgataa atgcttcaat aatattgaaa aaggaagagt   4260
atgagtattc aacatttccg tgtcgccctt attccctttt ttgcggcatt ttgccttcct   4320
gtttttgctc acccagaaac gctggtgaaa gtaaaagatg ctgaagatca gttgggtgca   4380
cgagtgggtt acatcgaact ggatctcaac agcggtaaga tccttgagag ttttcgcccc   4440
gaagaacgtt ttccaatgat gagcactttt aaagttctgc tatgtggcgc ggtattatcc   4500
cgtgttgacg ccgggcaaga gcaactcggt cgccgcatac actattctca gaatgacttg   4560
gttgacgcgt caccagtcac agaaaagcat cttacggatg gcatgacagt aagagaatta   4620
tgcagtgctg ccataaccat gagtgataac actgcggcca acttacttct gacaacgatc   4680
ggaggaccga aggagctaac cgcttttttg cacaacatgg gggatcatgt aactcgcctt   4740
gatcgttggg aaccggagct gaatgaagcc ataccaaacg acgagcgtga caccacgatg   4800
cctgcagcaa tggcaacaac gttgcgcaaa ctattaactg gcgaactact tactctagct   4860
tcccggcaac aattaataga ctggatggag gcggataaag ttgcaggacc acttctgcgc   4920
tcggcccttc cggctggctg gtttattgct gataaatctg gagccggtga gcgtgggtct   4980
cgcggtatca ttgcagcact ggggccagat ggtaagccct cccgtatcgt agttatctac   5040
acgacgggga gtcaggcaac tatggatgaa cgaaatagac agatcgctga gataggtgcc   5100
tcactgatta agcattggta actgtcagac caagtttact catatatact ttagattgat   5160
ttaaaacttc atttttaatt taaaaggatc taggtgaaga tcctttttga taatctcatg   5220
catgaccaaa atcccttaac gtgagttttc gttccactga gcgtcagacc ccgtagaaaa   5280
gatcaaagga tcttcttgag atcctttttt tctgcgcgta atctgctgct tgcaaacaaa   5340
aaaaccaccg ctaccagcgg tggtttgttt gccggatcaa gagctaccaa ctctttttcc   5400
gaaggtaact ggcttcagca gagcgcagat accaaatact gtccttctag tgtagccgta   5460
gttaggccac cacttcaaga actctgtagc accgcctaca tacctcgctc tgctaatcct   5520
gttaccagtg gctgctgcca gtggcgataa gtcgtgtctt accgggttgg actcaagacg   5580
atagttaccg gataaggcgc agcggtcggg ctgaacgggg ggttcgtgca cacagcccag   5640
cttggagcga acgacctaca ccgaactgag atacctacag cgtgagctat gagaaagcgc   5700
cacgcttccc gaagggagaa aggcggacag gtatccggta agcggcaggg tcggaacagg   5760
agagcgcacg agggagcttc caggggggaaa cgcctggtat ctttatagtc ctgtcgggtt   5820
tcgccacctc tgacttgagc gtcgattttt gtgatgctcg tcaggggggc ggagcctatg   5880
gaaaaacgcc agcaacgcgg cctttttacg gttcctggcc ttttgctggc cttttgctca   5940
catgttcttt cctgcgttat cccctgattc tgtggataac cgtattaccg cctttgagtg   6000
agctgatacc gctcgccgca gccgaacgac cgagcgcagc gagtcagtga gcgaggaagc   6060
ggaagagcgc ctgatgcggt attttctcct tacgcatctg tgcggtattt cacaccgcat   6120
atatggtgca ctctcagtac aatctgctct gatgccgcat agttaagcca gtatacactc   6180
cgctatcgct acgtgactgg gtcatggctg cgccccgaca cccgccaaca cccgctgacg   6240
cgccctgacg ggcttgtctg ctcccggcat ccgcttacag acaagctgtg accgtctccg   6300
ggagctgcat gtgtcagagg ttttcaccgt catcaccgaa acgcgcgagg cagctggcac   6360
gacaggtttc ccgactgg                                                  6378
```